(12) United States Patent
Riley et al.

(10) Patent No.: US 12,318,427 B2
(45) Date of Patent: Jun. 3, 2025

(54) METHODS AND COMPOSITIONS FOR MODULATION OF TAU PROTEINS

(71) Applicant: Sangamo Therapeutics, Inc., Richmond, CA (US)

(72) Inventors: Brigit E. Riley, Richmond, CA (US); Bryan Zeitler, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 1348 days.

(21) Appl. No.: 16/591,392

(22) Filed: Oct. 2, 2019

(65) Prior Publication Data

US 2020/0101133 A1   Apr. 2, 2020

Related U.S. Application Data

(60) Provisional application No. 62/740,162, filed on Oct. 2, 2018.

(51) Int. Cl.
| | | |
|---|---|---|
| A61K 38/17 | (2006.01) | |
| A61K 9/00 | (2006.01) | |
| C12N 15/86 | (2006.01) | |

(52) U.S. Cl.
CPC .......... *A61K 38/1709* (2013.01); *C12N 15/86* (2013.01); *A61K 9/0019* (2013.01); *C12N 2750/14143* (2013.01)

(58) Field of Classification Search
CPC .. A61K 38/1709; A61K 9/0019; C12N 15/86; C12N 2750/14143
See application file for complete search history.

(56) References Cited

U.S. PATENT DOCUMENTS

| | | | |
|---|---|---|---|
| 4,897,355 A | 1/1990 | Eppstein et al. | |
| 4,946,787 A | 8/1990 | Eppstein et al. | |
| 5,049,386 A | 9/1991 | Eppstein et al. | |
| 5,789,538 A | 8/1998 | Rebar et al. | |
| 5,925,523 A | 7/1999 | Dove et al. | |
| 6,007,988 A | 12/1999 | Choo et al. | |
| 6,008,336 A | 12/1999 | Hanson et al. | |
| 6,013,453 A | 1/2000 | Choo et al. | |
| 6,140,081 A | 10/2000 | Barbas | |
| 6,200,759 B1 | 3/2001 | Dove et al. | |
| 6,309,634 B1 | 10/2001 | Bankiewicz et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox, III et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,746,838 B1 | 6/2004 | Choo et al. | |
| 6,824,978 B1 | 11/2004 | Cox, III et al. | |
| 6,866,997 B1 | 3/2005 | Choo et al. | |
| 6,903,185 B2 | 6/2005 | Kim et al. | |
| 6,933,113 B2 | 8/2005 | Case et al. | |
| 6,953,575 B2 | 10/2005 | Bankiewicz et al. |
| 6,979,539 B2 | 12/2005 | Cox, III et al. |
| 7,013,219 B2 | 3/2006 | Case et al. |
| 7,074,596 B2 | 7/2006 | Darznkiewicz et al. |
| 7,153,949 B2 | 12/2006 | Kim et al. |
| 7,163,824 B2 | 1/2007 | Cox, III et al. |
| 7,182,944 B2 | 2/2007 | Bankiewicz |
| 7,198,951 B2 | 4/2007 | Gao et al. |
| 7,241,573 B2 | 7/2007 | Choo et al. |
| 7,241,574 B2 | 7/2007 | Choo et al. |
| 7,837,668 B2 | 11/2010 | Gasmi et al. |
| 7,851,216 B2 | 12/2010 | Choo et al. |
| 7,888,121 B2 | 2/2011 | Urnov et al. |
| 7,914,796 B2 | 3/2011 | Miller et al. |
| 8,034,598 B2 | 10/2011 | Miller |
| 8,092,429 B2 | 1/2012 | Gasmi et al. |
| 8,153,773 B2 | 4/2012 | Jemielity et al. |
| 8,309,355 B2 | 11/2012 | Bankiewicz et al. |
| 8,337,458 B2 | 12/2012 | Bankiewicz et al. |
| 8,409,861 B2 | 4/2013 | Guschin et al. |
| 8,586,526 B2 | 11/2013 | Gregory et al. |
| 8,597,912 B2 | 12/2013 | Collingwood et al. |
| 8,623,618 B2 | 1/2014 | Doyon et al. |
| 8,647,631 B2 | 2/2014 | Pfeifer et al. |
| 8,703,489 B2 | 4/2014 | Wang |
| 8,772,453 B2 | 7/2014 | Paschon et al. |
| 8,956,828 B2 | 2/2015 | Bonini et al. |
| 9,050,299 B2 | 6/2015 | Bankiewicz |
| 9,089,667 B2 | 7/2015 | Bankiewicz |
| 9,200,266 B2 | 12/2015 | Wang |
| 9,394,531 B2 | 7/2016 | Miller |
| 9,458,205 B2 | 10/2016 | Gregory et al. |
| 9,567,609 B2 | 2/2017 | Paschon et al. |

(Continued)

FOREIGN PATENT DOCUMENTS

| | | |
|---|---|---|
| AU | 2002330097 A1 | 4/2003 |
| CN | 104204225 A | 12/2014 |

(Continued)

OTHER PUBLICATIONS

Benihoud et al. "Adenovirus vectors for gene delivery" 1999, vol. 10: 440-447. (Year: 1999).*
Kang et al. 2008. "Novel Cancer Antiangiotherapy Using the VEGF Promoter-targeted Artificial Zinc-finger Protein and Oncolytic Adenovirus", Molecular Therapy. vol. 16, No. 6:1033-1040 (Year: 2008).*
Handel et al. "Versatile and Efficient Genome Editing in Human Cells by Combining Zinc-Finger Nucleases with Adeno-Associated Viral Vectors" Human Gene Therapy (2012) 23: 321-329 (Year: 2012).*
SantaCruz et al. "Tau Suppression in a Neurodegenerative Mouse Model Improves Memory Function" Science (2005) 309: 476-481) (Year: 2005).*

(Continued)

*Primary Examiner* — Neil P Hammell
*Assistant Examiner* — Kelly Nichet Hassell
(74) *Attorney, Agent, or Firm* — Snell & Wilmer L.L.P

(57) ABSTRACT

The present disclosure is in the field of diagnostics and therapeutics for Alzheimer's Disease.

9 Claims, 89 Drawing Sheets

Specification includes a Sequence Listing.

(56) References Cited

U.S. PATENT DOCUMENTS

| | | |
|---|---|---|
| 9,585,971 B2 | 3/2017 | Deverman et al. |
| 9,624,498 B2 | 4/2017 | Froelich et al. |
| 9,885,039 B2 | 2/2018 | Huang et al. |
| 10,563,184 B2 | 2/2020 | Miller et al. |
| 10,724,020 B2 | 7/2020 | Miller et al. |
| 10,793,856 B2 | 10/2020 | Kordasiewicz et al. |
| 11,504,389 B2 | 11/2022 | Ledeboer et al. |
| 2003/0021776 A1 | 1/2003 | Rebar et al. |
| 2004/0209277 A1 | 10/2004 | Lee et al. |
| 2006/0239966 A1 | 10/2006 | Tornøe et al. |
| 2009/0068164 A1 | 3/2009 | Segal et al. |
| 2009/0111119 A1 | 4/2009 | Doyon et al. |
| 2010/0257638 A1 | 10/2010 | Cai et al. |
| 2011/0016539 A1 | 1/2011 | Weinstein et al. |
| 2011/0023153 A1 | 1/2011 | Weinstein et al. |
| 2011/0082093 A1 | 4/2011 | Gregory et al. |
| 2011/0301073 A1 | 12/2011 | Gregory et al. |
| 2012/0195936 A1 | 8/2012 | Rudolph et al. |
| 2013/0130347 A1 | 5/2013 | Delisa et al. |
| 2013/0196373 A1 | 8/2013 | Gregory et al. |
| 2013/0253040 A1 | 9/2013 | Miller et al. |
| 2014/0357530 A1 | 12/2014 | Zhang et al. |
| 2015/0056177 A1 | 2/2015 | Liu et al. |
| 2015/0056705 A1 | 2/2015 | Conway et al. |
| 2015/0267205 A1 | 2/2015 | Conway et al. |
| 2015/0335708 A1 | 11/2015 | Froelich et al. |
| 2015/0353917 A1 | 12/2015 | Miller |
| 2016/0201089 A1 | 7/2016 | Gersbach et al. |
| 2016/0333063 A1 | 11/2016 | Hyman et al. |
| 2017/0035860 A1 | 2/2017 | Flynn |
| 2017/0119906 A1 | 5/2017 | Riley |
| 2018/0087072 A1 | 3/2018 | Miller et al. |
| 2018/0142215 A1 | 5/2018 | Eguchi et al. |
| 2018/0153921 A1 | 6/2018 | Ledeboer et al. |
| 2020/0101133 A1 | 4/2020 | Riley et al. |
| 2020/0109406 A1 | 4/2020 | Miller et al. |
| 2023/0242602 A1 | 8/2023 | Zeitler et al. |
| 2023/0270774 A1 | 8/2023 | Ledeboer et al. |

FOREIGN PATENT DOCUMENTS

| | | |
|---|---|---|
| CN | 106030310 A | 10/2016 |
| CN | 110214184 A | 9/2019 |
| CN | 110214184 B | 7/2024 |
| EP | 1683862 A1 | 7/2006 |
| EP | 3 080 611 | 10/2016 |
| JP | 2017505756 A | 2/2017 |
| KR | 1020160034340 | 3/2016 |
| KR | 1020180016970 A | 2/2018 |
| RU | 2582916 C2 | 2/2018 |
| WO | WO 1995/019431 A1 | 7/1995 |
| WO | WO 1996/006166 A1 | 2/1996 |
| WO | WO 1998/053057 A1 | 11/1998 |
| WO | WO 1998/053058 A1 | 11/1998 |
| WO | WO 1998/053059 A1 | 11/1998 |
| WO | WO 1998/053060 A1 | 11/1998 |
| WO | WO 1998/054311 A1 | 12/1998 |
| WO | WO 1999/045132 | 9/1999 |
| WO | WO 2000/027878 A1 | 5/2000 |
| WO | WO 2001/053480 | 7/2001 |
| WO | WO 2001/060970 A2 | 8/2001 |
| WO | WO 2001/088197 A2 | 11/2001 |
| WO | WO 2002/016536 A1 | 2/2002 |
| WO | WO 2002/099084 A2 | 12/2002 |
| WO | WO 2003/016496 A2 | 2/2003 |
| WO | WO 2005/004794 A2 | 1/2005 |
| WO | WO 2009/154686 | 12/2009 |
| WO | 2010/076939 A1 | 7/2010 |
| WO | WO 2010/079430 A1 | 7/2010 |
| WO | 2011/139349 | 11/2011 |
| WO | 2013/130824 | 9/2013 |
| WO | WO 2014/153236 A1 | 9/2014 |
| WO | WO 2015/031619 | 3/2015 |
| WO | 2015/153760 | 10/2015 |
| WO | 2020072677 | 4/2016 |
| WO | 2017/011556 | 1/2017 |
| WO | WO 2017/136049 | 8/2017 |
| WO | WO 2017/197141 A2 | 11/2017 |
| WO | WO 2018/039471 A2 | 3/2018 |
| WO | WO 2018/049009 A2 | 3/2018 |
| WO | 2018102665 A1 | 6/2018 |
| WO | 2020072684 | 4/2020 |
| WO | 2021/151012 | 7/2021 |

OTHER PUBLICATIONS

Couchie et al. "Primary structure of high molecular weight tau present in the peripheral nervous system" Proc. Nat. Acad. Sci. (1992) 89: 4378-4381 (Year: 1992).*

Lee et al. "Toward a Functional Annotation of the Human Genome Using Artificial Transcription Factors" Genome Res. (2003) 13: 2708-2716. (Year: 2003).*

Alerasool et al., "An Efficient KRAB Domain for CRISPRi Applications in Human Cells," Nature Methods (2020) 17:1093-6.

Alisky et al., "Gene Therapy for Amyotrophic Lateral Sclerosis and Other Motor Neuron Diseases," Hum Gene Ther. (2000) 11:2315-29.

Asuni et al., "Immunotherapy Targeting Pathological Tau Conformers in a Tangle Mouse Model Reduces Brain Pathology with Associated Functional Improvements," J Neurosci. (2007) 27(34):9115-29.

Bennett et al., "Enhanced Tau Aggregation in the Presence of Amyloid β," Am J Pathol. (2017) 187(7):1601-12.

Bird et al., "Methylation-Induced Repression—Belts, Braces, and Chromatin," Cell (1999) 99:451-54.

Cheng et al., "Tau Reduction Diminishes Spatial Learning and Memory Deficits after Mild Repetitive Traumatic Brain Injury in Mice," PLOS One (2014) 9(12):e115765.

Chern et al., "The Regulator of MAT2 (ROM2) Protein Binds to Early Maturation Promoters and Represses PvALF-Activated Transcription," Plant Cell (1996) 8(2):305-21.

Davidson et al., "A Model System for In Vivo Gene Transfer into the Central Nervous System Using an Adenoviral Vector," Nat Genet. (1993) 3:219-223.

Davidson et al., Recombinant Adeno-associated Virus Type 2, 4, and 5 Vectors: Transduction of Variant Cell Types and Regions in the Mammalian Central Nervous System, PNAS (2000) 97(7):3428-32.

Devos et al., "Antisense Oligonucleotides: Treating Neurodegeneration at the Level of RNA," Neurotherapeutics (2013) 10(3):486-97.

Devos et al., "Tau Reduction Prevents Neuronal Loss and Reverses Pathological Tau Deposition and Seeding in Mice with Tauopathy," Sci Transl Med. (2017) 9(374):eaag0481.

Deyi, "Screening of ZBTB1 Interacting Protein and 3'-UTR Insertion/deletion Polymorphism of RTN4 Gene and Lung Cancer Susceptibility Study," China Outstanding Master's Thesis Full Text Database (Electronic Journal) Basic Science Series (2013).

Guerrero-Munoz et al., "Tau Oligomers: The Toxic Player at Synapses in Alzheimer's Disease," Front Cell Neurosci. (2015) 9(464).

Hadaczek et al., "Eight Years of Clinical Improvement in MPTP-Lesioned Primates After Gene Therapy with AAV2-hAADC," Mol Ther. (2010) 18(8):1458-61.

Herrmann et al., "Clearing the Way for Tau Immunotherapy in Alzheimer's Disease," J Neurochem. (2015) 132:1-4.

Ittner et al., "Tau-targeting Passive Immunization Modulates Aspects of Pathology in Tau Transgenic Mice," J Neurochem. (2015) 132:135-45.

Knoepfler et al., "Sin Meets NuRD and Other Tails of Repression," Cell (1999) 99:447-50.

La Joie et al., "Prospective Longitudinal Atrophy in Alzheimer's Disease Correlates with the Intensity and Topography of Baseline Tau-PET," Sci Transl Med. (2020) 12(524).

Lopes et al., "Tau Protein is Essential for Stress-induced Brain Pathology," PNAS (2016) 113:E3755-63.

McKee et al., "The Neuropathology of Chronic Traumatic Encephalopathy," Brain Pathol. (2015) 25(3):350-64.

Miller et al., "Enhancing Gene Editing Specificity by Attenuating DNA Cleavage Kinetics," Nat Biotechnol. (2019) 37:945-52.

(56) References Cited

OTHER PUBLICATIONS

Niwa et al., "Efficient Selection for High-expression Transfectants with a Novel Eukaryotic Vector," Gene (1991) 108(2):193-99.
Roberson et al., "Reducing Endogenous Tau Ameliorates Amyloid β-Induced Deficits in an Alzheimer's Disease Mouse Model," Science (2007) 316:750-4.
Robertson et al., "DNMT1 Forms a Complex with Rb, E2F1 and HDAC1 and Represses Transcription from E2F-Responsive Promoters," Nature Genet. (2000) 25:338-42.
Stein et al., "Systemic and Central Nervous System Correction of Lysosomal Storage in Mucopolysaccharidosis Type VII Mice," J Vir. (1999) 73(4):3424-9.
Tyler et al., "The "Dark Side" of Chromatin Minireview Remodeling: Repressive Effects on Transcription," Cell (1999) 99:443-6.
Wu et al., "Functional Analysis of HD2 Histone Deacetylase Homologues in *Arabidopsis thaliana*," Plant J. (2000) 22(1):19-27.
Yanamandra et al., "Anti-tau Antibodies that Block Tau Aggregate Seeding in vitro Markedly Decrease Pathology and Improve Cognition in vivo," Neuron (2013) 80(2):402-14.
Zaiss et al., "Immunity to Adeno-associated Virus Vectors in Animals and Humans: a Continued Challenge," Gene Ther. (2008) 15:808-16.
Zhang, et al., "Synthetic Zinc Finger Transcription Factor Action at an Endogenous Chromosomal Site," The Journal of Biological Chemistry (2000) 275(43):33850-3860.
Ando, et al., "Stabilization of Microtubule-Unbound Tau via Tau Phosphorylation at SER262/356 by PAR-1/MARK Contributes to Augmentation of Ad-Related Phosphorylation and AB42-Induced Tau Toxicity," PLoS Genet 12(3):1-26, e1005917 (2016).
Benussi, et al., "Phenotypic Heterogeneity of Monogenic Frontotemporal Dementia," Front Ag Neuro 7(171): 1-19 (2015).
Beurdeley, et al., "Compact Designer Talens for Efficient Genome Engineering," Nat Commun 4(1762):1-8, doi:10.1038/ncomms2782 (2013).
Boch, et al., "Breaking The Code of DNA Binding Specificity of Tal-Type III Effectors," Science 326:1509-1512 (2009).
Bodea, et al., "Tau Physiology and Pathomechanisms in Frontotemporal Lobar Degeneration," J of Neurochem 138(Suppl 1):71-94 (2016).
Boissel, et al., "Megatals: A Rare-Cleaving Nuclease Architecture for Therapeutic Genome Engineering," Nucleic Acids Research 42(4):2591-2601, doi: 10.1093/nar/gkt1224 (2013).
Bonas, et al., "Genetic and Structural Characterization of The Avirulence Gene AVRBS3 From Xanthomonas Campestris PV. Vesicatoria," Mol Gen Genet 218:127-136 (1989).
Brouns, et al., "Small CRISPR RNAS Guide Antiviral Defense in Prokaryotes," Science 321:960-964 (2008).
Burstein, et al., "New CRISPR-Cas Systems From Uncultivated Microbes," Nature 542(7640):237-241 (2017).
Carstens, et al., "Perineuronal Nets Suppress Plasticity of Excitatory Synapses on CA2 Pyramidal Neurons," J Neurosci. 36(23):6312-6320 (2016).
Cebrian-Serrano, et al., "CRISPR-Cas Orthologues and Variants: Optimizing the Repertoire, Specificity and Delivery of Genome Engineering Tools," Mamm Genome 28(7):247-261 (2017).
Cong, et al., "Multiplex Genome Engineering Using CRISPR/Cas Systems," Science 339(6121): 819-823, doi: 10.1126/science. 1231143 (2013).
Conrad, et al., "A Polymorphic Gene Nested Within an Intron of The Tau Gene: Implications for Alzheimer's Disease," Proc Natl Acad Sci U S A. 99(11):7751-7756 (2002).
De Calignon, et al., "Propagation of Tau Pathology in a Model of Early Alzheimer's Disease," Neuron 73:685-697 (2012).
DeVos, et al., "Antisense Reduction of Tau in Adult Mice Protects Against Seizures," Journal of NeuroScience 33(31):12887-12897 (2013).
Esvelt, et al., "Orthogonal CAS9 Proteins for RNA-Guided Gene Regulation and Editing," Nature Methods 10(11):1116 (2013).
Fagerlund, et al., "The Cpf1 CRISPR-Cas Protein Expands Genome-Editing Tools," Genome Biology 16:251 (2015).
Ferraro, et al., "Mapping Murine Loci for Seizure Response to Kainic Acid," Mamm Genome 8(3):200-208 (1997).
Fonfara, et al., "Phylogeny of CAS9 Determines Functional Exchangeability of Dual-RNA and CAS9 Among Orthologous Type II CRISPR-Cas Systems," Nucleic Acids Research 42(4):2377-2590 (2013).
Fu, et al., "Improving CRISPR-Cas Nuclease Specificity Using Truncated Guide RNAS," Nature Biotechnol 32(3):279-284 (2014).
Gheyara, et al., "Tau Reduction Prevents Disease in a Mouse Model of Dravet Syndrome," Ann Neurol 76(3):443-456 (2014).
Godde, et al., "The Repetitive DNA Elements Called CRISPRS and Their Associated Genes: Evidence of Horizontal Transfer Among Prokaryotes," J Mol Evol 62:718-729 (2006).
Gurda, et al., "Evaluation of AAV-Mediated Gene Therapy for Central Nervous System Disease in Canine Mucopolysaccharidosis VII," Molecular Therapy 24(2):206-216 (2016).
Haft, et al., "A Guild of 45 CRISPR-Associated (Cas) Protein Families and Multiple CRISPR/Cas Subtypes Exist in Prokaryotic Genomes," PLoS Computational Biology 1(6):e60 (2005).
Hale, et al., "Prokaryotic Silencing (PSI)RNAS in Pyrococcus Furiosus," RNA 14:2572-2579 (2008).
Hardy, et al., "The Amyloid Hypothesis of Alzheimer's Disease: Progress and Problems on The Road to Therapeutics," Science 297:353-356 (2002).
Heuer, et al., "Repeat Domain Diversity of AVRBS3-Like Genes in Ralstonia Solanacearum Strains and Association With Host Preferences in The Field," Applied and Environmental Microbiology 73(13):4379-4384 (2007).
Hilton, et al., "Epigenome Editing by a CRISPR/Cas9-Based Acetyltransferase Activates Genes From Promoters and Enhancers," Nat Biotechnol 33(5):510-517 (2015).
Hsiao, et al., "Upregulation of Haploinsufficient Gene Expression in the Brain by Targeting a Long Non-Coding RNA Improves Seizure Phenotype in a Model of Dravet Syndrome," EBioMedicine 9:257-277 (2016).
Hsu, et al., "DNA Targeting Specificity of RNA-Guided CAS9 Nucleases," Nat Biotechnol 31(9):827-832, doi: 10.1038/nbt.2647 (2013).
Hwang, et al., "Efficient in Vivo Genome Editing Using RNA-Guided Nucleases," Nat Biotechnol 31(3):227-229 (2013).
Hyman, "Tau Propagation, Different Tau Phenotypes, and Prion-Like Properties of Tau," Neuron 82:1189-1190 (2014).
Jackson, et al., "Initial Gene Vector Dosing for Studying Symptomatology of Amyotrophic Lateral Sclerosis in Non-Human Primates," J. Med Primatol 44(2):66-75 (2015).
Jansen, et al., "Identification of Genes That are Associated With DNA Repeats in Prokaryotes," Molecular Microbiology 43(6):1565-1575 (2002).
Jinek, et al., "A Programmable Dual-RNA-Guided DNA Endonuclease in Adaptive Bacterial Immunity," Science 337:816-821 (2012).
Johnston, et al., "Symptomatic Models of Parkinson's Disease and L-Dopa-Induced Dyskinesia in Non-Human Primates," Curr Top Behav Neurosci 22:221-235 (2015).
Kabadi, et al., "Engineering Synthetic Tale and CRISPR/CAS9 Transcription Factors for Regulating Gene Expression," Methods 69(2):188-197 (2014).
Kadiyala, et al., "Spatiotemporal Differences in the C-FOS Pathway Between C57BL/6J and DBA/2J Mice Following Flurothyl-Induced Seizures: A Dissociation of Hippocampal FOS From Seizure Activity," Epilepsy Res 109:183-196 (2015).
Kay, et al., "A Bacterial Effector Acts as a Plant Transcription Factor and Induces a Cell Size Regulator," Science 318:648-651 (2007).
Kleinstiver, et al., "High-Fidelity CRISPR-CAS9 Variants With Undetectable Genome-Wide Off-Targets," Nature 529(7587):490-495 (2016).
Kormann, et al., "Expression of Therapeutic Proteins After Delivery of Chemically Modified MRNA in Mice," Nature Biotechnology 29(2):154-157 (2011).
Laganiere, et al., "An Engineered Zinc Finger Protein Activator of the Endogenous Glial Cell Line-Derived Neurotrophic Factor Gene Provides Functional Neuroprotection in a Rat Model of Parkinson's Disease," Journal of Neuroscience 30(49):16469-16474 (2010).

(56) References Cited

OTHER PUBLICATIONS

Li, et al., "Application of App/OS1 Transgenic Mouse Model for Alzheimer's Disease," *J Alzheimers Dis Parkin* 5(3):4 pgs., doi: 10.4172/2161-0460.1000201 (2015).
Lillestøl, et al., "A Putative Viral Defence Mechanism in Archaeal Cells," *Archaea* 2:59-72 (2006).
Liu, et al., "Regulation of an Endogenous Locus Using a Panel of Designed Zinc Finger Proteins Targeted to Accessible Chromatin Regions," *Journal of Biological Chemistry* 276(14):11323-11334 (2001).
Liu, et al., "Vectored Intracerebral Immunization With the Anti-Tau Monoclonal Antibody PHF1 Markedly Reduces Tau Pathology in Mutant Tau Transgenic Mice," *Journal Neuroscience* 36(49):12425-12435 (2016).
Ma, et al., "Rational Design of Mini-CAS9 for Transcriptional Activation," *ACS Synth Biol* 7(4):978-985 (2018).
Makarova, et al., "A DNA Repair System Specific for Thermophilic Archaea and Bacteria Predicted by Genomic Context Anlysis," *Nucleic Acids Research* 30(2):482-496 (2002).
Makarova, et al., "A Putative RNA-Interference-Based Immune System in Prokaryotes: Computational Analysis of The Predicted Enzymatic Machinery, Functional Analogies With Eukaryotic RNAI, and Hypothetical Mechanisms of Action," *Biology Direct* 1(7):1-26 (2006).
Myers, et al., "Effects of Acute and Chronic Paleocerebellar Stimulation on Experimental Models of Epilepsy in The CAT: Studies With Enflurane, Pentylenetetrazol, Penicillin, and Chloralosed," *Epilepsia* 16(2):257-67 (1975).
Moscou, et al., "A Simple Cipher Governs DNA Recognition By Tal Effectors," *Science* 326:1501 (2009).
Park, et al., "Quantitative Expression Analysis of App Pathway and Tau Phosphorylation-Related Genes in The ICV STZ-Induced Non-Human Primate Model of Sporadic Alzheimer's Disease," *Int J Mol Sci* 16(2):2386-2402 (2015).
Polydoro, et al., "Reversal of Neurofibrillary Tangles and Tau-Associated Phenotype in The Rtgtauec Model of Early Alzheimer's Disease," *Journal of Neuroscience* 33(33):13300-13311 (2013).
Pooler, et al., "Amyloid Accelerates Tau Propagation and Toxicity in a Model of Early Alzheimer's Disease," *Acta Neuropathologica Communications* 3(14):1, doi: 10.1186/s40478-015-0199-x (2015).
Ramalingam, et al., "Generation and Genetic Engineering of Human Induced Pluripotent Stem Cells Using Designed Zinc Finger Nucleases," *Stem Cells and Development* 22(4):595-610 (2013).
Remacle, et al., "New Mode of DNA Binding of Multi-Zinc Finger Transcription Factors: Deltaefi Family Members Bind With Two Hands to Two Target Sites," *EMBO Journal* 18(18):5073-5084 (1999).
Sander, et al., "CRISPR-Cas Systems for Genome Editing, Regulation and Targeting," *Nature Biotechnol* 32(4):347-355 (2014).
Scholz, et al., "Genetics Underlying Atypical Parkinsonism and Related Neurodegenerative Disorders," *Int J. Mol Sci* 16(10):24629-24655 (2015).
Schornack, et al., "Gene-for-Gene-Mediated Recognition of Nuclear-Targeted AVRBS3-Like Bacterial Effector Proteins," *Journal of Plant Physiology* 163(3):256-272 (2006).
Schutt, et al., "Dogs With Cognitive Dysfunction as a Spontaneous Model for Early Alzheimer's Disease: A Translational Study of Neuropathological and Inflammatory Markers," *J Alzheimer's Dis* 52(2):433-449 (2016).
Sheng, et al., "Structure-Based Cleavage Mechanism of Thermus Thermophilus Argonaute DNA Guide Strand-Mediated DNA Target Cleavage," *Proc. Natl. Acad. Sci. U.S.A.* 111(2):652-657 (2014).
Sorek, et al., "CRISPR—A Widespread System That Provides Acquired Resistance Against Phages in Bacteria and Archaea," *Nature Reviews Microbiology* 6:181-186 (2008).
Sorrentino, et al., "The Dark Sides of Amyloid in Alzheimer's Disease Pathogenesis," *FEBS Lett* 588:641-652 (2014).
Spires-Jones, et al., "The Intersection of Amyloid Beta and Tau at Synapses in Alzheimer's Disease," *Neuron* 82(4):756-771 (2014).
Swarts, et al., "DNA-Guided DNA Interference by a Prokaryotic Argonaute," *Nature* 507(7491):258-261 (2014).
Takeda, et al., "Neuronal Uptake and Propagation of a Rare Phosphorylated High-Molecular-Weight Tau Derived From Alzheimer's Disease Brain," *Nature Communications* 6:8490, doi: 10.1038/ncomms9490 (2015).
Tang, et al., "Identification of 86 Candidates for Small Non-Messenger RNAS From the Archaeon Archaeoglobus Fulgidus," *Proc. Natl. Acad. Sci.* 99(11):7536-7541 (2002).
Tang, et al., "Identification of Novel Non-Coding RNAS as Potential Antisense Regulators in the Archaeon Sulfolobus Solfataricus," *Molecular Microbiology* 55(2):469-481 (2005).
Troung, et al., "Development of an Intein-Mediated Split-CAS9 System for Gene Therapy," *Nucl Acid Res* 43(13):6450-8 (2015).
Van Dijk, et al., "Integrative Neurobiology of Metabolic Diseases, Neuroinflammation, and Neurodegeneration," *Frontiers in Neuroscience* 9(173):1-19 (2015).
Varatharajah, et al., "Seizure Forecasting and the Preictal State in Canine Epilepsy," *Int J Neural Syst* 27(1):1650046 (2017).
Webster, et al., "Using Mice to Model Alzheimer's Dementia: An Overview of The Clinical Disease and The Preclinical Behavioral Changes in 10 Mouse Models," *Front Genet* 5(99):1-23, doi: 10.3389f/gene.2014.00088 (2014).
Wegmann, et al., "Removing Endogenous Tau Does Not Prevent Tau Propagation yet Reduces Its Neurotoxicity," *EMBO J.* 34(24):3028-3041 (2015).
Wu, et al., "Genome-Wide Binding of The CRISPR Endonuclease CAS9 in Mammalian Cells," *Nature Biotechnology* 32(7):670-6, doi: 10.1038/nbt2889 (2014).
Yang, et al., "Towards a Transgenic Model of Huntington's Disease in a Non-Human Primate," *Nature* 453(7197):921-924 (2008).
Zeitler, et al., "Allele-Selective Transcriptional Repression of Mutant HTT for The Treatment of Huntington's Disease," *Nature Medicine* 25(7):1131-1142 (2019).
Zetsche, et al., "A Split-CAS9 Architecture for Inducible Genome Editing and Transcription Modulation," *Nat Biotechnol* 33(2):139-142 (2015).
Zhang, et al., "A Designed Zinc-Finger Transcriptional Repressor of Phospholamban Improves Function of The Failing Heart," *Mol Ther* 20(8):1508-1515 (2012).
Bannister et al., "Regulation of Chromatin by Histone Modifications," *Cell Res.* (21)3: 381-395 (2011).
Gersbach et al., "Synthetic Zinc Finger Proteins: The Advent of Targeted Gene Regulation and Genome Modification Technologies," *Acc Chem Res.* 47(8): 2309 2318 (2014).
Heman-Ackah et al., "Precision Modulation of Neurodegenerative Disease-Related Gene Expression in Human PSC-Derived Neurons," *Sci Rep.* 6(28420): 1 12 (2016).
Kimura et al., "Physiological and Pathological Phosphorylation of Tau by CDK5," *Front in Mol Neurosci.* 7(65):1-10 (2014).
Kouzarides, "Chromatin Modifications and Their Function," *Cell* 128(4):693-705 (2007).
Nimsanor et al., "Generation of an Isogenic, Gene-Corrected IPSC Line from a Pre-Symptomatic 28-Year-Old Woman with the R406W Mutation in the Microtubule Associated Protein Tau (MAPT) Gene," *Stem Cell Res.* 17(3):600-602 (2016).
Noble et al., "The Importance of Tau Phosphorylation for Neurodegenerative Diseases," *Front. in Neurol.* 4(83):1-11 (2013).
Olsson et al., "Characterization of Intermediate Steps in Amyloid Beta (Aβ) Production Under Near-Native Conditions," *J of Biolog Chem.* 289(3):1540-1550 (2014).
Ong et al., "Enhancer Function: New Insights into the Regulation of Tissue-Specific Gene Expression," *Nat Rev Genet.* 12(4):283-293 (2011).
Wang et al., "RBFOX3/Neun is Required for Hippocampal Circuit Balance and Function," *Sci Rpts.* 5(17383):1-16 (2015).
Wegmann, et al. "Persistent repression of tau in the brain using engineered zinc finger protein transcription factors," *Sci. Adv.* (2021) 7(12):1-19.
Perez, et al., "Management of Neuroinflammatory Responses to AAV-Mediated Gene Therapies for Neurodegenerative Diseases," *Brain Sci.* (2020) 10(2):119.

(56) References Cited

OTHER PUBLICATIONS

Hocquemiller, et al., "Adeno-Associated Virus-Based Gene Therapy for CNS Diseases," Human Gene Therapy (2016) 27(7):478-97.
Golebiowski, et al., "Direct Intracranial Injection of AAVrh8 Encoding Monkey β-N-Acetylhexosaminidase Causes Neurotoxicity in the Primate Brain," Human Gene Therapy (2017) 28(6): 510-22.
Zeitler, et al., "Sustained Tau Reduction via Zinc Finger Protein Transcription Factors as a Potential Next-Generation Therapy for Alzheimer's Disease and Other Tauopathies," ASGCT 20th Annual Meeting (2017), Retrieved from the Internet: URL:https://www.abstractsonline.com/pp8/#:/4399/presentation/1333>.
Caillet-Boudin, et al., "Regulation of Human MAPT Gene Expression," Molecular Neurodegeneration (2015) 10:28.
Yamamoto, et al., "Genome Editing with Programmable Site-Specific Nucleases," Uirusu (Virus) (2014) 64(1):75-82.
Asokan et al., "The AAV Vector Toolkit: Poised at the Clinical Crossroads," (2012) Molecular Therapy 20(4) 699-708.
U.S. Appl. No. 18/046,327, filed Oct. 13, 2022, Ledeboer.
U.S. Appl. No. 17/791,395, filed Jul. 7, 2022, Zeitler.
U.S. Appl. No. 16/591,445, filed Oct. 2, 2019, Miller.
JP; Notice of Allowance dated Mar. 29, 2023 for Application No. 2019-529263.
JP; Notice of Final Rejection dated Nov. 29, 2022 for Application No. 2019-529263.
JP; Notice of Reasons for Rejection dated Jan. 28, 2022 for Application No. 2019-529263.
JP; Official Action dated Jan. 10, 2024 for Application No. 2023-53704.
JP; Official Action dated Oct. 3, 2023 for Application No. 2021-518063.
KR; Notification of Grounds for Refusal dated Sep. 13, 2022 for Application No. 10-2019-7016870.
MX; First Office Action Report dated Oct. 3, 2023 for Application No. MX/a/2019/006426.
MX; Notice of Allowance dated Jan. 17, 2024 for Application No. MX/a/2019/006426.
PCT; International Preliminary Report on Patentability dated Aug. 4, 2022 for Application No. PCT/US2021/014780 (12 pages).
PCT; International Preliminary Report on Patentability dated Jun. 4, 2019 for Application No. PCT/US2017/064181 (5 pages).
PCT; International Search Report dated Apr. 26, 2018 for Application No. PCT/US2017064181 (5 pages).
PCT; International Search Report dated Jul. 8, 2021 for Application No. PCT/US2021/014780 (11 pages).
CN: First Office Action dated Jun. 26, 2024 for Application No. 201980079236.X (Machine Translation).
Zhang et al., "Cell-to-cell transmission of misfolded Tau protein in neurodegenerative diseases and possible treatment strategies," Journal of Alzheimer's Disease and Related Diseases, 4(2) (Apr. 5, 2021) Machine Translation.
AU: First Examination Report dated Feb. 15, 2023 in Application No. 2017367722.
AU: Notice of Acceptance dated Jan. 19, 2024 for Application No. 2017367722.
Beshnova et al., "Regulation of the Nucleosome Repeat Length In Vivo by the DNA Sequence, Protein Concentrations and Long-Range Interactions," (2014) PLoS Comput Biol 10(7):1-14 e1003698.
CA: First Office Action dated Feb. 7, 2024 for Application No. 3,043,635.
CN: First Office Action dated Jun. 20, 2024 for Application No. 201980077887.5 (Machine Translation).
CN: Third Office Action dated Nov. 21, 2023 for Application No. 201780084345.1.
EPO: Examination Report dated Jul. 11, 2024 for Application No. 19868538.0.
EPO: Examination Report dated May 22, 2024 for Application No. 17876620.0.
EPO: Extended Examination Report dated May 9, 2022 for Application No. 19868538.0.
EPO: European Search Report dated Apr. 14, 2020 for Application No. 17876620.0.
IL: Notice before Acceptance dated May 16, 2023 for Application No. 266862.
IL: Notice of Deficiencies dated Aug. 7, 2023 for Application No. 281972.
IL: Notice of Deficiencies dated Aug. 13, 2024 for Application No. 281972.
IL: Notice of Deficiencies dated Sep. 14, 2022 for Application No. 266862.
JP: Final Office Action dated Jun. 4, 2024 for Application No. 2021-518086 (Summary and English Machine Translation).
JP: Notice of Allowance dated Mar. 29, 2023 for Application No. 2019-529263 (English Translation).
JP: Notice of Final Rejection dated Nov. 29, 2022 for Application No. 2019-529263 (English Translation).
JP: Notice of Reasons for Rejection dated Jan. 28, 2022 for Application No. 2019-529263 (English Translation).
JP: Office Action dated Jul. 23, 2024 for Application No. 2021-518063 (Summary and English Machine Translation).
JP: Office Action dated Oct. 3, 2023 for Application No. 2021-518063 (English Translation).
JP: Official Action dated Jan. 10, 2024 for Application No. 2023-53704 (English Translation).
KR: Decision for Patent Grant dated Apr. 15, 2024 for Applicaton No. 10-2019-7016870 (English Translation).
KR: Notification of Grounds for Refusal dated Sep. 13, 2022 for Application No. 10-2019-7016870 (English Translation).
MX: First Office Action Report dated Oct. 3, 2023 for Application No. MX/a/2019/006426 (English Translation).
MX: Notice of Allowance dated Jan. 17, 2024 for Application No. MX/a/2019/006426 (Machine Translation).
PCT: International Preliminary Report on Patentability for Application No. PCT/US2017/064181 dated Jun. 4, 2019 (5 pages).
PCT: International Preliminary Report on Patentability for Application No. PCT/US2019/054339 dated Sep. 11, 2020.
PCT: International Preliminary Report on Patentability for Application No. PCT/US2019/054347 dated Apr. 15, 2021.
PCT: International Preliminary Report on Patentability for Application No. PCT/US2021/014780 dated Aug. 4, 2022 (12 pages).
PCT: International Search Report for Application No. PCT/US2017064181 dated Apr. 26, 2018 (5 pages).
PCT: International Search Report for Application No. PCT/US2019/054339 dated Jan. 23, 2020.
PCT: International Search Report for Application No. PCT/US2019/054347 dated Jan. 23, 2020.
PCT: International Search Report for Application No. PCT/US2021/014780 dated Jul. 8, 2021 (11 pages).
SG: Written Opinion dated Mar. 29, 2024 for Application No. SG11202103314Q (6 pages).
Snowden et al., "Gene-Specific Targeting of H3K9 Methylation is Sufficient for Initiating Repression In Vivo," (2002) Current Biology 12:2159-66.
USPTO: Non-Final Office Action dated Nov. 16, 2023 for U.S. Appl. No. 16/591,445.
CA: Second Office Action dated Mar. 14, 2025 for Application No. 3,043,635.
EPO: Extended Examination Report dated Feb. 25, 2025 for Application No. 19868538.0.
KR: Preliminary Rejection dated Mar. 19, 2025 in Application No. 10-2021-7013168 (Machine English Translation).
KR: Preliminary Rejection dated Mar. 20, 2025 in Application No. 10-2021-7013170 (Machine English Translation).

* cited by examiner

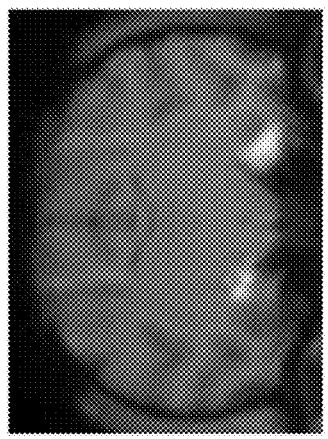
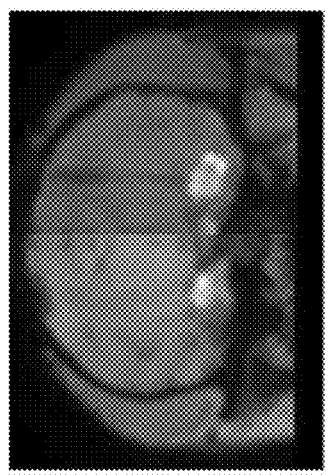
MRI from Slice ~7
Baseline method: VEH + ZFP negative animals
FIG.5C

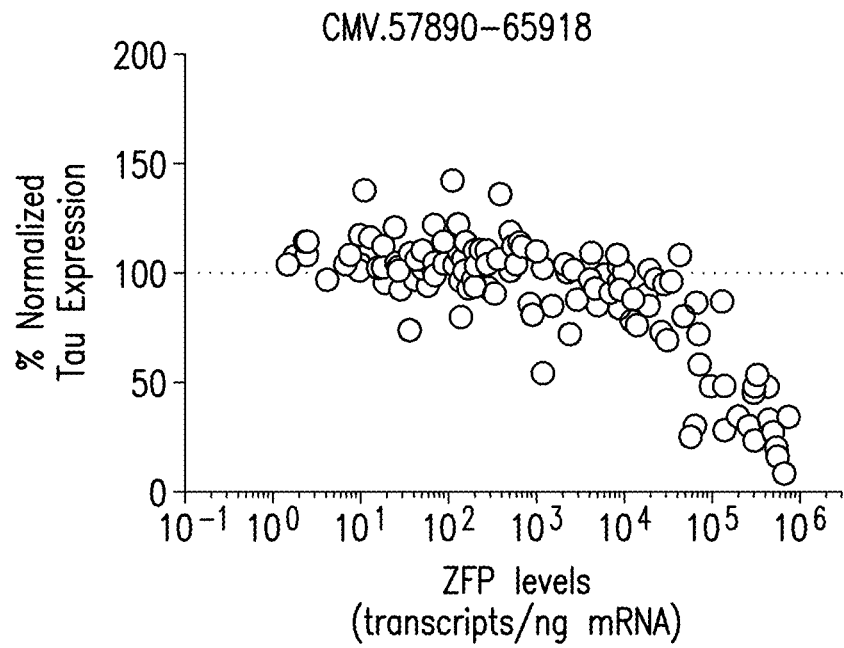
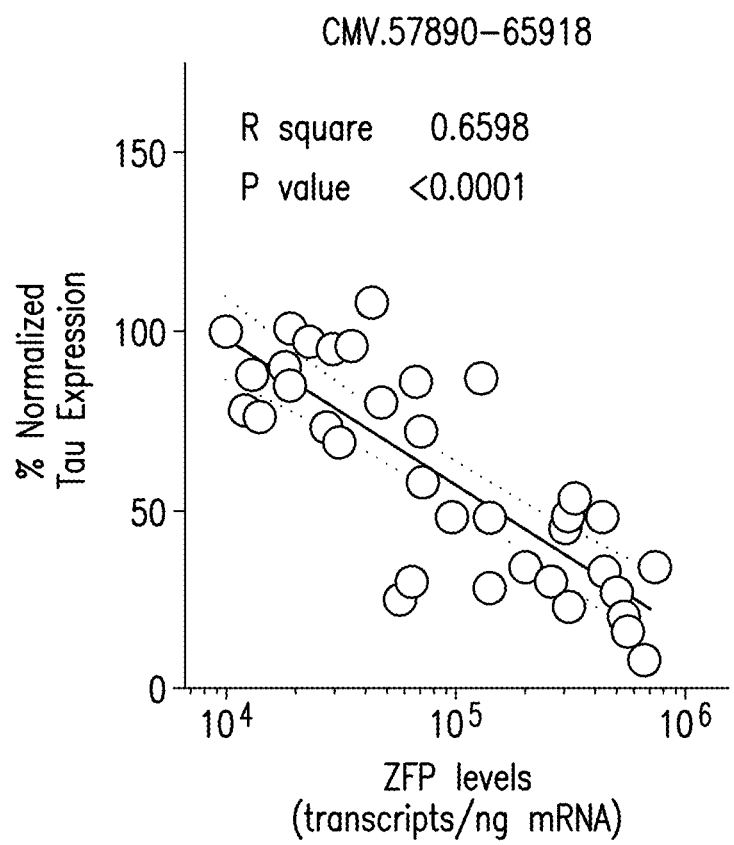
Baseline method: VEH + ZFP negative
FIG.13B

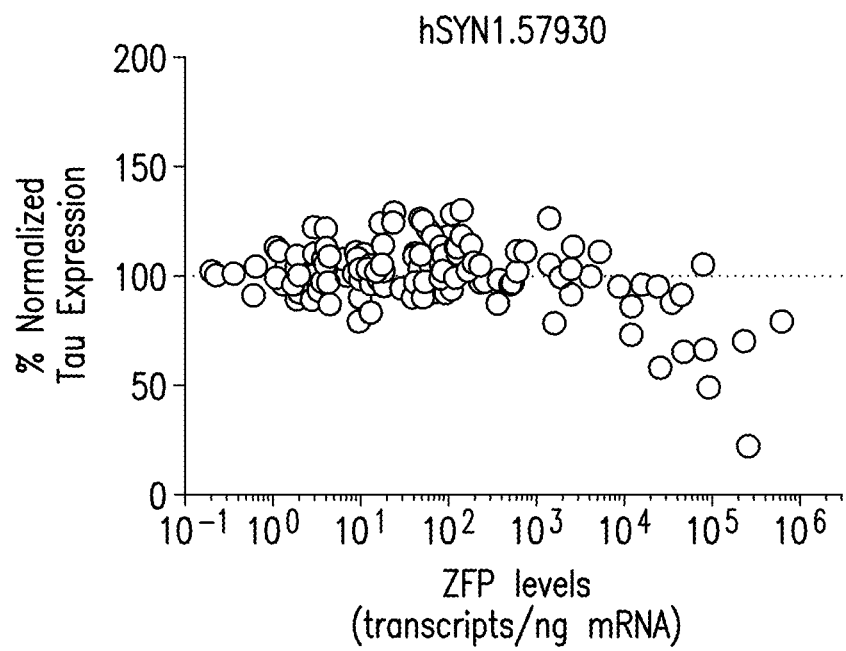
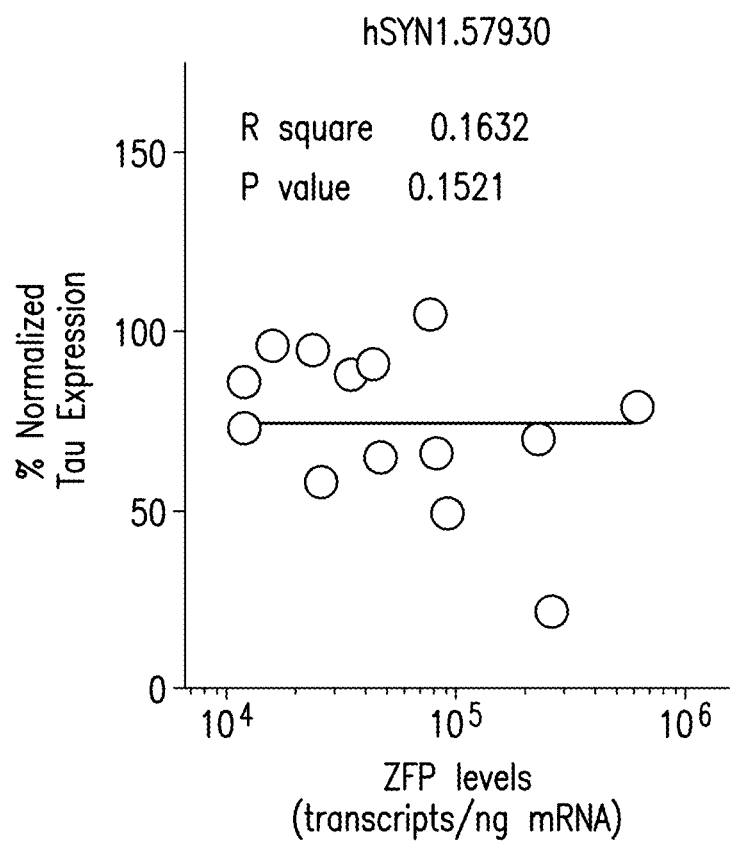
Baseline method: VEH + ZFP negative
FIG.13C

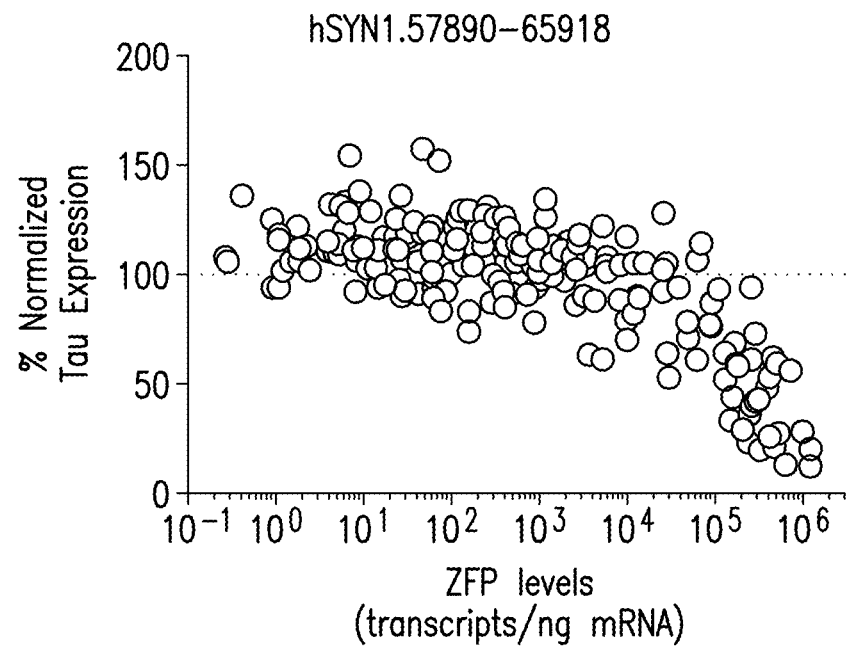
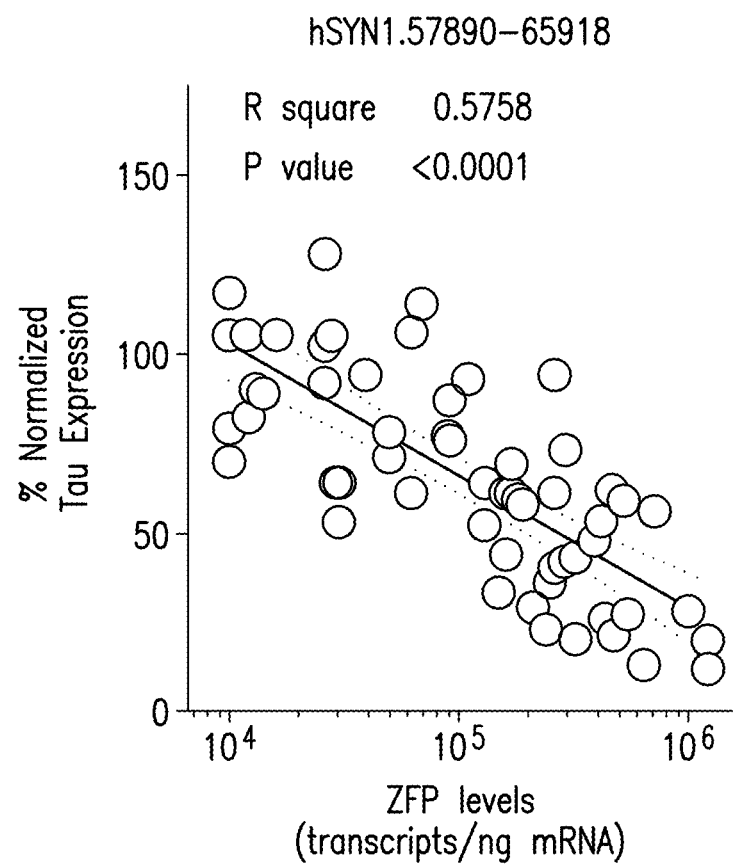
FIG.15A

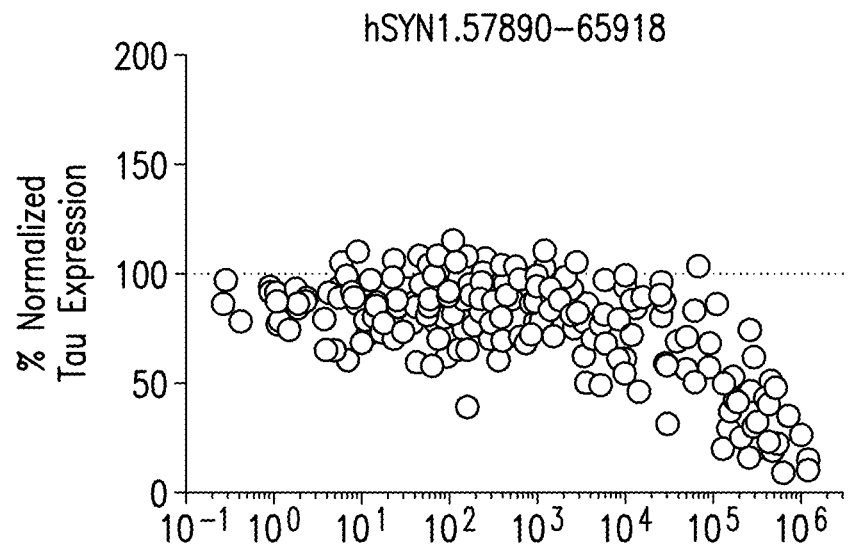
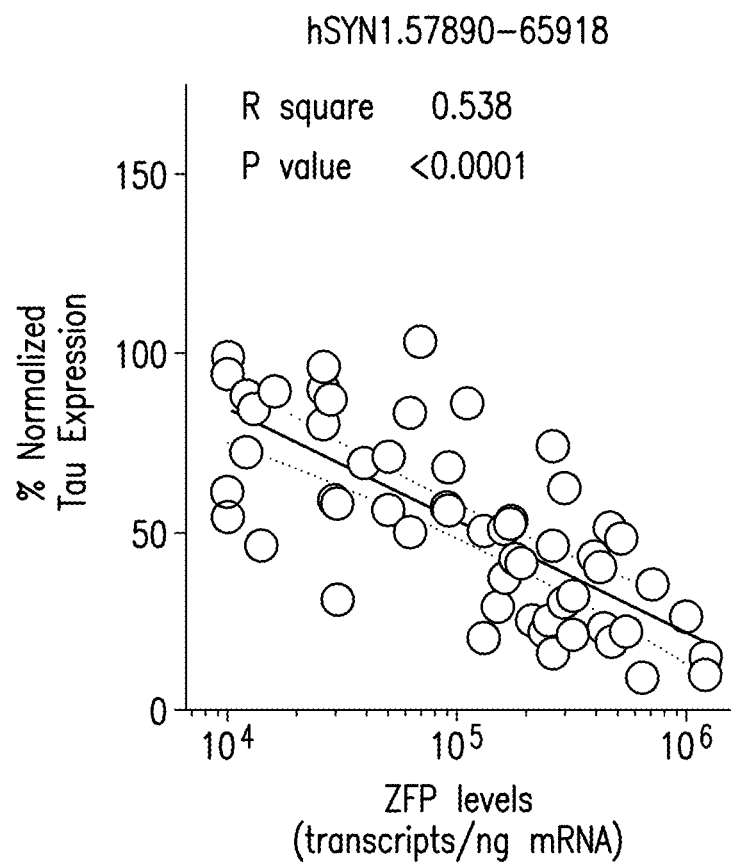
Baseline method: Unscaled
FIG.17A

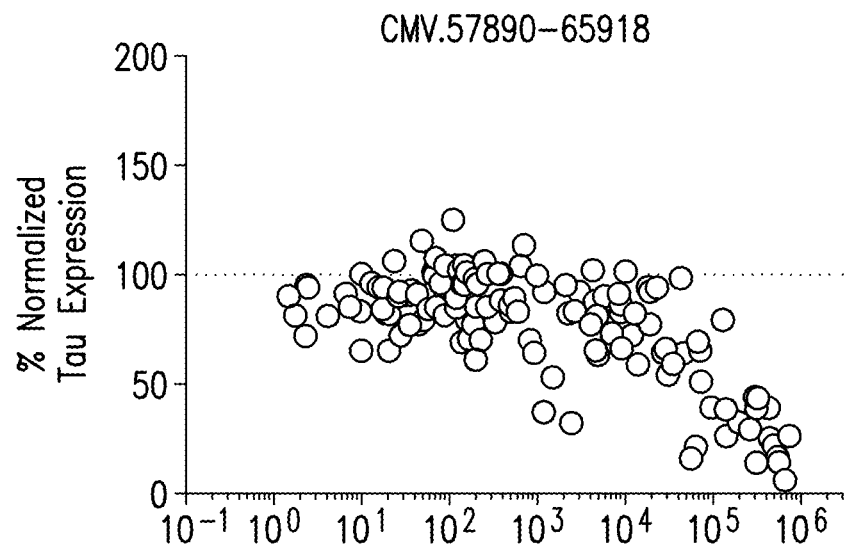
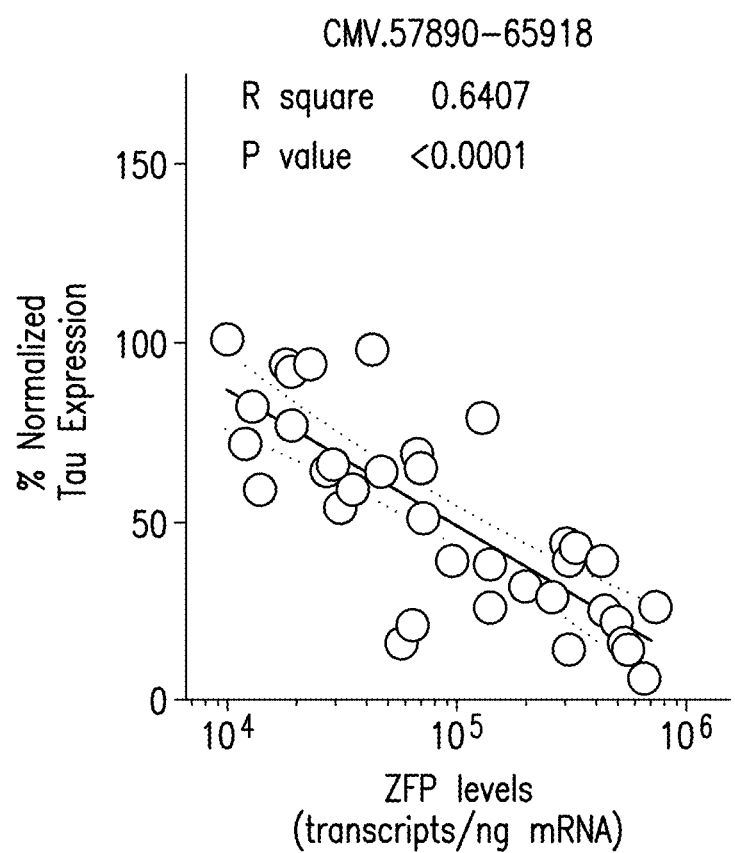
FIG.17B

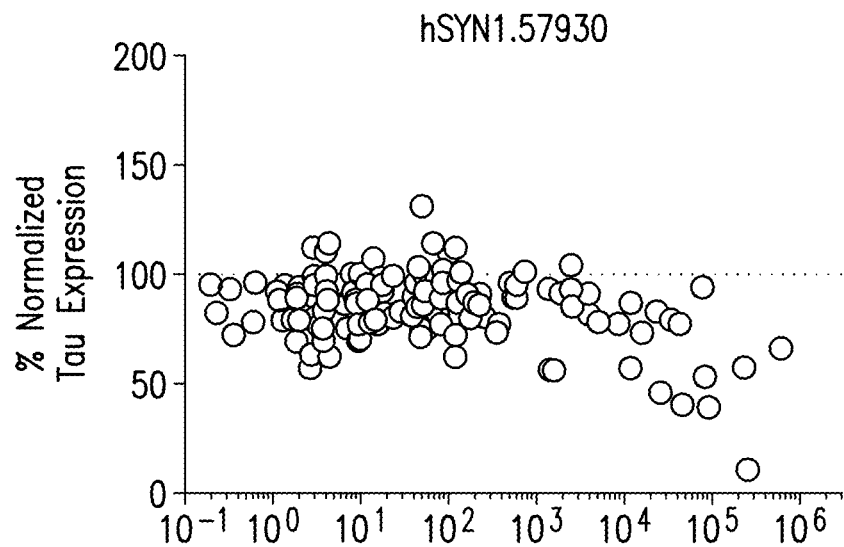
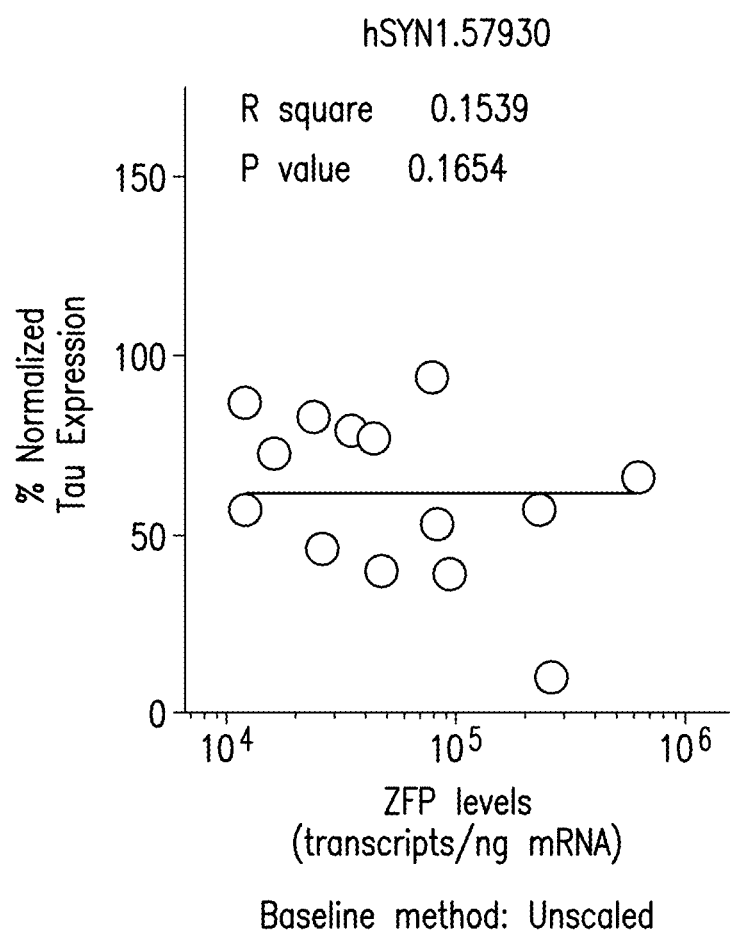
FIG.17C

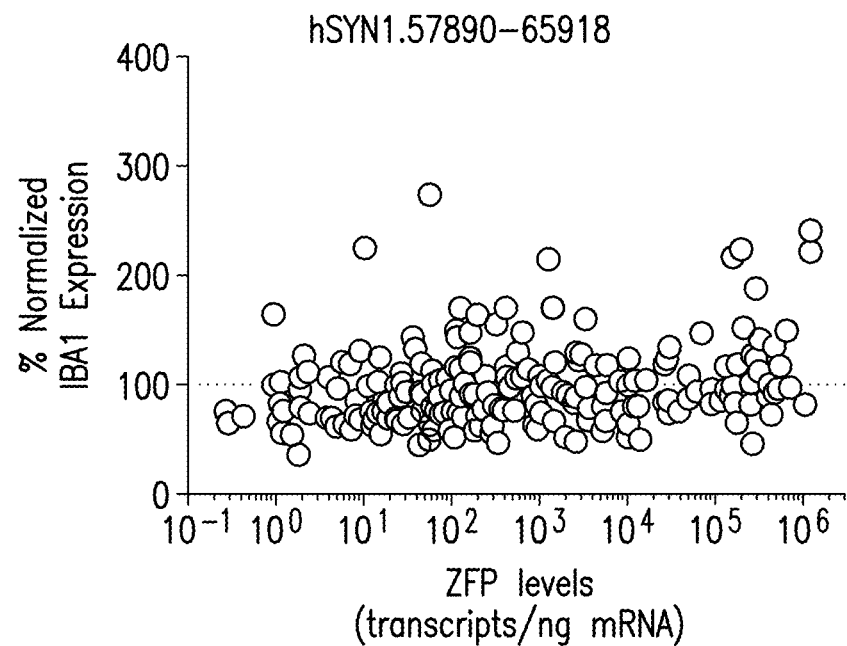
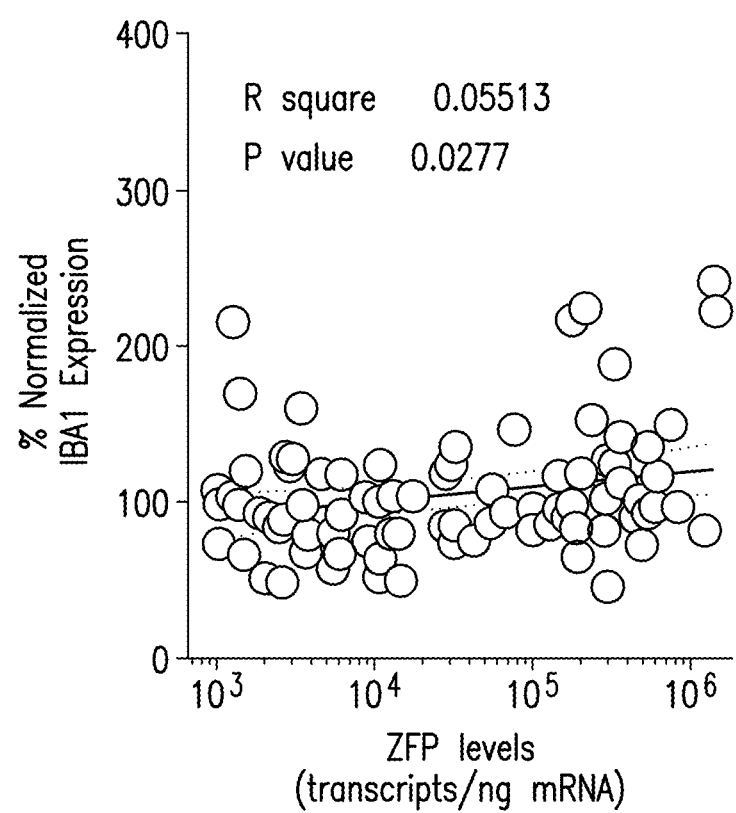
FIG.19A

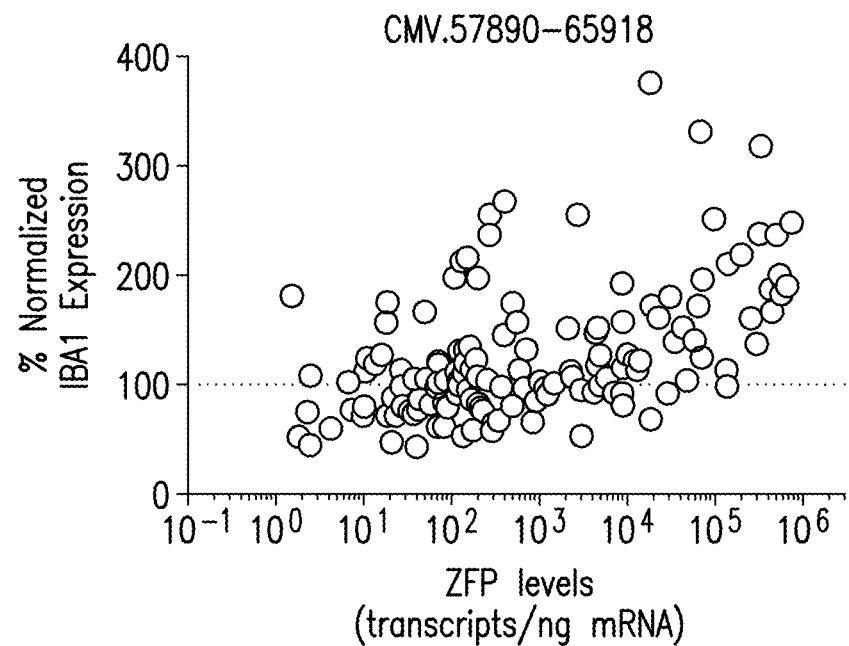
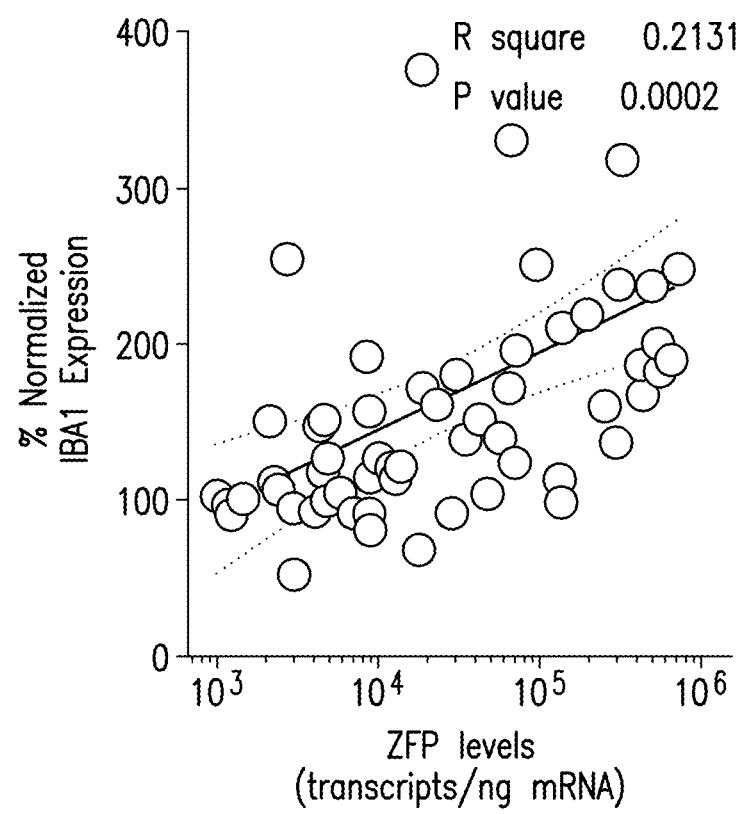
FIG.19B

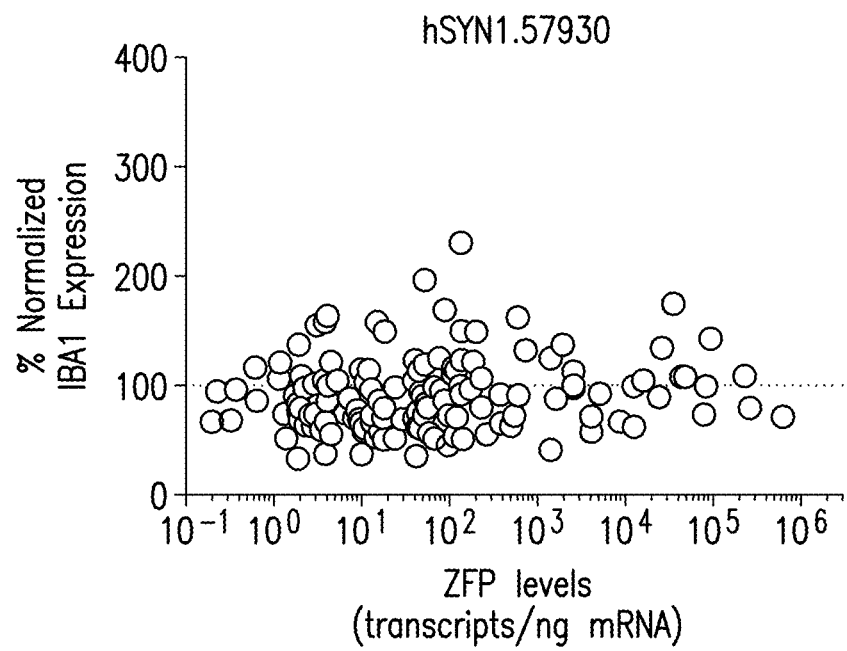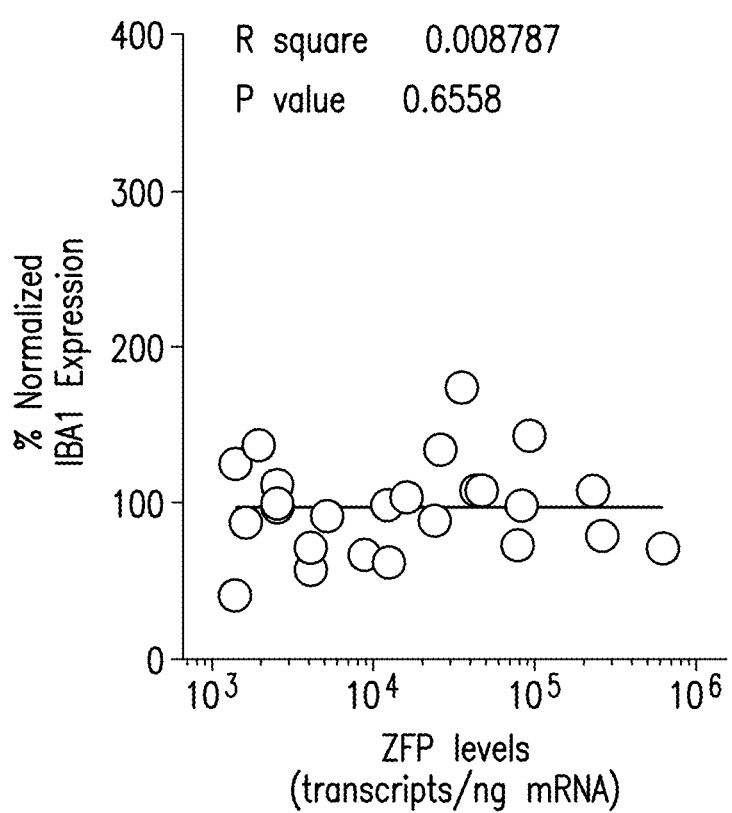
FIG.19C

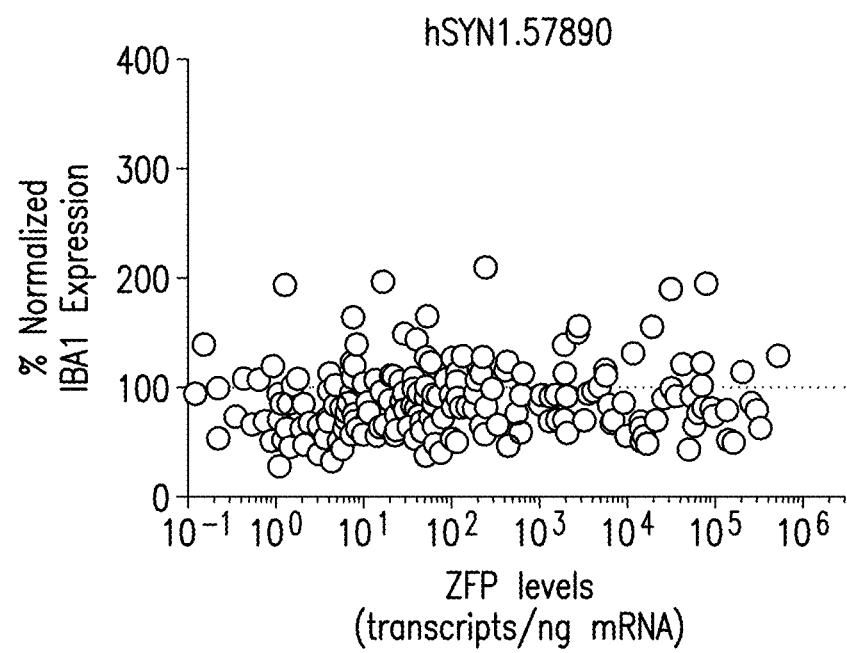
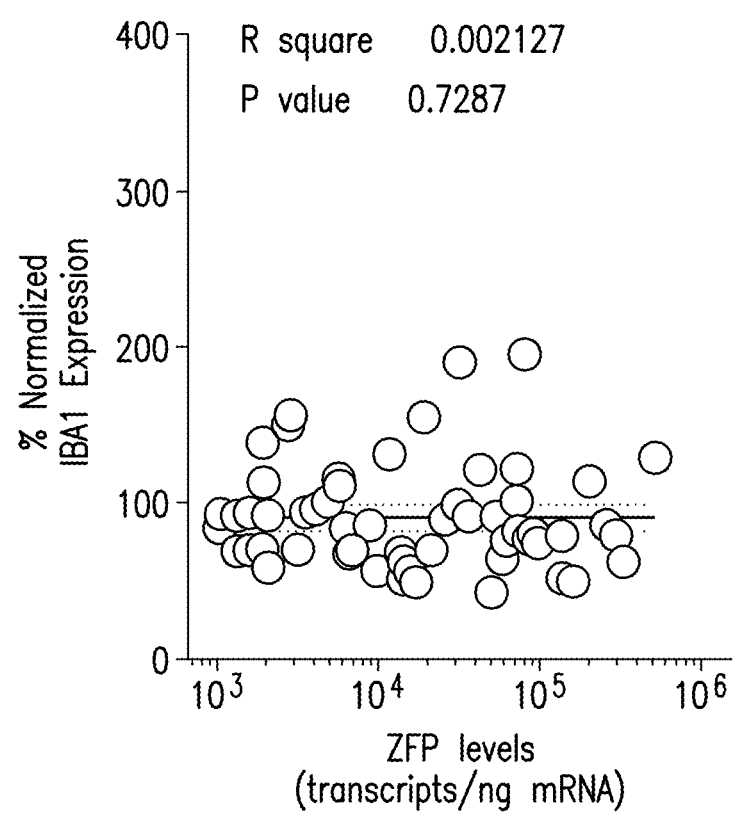
FIG.19D

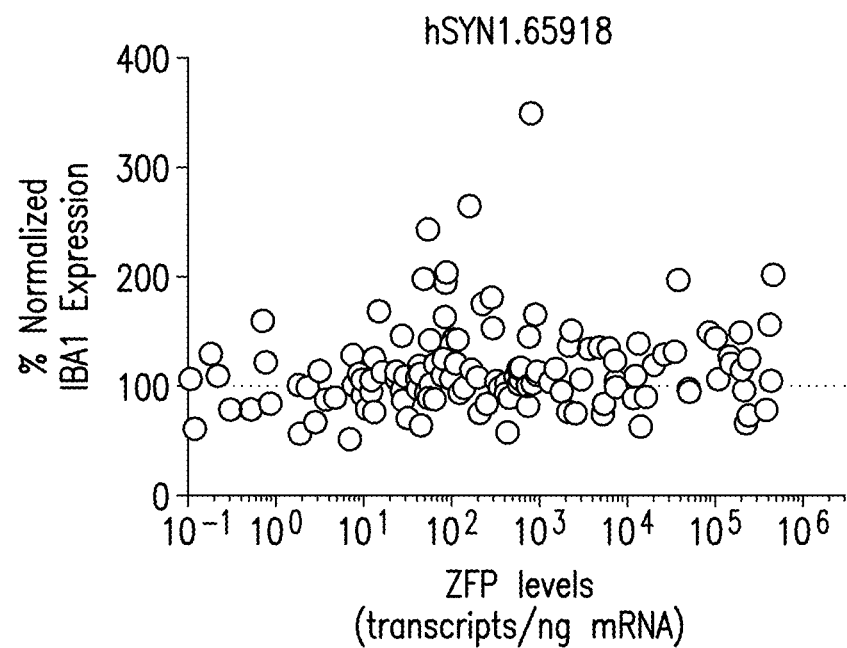
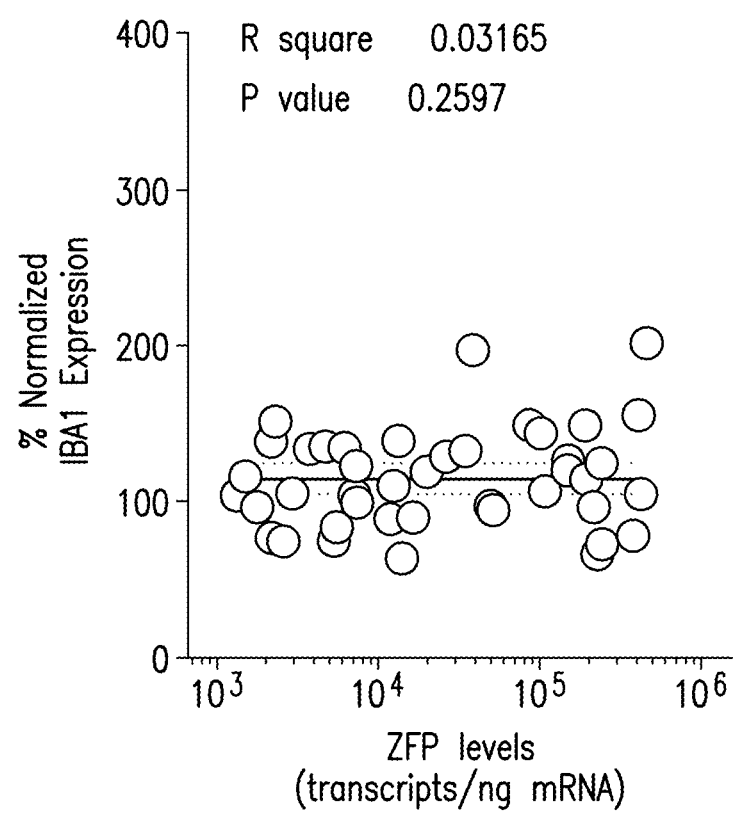
FIG.19E

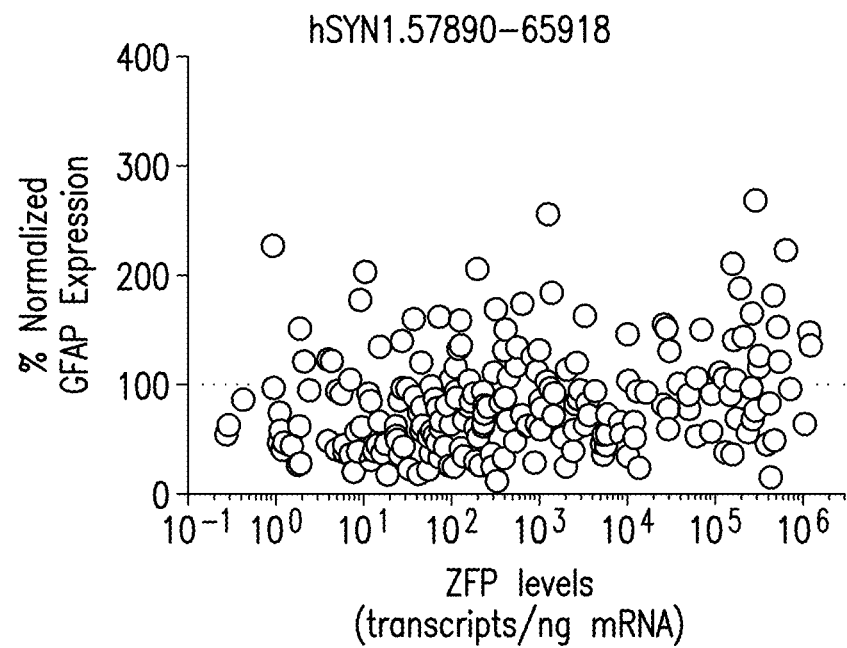
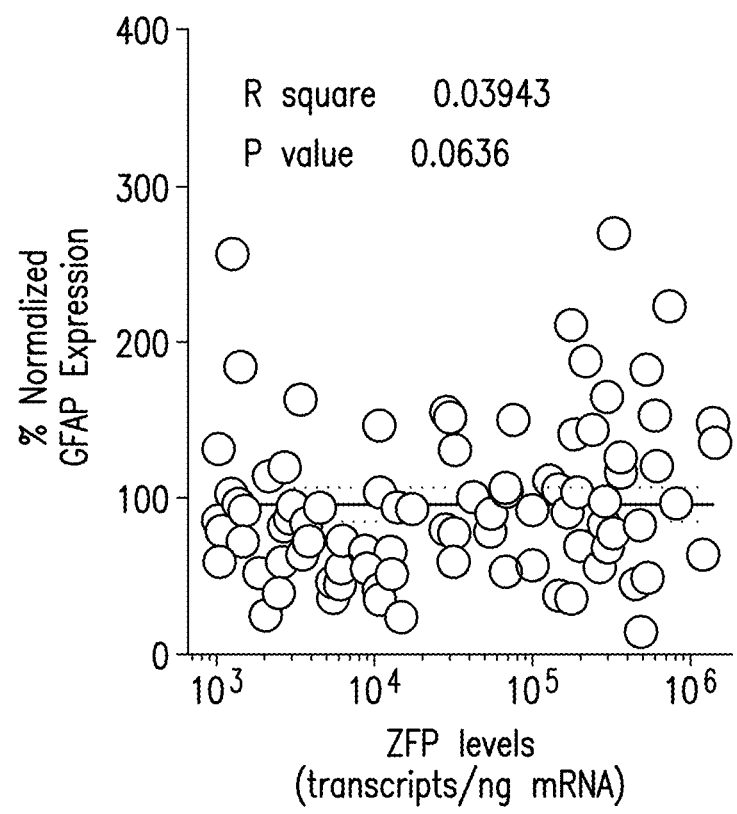
FIG.19G

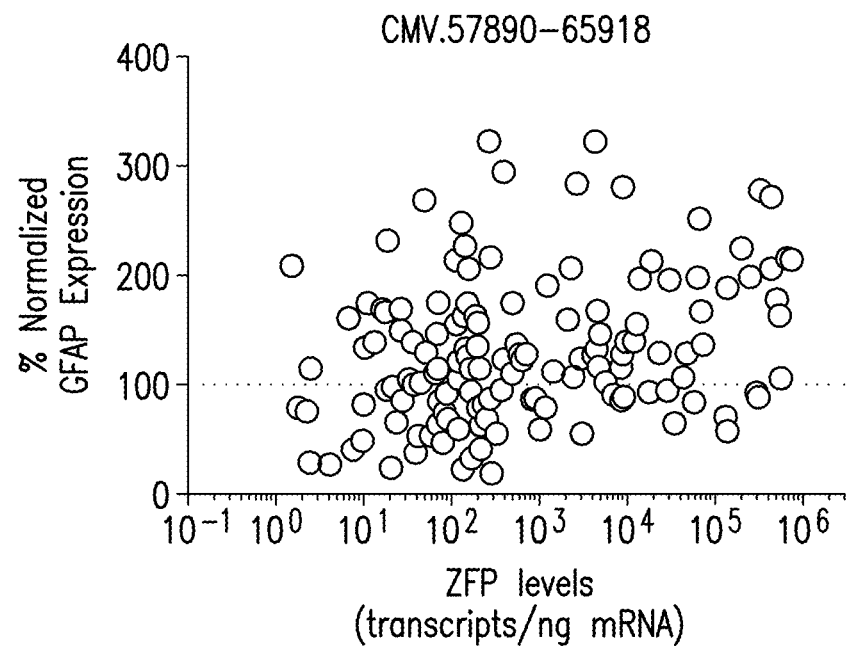
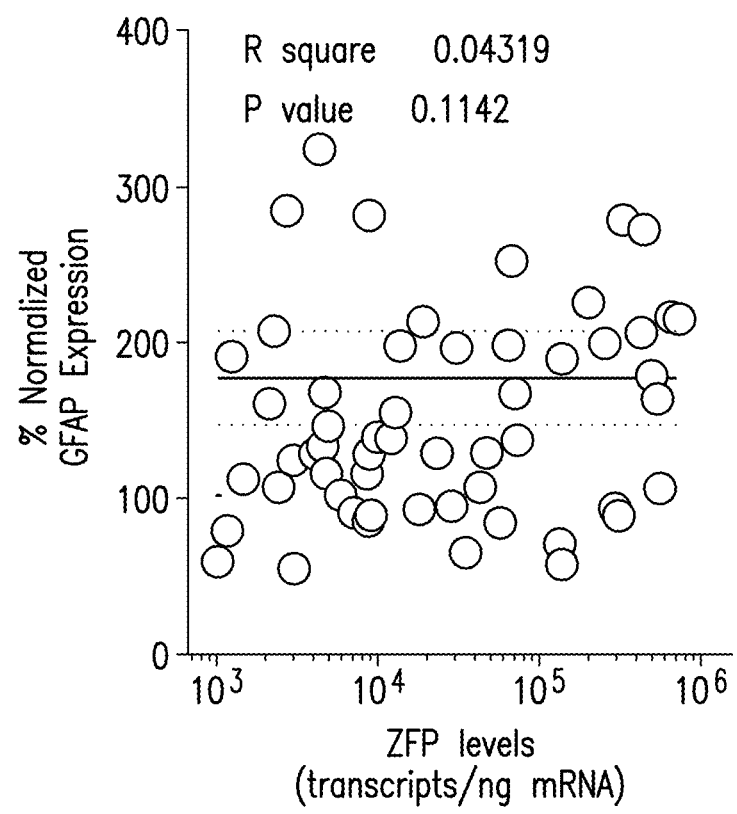
FIG.19H

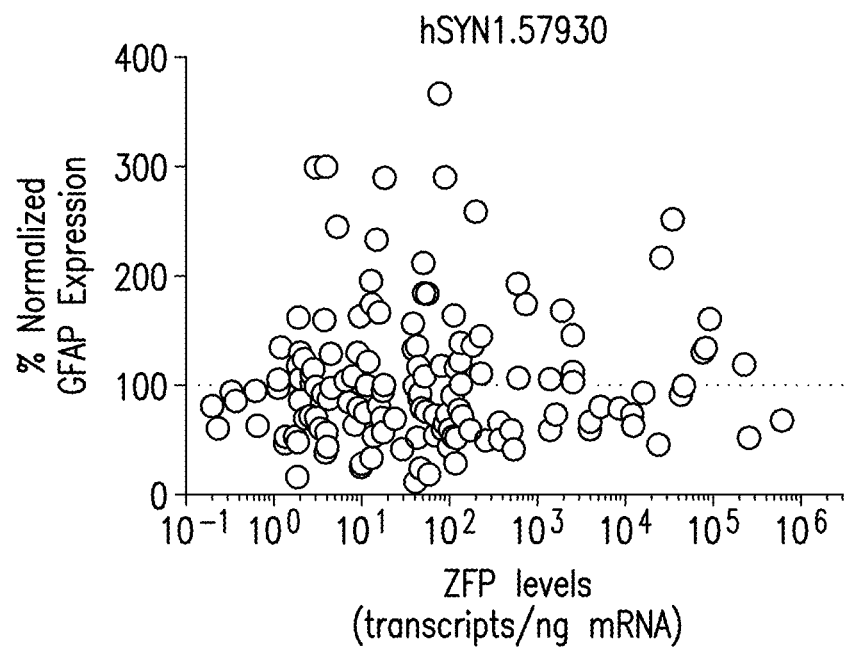
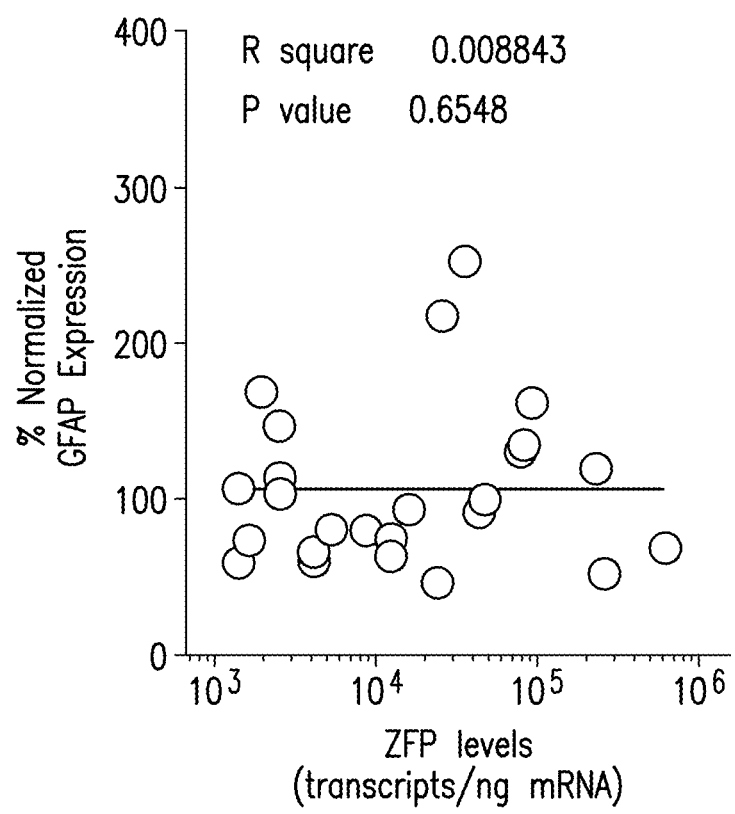
FIG.19I

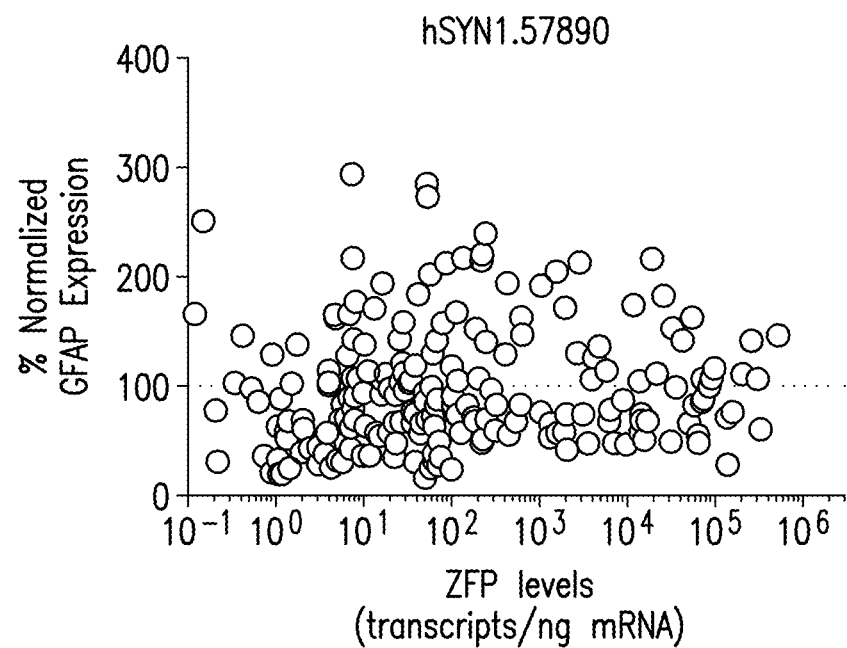
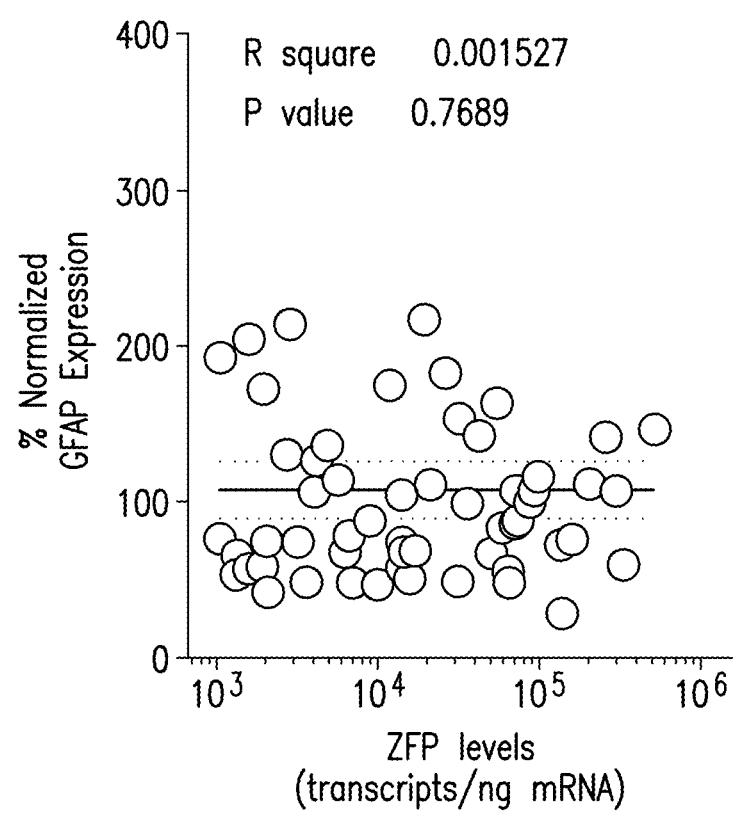
FIG.19J

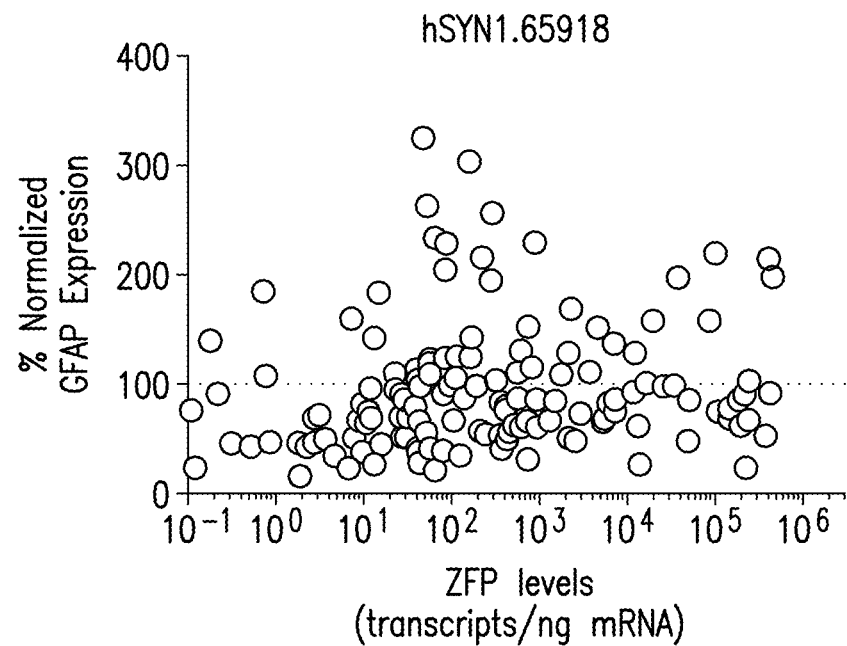
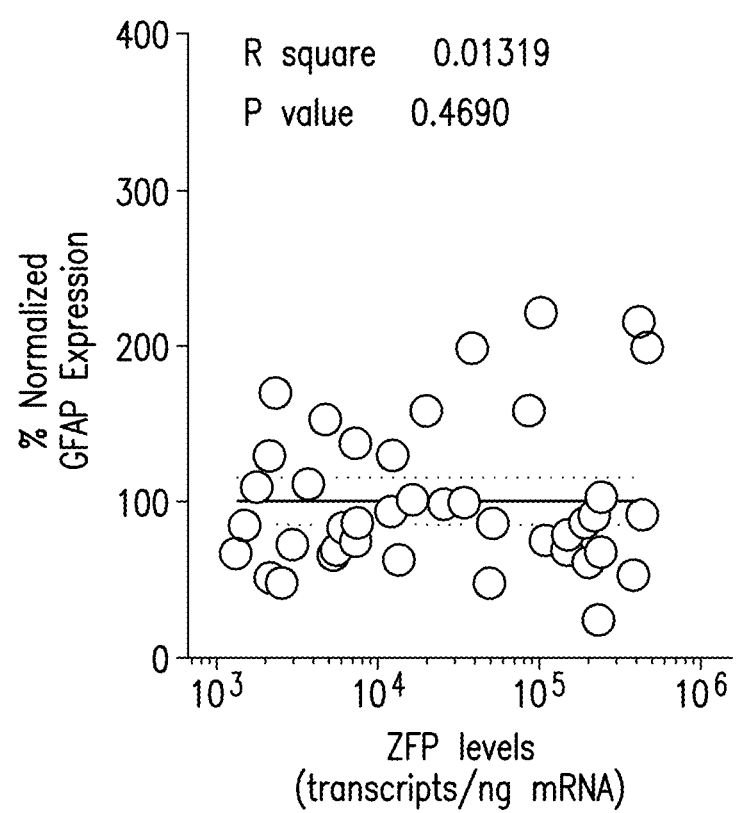
FIG. 19K

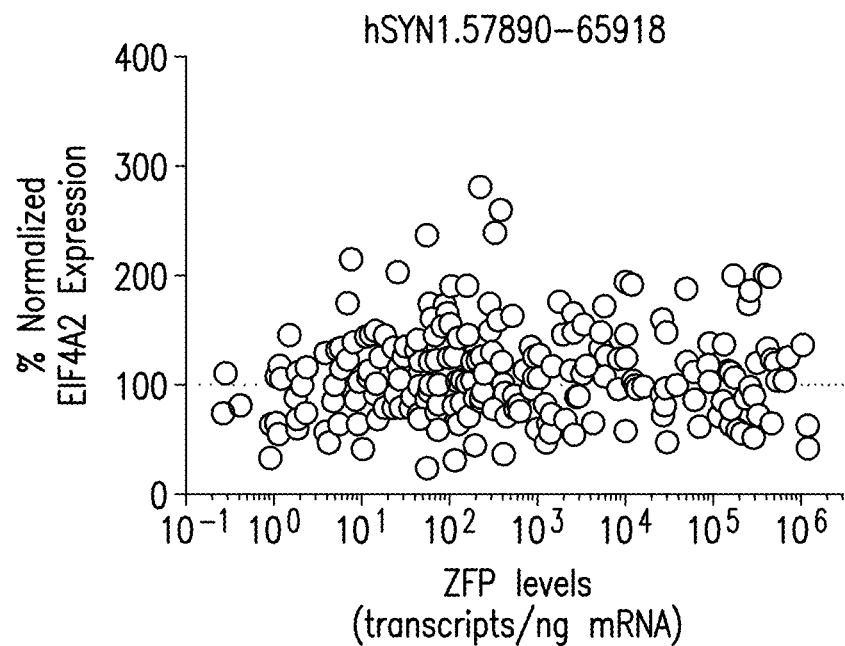
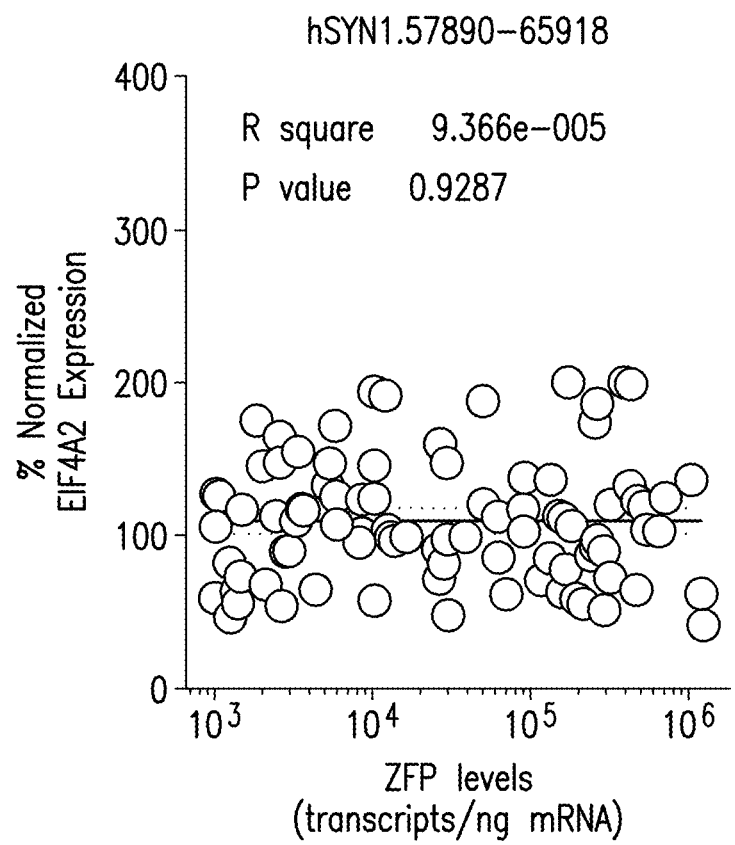
FIG.21A

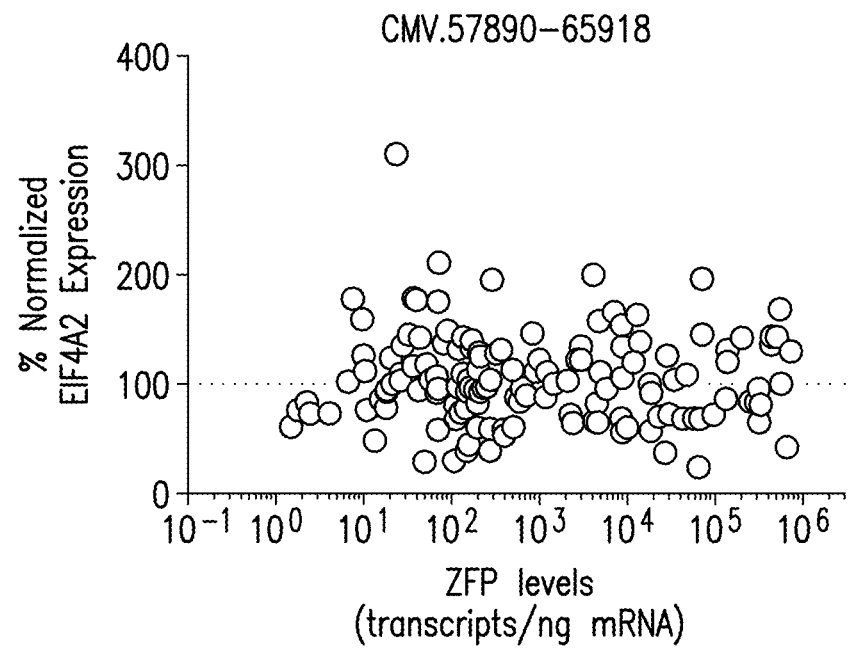
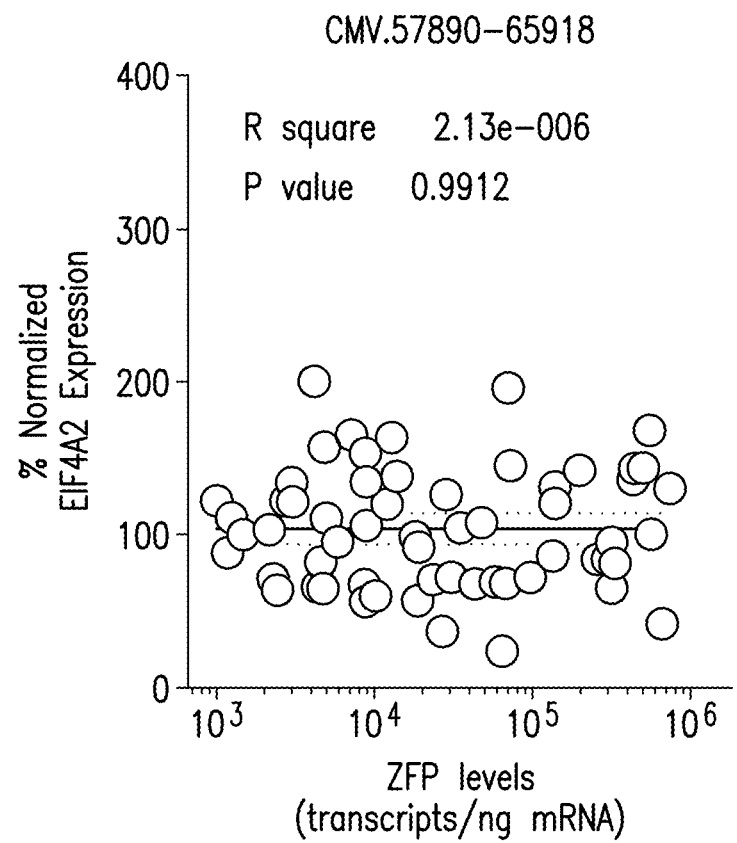
FIG.21B

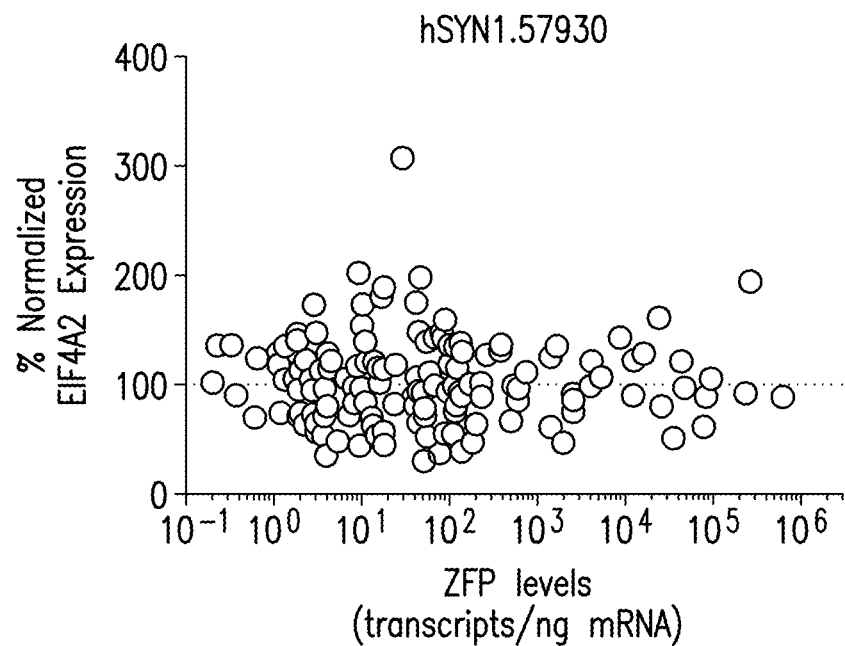
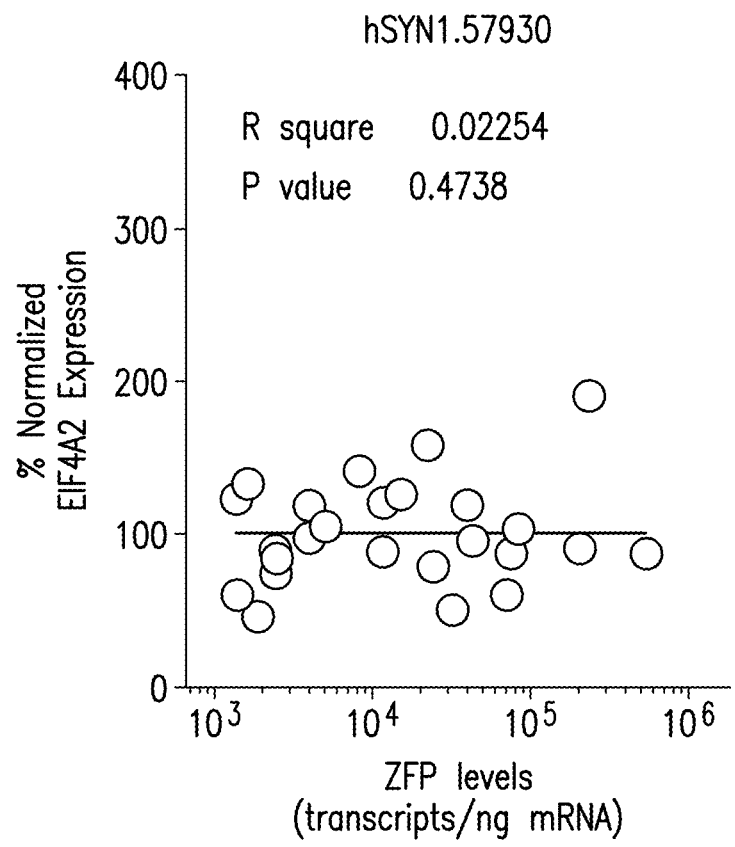
FIG.21C

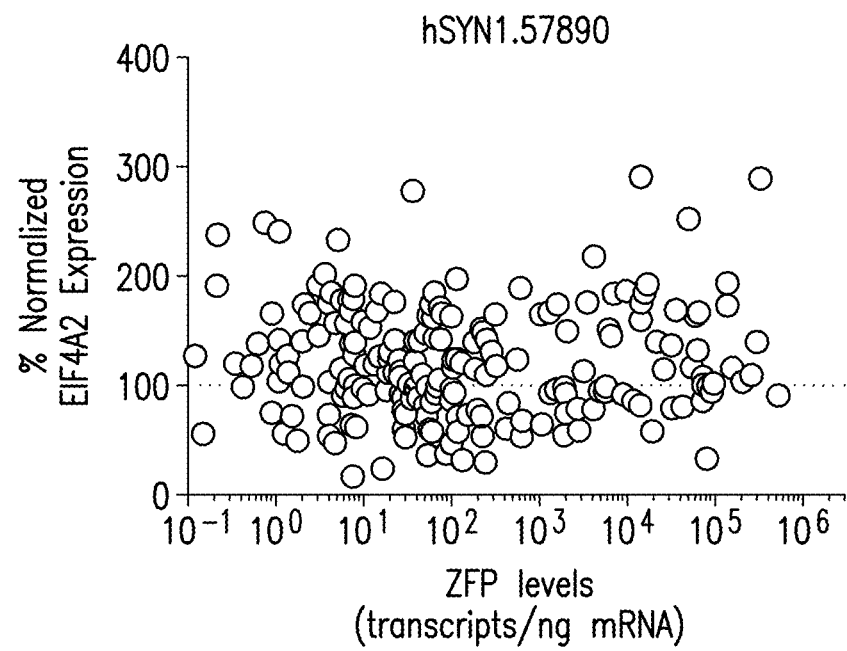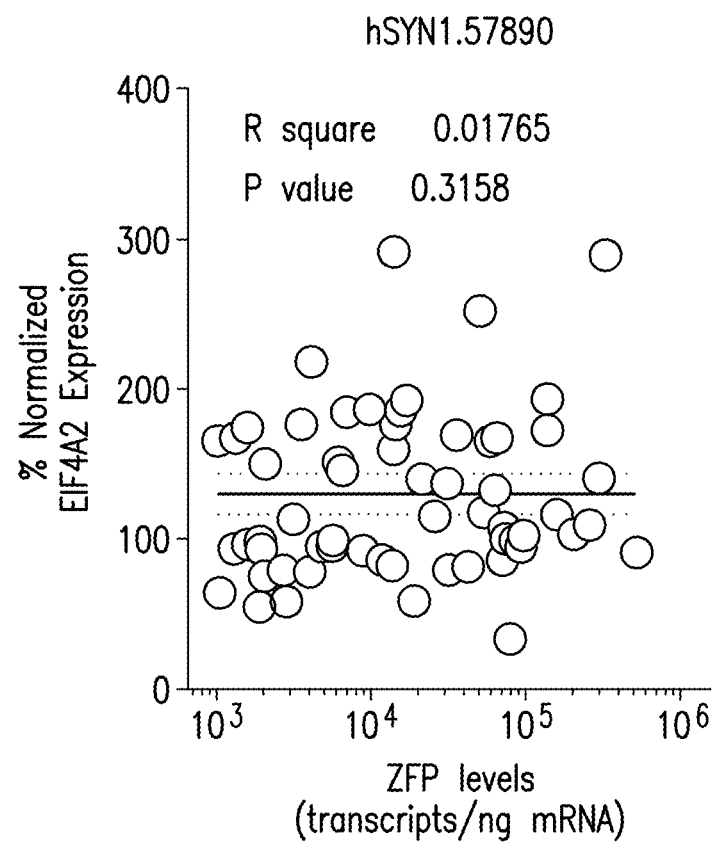
FIG.21D

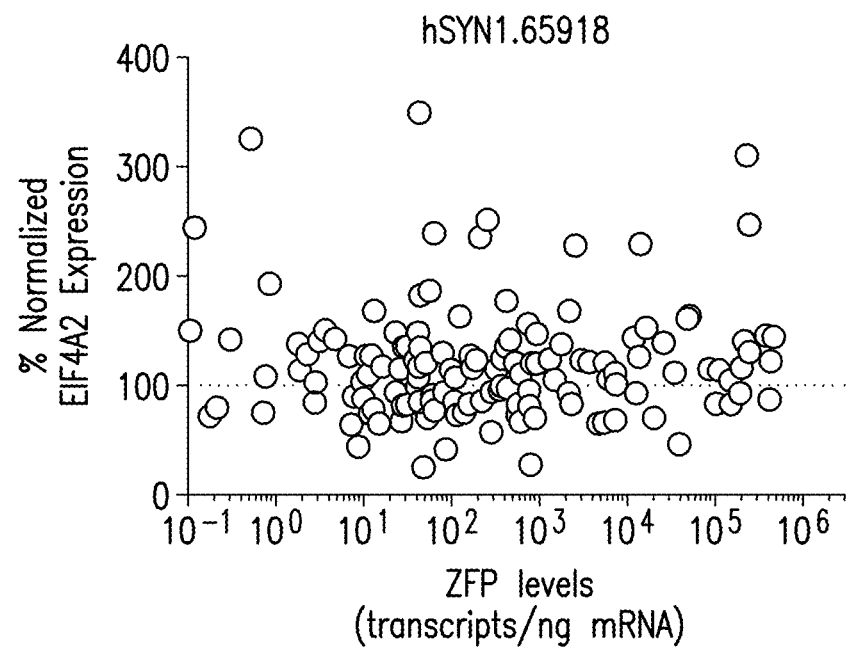
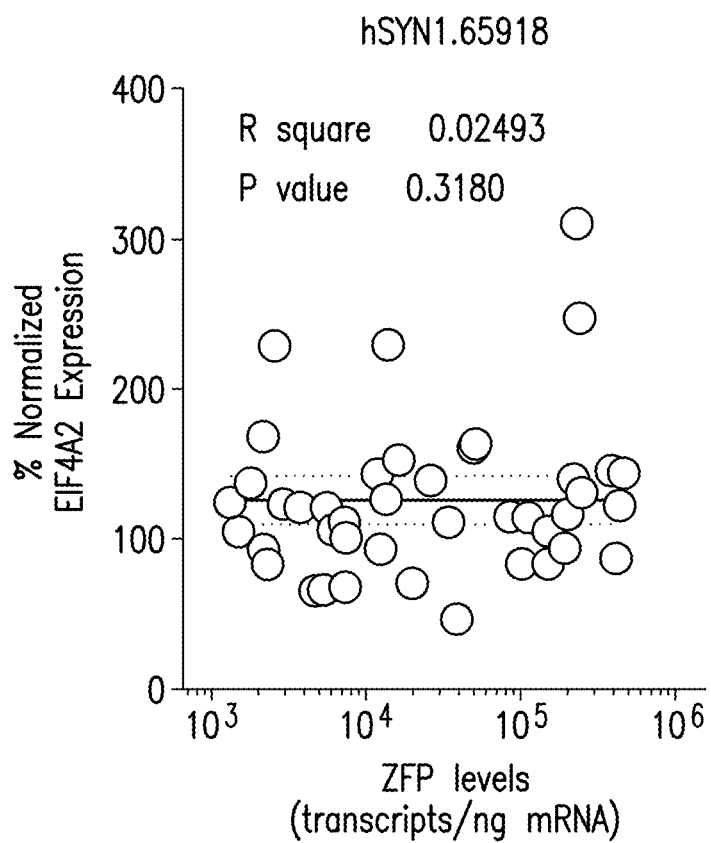
FIG.21E

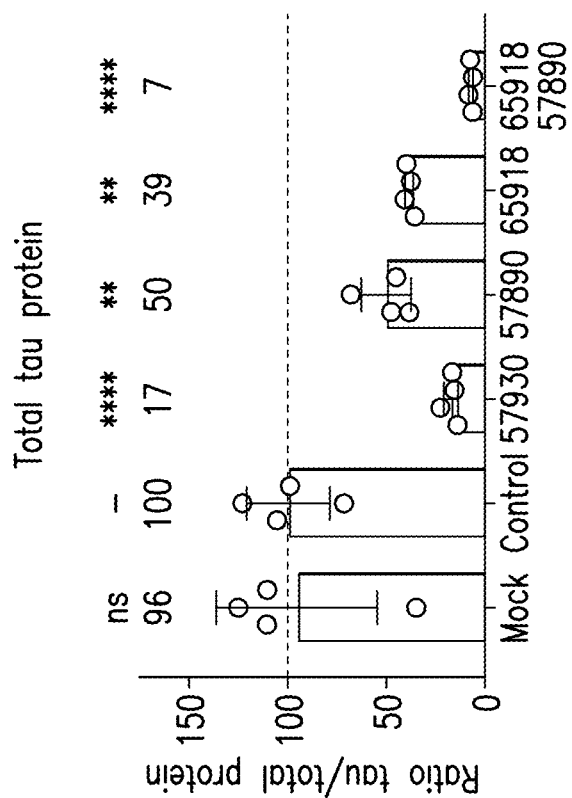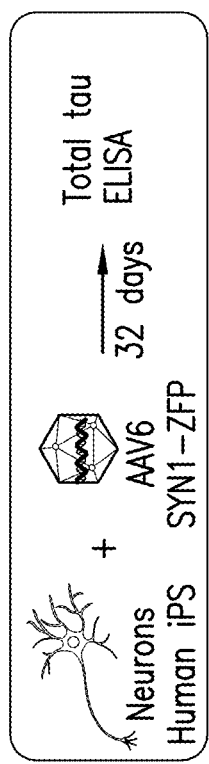
FIG.22

METHODS AND COMPOSITIONS FOR MODULATION OF TAU PROTEINS

CROSS-REFERENCE TO RELATED APPLICATIONS

The present application claims the benefit of U.S. Provisional Application No. 62/740,162, filed Oct. 2, 2018, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Oct. 28, 2019, is named 8325-0182_SL.txt and is 2,939 bytes in size.

TECHNICAL FIELD

The present disclosure is in the field of compositions and methods for modulating tau expression, including for the treatment and/or prevention of tauopathies such as Alzheimer's Disease.

BACKGROUND

Abnormal levels and/or aggregation of tau protein, a microtubule-associated protein (also referred to as MAPT) that can accumulate in neurofibrillary tangles (NFT), has been implicated in a number of conditions, collectively referred to as tauopathies. These include Alzheimer's Disease (AD), Frontotermporal dementia (FTD, see Benussi et al. (2015) Front Aging Neurosci. 7 (171): 1-19)), Progressive Supranuclear Palsy (PSP), intractable genetic epilepsies (e.g. Dravet syndrome, see Gheyara et al. (2014) Ann Neurol 76:443-456), traumatic brain injury (TBI) and Corticobasal degeneration (CBD, see Scholz and Bras (2015) Int J. Mol Sci 16 (10): 24629-24655). Previous studies have shown that a reduction of tau protein expression in adult mice using antisense oligonucleotides administered directly into the cerebral spinal fluid (CSF) caused a complete or partial reduction in tau protein levels and also protected the treated mice from chemically induced seizures in terms of seizure severity (DeVos et al. (2013) J of NeuroSci 33 (31): 12887). In AD, for instance, there is a direct correlation between the presence of tau NFT in the brain and cognitive decline (Spires-Jones and Hyman (2014) Neuron 82:756).

It has also been suggested that tau protein may have prion like properties, as misfolded, highly phosphorylated tau protein is more easily taken up by neurons and may propagate the disease throughout the brain, and that this misfolded tau protein isolated from brains of AD patients can be readily taken up by mouse neurons (Takeda et al. (2015) Nat Comm doi: 10.1038/ncomms9490; Hyman (2014) Neuron 82:1189). Entorhinal cortex-limited expression of a tangle-associated human tau protein in a transgenic mouse model led to the misfolding of mouse tau protein and aggregation of that tau protein in neurons without any detectable human tau protein expression (de Calignon et al. (2012) Neuron 73:685-697). This work suggests that the misfolded human protein is able to 'seed' misfolding and cause aggregation of the mouse proteins. Further, genetic reduction or loss of endogenous mouse tau is protective against neuropathological toxicity caused by overexpression of a mutant human tau transgene (Wegmann et al. (2015) EMBO J. 34 (24): 3028-41).

An estimated 5.3 million Americans have Alzheimer's Disease (AD) making it one of the top ten causes of death in America, and it is estimated by the year 2050, there will be 106.2 million people worldwide with the disease (van Dijk et al. (2015) Front Neurosci 9:173). The disease is more prevalent in women (two thirds of cases), and people of African or Hispanic descent are more likely to develop AD than people of Caucasian descent. The causes of AD appear to be related to genetics (especially for early onset, 5% of cases) and environmental and lifestyle factors. Typically, the disease is diagnosed in a person's mid-sixties. Although by the time a diagnosis is made, the disease has been progressing for years or even decades. The disease progresses over time, and thus far no therapeutic interventions have been identified that curtail or reverse the effects of the disease.

Repression or activation of disease-associated genes has been accomplished through the use of engineered transcription factors. Methods of designing and using engineered zinc finger transcription factors (ZFP-TF) are well documented (see for example U.S. Pat. No. 6,534,261), and more recently both transcription activator like effector transcription factors (TALE-TF) and clustered regularly interspaced short palindromic repeat Cas 9 based transcription factors (CRISPR-Cas-TF) have also been described (see review Kabadi and Gersbach (2014) Methods 69 (2): 188-197). Non-limiting examples of targeted genes include phospholamban (Zhang et al. (2012) Mol Ther 20 (8): 1508-1515), GDNF (Laganiere et al. (2010) J. Neurosci 30 (49): 16469) and VEGF (Liu et al. (2001) J Biol Chem 276:11323-11334). In addition, activation of genes has been achieved by use of a CRIPSR/Cas-acetyltransferase fusion (Hilton et al. (2015) Nat Biotechnol 33 (5): 510-517). Engineered TFs that repress gene expression (repressors) have also been shown to be effective in treating trinucleotide disorders such as Huntingtin's Disease (HD). See, e.g., U.S. Pat. No. 8,956,828 and U.S. Patent Publication No. 2015/0335708. U.S. Patent Publication No. 2018/0153921 discloses tau modulators.

However, improved compositions and methods for the diagnosis, prevention, and/or treatment of tauopathies are still needed. Thus, compositions and methods for the prevention and/or treatment of tauopathies, including AD, are described herein.

SUMMARY

Disclosed herein are methods and compositions for diagnosing, preventing and/or treating one or more tauopathies, such as Alzheimer's Disease (AD). In particular, provided herein are methods and compositions for modifying (e.g., modulating expression of) a tau allele so as to treat at least one tauopathy such as AD, including engineered transcription factor repressors (that repress tau protein expression). Further, these methods and compositions can be used to modify a MAPT allele for the treatment and/or prevention of other tauopathies, including AD, FTD, PSP, CBD and/or seizures. Additionally, the use of two or more tau repressors provides a surprising and unexpected synergistic effect as compared to the use of single repressors. In particular, provided herein are methods and compositions for detecting, reducing and/or eliminating tau protein aggregates in vivo in a subject with a tauopathy.

Thus, described herein are genetic modulators of a microtubule associated protein tau (MAPT) gene for use in modulating tau expression in vivo. The modulator comprises at least one fusion molecule comprising a DNA-binding domain that binds to a target site of at least 12 nucleotides in the MAPT gene; and functional domain (e.g., a transcriptional regulatory domain (such as a repression domain or an activation domain) or nuclease domain). Any DNA-binding domain can be used, including but not limited to, a zinc finger protein (ZFP), a TAL-effector domain protein (TALE), a single guide RNA (of a CRISPR system), an Argonaute protein and the like. In certain embodiments, the DNA-binding domain is a zinc finger protein DNA-binding domain, for example, a ZFP-TF, namely a fusion protein comprising a ZFP that binds specifically to a tau allele and a transcriptional repression domain (e.g., KOX, KRAB, etc.). In certain embodiments, the zinc finger protein DNA-binding domains have the recognition helices in the proteins shown in Table 1, including but not limited to, ZFPs designated 57890, 65918, 57930. In any of the compositions and methods described herein, two or more genetic modulators are used (e.g., 65918 in combination with 57890). The two or more fusion proteins may bind to different target sites and comprise the same or different functional domains. The two or more tau repressors may provide a surprising and unexpected synergistic effect as compared to the use of single repressors. Alternatively, the two or more fusion proteins as described herein may bind to the same target site but include different functional domains. In some instances, three or more fusion proteins are used, in others, four or more fusion proteins are used, while in others, 5 or more fusion proteins are used. In preferred embodiments, the two or more, three or more, four or more, or five or more fusion proteins are delivered to the cell as nucleic acids (e.g., rAAV). One or more nucleic acids (e.g., AAV vectors) may be used to deliver the tau repressors described herein. In certain embodiments, the tau repressor comprises two or more tau repressors carried by a single nucleic acid vector (e.g., an AAV vector) in which the repressor-encoding sequences are separated by a 2A (e.g., T2a) sequence. In these embodiments, the sequences encoding the two or more tau repressors may be in any order (e.g., 65918 repressor-T2a-57890 repressor or 57890 repressor-T2A-65918 repressor). In preferred embodiments, the fusion proteins cause a repression of the expression of the targeted gene. In some embodiments, two fusion proteins are administered at doses where each protein is active on its own but in combination, the repression activity is additive. In preferred embodiments, two fusion proteins are administered at doses where neither is active on its own, but in combination, the repression activity is synergistic.

The genetic modulators described herein may be provided to the subject in any form, including in polynucleotide and/or protein form as well as pharmaceutical compositions comprising such polynucleotides and/or proteins.

In some aspects, the genetic modulators (or a component thereof, for example the DNA binding protein) is provided in polynucleotide form. In certain embodiments, the polynucleotide is a gene delivery vector comprising any of the polynucleotides (e.g., encoding the genetic modulators (repressors)) as described herein. In certain embodiments, the vector is an adenovirus vector (e.g., an Ad5/F35 vector), a lentiviral vector (LV) including integration competent or integration-defective lentiviral vectors, or an adenovirus associated viral vector (AAV). In certain embodiments, the genetic modulator(s) are carried on at least one AAV vector (or pseudotype or variant thereof), including but not limited to one or more AAV1, AAV2, AAV3, AAV4, AAV5, AAV6, AAV8, AAV 8.2, AAV9, AAV rh10, pseudotypes of these vectors (e.g., as AAV2/8, AAV2/5, AAV2/6, AAV2/9, etc.), including AAV vector variants known in the art (e.g. U.S. Pat. Nos. 9,585,971 and 7,198,951; U.S. Patent Publication No. 2017/0119906). In some embodiments, the AAV vector is an AAV variant capable of crossing the blood-brain barrier (e.g. U.S. Pat. No. 9,585,971).

In certain embodiments, provided herein are genetic modulators of tau that are comprised of one or more vectors, including viral and non-viral gene delivery vehicles (e.g., as mRNA, plasmids, AAV vectors, lentiviral vectors, Ad vectors), encoding the genetic modulators as described herein (or one or more components thereof on the same or different polynucleotides). In certain embodiments, the polynucleotide is an mRNA. In some aspects, the mRNA may be chemically modified (See e.g., Kormann et al. (2011) *Nature Biotechnology* 29 (2): 154-157). In other aspects, the mRNA may comprise a cap (e.g. an ARCA cap (see U.S. Pat. Nos. 7,074,596 and 8,153,773)). In further embodiments, the mRNA may comprise a mixture of unmodified and modified nucleotides (see U.S. Patent Publication No. 2012/0195936).

Pharmaceutical compositions and isolated cells comprising one or more of the genetic modulators, one or more polynucleotides, and/or one or more gene delivery vehicles are also provided. In certain embodiments, the pharmaceutical composition comprises two or more genetic modulators. For example, certain compositions include a nucleic acid comprising a sequence that encodes one of the tau modulating ZFPs, Cas or TALEs described herein operably linked to a regulatory sequence, combined with a pharmaceutically acceptable carrier or diluent, where the regulatory sequence allows for expression of the nucleic acid in a cell. In certain embodiments, the ZFPs, CRISPR/Cas or TALEs encoded are specific for a mutant or wild type MAPT allele. In some embodiments, pharmaceutical compositions comprise ZFPs, CRISPR/Cas or TALEs that modulate a mutant or wild type MAPT allele. Protein-based compositions include one of more ZFPs, CRISPR/Cas or TALEs as disclosed herein and a pharmaceutically acceptable carrier or diluent.

In other embodiments, methods and uses for repressing MAPT expression in a subject in need thereof, including by providing to the subject one or more polynucleotides, one or more gene delivery vehicles, and/or a pharmaceutical composition are described herein. In certain embodiments, the compositions described herein are used to repress MAPT expression in the subject, including for treatment and/or prevention of a tauopathy (e.g., by reducing the amount of tau in the subject). The compositions described herein reduce tau levels for sustained periods of time (4 weeks, 3 months, 6 months to year or more) in the brain (including but not limited to the frontal cortical lobe, the prefrontal cortex, parietal cortical lobe, occipital cortical lobe, temporal cortical lobe including by not limited to the entorhinal cortex, hippocampus, brain stem, striatum, thalamus, midbrain, cerebellum) and spinal cord (including but not limited to the lumbar, thoracic and cervical regions). The compositions described herein may be provided to the subject by any administration means, including but not limited to, intracerebroventricular, intrathecal, intracranial, intravenous, orbital (retro-orbital (RO)), intranasal and/or intracisternal administration. Kits comprising one or more of the compositions (e.g., genetic modulators, polynucleotides, pharmaceutical compositions and/or cells) as described herein as well as instructions for use of these compositions are also provided.

Thus, provided herein are methods for treating and/or preventing a tauopathy such as Alzheimer's Disease or seizure using the methods and compositions described herein. In some embodiments, the methods involve compositions where the polynucleotides and/or proteins (or pharmaceutical compositions comprising the polynucleotides and/or proteins) may be delivered using a viral vector, a non-viral vector (e.g., plasmid) and/or combinations thereof. Administration of compositions as described herein (proteins, polynucleotides, cells and/or pharmaceutical compositions comprising these proteins, polynucleotides and/or cells) result in a therapeutic (clinical) effect, including, but not limited to, amelioration or elimination of any the clinical symptoms associated with AD, tauopathies or seizure as well as an increase in function and/or number of CNS cells (e.g., neurons, astrocytes, myelin, etc.). In certain embodiments, the compositions and methods described herein reduce tau gene and/or protein expression (as compared to controls not receiving the artificial repressors as described herein) by at least 30%, or 40%, preferably by at least 50%, even more preferably by at least 70%, or at least 80% or at least 90%, or at least 95% or greater that 95%. In some embodiments, at least 50% reduction is achieved.

Delivery may be to any brain region, for example, the hippocampus or entorhinal cortex by any suitable means including via the use of a cannula or any other delivery technology. Any AAV vector may provide widespread delivery of the repressor to the brain of the subject, including via anterograde and retrograde axonal transport to brain regions not directly administered by the vector (e.g., delivery to the putamen results in delivery to other structures such as the cortex, substantia nigra, thalamus, etc.). In certain embodiments, the subject is a human and in other embodiments, the subject is a non-human primate (NHP). The administration may be in a single dose, or in a series of doses given at the same time, or in multiple administrations (at any timing between administrations).

Furthermore, in any of the methods described herein, the repressors can be delivered at any concentration (dose) that provides the desired effect. In preferred embodiments, the repressor is delivered using an adeno-associated virus (AAV) vector at 10,000-500,000 vector genomes/cell (or any value therebetween). In certain embodiments, the repressor is delivered using a lentiviral vector at a multiplicity of infection (MOI) between 250 and 1,000 (or any value therebetween). In other embodiments, the repressor is delivered using a plasmid vector at 0.01-1,000 ng/100,000 cells (or any value therebetween). In other embodiments, the repressor is delivered as mRNA at 0.01-3000 ng/number of cells (e.g., 50,000-200,000 (e.g., 100,000) cells (or any value therebetween). In other embodiments, the repressor is delivered using an adeno-associated virus (AAV) vector at a fixed volume of 1-300 ul to the brain parenchyma at 1E10-1E14 VG/ml (or any value therebetween). In other embodiments, the repressor is delivered using an adeno-associated virus (AAV) vector at a fixed volume of 0.5-10 ml to the CSF at 1E10-1E14 VG/ml (or any value therebetween).

Thus, in other aspects, described herein is a method of preventing and/or treating a tauopathy (e.g., AD) in a subject, the method comprising administering a repressor of a tau allele to the subject using one or more AAV vectors. In certain embodiments, the AAV encoding the repressor is administered to the CNS (brain and/or CSF) via any delivery method including but not limited to, intracereboventricular, intrathecal, intracranial, intravenous, intranasal, retro-orbital, or intracisternal delivery. In other embodiments, the AAV encoding the repressor is administered directly into the parenchyma (e.g., hippocampus and/or entorhinal cortex) of the subject. In other embodiments, the AAV encoding the repressor is administered intravenously (IV). In any of the methods described herein, the administering may be done once (single administration) or may be done multiple times (with any time between administrations) at the same or different doses per administration. When administered multiple times, the same or different dosages and/or delivery vehicles of modes of administration may be used (e.g., different AAV vectors administered IV and/or ICV). The methods include methods of reducing the aggregation of tau in the subject (e.g., reducing NFTs characteristic of tau aggregation) for example in AD neurons of a subject with AD; methods of reducing apoptosis in a neuron or population of neurons (e.g., an AD neuron or population of AD neurons); methods of reducing neuronal hyperexcitability; methods of reducing amyloid beta induced toxicity (e.g. synapse loss and/or neuritic dystrophy); and/or methods of reducing loss to one or more cognitive functions in AD subjects, all in comparison with a subject not receiving the method, or in comparison to the subject themselves prior to receiving the methods. Thus, the methods described herein result in reduction in biomarkers and/or symptoms of tauopathies, including one or more of the following: neurotoxicity, pathological tau species (e.g., NFTs or phosphorylated tau), neurofilament light chain (Nfl), CSF tau, gliosis, dystrophic neurites, spine loss, excitotoxicity, cortical and hippocampal shrinkage, volumetric changes associated with the region impacted by the specific tauopathy, dendritic tau accumulation, cognitive (e.g., the radial arm maze and the Morris water maze in rodent models, fear conditioning, etc.), and/or motor deficits.

In some aspects, methods and compositions for reducing the amount of a pathogenic tau species in a cell are provided. In some embodiments, the methods result in a reduction of hyperphosphorylated tau. In some instances, the reduction of hyperphosphorylated tau results in a reduction of soluble or granular tau. In other embodiments, the reduction of pathogenic tau species decreases tau aggregation and causes a reduction in neurofibrillary tangles (NFTs) as compared to a cell or subject that has not been treated following the methods and/or with the compositions of described herein. In further embodiments, the methods of reversing the amount of NFTs observed in a cell are provided. In still further embodiments, the methods and compositions of the invention cause a slowing of the propagation of pathogenic tau species (e.g., NFTs, hyperphosphorylated tau) within the brain of a subject. In some embodiments, propagation of pathogenic tau across the brain is halted, and in other embodiments, propagation of pathogenic tau across the brain is reversed. In further embodiments, the number of dystrophic neurites associated with amyloid β plaques in the brain is reduced. In some embodiments, the number of dystrophic neurites is reduced to the levels found in an age-matched wild type brain. In further embodiments, provided herein are methods and compositions for reducing hyperphosphorylated tau associated with amyloid β plaques in the brain of a subject.

In some embodiments, following administration to the subject, the sequence encoding a genetic modulator (genetic repressor) as described herein (e.g., ZFP-TF, TALE-TF or CRISPR/Cas-TF) is inserted (integrated) into the genome while in other embodiments the sequence encoding the repressor is maintained episomally. In some instances, the nucleic acid encoding the TF fusion is inserted (e.g., via nuclease-mediated integration) at a safe harbor site comprising a promoter such that the endogenous promoter drives expression. In other embodiments, the repressor (TF) donor sequence is inserted (via nuclease-mediated integration) into a safe harbor site and the donor sequence comprises a promoter that drives expression of the repressor. In some embodiments, the sequence encoding the genetic modulator is maintained extrachromosomally (episomally) after delivery, and may include a heterologous promoter. The promoter may be a constitutive or inducible promoter. In some embodiments, the promoter sequence is broadly expressed while in other embodiments, the promoter is tissue or cell/type specific. In preferred embodiments, the promoter sequence is specific for neuronal cells. In other preferred embodiments, the promoter chosen is characterized in that it has low expression. Non-limiting examples of preferred promoters include the neural specific promoters NSE, Synapsin, CAMKiia and MECPs. Non-limiting examples of ubiquitous promoters include CMV, CAG and Ubc. Further embodiments include the use of self-regulating promoters as described in U.S. Patent Publication No. 2015/0267205.

In any of the methods described herein, the method can yield about 50% or greater, about 55% or greater, about 60% or greater, about 65% or greater, about 70% or greater, about 75% or greater, about 85% or greater, about 90% or greater, about 92% or greater, about 95% or greater, 98% or greater, or 99% or greater repression of the tau alleles in one or more AD neurons of the subject.

In certain aspects, described are methods of preventing and/or treating a tauopathy using the methods and compositions described herein. In certain embodiments, use of an artificial transcription factor (e.g., a zinc finger protein (ZFP-TF), a TALE (TALE-TF), and/or CRISPR/Cas-TF), optionally a ZFP-TF comprising a ZFP designated 65918, 57890, and/or 57930) that modulates (e.g., represses) MAPT gene expression and/or tau protein levels in the central nervous system (CNS) of a subject is used for the prevention and/or treatment of tauopathy (e.g., Alzheimer's Disease (AD), Frontotermporal Dementia, Progressive Supranuclear Palsy, traumatic brain injury (TBI), seizure disorders and/or Corticobasal Degeneration), preferably wherein the symptoms of the tauopathy are reduced or eliminated, optionally by reducing the occurrence of neural tangles in the brain of the subject. In any of the methods and uses described herein, the artificial transcription factor(s) is (are) delivered to the CNS (e.g., brain or spinal cord) of the subject by a viral vector, such as an AAV vector (e.g., AAV9), for example intravenously or to the CNS, optionally into the striatum or hippocampus in one or both hemispheres of the brain of the subject. In certain embodiments, the AAV vector comprises a CMV or synapsin (SYN) promoter. In still further embodiments, artificial transcription factors reduce MAPT gene expression and/or tau levels in the brain of the primate subject by 50% or more, optionally 70% or more, and up to 99% as compared to untreated subjects. In any of the embodiments described herein, the artificial transcription factor is carried by an AAV vector comprising a CMV or SYN promoter at 6E11 rAAV vector genomes per hemisphere.

Also provided is a kit comprising one or more of the AAV tau-modulators (e.g., repressors) and/or polynucleotides comprising components of and/or encoding the tau-modulators (or components thereof) as described herein. The kits may further comprise cells (e.g., neurons), reagents (e.g., for detecting and/or quantifying tau protein, for example in CSF) and/or instructions for use, including the methods as described herein.

Thus, provided herein is a composition comprising two or more artificial zinc finger protein transcription factors (ZFP-TFs) that repress MAPT expression (e.g., the ZFPs designated 65918 in combination with 57890 or 57930). The compositions comprising two or more ZFP-TFs may repress MAPT expression 1-, 2-, 3-, 4-, 5-, 6-, 7-, 8-, 9-, 10-fold or more as compared to single repressors and/or untreated controls (subjects). The composition typically comprises one or more polynucleotides encoding the two or more ZFP-TFs are encoded by polynucleotides, which may be carried by one or more viral (e.g., AAV such as AAV9) vectors, for example a single AAV vector comprising a polynucleotide encoding both of the ZFP-TFs or separate AAV vectors encoding each of the ZFP-TFs. Any promoters may be used to drive expression of the ZFP-TFs including but not limited to CMV and/or synapsin (SYN) promoter. One or more compositions (e.g., one or more AAV vectors comprising sequences encoding the two or more ZFP-TFs) described herein may be used to for the prevention and/or treatment of tauopathy (e.g., Alzheimer's Disease (AD), Frontotermporal Dementia, Progressive Supranuclear Palsy, traumatic brain injury (TBI), seizure disorders and/or Corticobasal Degeneration) in a subject in need thereof, optionally wherein the symptoms of the tauopathy are reduced or eliminated, optionally by reducing the occurrence of neural tangles in the brain of the subject. The compositions may be administered to the subject intravenously or to the CNS (e.g., into the striatum or hippocampus in one or both hemispheres of the brain of the subject), optionally wherein the one or more AAV vectors are administered at between about 1E10 to 6E11 rAAV vector genomes per hemisphere. Expression of two or more ZFP-TFs of the composition reduce MAPT gene expression and/or tau levels in the brain of the primate subject by 50% or more, optionally 70% or more, and up to 99% as compared to untreated subjects.

BRIEF DESCRIPTION OF THE DRAWINGS

FIG. 3A shows results for punch 037; FIG. 3B shows results for punch 039; and FIG. 3C shows results for punch 061, each sample (punch) from the hippocampus. The top plot in each panel shows % normalized tau repression (left axis) and the bottom plot in each panel shows ZFP mRNA levels (copies/ng mRNA) (right axis).

FIG. 5A through FIG. 5C depict tau expression and ZFP levels and corresponding MRI images in control and treated NHP subjects. FIG. 5A and FIG. 5B are graphs showing tau expression and ZFP levels, with a focus on punches from brain slice 7 showing the cortex and hippocampus in control ("Vehicle" as shown in the FIG. 5A) and a NHP subject treated with tau repressors 65918 ("918") and 57890 ("890") carried by an AAV vector (AAV9) where expression of the repressors (918 and 890) is driven by the synapsin (SYN1) promoter and the repressors are linked by a T2A cleavage peptide. The top plot in FIG. 5A and FIG. 5B show % normalized tau repression and the bottom plot in FIG. 5A and FIG. 5B show ZFP mRNA levels (copies/ng mRNA). FIG. 5C depicts MRI scans from the same control (left image) and treated (right image) subjects at the level of the injection track. A co-infused gadolinium tracer is evident in the hippocampal region in both hemispheres.

FIG. 6A through FIG. 6O are graphs depicting tau expression and ZFP levels in samples taken from control and treated NHP subjects. FIG. 6A through FIG. 6C show results from control subjects (NHP01 as shown in FIG. 6A, NHP02 as shown in FIG. 6B and NHP03 as shown in FIG. 6C). FIG. 6G through FIG. 6J show results from subjects (NHP07 and NHP08) treated with genetic repressors 65918 ("918") and 57890 ("890") carried by an AAV vector (AAV9) where expression of the repressor (918 and 890) is driven by a CMV promoter ("CMV.918-890") (FIG. 6G and FIG. 6H), and subjects (NHP09 and NHP10) treated with the genetic repressor 57930 ("930") carried by an AAV vector (AAV9) where expression of the repressor (930) is driven by a synapsin (SYN1) promoter ("SYN1.930") (FIG. 6I and FIG. 6J). FIG. 6N and FIG. 6O show results from subjects (NHP14 as shown in FIG. 6N and NHP15 as shown in FIG. 6O) treated with 65918 ("918") carried by an AAV vector (AAV9) where expression of the repressor is driven by the synapsin (SYN1) promoter ("SYN1.918"). The top plot in each graph shows % normalized tau repression and the bottom plot in each graph shows ZFP mRNA levels (copies/ng mRNA).

FIG. 7A, FIG. 7B and FIG. 7C show control subjects ("vehicle") and FIG. 7D, FIG. 7E and FIG. 7F show all treated subjects ("All AAV-treated NHPs").

For this analysis, tau expression is scaled to the average of the Vehicle-treated animals and ZFP-treated animals without detectable ZFP expression.

Figure 13A:
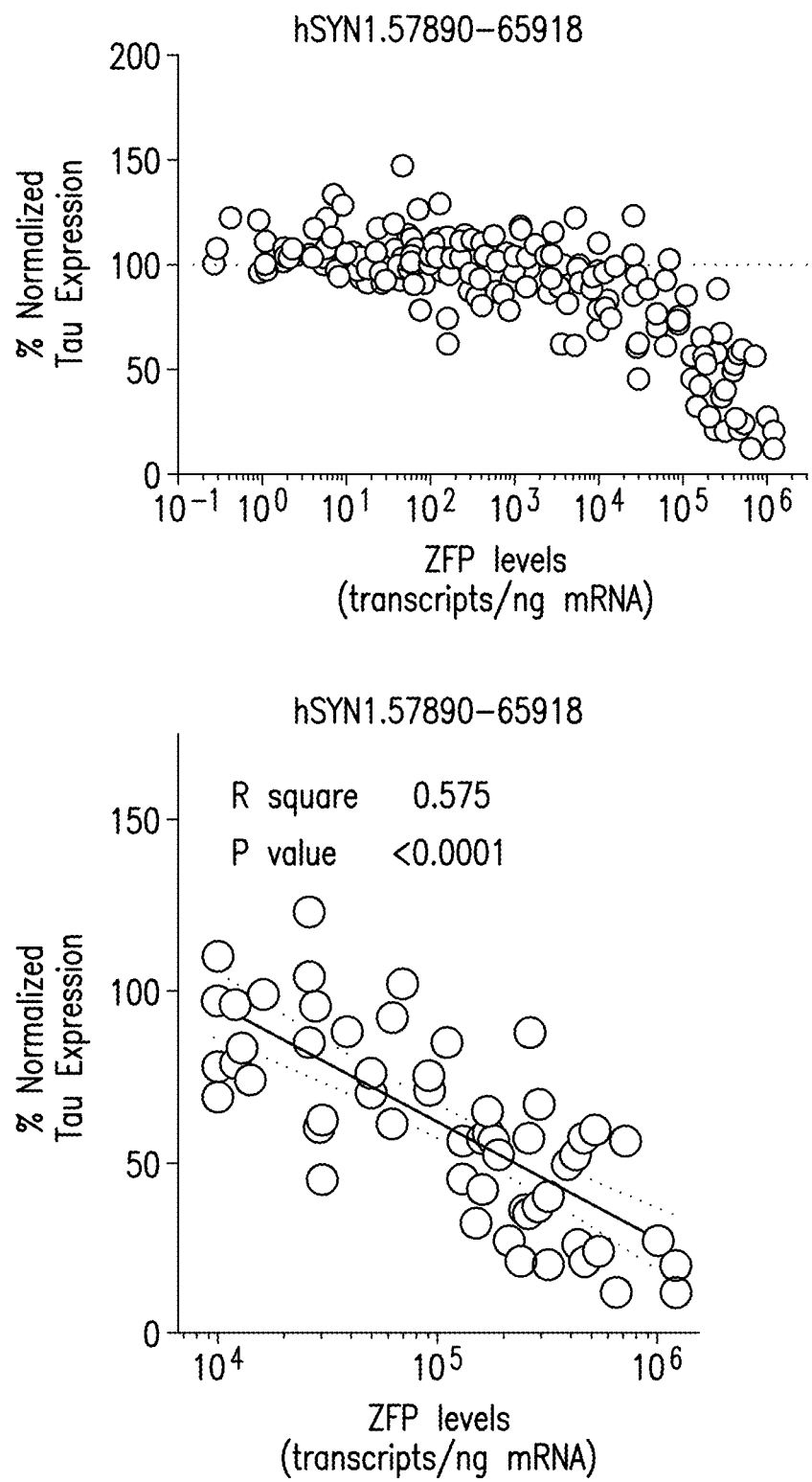
Figure 13D:
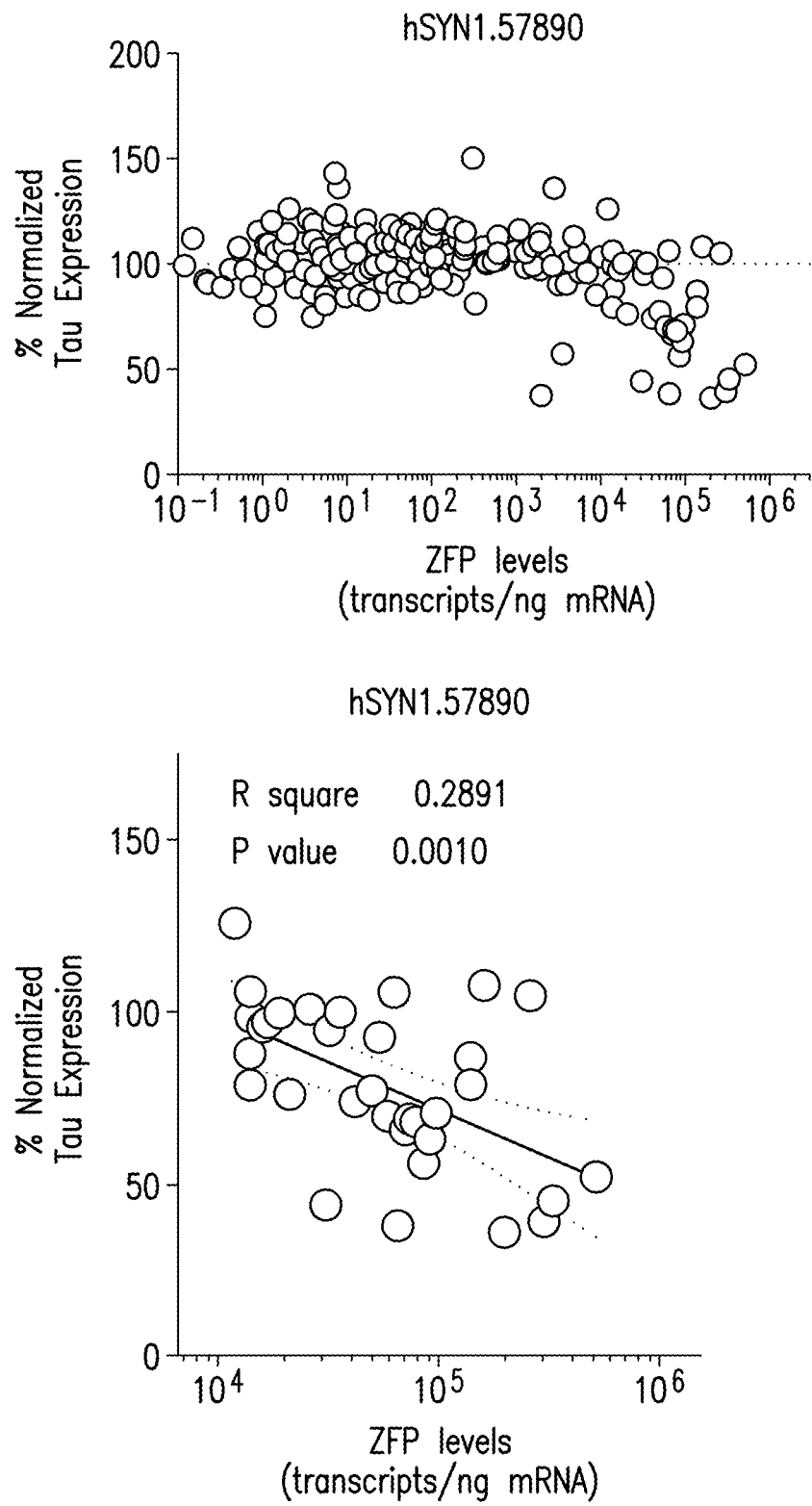
Figure 13E:
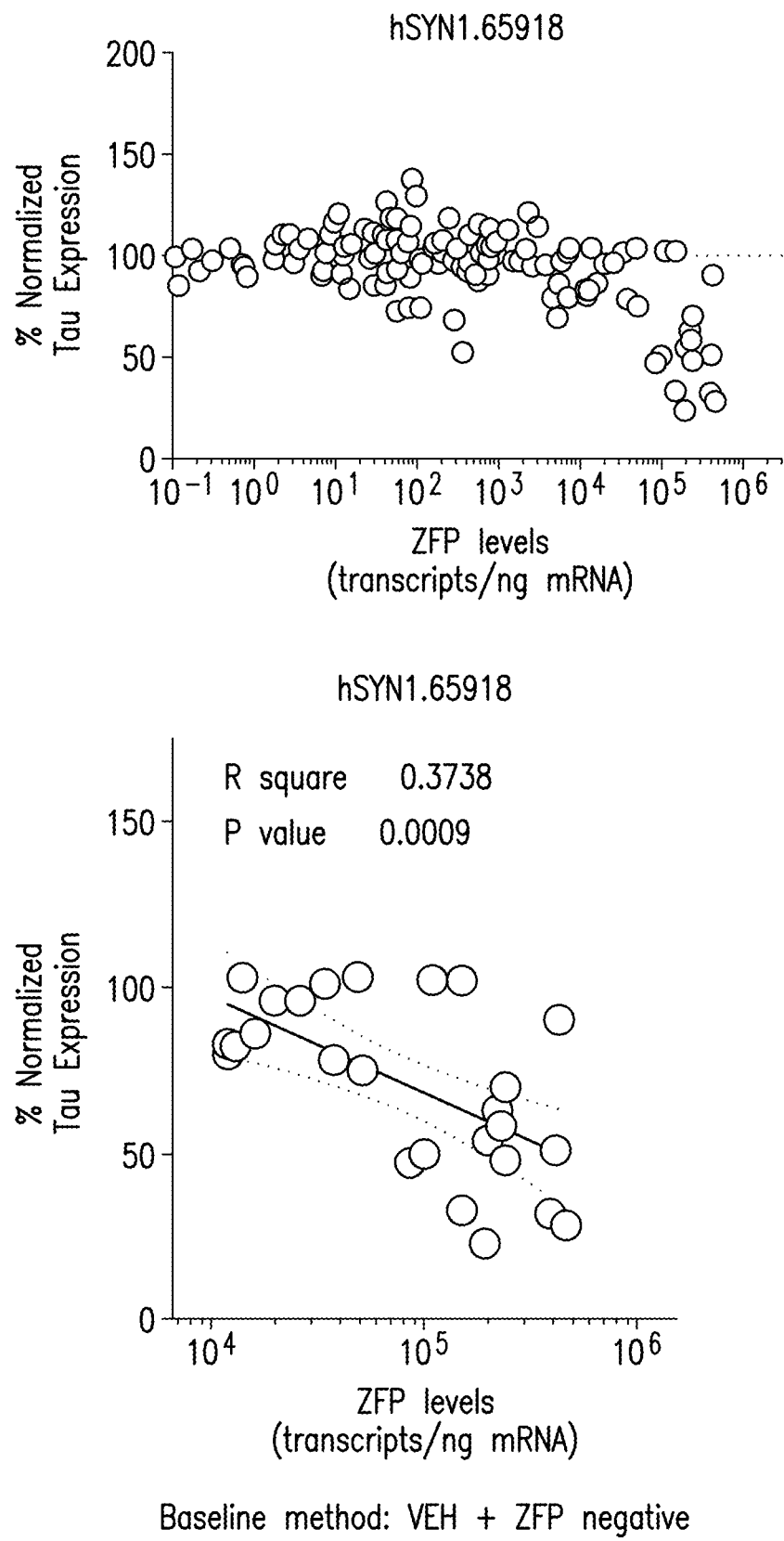

FIG. 13A through FIG. 13E are correlation plots showing tau expression at the indicated ZFP transcript levels for the indicated treatment groups. FIG. 13A shows results for groups treated with hSYN1.57890-65918; FIG. 13B shows results for groups treated with CMV.57890-65918; FIG. 13C shows results for groups treated with hSYN1.57930; FIG. 13D shows results for groups treated with hSYN1.57890; and FIG. 13E shows results for groups treated with hSYN.65918. For this analysis, tau expression levels for each punch are scaled to the average of the three vehicle-treated animals. The top panels of each of FIG. 13A through 13E show the relationship across all ZFP mRNA levels; the bottom panels of each of FIG. 13A through 13E show only the range of ZFP expression associated with tau reduction, approximately 1E4-1E6 ZFP transcripts/ng mRNA. Also shown are R-squared and P values. For this analysis, tau expression is scaled to the average of the vehicle-treated animals and ZFP-treated animals without detectable ZFP expression.

Figure 14:
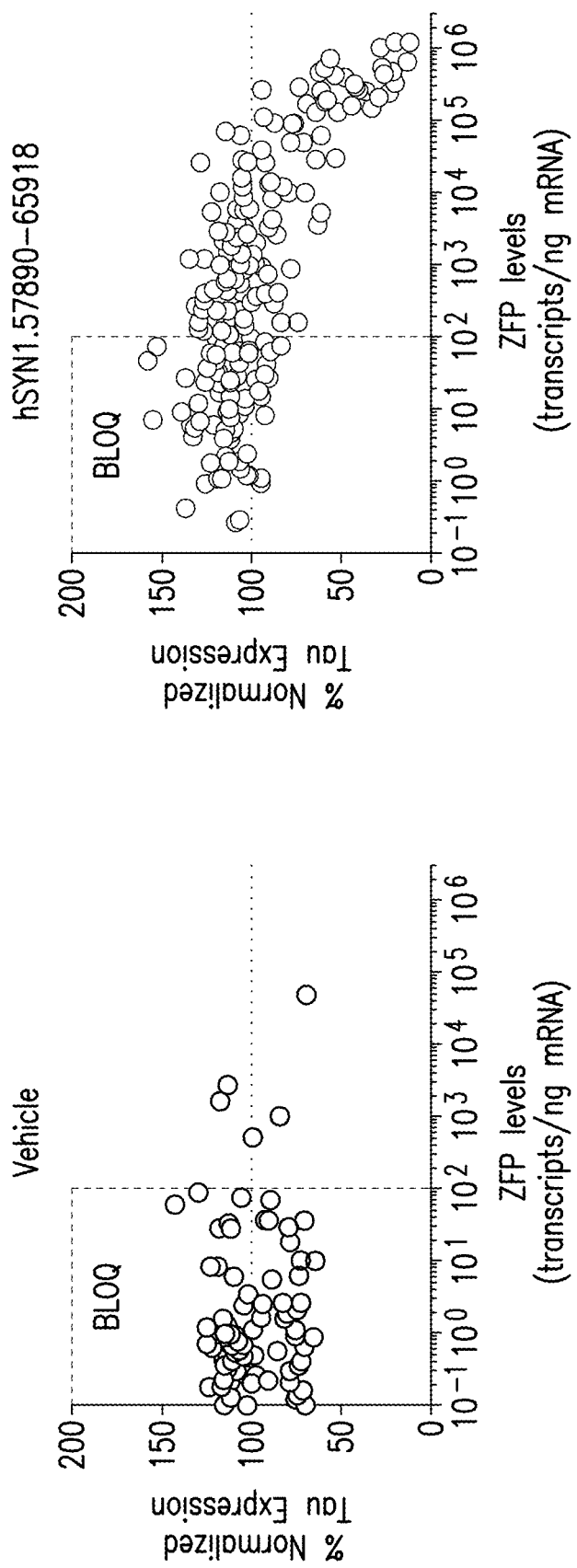

FIG. 14 are correlation plots showing tau expression and ZFP transcript levels in control subjects (left panel-"Vehicle") and subjects treated with AAV vectors encoding the 65918 and 57890 genetic repressors, where expression is driven by a synapsin promoter ("hSYN1.5789-65918"). The limit of the ZFP qRT-PCR assay for absolute quantitation is approximately 1E2 transcripts/ng mRNA which is indicated by Below Limit of Quantitation (BLOQ). In contrast to FIG. 12, for this analysis, tau expression levels are scaled to the average of the three vehicle-treated animals.

Figure 15B:
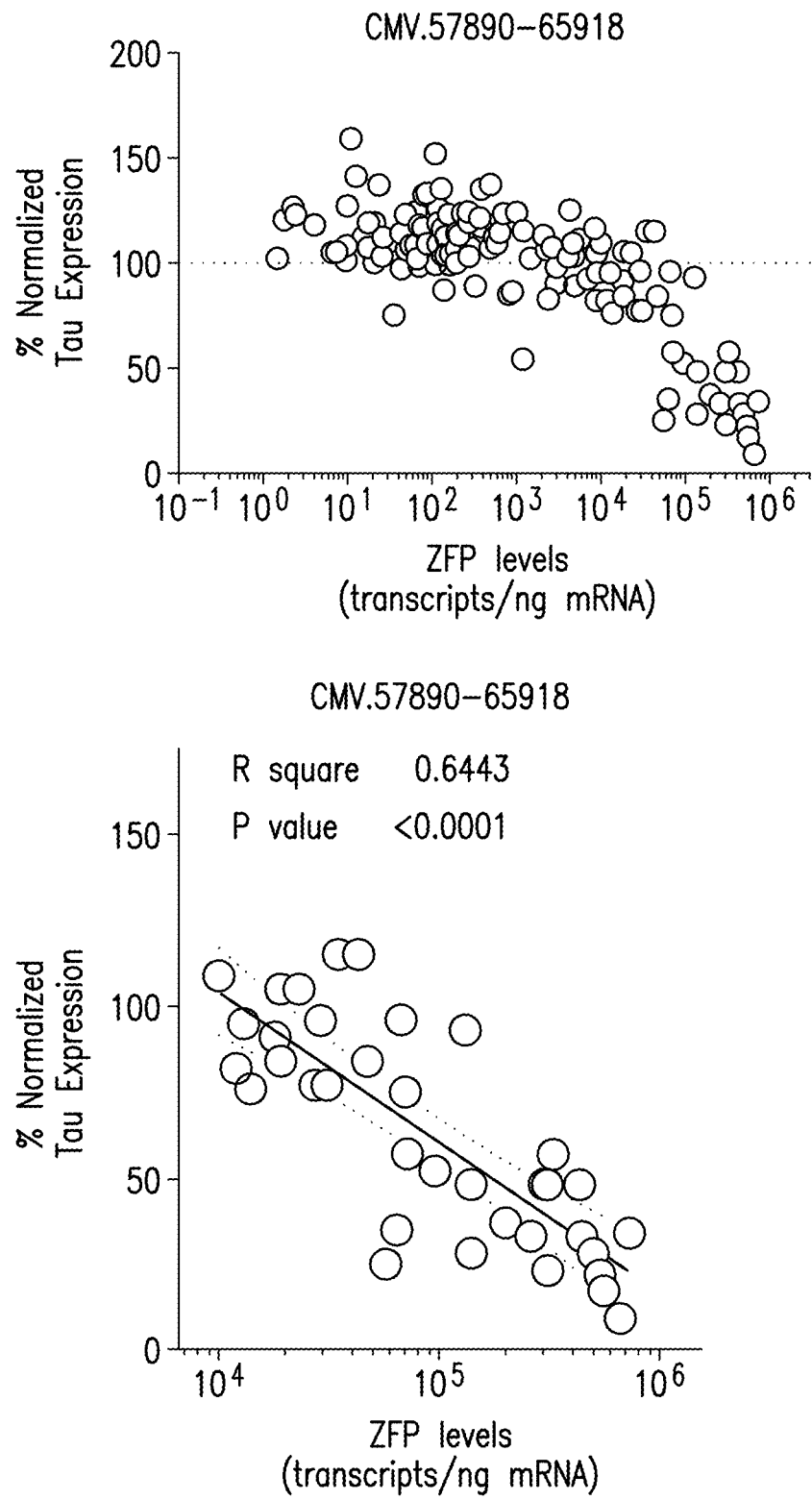
Figure 15C:
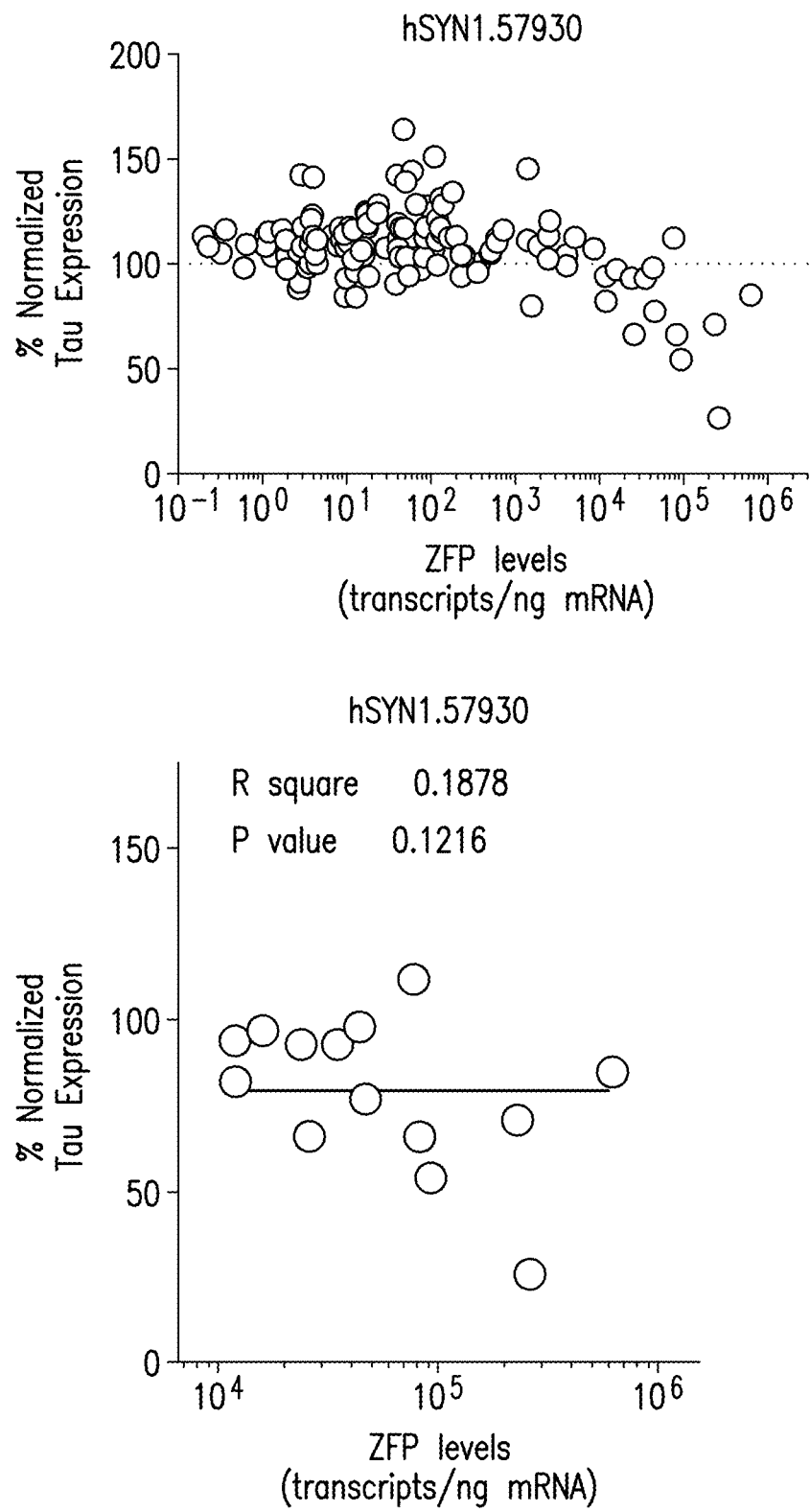
Figure 15D:
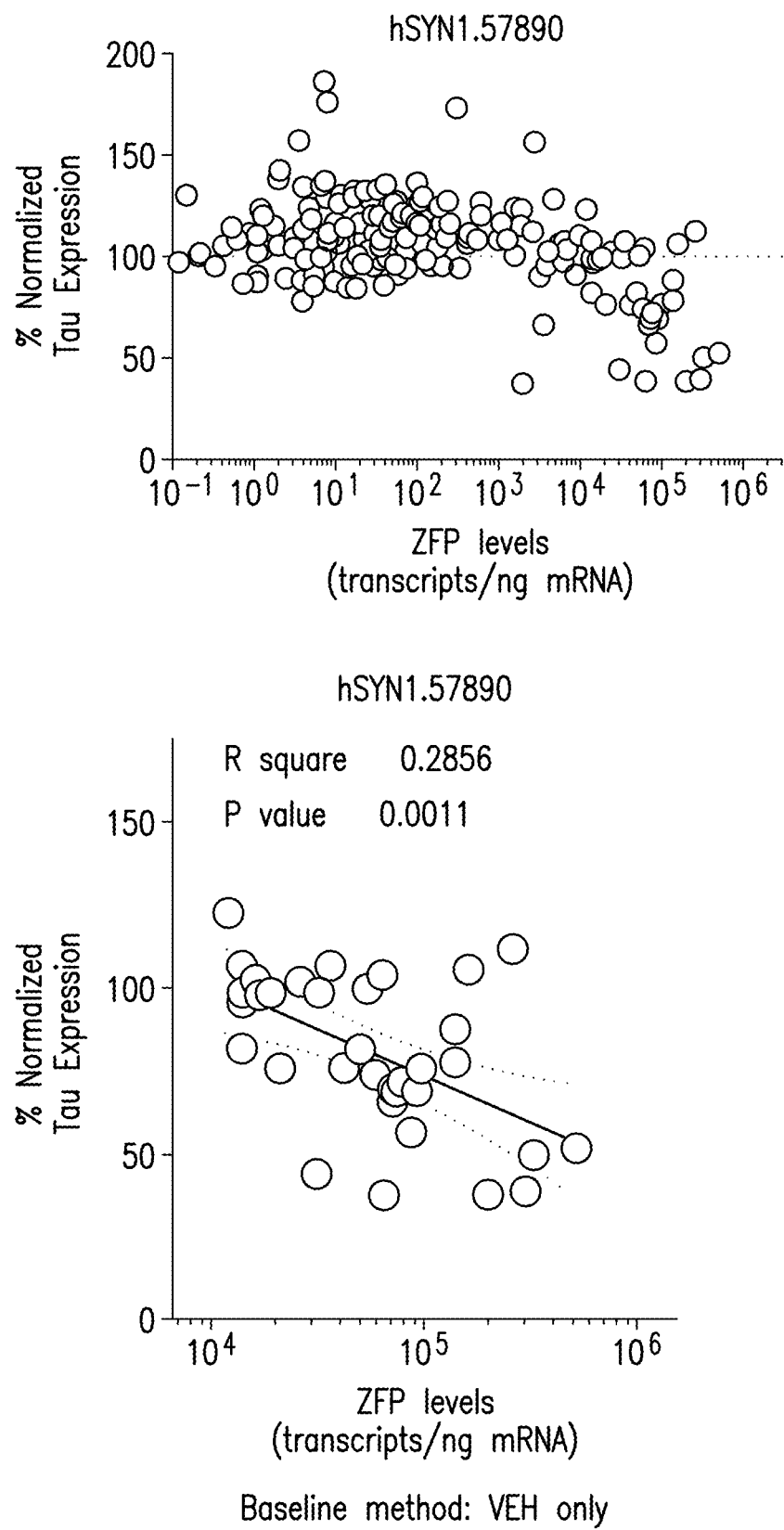
Figure 15E:
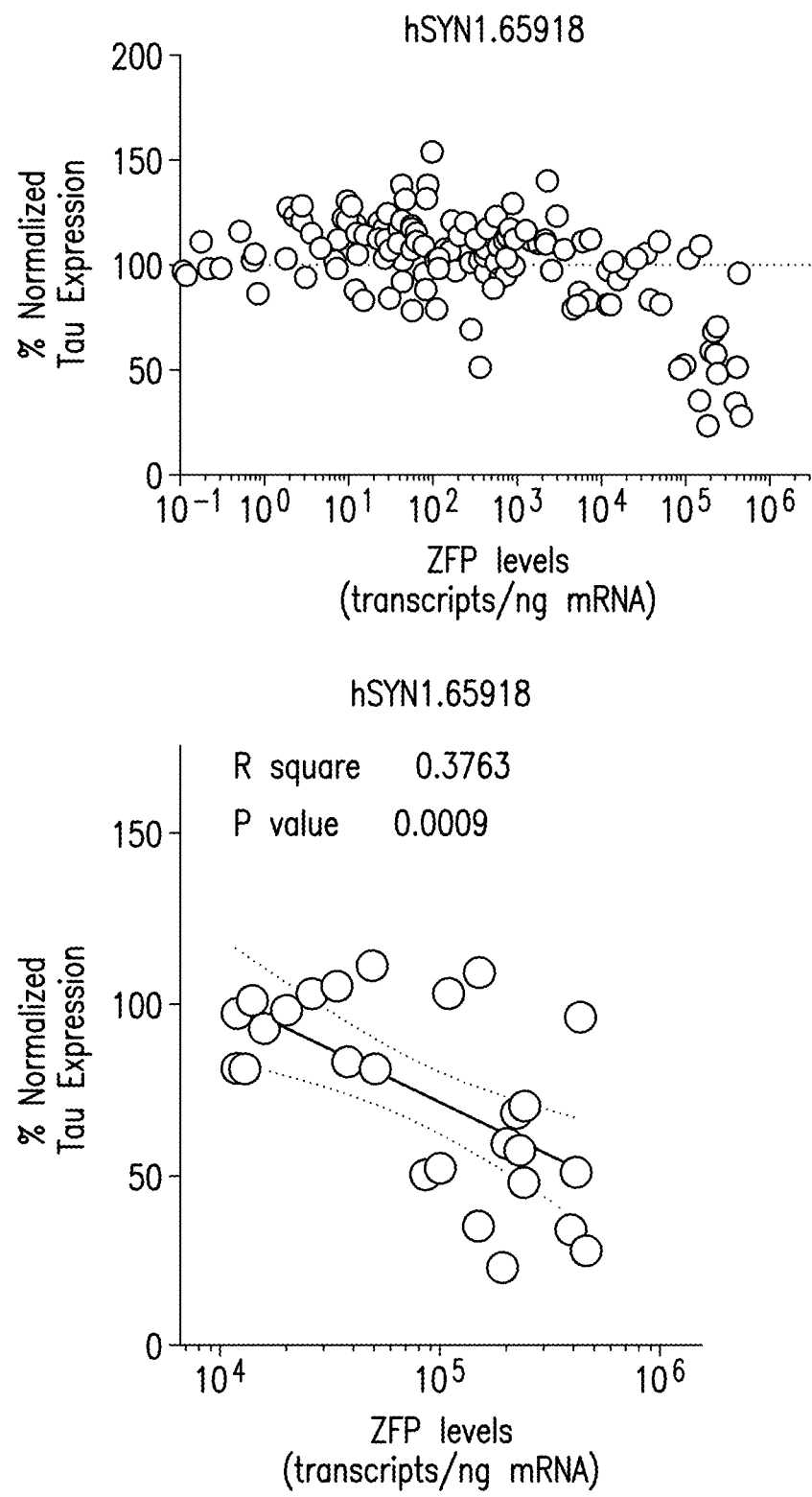

FIG. 15A through FIG. 15E are correlation plots showing tau expression at the indicated ZFP transcript levels for the indicated treatment groups: FIG. 15A shows results for groups treated with hSYN1.57890-65918; FIG. 13B shows results for groups treated with CMV.57890-65918; FIG. 15C shows results for groups treated with hSYN1.57930; FIG. 15D shows results for groups treated with hSYN1.57890; and FIG. 15E shows results for groups treated with hSYN.65918. For this analysis, tau expression levels for each punch are scaled to the average of the three vehicle-treated animals. The top panels of each of FIG. 15A through FIG. 15E show the relationship across all ZFP mRNA levels; the bottom panels of each of FIG. 15A through FIG. 15E show only the range of ZFP expression associated with tau reduction, approximately 1E4-1E6 ZFP transcripts/ng mRNA. Also shown are R-squared and P values. In contrast to FIG. 13A through FIG. 13E, for this analysis, tau expression levels are scaled to the average of the three vehicle-treated animals.

Figure 16:
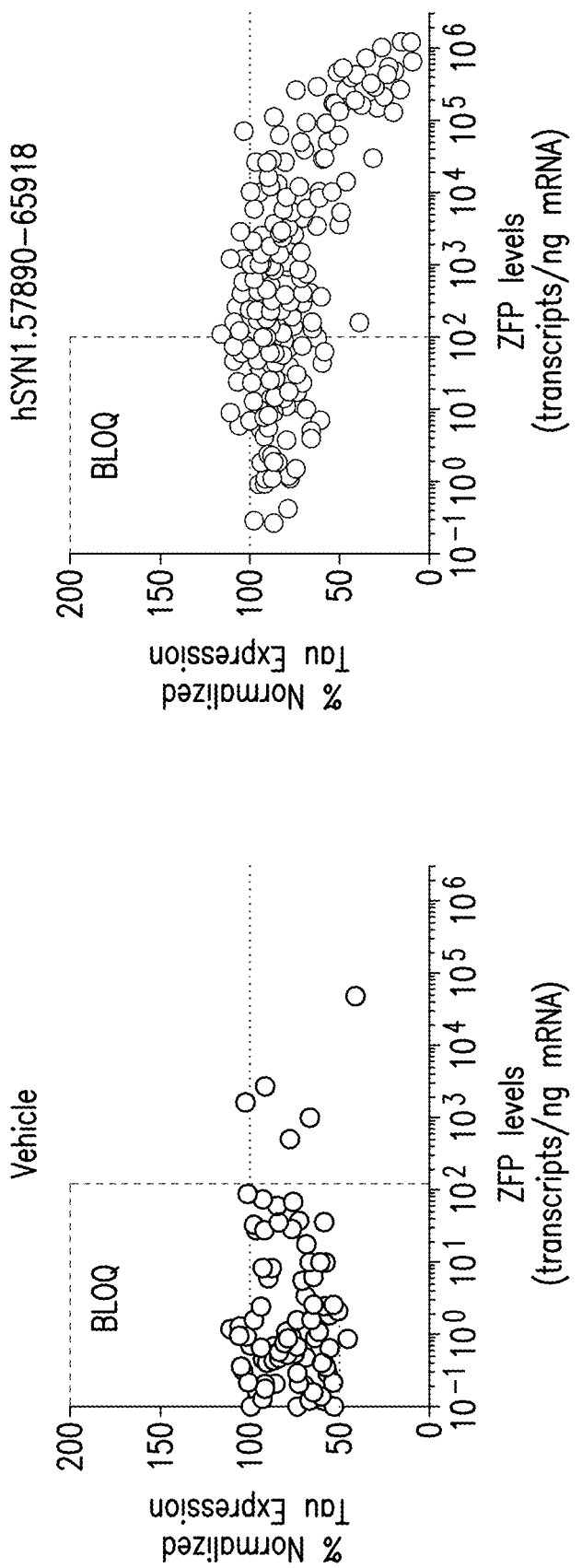

FIG. 16 are correlation plots showing tau expression and ZFP transcript levels in control subjects (left panel-"Vehicle") and subjects treated with AAV vectors encoding the 65918 and 57890 genetic repressors, where expression is driven by a synapsin promoter ("hSYN1.5789-65918"). The limit of the ZFP qRT-PCR assay for absolute quantitation is approximately 1E2 transcripts/ng mRNA which is indicated by Below Limit of Quantitation (BLOQ). For this analysis, tau expression levels were not scaled to correct for baseline tau levels in untreated or ZFP-negative animals.

Figure 17D:
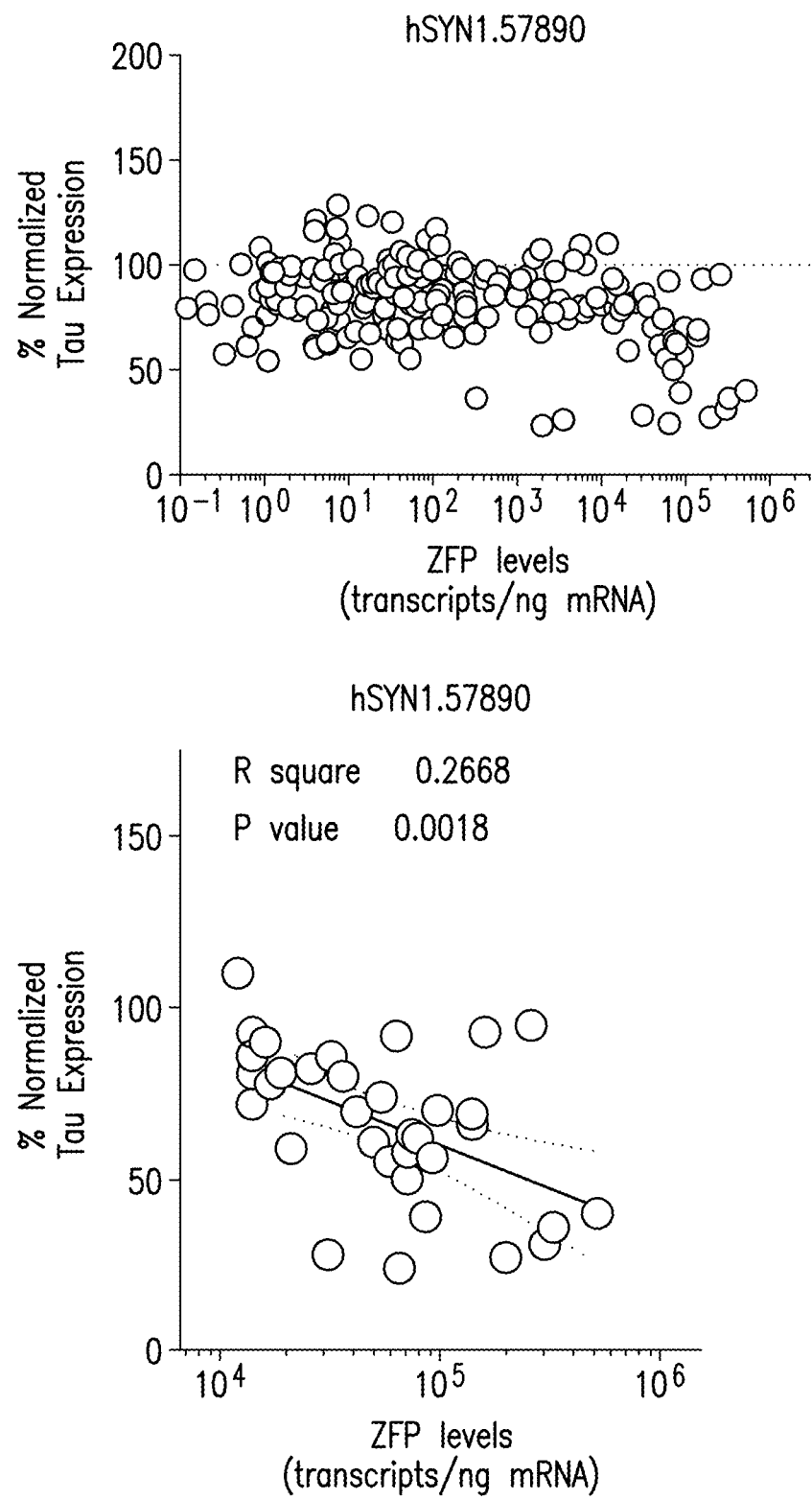
Figure 17E:
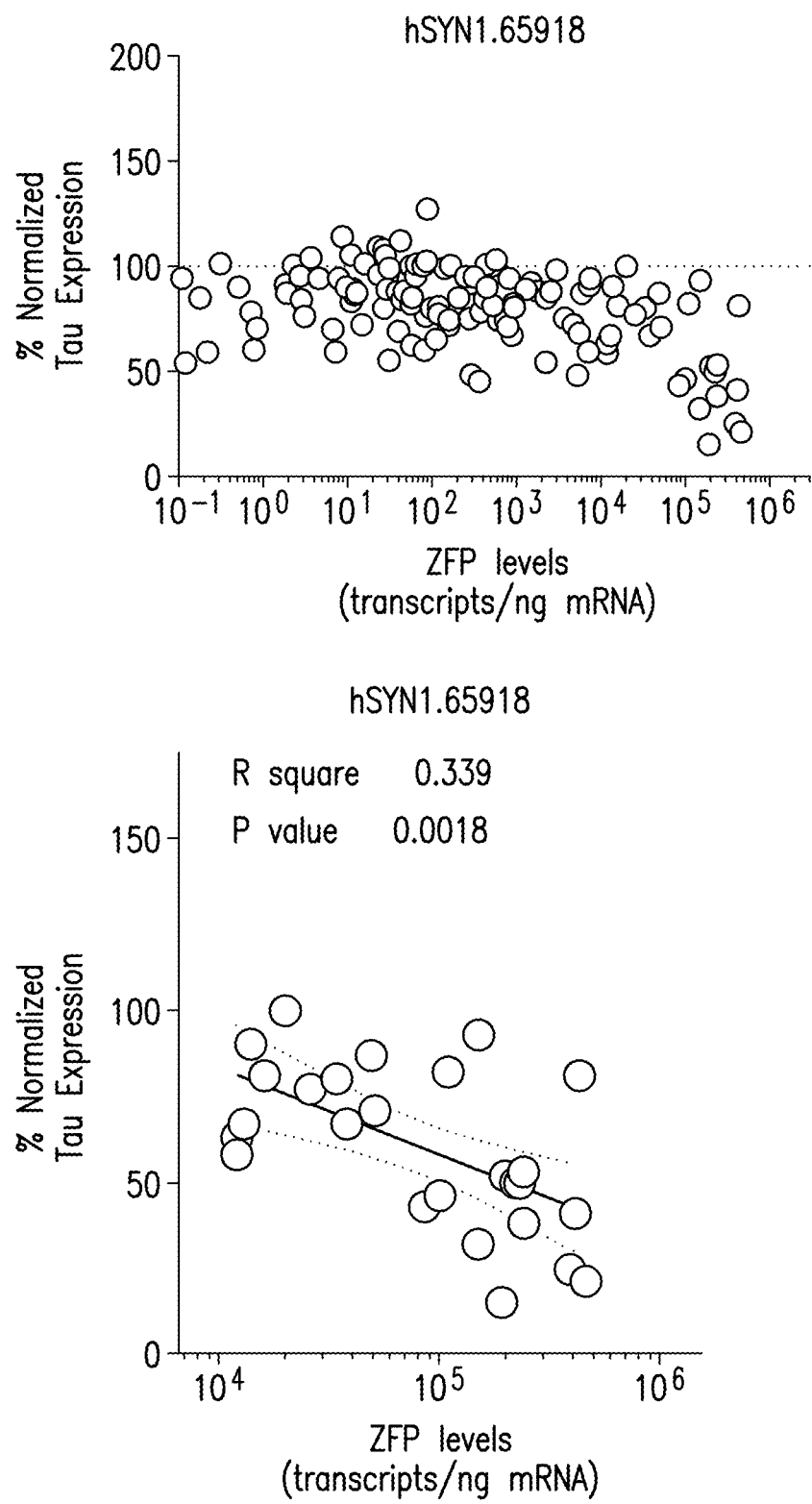

FIG. 17A through FIG. 17E are correlation plots showing tau expression at the indicated ZFP transcript levels for the indicated treatment groups: FIG. 17A shows results for groups treated with hSYN1.57890-65918; FIG. 17B shows results for groups treated with CMV.57890-65918; FIG. 17C shows results for groups treated with hSYN1.57930; FIG. 17D shows results for groups treated with hSYN1.57890; and FIG. 17E shows results for groups treated with hSYN.65918. For this analysis, tau expression levels for each punch are scaled to the average of the three Vehicle-treated animals. The top panels of each of FIG. 17A through FIG. 17E show the relationship across all ZFP mRNA levels; the bottom panels of each of FIG. 17A through FIG. 17E show only the range of ZFP expression associated with tau reduction, approximately 1E4-1E6 ZFP transcripts/ng mRNA. Also shown are R-squared and P values. For this analysis, tau expression levels were not scaled to correct for baseline tau levels in untreated or ZFP-negative animals.

Figure 18A:
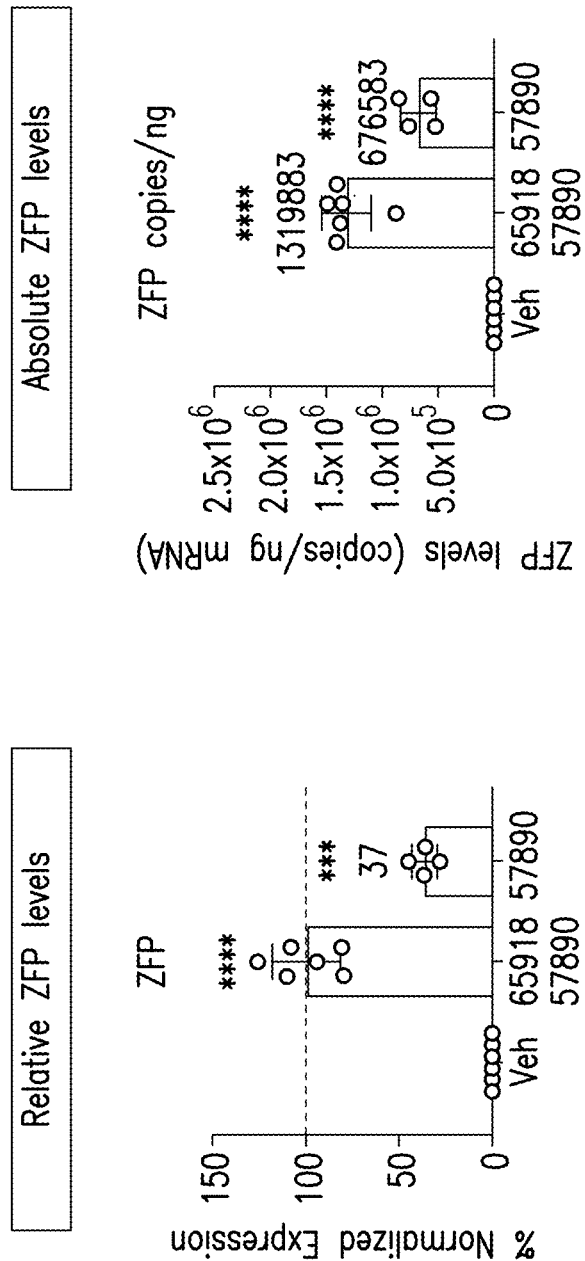
Figure 18B:
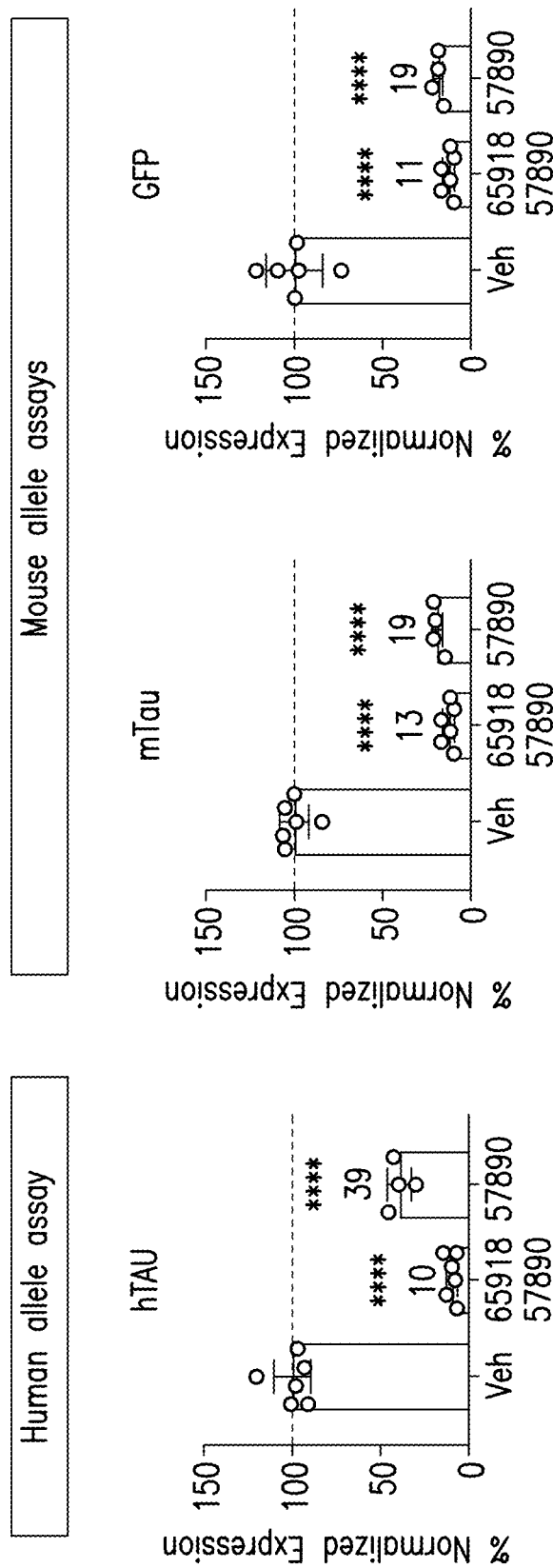
Figure 18C:
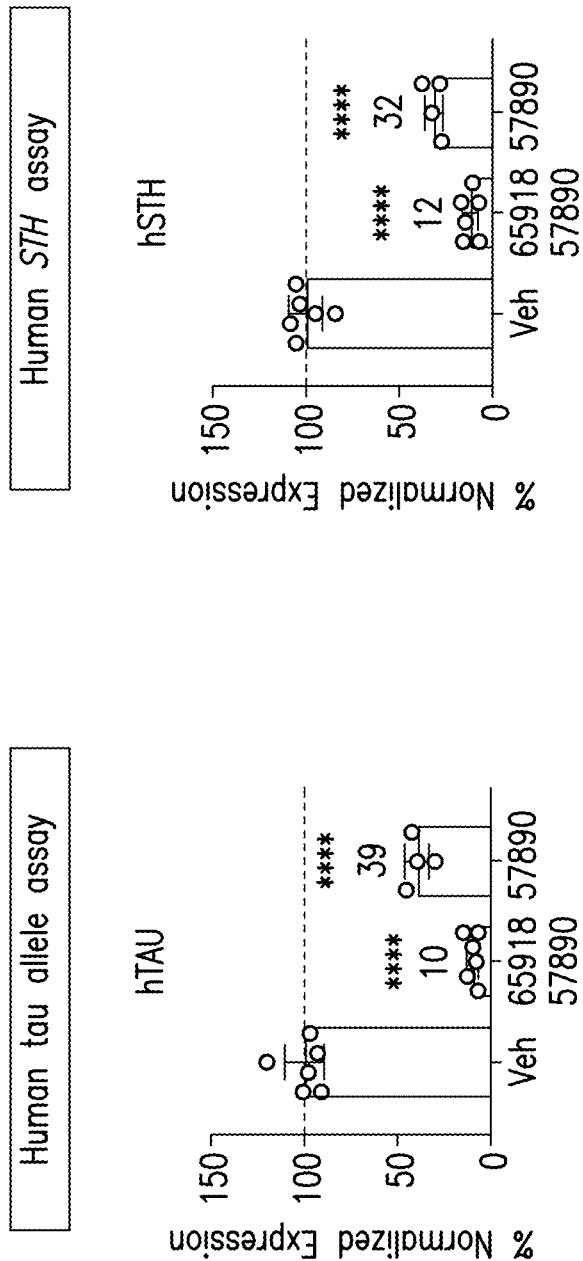
Figure 18D:
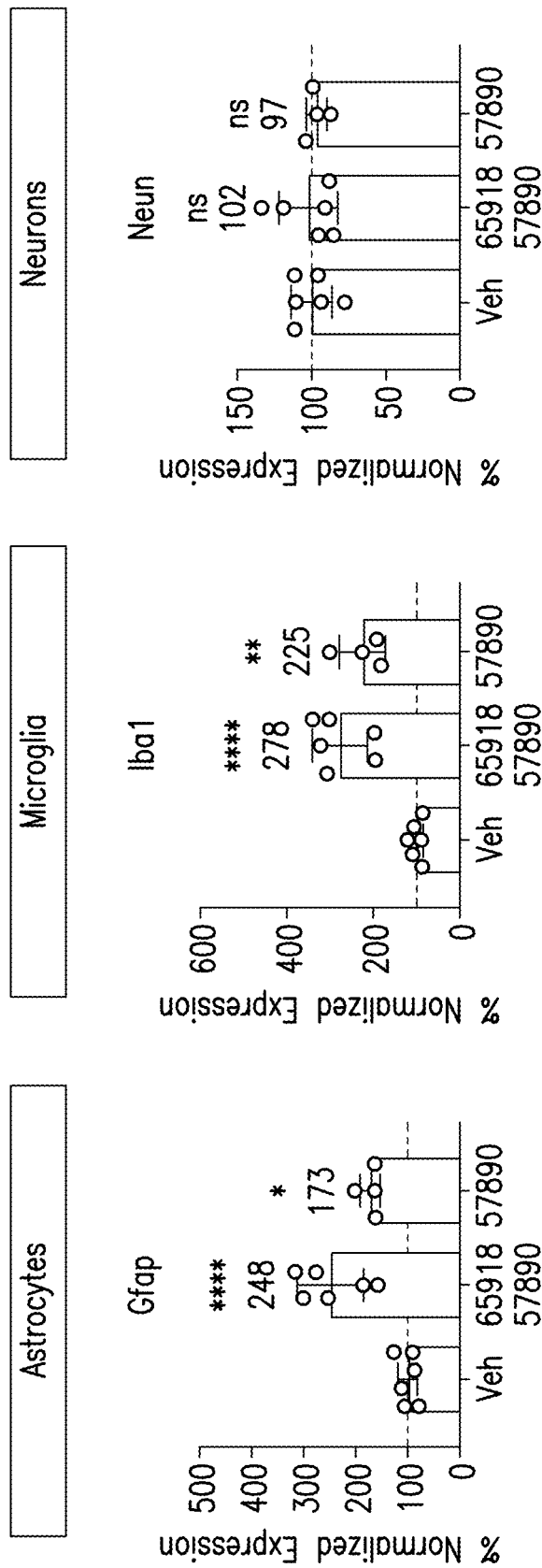

FIG. 18A through FIG. 18D are bar graphs depicting results from humanized Tau mice treated with tau ZFP-TFs as described herein. FIG. 18A shows relative (left graph) and absolute (right graph) ZFP levels of mice treated with the indicated constructs. As shown, mice treated with the synergistic combination of 65918 and 57890 showed expression levels 2x higher than 57890 alone. FIG. 18B shows human tau ("hTAU", left graph), mouse tau ("mTAU", middle graph) and GFP (right graph) expression levels in mice treated with the indicated constructs. As shown, human tau mRNA was repressed by ~90% by 65918-T2a-57890 as compared to ~60% repression by 57890. Likewise, mouse tau mRNA was repressed ~87% by 65918-T2a-57890 as compared to 81% repression by 57890 alone. FIG. 18C depicts expression of hTAU (left graph) and human Saitohin ("hSTH", right graph) in the humanized tau mice treated under the indicated conditions. Similar levels of human tau and STH reduction were observed consistent with the fact that STH is nested within tau and, therefore, the two genes are coregulated. FIG. 18D shows expression levels of GFAP (astrocyte marker) (left graph), IBA1 (microglia marker) (middle graph) and NeuN (neuronal marker) (right graph) of humanized Tau mice treated with the indicated constructs.

Figure 19F:
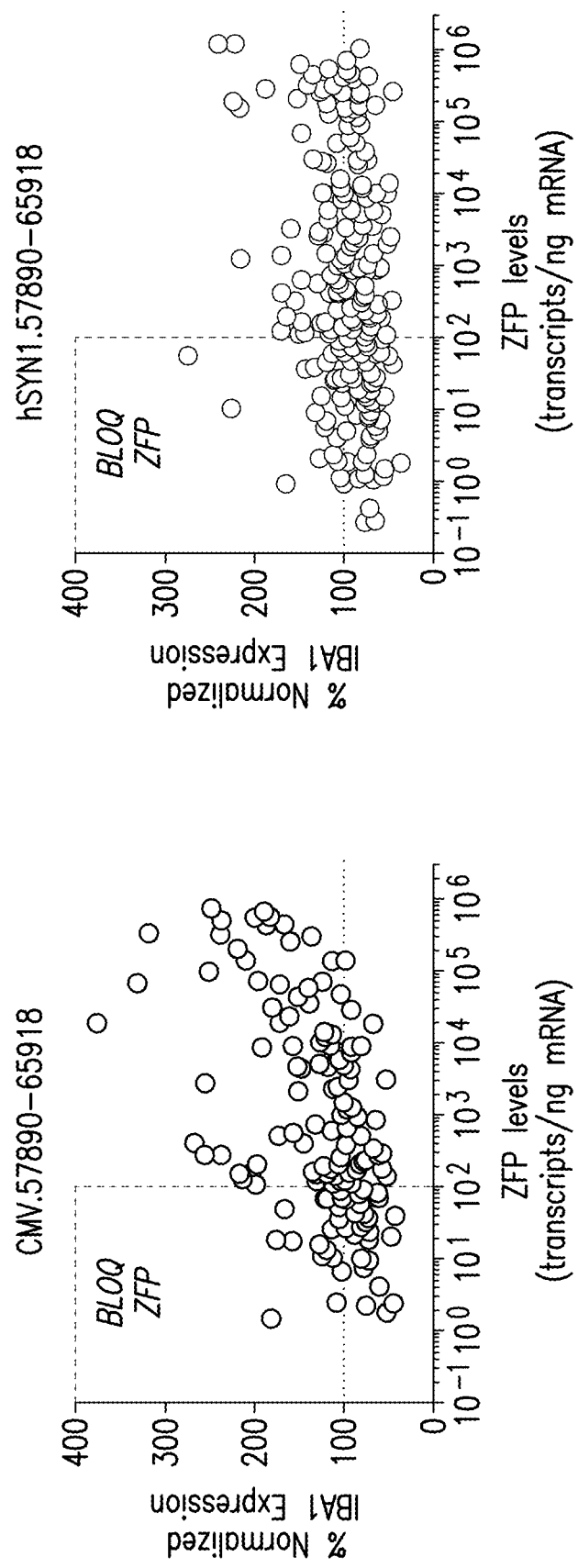

FIG. 19A through FIG. 19K are graphs depict increased microglial and astrocyte marker expression levels in non-human primates (NHP) following treatment with the indicated tau-specific ZFP-TF expressed from a ZFP-TF construct including either a CMV or synapsin (SYN) promoter. FIG. 19A through FIG. 19F show ionized calcium-binding adapter molecule 1 (IBA1) levels, a marker of microglia in the indicated treatment groups: FIG. 19A shows group treated with hSYN1.57890-65918; FIG. 19B shows results for groups treated with CMV.57890-65918; FIG. 19C shows results for groups treated with hSYN1.57930; FIG. 19D shows results for groups treated with hSYN1.57890; FIG. 19E shows results for groups treated with hSYN.65918; and FIG. 19F shows side by side results for groups treated with CMV.57890-65918 (left panel) and hSYN1.57890-65918 (right panel). Microglial activation is indicative of an inflammatory response. FIG. 19G through FIG. 19K show astrocyte activation (as measured by GFAP levels) in the indicated treatment groups: FIG. 19G shows results for groups treated with hSYN1.57890-65918; FIG. 19H shows results for groups treated with CMV.57890-65918; FIG. 19I shows results for groups treated with hSYN1.57930; FIG. 19J shows results for groups treated with hSYN1.57890; and FIG. 19K shows results for groups treated with hSYN.65918. As shown, no ZFP dependent elevation in microglial or astrocyte levels was seen for any of the constructs comprising the SYN promoter, while microglial and astrocyte markers were elevated with constructs comprising the CMV promoter.

Figure 20A:
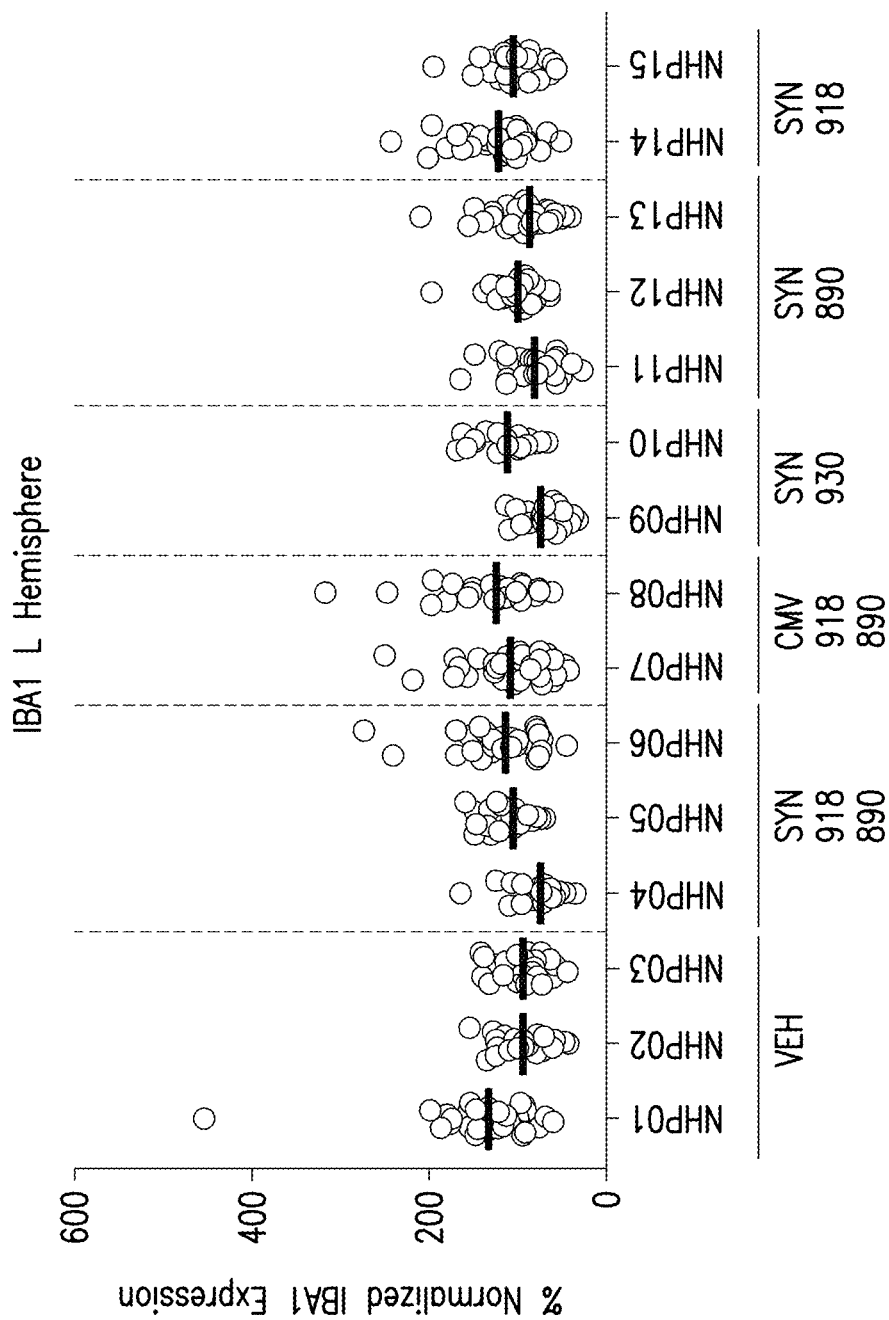
Figure 20B:
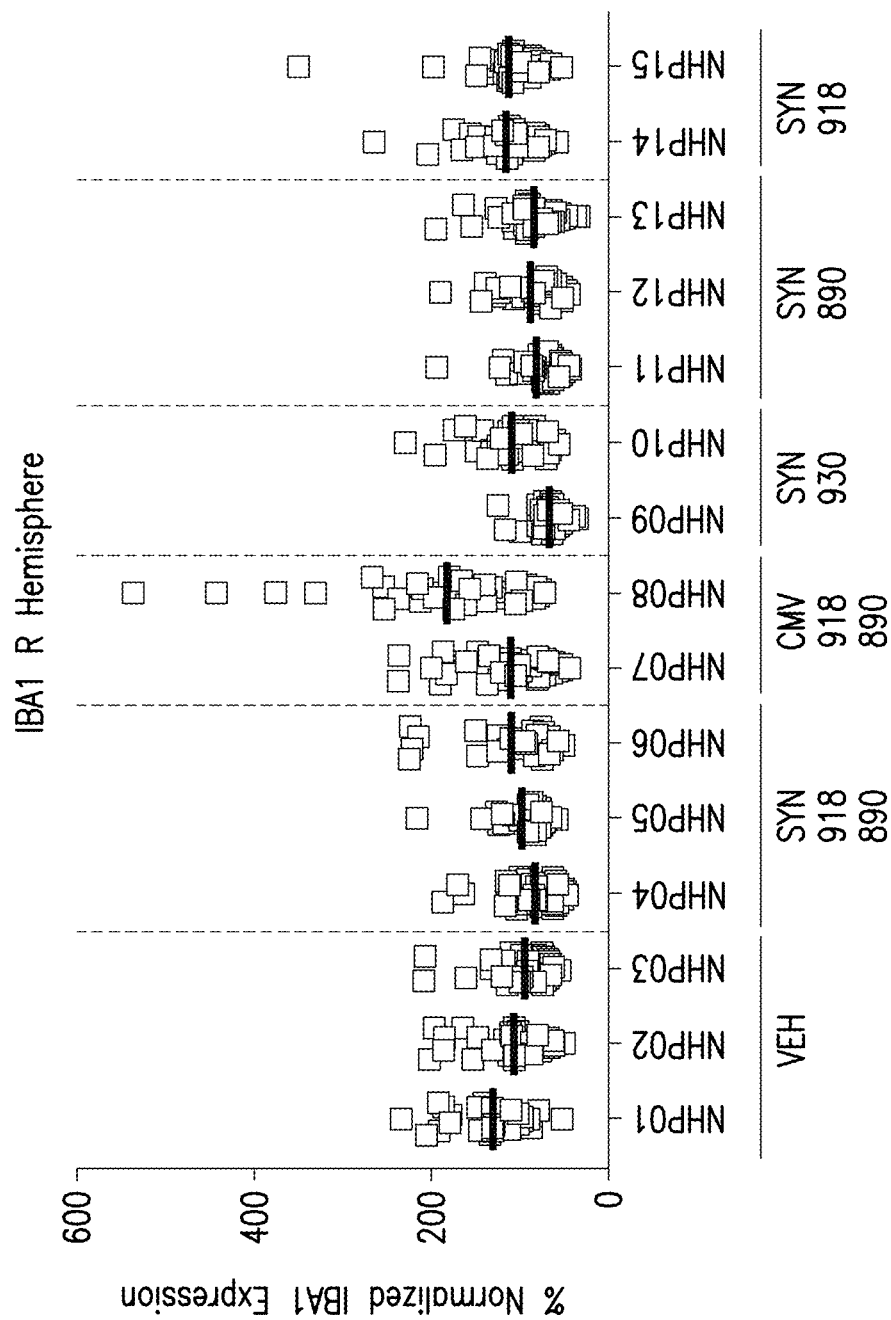
Figure 20C:
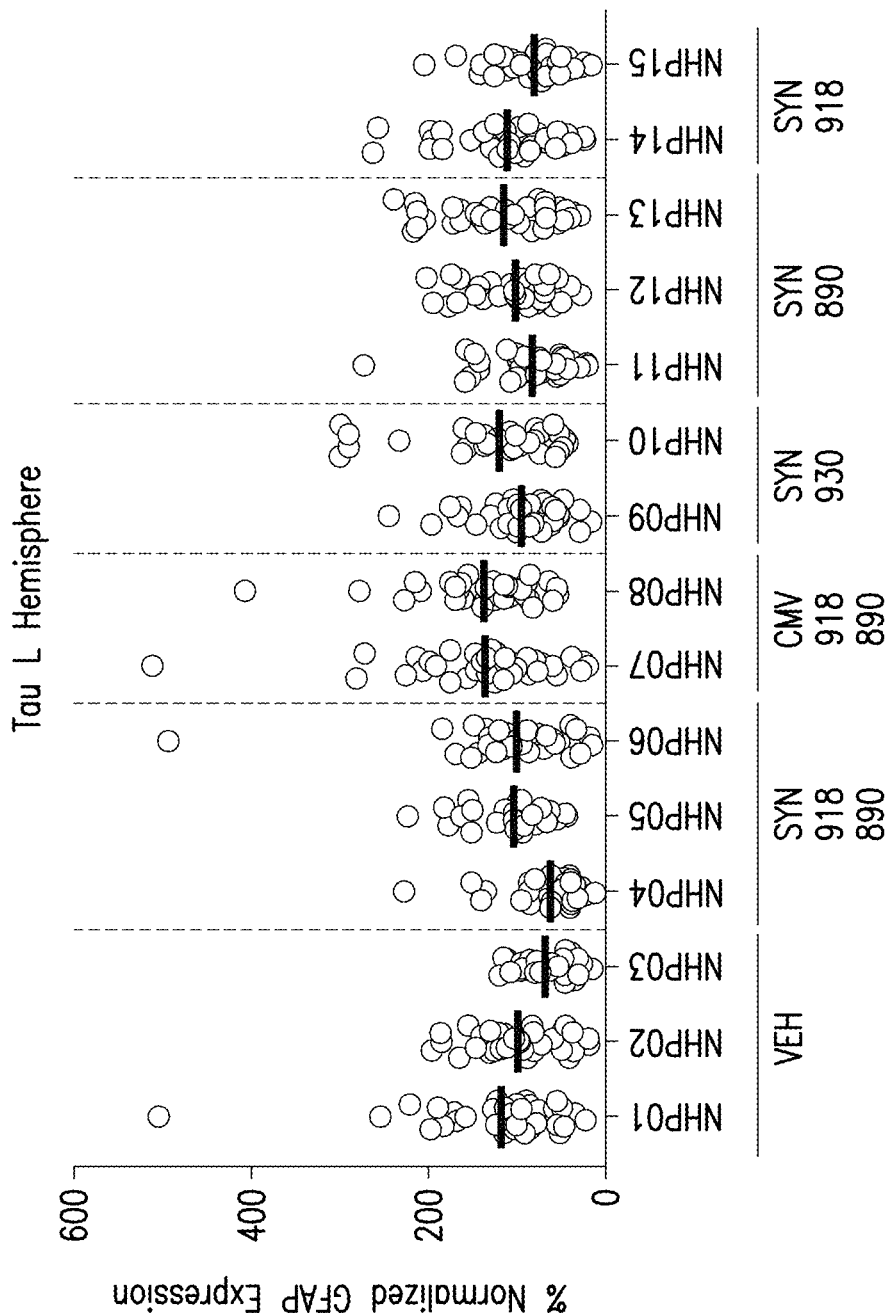
Figure 20D:
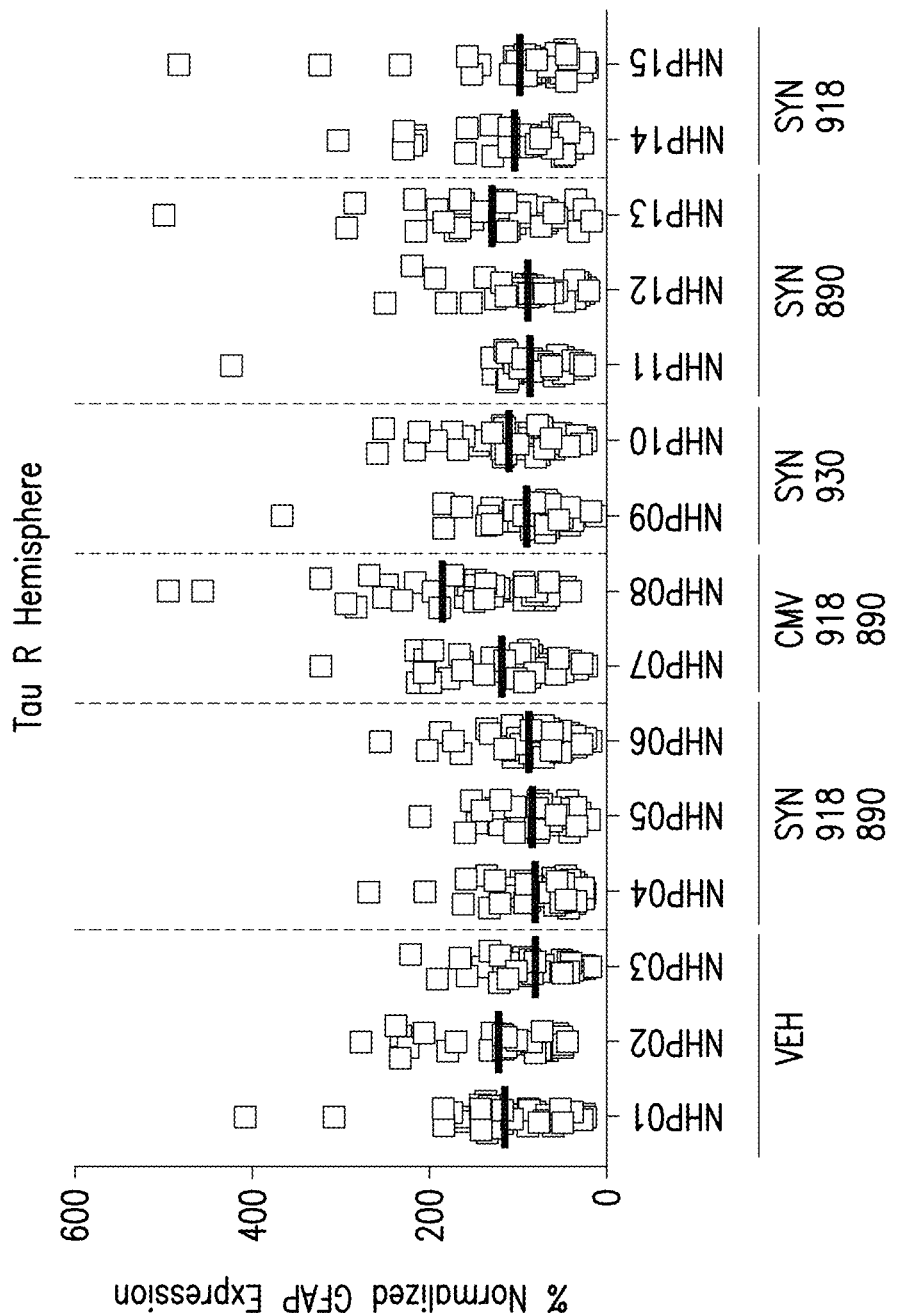

FIG. 20A through FIG. 20D are graphs showing bulk levels of IBA1 (FIG. 20A and FIG. 20B) and GFAP (FIG. 20C and FIG. 20D) in left ("L") (FIG. 20A and FIG. 20C)

and right ("R") (FIG. 20B and FIG. 20D) hemispheres of the primates treated as indicated. As shown while IBA1 and GFAP levels vary between NHP, no major bulk effect was observed for any treatment group.

FIG. 21A through FIG. 21E are graphs depicting normalized expression of the housekeeping gene EIF4a2 to ZFP in subjects treated under the indicated conditions. FIG. 21A shows results for groups treated with hSYN1.57890-65918; FIG. 21B shows results for groups treated with CMV.57890-65918; FIG. 21C shows results for groups treated with hSYN1.57930; FIG. 21D shows results for groups treated with hSYN1.57890; and FIG. 21E shows results for groups treated with hSYN.65918. As shown, there was no correlation with the levels of a housekeeping gene (EIF4A2) and ZFP expression in any of the treatment groups.

FIG. 22 is a graph depicting total tau protein levels in human iPSC-derived (IPS) neurons under the indicated conditions. "Mock" refers to cells that were transfected with empty AAV vectors; "control" refers to cells transfected with AAV vector encoding a ZFP that does not target tau; "57930" refers to cells treated with an AAV vector encoding the 57930 repressor; "57890" refers to cells treated with an AAV vector encoding the 57890 repressor; "65918" refers to cells treated with an AAV vector encoding the 65918 repressor; and "65918/57890" refers to cells treated with an AAV vector encoding both the 65918 and 57890 repressors. All AAV constructs encoding the ZFP repressors comprised a synapsin promoter (SYN1) driving expression of the repressor. Tau protein levels evaluated by ELISA 32 days post AAV vector administration.

DETAILED DESCRIPTION

Disclosed herein are compositions and methods for the prevention and/or treatment of tauopathies. In particular, the compositions and methods described herein are used to repress the expression of a MAPT (tau) protein to prevent or treat tauopathies such as Alzheimer's Disease (AD), Frontotermporal Dementia, Progressive Supranuclear Palsy, traumatic brain injury (TBI), seizure disorders and/or Corticobasal Degeneration. The MAPT repressors (e.g., MAPT-modulating transcription factors, such as MAPT-modulating transcription factors comprising zinc finger proteins (ZFP TFs), TALEs (TALE-TF), and/or CRISPR/Cas-TFs), modify the CNS such that the effects and/or symptoms of the tauopathy is reduced or eliminated, for example by reducing the aggregation of tau in the brain of a subject with a tauopathy (e.g., AD) and reducing the occurrence of neural tangles. In preferred embodiments, the MAPT-modulating transcription factors are delivered to the brain by a viral vector such as an AAV. AAV has been shown to be well suited for brain delivery, so use of these viral vectors to deliver MAPT modulating transcription factors is especially useful for the treatment of diseases such as Alzheimer's Disease associated with the inappropriate expression and thereby aggregation of tau protein.

The Microtubule Associated Protein Tau (MAPT) is closely linked to the pathogenesis of several neurodegenerative disorders, including Alzheimer's Disease, Progressive Supranuclear Palsy, and Frontotemporal Dementia. While genetic and antisense-based tau lowering approaches have proven efficacious and well tolerated in mice, the development of a single-administration, intracellular tau-targeted therapy remains a long-standing goal. Advances in Zinc Finger Protein (ZFP) design and AAV delivery have created new potential for a one-time, DNA-targeted therapy for neurodegenerative disease. ZFP repressors targeting the mouse, nonhuman primate (NHP), and human tau transcriptional regulatory elements were delivered to the mouse and NHP brain using AAV vectors. MAPT-targeted ZFPs reduced mouse and human tau by up to 99% with no detectable off-target gene regulation in primary and iPSC neurons. Intrahippocampal ZFP delivery to adult mice resulted in >90% tau reduction. Intravenous ZFP administration reduced tau levels by 50-70% across the entire brain. ZFP expression and mouse tau reduction were stable out to at least six months with no detectable off-targets, resulted in >80% lowering of CSF-tau, and reduced dystrophic neurites by 50% in APP/PS1 mice. Bilateral, real-time MRI-guided stereotaxis was used to deliver the ZFPs to the NHP hippocampus which was well tolerated and resulted in up to >80% tau lowering in the hippocampus and entorhinal cortex. ZFP levels were strongly correlated with tau reduction. The potency, efficacy, specificity and tolerability of ZFPs show they achieve permanent tau down-regulation for the treatment of human tauopathies.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. *MOLECULAR CLONING: A LABORATORY MANUAL*, Second edition, Cold Spring Harbor Laboratory Press, 1989 and Third edition, 2001; Ausubel et al., *CURRENT PROTOCOLS IN MOLECULAR BIOLOGY*, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; *METHODS IN ENZYMOLOGY*, Vol. 304, "Chromatin" (P.M. Wassarman and A. P. Wolffe, eds.), Academic Press, San Diego, 1999; and METHODS IN MOLECULAR BIOLOGY, Vol. 119, "Chromatin Protocols" (P.B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acid.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526.

"TtAgo" is a prokaryotic Argonaute protein thought to be involved in gene silencing. TtAgo is derived from the bacteria *Thermus thermophilus*. (See, e.g., Swarts et al. (2014) *Nature* 507 (7491): 258-261, G. Sheng et al. (2014) *Proc. Natl. Acad. Sci. U.S.A.* 111 (2): 652). A "TtAgo system" is all the components required including, for example, guide DNAs for cleavage by a TtAgo enzyme. "Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

DNA-binding domains such as sgRNAs, zinc finger binding domains or TALE DNA binding domains can be "engineered" to bind to a predetermined nucleotide sequence, for example via design of a sgRNA that binds to a selected target site or by engineering (altering one or more amino acids) of the recognition helix region of a naturally occurring zinc finger protein or by engineering the RVDs of a TALE protein. Therefore, engineered zinc finger proteins or TALEs are proteins that are non-naturally occurring. Non-limiting examples of methods for engineering DNA-binding domains are design and selection. A "designed" zinc finger protein or TALE is a protein not occurring in nature whose design/composition results principally from rational criteria. Rational criteria for design include application of substitution rules and computerized algorithms for processing information in a database storing information of existing ZFP designs and binding data. A "selected" zinc finger protein or TALE is a protein not found in nature whose production results primarily from an empirical process such as phage display, interaction trap or hybrid selection. See, for example, U.S. Pat. Nos. 8,586,526; 6,140,081; 6,453,242; 6,746,838; 7,241,573; 6,866,997; 7,241,574; and 6,534,261; see also International Patent Publication No. WO 03/016496.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid. The term also includes systems in which a polynucleotide component associates with a polypeptide component to form a functional molecule (e.g., a CRISPR/Cas system in which a single guide RNA associates with a functional domain to modulate gene expression).

Expression of a fusion protein in a cell can result from delivery of the fusion protein to the cell or by delivery of a polynucleotide encoding the fusion protein to a cell, where the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "multimerization domain" (also referred to as a "dimerization domain" or "protein interaction domain") is a domain incorporated at the amino, carboxy or amino and carboxy terminal regions of a ZFP TF or TALE TF. These domains allow for multimerization of multiple ZFP TF or TALE TF units such that larger tracts of trinucleotide repeat domains become preferentially bound by multimerized ZFP TFs or TALE TFs relative to shorter tracts with wild-type numbers of lengths. Examples of multimerization domains include leucine zippers. Multimerization domains may also be regulated by small molecules where the multimerization domain assumes a proper conformation to allow for interaction with another multimerization domain only in the presence of a small molecule or external ligand. In this way, exogenous ligands can be used to regulate the activity of these domains.

A "gene" for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALE protein as described herein. Thus, gene inactivation may be partial or complete.

A "genetic modulator" refers to any molecule that alters the expression and/or sequence of one or more genes. Non-limiting examples of genetic modulators include transcription factors (such as artificial transcription factors as described herein) that bind to the target gene and alter its expression and nucleases that modify the sequence of the target gene, which in turn alters its expression (e.g., inactivation of the target via insertions and/or deletions). Thus, a genetic modulator may be a genetic repressor (that represses and/or inactivates gene expression) or a genetic activator.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion molecule in which a ZFP or TALE DNA-binding domain is fused to an activation domain, the ZFP or TALE DNA-binding domain and the activation domain are in operative linkage if, in the fusion polypeptide, the ZFP or TALE DNA-binding domain portion is able to bind its target site and/or its binding site, while the activation domain is able to upregulate gene expression. ZFPs fused to domains capable of regulating gene expression are collectively referred to as "ZFP-TFs" or "zinc finger transcription factors", while TALEs fused to domains capable of regulating gene expression are collectively referred to as "TALE-TFs" or "TALE transcription factors." When a fusion polypeptide in which a ZFP DNA-binding domain is fused to a cleavage domain (a "ZFN" or "zinc finger nuclease"), the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site. When a fusion polypeptide in which a TALE DNA-binding domain is fused to a cleavage domain (a "TALEN" or "TALE nuclease"), the TALE DNA-binding domain and the cleavage domain are in operative linkage if, in the fusion polypeptide, the TALE DNA-binding domain portion is able to bind its target site and/or its binding site, while the cleavage domain is able to cleave DNA in the vicinity of the target site. With respect to a fusion molecule in which a Cas DNA-binding domain (e.g., single guide RNA) is fused to an activation domain, the Cas DNA-binding domain and the activation domain are in operative linkage if, in the fusion polypeptide, the Cas DNA-binding domain portion is able to bind its target site and/or its binding site, while the activation domain is able to up-regulate gene expression. When a fusion polypeptide in which a Cas DNA-binding domain is fused to a cleavage domain, the Cas DNA-binding domain and the cleavage domain are in operative linkage if, in the fusion polypeptide, the Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and International Patent Publication No. WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

Throughout this specification and embodiments, the words "have" and "comprise," or variations such as "has," "having," "comprises," or "comprising," will be understood to imply the inclusion of a stated integer or group of integers but not the exclusion of any other integer or group of integers. All publications and other references mentioned herein are incorporated by reference in their entirety. Although a number of documents are cited herein, this citation does not constitute an admission that any of these documents forms part of the common general knowledge in the art. As used herein, the term "approximately" or "about" as applied to one or more values of interest refers to a value that is similar to a stated reference value. In certain embodiments, the term refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context.

Tau and Alzheimer's Disease

The tau protein is encoded by the MAPT gene which comprises 16 exons. Interestingly, exons 1, 4, 5, 7, 9, 11 and 12 and constitutively expressed whereas exons 2, 3, and 10 can be present in tau protein species derived from alternatively spliced variants, leading to the presence of six different tau protein isoforms in the adult brain. Tau binds to microtubules via 3 or 4 repeated tubulin-binding motifs in the C-terminal half of the protein, and is thought to stabilize the tubules where tau4R (4 tubulin binding motifs) is thought to interact more strongly with microtubules that tau3R. The ratio of 3R to 4R is generally stable but can be affected in pathological states. The tau form that interacts with microtubules is phosphorylated and it appears that hyperphosphorylation causes the tau to detach from microtubules. Hyperphosphoylated tau can be sequestered in the cell, which then leads to conformational changes in the protein and to aggregation. These aggregates may be the initial step in the formation of pathogenic neurofibrillary tangles (NFTs), however, hyperphosphorylated tau may be pathogenic in a soluble form as well as when present in the tangles (Bodea et al. (2016) J of Neurochem 138 (Suppl 1): 71-94). NFTs are restricted to the entorhinal cortex and medial temporal lobe in the early stages of AD, and by the time of severe clinical symptoms of the disease present, NFTs are widespread throughout the brain. Coincident with the presence of abundant NFTs, widespread distribution of amyloid plaques also occurs. In fact, it appears that the amyloid deposition in the cortex leads to an increase in the speed of tau propagation and the spread of NFT to distal regions of the brain. As tau tangles spread, there is a concomitant increase in neuronal loss (Pooler et al. (2015) Acta Neuropathol Commun 3:14, doi: 10.1186/s40478-015-0199-x).

Tau has 95 amino acid residues that are capable of being phosphorylated, and several kinases have been identified that may be responsible for tau phosphorylation, which may be possible target candidates for new therapeutics, including glycogen synthase-3, cyclin-dependent kinase 5, members of the MAPK family, extracellular-regulated kinase, c-Jun N-terminal kinase and microtubule-affinity regulating kinase (Bodea (2016) ibid).

Amyloid β protein (AB) is the major constituent of senile plaques, which together with NFTs, are the hallmarks of a neuropathological confirmation of Alzheimer's Disease. AB is a peptide that has between 39 and 42 amino acid chains; the 42 amino acids form aggregates more avidly and is thought to be implicated in the pathogenesis of the disease and is the basis of the amyloid hypothesis (the proposal that accumulation of AB in the brain is the primary cause of AD, see review Hardy and Selkoe (2002) Science 297:353). Aßs are products of the proteolytic cleavage of amyloid precursor protein (APP), a ubiquitous, glycosylated, sulfated, and phosphorylated integral membrane protein (Sorrentino et al. (2014) FEBS Lett 588:641-652). However, it is becoming clear that the pathogenesis leading to AD is extremely complex and that the pathogenesis of Aß accumulation may play a role in abnormal tau behavior (Ando et al. (2016) PLOS Genet 12 (3): e1005917.

Reduction of tau in the brain has been shown to improve the pathology of AD. Regulated suppression of a tau transgene expression in a murine AD model demonstrated a reduction of transgene associated tau aggregates and a decrease in the concentration of hyperphosphorylated tau and NFT. In fact, this work also showed a loss in overall NFT, indicating that the accumulation of NFT may be reversible (Polydoro et al. (2013) J of Neurosci 33 (33): 13300-13311). Additionally, studies performed with an intracellular anti-tau antibody delivered via AAV directly through intrahippocampal administration demonstrated a reduction in insoluble tau species, NFT and a rescue of the hippocampal atrophy that is observed in the untreated mouse model (Liu et al. (2016) J Neurosci 36 (49): 12425-12435).
DNA-Binding Domains The methods described herein make use of compositions, for example tau-modulating transcription factors, comprising a DNA-binding domain that specifically binds to a target sequence in a tau (MATP) gene. Any polynucleotide or polypeptide DNA-binding domain can be used in the compositions and methods disclosed herein, for example DNA-binding proteins (e.g., ZFPs or TALEs) or DNA-binding polynucleotides (e.g., single guide RNAs). Thus, genetic modulators (repressors) of tau genes are described.

In certain embodiments, the tau-repressor, or DNA binding domain therein, comprises a zinc finger protein. Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; and International Patent Publication Nos. WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536; and WO 03/016496.

Tau target sites typically include at least one zinc finger but can include a plurality of zinc fingers (e.g., 2, 3, 4, 5, 6 or more fingers). Usually, the ZFPs include at least three fingers. Certain of the ZFPs include four, five or six fingers, while some ZFPs include 8, 9, 10, 11 or 12 fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains. In some embodiments, the fusion protein comprises two ZFP DNA binding domains linked together. These zinc finger proteins can thus comprise 8, 9, 10, 11, 12 or more fingers. In some embodiments, the two DNA binding domains are linked via an extendable flexible linker such that one DNA binding domain comprises 4, 5, or 6 zinc fingers and the second DNA binding domain comprises an additional 4, 5, or 5 zinc fingers. In some embodiments, the linker is a standard inter-finger linker such that the finger array comprises one DNA binding domain comprising 8, 9, 10, 11 or 12 or more fingers. In other embodiments, the linker is an atypical linker such as a flexible linker. The DNA binding domains are fused to at least one regulatory domain and can be thought of as a 'ZFP-ZFP-TF' architecture. Specific examples of these embodiments can be referred to as "ZFP—ZFP-KOX" which comprises two DNA binding domains linked with a flexible linker and fused to a KOX repressor and "ZFP—KOX-ZFP-KOX" where two ZFP-KOX fusion proteins are fused together via a linker.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

A ZFP can be operably associated (linked) to one or more transcriptional regulatory (e.g., repression domains) to form a ZF-TF (e.g., repressor). Methods and compositions can also be used to increase the specificity of a ZFP for its intended target relative to other unintended cleavage sites, known as off-target sites for example by mutations to the ZFP backbone as described in U.S. Patent Publication No. 2018/0087072. Thus, tau repressors described herein can comprise mutations in one or more of their DNA binding domain backbone regions and/or one or more mutations in their transcriptional regulatory domains. These ZFPs can include mutations to amino acid within the ZFP DNA binding domain ('ZFP backbone') that can interact non-specifically with phosphates on the DNA backbone, but they do not comprise changes in the DNA recognition helices. Thus, the invention includes mutations of cationic amino acid residues in the ZFP backbone that are not required for nucleotide target specificity. In some embodiments, these mutations in the ZFP backbone comprise mutating a cationic amino acid residue to a neutral or anionic amino acid residue. In some embodiments, these mutations in the ZFP backbone comprise mutating a polar amino acid residue to a neutral or non-polar amino acid residue. In preferred embodiments, mutations at made at position (−5), (−9) and/or position (−14) relative to the DNA binding helix. In some embodiments, a zinc finger may comprise one or more mutations at (−5), (−9) and/or (−14). In further embodiments, one or more zinc finger in a multi-finger zinc finger protein may comprise mutations in (−5), (−9) and/or (−14). In some embodiments, the amino acids at (−5), (−9) and/or (−14) (e.g. an arginine (R) or lysine (K)) are mutated to an alanine (A), leucine (L), Ser(S), Asp (N), Glu (E), Tyr (Y) and/or glutamine (Q).

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22:1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 2007/0117128.

"Two handed" zinc finger proteins are those proteins in which two clusters of zinc finger DNA binding domains are separated by intervening amino acids so that the two zinc finger domains bind to two discontinuous target sites. An example of a two handed type of zinc finger binding protein is SIP1, where a cluster of four zinc fingers is located at the amino terminus of the protein and a cluster of three fingers is located at the carboxyl terminus (see Remacle et al. (1999) *EMBO Journal* 18 (18): 5073-5084). Each cluster of zinc fingers in these proteins is able to bind to a unique target sequence and the spacing between the two target sequences can comprise many nucleotides. Two-handed ZFPs may include a functional domain, for example fused to one or both of the ZFPs. Thus, it will be apparent that the functional domain may be attached to the exterior of one or both ZFPs or may be positioned between the ZFPs (attached to both ZFPs).

In certain embodiments, the DNA-binding domain comprises a naturally occurring or engineered (non-naturally occurring) TAL effector (TALE) DNA binding domain. See, e.g., U.S. Pat. No. 8,586,526, incorporated by reference in its entirety herein. In certain embodiments, the TALE DNA-binding protein comprises binds to 12, 13, 14, 15, 16, 17, 18, 19, 20 or more contiguous nucleotides of a tau target site as shown in U.S. Patent Publication No. 2018/0153921. The RVDs of the TALE DNA-binding protein that binds to a tau target site may be naturally occurring or non-naturally occurring RVDs. See, U.S. Pat. Nos. 8,586,526 and 9,458,205.

The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et al. (2007) *Science* 318:648-651). These proteins contain a DNA binding domain and a transcriptional activation domain. One of the most well characterized TALEs is AvrBs3 from *Xanthomonas* campestgris pv. Vesicatoria (see Bonas et al. (1989) *Mol Gen Genet* 218:127-136 and International Patent Publication No. WO 2010/079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack et al. (2006) *J Plant Physiol* 163 (3): 256-272). In addition, in the phytopathogenic bacteria *Ralstonia solanacearum*, two genes, designated brg11 and hpx17, have been found that are homologous to the AvrBs3 family of *Xanthomonas* in the *R. solanacearum* biovar 1 strain GMI1000 and in the biovar 4 strain RS1000 (See Heuer et al. (2007) *Appl and Envir Micro* 73 (13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Specificity of these TALEs depends on the sequences found in the tandem repeats. The repeated sequence comprises approximately 102 bp and the repeats are typically 91-100% homologous with each other (Bonas et al., ibid). Polymorphism of the repeats is usually located at positions 12 and 13 and there appears to be a one-to-one correspondence between the identity of the hypervariable diresidues at positions 12 and 13 with the identity of the contiguous nucleotides in the TALE's target sequence (see Moscou and Bogdanove (2009) *Science* 326:1501 and Boch et al. (2009) *Science* 326:1509-1512). Experimentally, the code for DNA recognition of these TALEs has been determined such that an HD sequence at positions 12 and 13 leads to a binding to cytosine (C), NG binds to T, NI to A, C, G or T, NN binds to A or G, and NG binds to T. These DNA binding repeats have been assembled into proteins with new combinations and numbers of repeats, to make artificial transcription factors that are able to interact with new sequences. In addition, U.S. Pat. No. 8,586,526 and U.S. Patent Publication No. 2013/0196373, incorporated by reference in their entireties herein, describe TALEs with N-cap polypeptides, C-cap polypeptides (e.g., +63, +231 or +278) and/or novel (atypical) RVDs.

Exemplary TALEs are described in U.S. Pat. Nos. 8,586,526 and 9,458,205, incorporated by reference in their entireties.

In certain embodiments, the DNA binding domains include a dimerization and/or a multimerization domain, for example a coiled-coil (CC) and dimerizing zinc finger (DZ). See, U.S. Patent Publication No. 2013/0253040.

In still further embodiments, the DNA-binding domain comprises a single-guide RNA of a CRISPR/Cas system, for example sgRNAs as disclosed in 20150056705.

Compelling evidence has recently emerged for the existence of an RNA-mediated genome defense pathway in archaea and many bacteria that has been hypothesized to parallel the eukaryotic RNAi pathway (for reviews, see Godde and Bickerton (2006) *J. Mol. Evol.* 62:718-729; Lillestol et al. (2006) *Archaea* 2:59-72; Makarova et al. (2006) *Biol. Direct* 1:7; Sorek et al. (2008) *Nat. Rev. Microbiol.* 6:181-186). Known as the CRISPR-Cas system or prokaryotic RNAi (pRNAi), the pathway is proposed to arise from two evolutionarily and often physically linked gene loci: the CRISPR (clustered regularly interspaced short palindromic repeats) locus, which encodes RNA components of the system, and the cas (CRISPR-associated) locus, which encodes proteins (Jansen et al. (2002) *Mol. Microbiol.* 43:1565-1575; Makarova et al. (2002) *Nucleic Acids Res.* 30:482-496; Makarova et al. (2006) *Biol. Direct* 1:7; Haft et al. (2005) *PLOS Comput. Biol.* 1: e60). CRISPR loci in microbial hosts contain a combination of CRISPR-associated (Cas) genes as well as non-coding RNA elements capable of programming the specificity of the CRISPR-mediated nucleic acid cleavage. The individual Cas proteins do not share significant sequence similarity with protein components of the eukaryotic RNAi machinery, but have analogous predicted functions (e.g., RNA binding, nuclease, helicase, etc.) (Makarova et al. (2006) *Biol. Direct* 1:7). The CRISPR-associated (cas) genes are often associated with CRISPR repeat-spacer arrays. More than forty different Cas protein families have been described. Of these protein families, Cas1 appears to be ubiquitous among different CRISPR/Cas systems. Particular combinations of cas genes and repeat structures have been used to define 8 CRISPR subtypes (*E. coli*, Y. pest, N. meni, D. vulg, T. neap, H. mari, A. pern, and M. tube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

The Type II CRISPR, initially described in *S. pyogenes*, is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences where processing occurs by a double strand-specific RNase III in the presence of the Cas9 protein. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. In addition, the tracrRNA must also be present as it base pairs with the crRNA at its 3' end, and this association triggers Cas9 activity. Finally, Cas9 mediates cleavage of target DNA to create a double-stranded break within the protospacer. Activity of the CRISPR/Cas system comprises three steps: (i) insertion of alien DNA sequences into the CRISPR array to prevent future attacks, in a process called 'adaptation,' (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system.

Type II CRISPR systems have been found in many different bacteria. BLAST searches on publically available genomes by Fonfara et al. (2013) *Nuc Acid Res* 42 (4): 2377-2590 found Cas9 orthologs in 347 species of bacteria. Additionally, this group demonstrated in vitro CRISPR/Cas cleavage of a DNA target using Cas9 orthologs from *S. pyogenes, S. mutans, S. therophilus, C. jejuni, N. meningitides, P. multocida* and *F. novicida*. Thus, the term "Cas9" refers to an RNA guided DNA nuclease comprising a DNA binding domain and two nuclease domains, where the gene encoding the Cas9 may be derived from any suitable bacteria.

The Cas9 protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand. The Cas 9 nuclease can be engineered such that only one of the nuclease domains is functional, creating a Cas nickase (see Jinek et al. (2012) *Science* 337:816). Nickases can be generated by specific mutation of amino acids in the catalytic domain of the enzyme, or by truncation of part or all of the domain such that it is no longer functional. Since Cas 9 comprises two nuclease domains, this approach may be taken on either domain. A double strand break can be achieved in the target DNA by the use of two such Cas 9 nickases. The nickases will each cleave one strand of the DNA and the use of two will create a double strand break.

The requirement of the crRNA-tracrRNA complex can be avoided by use of an engineered "single-guide RNA" (sgRNA) that comprises the hairpin normally formed by the annealing of the crRNA and the tracrRNA (see Jinek et al., ibid and Cong et al. (2013) Sciencexpress/10.1126/science.1231143). In S. pyogenes, the engineered tracrRNA:crRNA fusion, or the sgRNA, guides Cas9 to cleave the target DNA when a double strand RNA: DNA heterodimer forms between the Cas associated RNAs and the target DNA. This system comprising the Cas9 protein and an engineered sgRNA containing a PAM sequence has been used for RNA guided genome editing (see Ramalingam et al. (2013) *Stem Cells and Development* 22 (4): 595-610) and has been useful for zebrafish embryo genomic editing in vivo (see Hwang et al. (2013) *Nature Biotechnology* 31 (3): 227) with editing efficiencies similar to ZFNs and TALENs.

The primary products of the CRISPR loci appear to be short RNAs that contain the invader targeting sequences, and are termed guide RNAs or prokaryotic silencing RNAs (psiRNAs) based on their hypothesized role in the pathway (Makarova et al. (2006) *Biol. Direct* 1:7; Hale et al. (2008) *RNA*, 14:2572-2579). RNA analysis indicates that CRISPR locus transcripts are cleaved within the repeat sequences to release ~60- to 70-nt RNA intermediates that contain individual invader targeting sequences and flanking repeat fragments (Tang et al. (2002) *Proc. Natl. Acad. Sci.* 99:7536-7541; Tang et al. (2005) *Mol. Microbiol.* 55:469-481; Lillestol et al. (2006) *Archaea* 2:59-72; Brouns et al. (2008) *Science* 321:960-964; Hale et al. (2008) *RNA,* 14:2572-2579). In the archaeon *Pyrococcus furiosus*, these intermediate RNAs are further processed to abundant, stable ~35- to 45-nt mature psiRNAs (Hale et al. (2008) *RNA,* 14:2572-2579).

The requirement of the crRNA-tracrRNA complex can be avoided by use of an engineered "single-guide RNA" (sgRNA) that comprises the hairpin normally formed by the annealing of the crRNA and the tracrRNA (see Jinek et al. (2012) *Science* 337:816 and Cong et al. (2013) Sciencexpress/10.1126/science.1231143). In S. pyrogenes, the engineered tracrRNA: crRNA fusion, or the sgRNA, guides Cas9 to cleave the target DNA when a double strand RNA: DNA heterodimer forms between the Cas associated RNAs and the target DNA. This system comprising the Cas9 protein and an engineered sgRNA containing a PAM sequence has been used for RNA guided genome editing (see Ramalingam, ibid) and has been useful for zebrafish embryo genomic editing in vivo (see Hwang et al. (2013) *Nature Biotechnology* 31 (3): 227) with editing efficiencies similar to ZFNs and TALENs.

Chimeric or sgRNAs can be engineered to comprise a sequence complementary to any desired target. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In certain embodiments, the sgRNA comprises a sequence that binds to 12, 13, 14, 15, 16, 17, 18, 19, 20 or more contiguous nucleotides of a tau target site as shown in U.S. Publication No. 20180153921. In some embodiments, the RNAs comprise 22 bases of complementarity to a target and of the form G [n19], followed by a protospacer-adjacent motif (PAM) of the form NGG or NAG for use with a *S. pyogenes* CRISPR/Cas system. Thus, in one method, sgRNAs can be designed by utilization of a known ZFN target in a gene of interest by (i) aligning the recognition sequence of the ZFN heterodimer with the reference sequence of the relevant genome (human, mouse, or of a particular plant species); (ii) identifying the spacer region between the ZFN half-sites; (iii) identifying the location of the motif G [N20] GG that is closest to the spacer region (when more than one such motif overlaps the spacer, the motif that is centered relative to the spacer is chosen); (iv) using that motif as the core of the sgRNA. This method advantageously relies on proven nuclease targets. Alternatively, sgRNAs can be designed to target any region of interest simply by identifying a suitable target sequence the conforms to the G [n20] GG formula. Along with the complementarity region, an sgRNA may comprise additional nucleotides to extend to tail region of the tracrRNA portion of the sgRNA (see Hsu et al. (2013) *Nature Biotech* doi: 10.1038/nbt.2647). Tails may be of +67 to +85 nucleotides, or any number therebetween with a preferred length of +85 nucleotides. Truncated sgRNAs may also be used, "tru-gRNAs" (see Fu et al. (2014) *Nature Biotech* 32 (3): 279). In tru-gRNAs, the complementarity region is diminished to 17 or 18 nucleotides in length.

Further, alternative PAM sequences may also be utilized, where a PAM sequence can be NAG as an alternative to NGG (Hsu 2013, ibid) using a *S. pyogenes* Cas9. Additional PAM sequences may also include those lacking the initial G (Sander and Joung (2014) *Nature Biotech* 32 (4): 347). In addition to the *S. pyogenes* encoded Cas9 PAM sequences, other PAM sequences can be used that are specific for Cas9 proteins from other bacterial sources. For example, the PAM sequences shown below (adapted from Sander and Joung, ibid, and Esvelt et al. (2013) *Nat Meth* 10 (11): 1116) are specific for these Cas9 proteins:

| Species | PAM |
| --- | --- |
| S. pyogenes | NGG |
| S. pyogenes | NAG |
| S. mutans | NGG |
| S. thermophilius | NGGNG |
| S. thermophilius | NNAAAW |
| S. thermophilius | NNAGAA |
| S. thermophilius | NNNGATT |
| C. jejuni | NNNNACA |
| N. meningitides | NNNNGATT |
| P. multocida | GNNNCNNA |
| F. novicida | NG |

Thus, a suitable target sequence for use with a *S. pyogenes* CRISPR/Cas system can be chosen according to the following guideline: [n17, n18, n19, or n20] (G/A) G. Alternatively the PAM sequence can follow the guideline G [n17, n18, n19, n20] (G/A) G. For Cas9 proteins derived from non-*S. pyogenes* bacteria, the same guidelines may be used where the alternate PAMs are substituted in for the *S. pyogenes* PAM sequences.

Most preferred is to choose a target sequence with the highest likelihood of specificity that avoids potential off target sequences. These undesired off target sequences can be identified by considering the following attributes: i) similarity in the target sequence that is followed by a PAM sequence known to function with the Cas9 protein being utilized; ii) a similar target sequence with fewer than three mismatches from the desired target sequence; iii) a similar target sequence as in ii), where the mismatches are all located in the PAM distal region rather than the PAM proximal region (there is some evidence that nucleotides 1-5 immediately adjacent or proximal to the PAM, sometimes referred to as the 'seed' region (Wu et al. (2014) *Nature Biotech* doi: 10.1038/nbt2889) are the most critical for recognition, so putative off target sites with mismatches located in the seed region may be the least likely be recognized by the sg RNA); and iv) a similar target sequence where the mismatches are not consecutively spaced or are spaced greater than four nucleotides apart (Hsu 2013, ibid). Thus, by performing an analysis of the number of potential off target sites in a genome for whichever CRIPSR/Cas system is being employed, using these criteria above, a suitable target sequence for the sgRNA may be identified.

In some embodiments, the CRISPR-Cpf1 system is used. The CRISPR-Cpf1 system, identified in *Francisella* spp, is a class 2 CRISPR-Cas system that mediates robust DNA interference in human cells. Although functionally conserved, Cpf1 and Cas9 differ in many aspects including in their guide RNAs and substrate specificity (see Fagerlund et al. (2015) *Genom Bio* 16:251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term "Cas" includes both Cas9 and Cfp1 proteins. Thus, as used herein, a "CRISPR/Cas system" refers both CRISPR/Cas and/or CRISPR/Cfp1 systems, including both nuclease, nickase and/or transcription factor systems.

In some embodiments, other Cas proteins may be used. Some exemplary Cas proteins include Cas9, Cpf1 (also known as Cas12a), C2c1, C2c2 (also known as Cas13a), C2c3, Cas1, Cas2, Cas4, CasX and CasY; and include engineered and natural variants thereof (Burstein et al. (2017) *Nature* 542:237-241) for example HF1/spCas9 (Kleinstiver et al. (2016) *Nature* 529:490-495; Cebrian-Serrano and Davies (2017) *Mamm Genome* 28 (7): 247-261); split Cas9 systems (Zetsche et al. (2015) *Nat Biotechnol* 33 (2): 139-142), trans-spliced Cas9 based on an intein-extein system (Troung et al. (2015) *Nucl Acid Res* 43 (13): 6450-8); mini-SaCas9 (Ma et al. (2018) *ACS Synth Biol* 7 (4): 978-985). Thus, in the methods and compositions described herein, it is understood that the term "Cas" includes all Cas variant proteins, both natural and engineered. Thus, as used herein, a "CRISPR/Cas system" refers to any CRISPR/Cas system, including both nuclease, nickase and/or transcription factor systems.

In certain embodiments, the Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. In some aspects, a functional derivative may comprise a single biological property of a naturally occurring Cas protein. In other aspects, a function derivative may comprise a subset of biological properties of a naturally occurring Cas protein. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Exemplary CRISPR/Cas nuclease systems targeted to specific genes (including safe harbor genes) are disclosed for example, in U.S. Patent Publication No. 2015/0056705.

Thus, the nuclease comprises a DNA-binding domain in that specifically binds to a target site in any gene into which it is desired to insert a donor (transgene) in combination with a nuclease domain that cleaves DNA.

Tau Gene Modulators

The tau DNA-binding domains may be fused to or otherwise associate with any additional molecules (e.g., polypeptides) for use in the methods described herein. In certain embodiments, the methods employ fusion molecules comprising at least one DNA-binding molecule (e.g., ZFP, TALE or single guide RNA) and a heterologous regulatory (functional) domain (or functional fragment thereof).

In certain embodiments, the functional domain of the tau modulator comprises a transcriptional regulatory domain. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases), protein degradation modifiers (de-ubiquitinases, ligases, degrons) and their associated factors and modifiers. See, e.g., U.S. Publication No. 2013/0253040, incorporated by reference in its entirety herein.

Suitable domains for achieving activation include the HSV VP16 activation domain (see, e.g., Hagmann et al. (1997) *J. Virol.* 71:5952-5962) nuclear hormone receptors (see, e.g., Torchia et al. (1998) *Curr. Opin. Cell. Biol.* 10:373-383); the p65 subunit of nuclear factor kappa B (Bitko & Barik (1998) *J. Virol.* 72:5610-5618 and Doyle & Hunt (1997) *Neuroreport* 8:2937-2942); Liu et al. (1998) *Cancer Gene Ther.* 5:3-28), or artificial chimeric functional domains such as VP64 (Beerli et al. (1998) *Proc. Natl. Acad. Sci. USA* 95:14623-33), and degron (Molinari et al. (1999) *EMBO J.* 18:6439-6447). Additional exemplary activation domains include, October 1, Oct-2A, Sp1, AP-2, and CTF1 (Seipel et al. (1992) *EMBO J.* 11:4961-4968) as well as p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5,-6,-7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

Exemplary repression domains that can be used to make tau repressors include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

In some instances, the domain is involved in epigenetic regulation of a chromosome. In some embodiments, the domain is a histone acetyltransferase (HAT), e.g. type-A, nuclear localized such as MYST family members MOZ, Ybf2/Sas3, MOF, and Tip60, GNAT family members Gcn5 or pCAF, the p300 family members CBP, p300 or Rtt109 (Berndsen and Denu (2008) *Curr Opin Struct Biol* 18 (6): 682-689). In other instances the domain is a histone deacetylase (HDAC) such as the class I (HDAC-1, 2, 3, and 8), class II (HDAC IIA (HDAC-4, 5, 7 and 9), HDAC IIB (HDAC 6 and 10)), class IV (HDAC-11), class III (also known as sirtuins (SIRTs); SIRT1-7) (see Mottamal et al. (2015) *Molecules* 20 (3): 3898-3941). Another domain that is used in some embodiments is a histone phosphorylase or kinase, where examples include MSK1, MSK2, ATR, ATM, DNA-PK, Bub1, VprBP, IKK-a, PKCB1, Dik/Zip, JAK2, PKC5, WSTF and CK2. In some embodiments, a methylation domain is used and may be chosen from groups such as Ezh2, PRMT1/6, PRMT5/7, PRMT 2/6, CARM1, set7/9, MLL, ALL-1, Suv 39h, G9a, SETDB1, Ezh2, Set2, Dot1, PRMT 1/6, PRMT 5/7, PR-Set7 and Suv4-20h. Domains involved in sumoylation and biotinylation (Lys9, 13, 4, 18 and 12) may also be used in some embodiments (review see Kousarides (2007) *Cell* 128:693-705).

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, IL) Catalogue. Methods and compositions for making fusions between a minor groove binder and a polypeptide have been described. Mapp et al. (2000) *Proc. Natl. Acad. Sci. USA* 97:3930-3935. Likewise, CRISPR/Cas TFs and nucleases comprising a sgRNA nucleic acid component in association with a polypeptide component function domain are also known to those of skill in the art and detailed herein.

The fusion molecule may be formulated with a pharmaceutically acceptable carrier, as is known to those of skill in the art. See, for example, *Remington's Pharmaceutical Sciences,* 17th ed., 1985; and co-owned International Patent Publication No. WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

In certain embodiments, the fusion molecule comprises a DNA-binding domain and a nuclease domain to create functional entities that are able to recognize their intended nucleic acid target through their engineered (ZFP or TALE or sgRNA) DNA binding domains and create nucleases (e.g., zinc finger nuclease or TALE nucleases or CRISPR/Cas nucleases) cause the DNA to be cut near the DNA binding site via the nuclease activity. This cleavage results in inactivation (repression) of a tau gene. Thus, tau repressors also include tau nucleases.

Thus, the methods and compositions described herein are broadly applicable and may involve any nuclease of interest. Non-limiting examples of nucleases include meganucleases, TALENs and zinc finger nucleases. The nuclease may comprise heterologous DNA-binding and cleavage domains (e.g., zinc finger nucleases; TALENs; meganuclease DNA-binding domains with heterologous cleavage domains, sgRNAs in association with nuclease domains) or, alternatively, the DNA-binding domain of a naturally-occurring nuclease may be altered to bind to a selected target site (e.g., a meganuclease that has been engineered to bind to site different than the cognate binding site).

The nuclease domain may be derived from any nuclease, for example any endonuclease or exonuclease. Non-limiting examples of suitable nuclease (cleavage) domains that may be fused to tau DNA-binding domains as described herein include domains from any restriction enzyme, for example a Type IIS Restriction Enzyme (e.g., FokI). In certain embodiments, the cleavage domains are cleavage half-domains that require dimerization for cleavage activity. See, e.g., U.S. Pat. Nos. 8,586,526; 8,409,861; and 7,888,121, incorporated by reference in their entireties herein. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing.

The nuclease domain may also be derived any meganuclease (homing endonuclease) domain with cleavage activity may also be used with the nucleases described herein, including but not limited to I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII.

In certain embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the meganuclease (e.g., TevI) nuclease domain (see Beurdeley et al. (2013) *Nat Comm* 4 (1762): 1-8, DOI: 10.1038/ncomms2782).

In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al. (2013) *Nucl Acid Res* 42 (4): 2591-2601, doi: 10.1093/nar/gkt1224).

In addition, the nuclease domain of the meganuclease may also exhibit DNA-binding functionality. Any TALENs may be used in combination with additional TALENs (e.g., one or more TALENs (cTALENs or FokI-TALENs) with one or more mega-TALs) and/or ZFNs.

In addition, cleavage domains may include one or more alterations as compared to wild-type, for example for the formation of obligate heterodimers that reduce or eliminate off-target cleavage effects. See, e.g., U.S. Pat. Nos. 7,914,796; 8,034,598; and 8,623,618, incorporated by reference in their entireties herein.

Nucleases as described herein may generate double- or single-stranded breaks in a double-stranded target (e.g., gene). The generation of single-stranded breaks ("nicks") is described, for example in U.S. Pat. Nos. 8,703,489 and 9,200,266, incorporated herein by reference which describes how mutation of the catalytic domain of one of the nucleases domains results in a nickase.

Thus, a nuclease (cleavage) domain or cleavage half-domain can be any portion of a protein that retains cleavage activity, or that retains the ability to multimerize (e.g., dimerize) to form a functional cleavage domain.

Alternatively, nucleases may be assembled in vivo at the nucleic acid target site using so-called "split-enzyme" technology (see e.g. U.S. Patent Publication No. 2009/0068164). Components of such split enzymes may be expressed either on separate expression constructs, or can be linked in one open reading frame where the individual components are separated, for example, by a self-cleaving 2A peptide (e.g., T2A) or IRES sequence. Components may be individual zinc finger binding domains or domains of a meganuclease nucleic acid binding domain.

Nucleases can be screened for activity prior to use, for example in a yeast-based chromosomal system as described in U.S. Patent Publication No. 2009/0111119. Nuclease expression constructs can be readily designed using methods known in the art.

Expression of the fusion proteins (or component thereof) may be under the control of a constitutive promoter or an inducible promoter, for example the galactokinase promoter which is activated (de-repressed) in the presence of raffinose and/or galactose and repressed in presence of glucose. Non-limiting examples of preferred promoters include the neural specific promoters NSE, Synapsin, CAMKiia and MECPs. Non-limiting examples of ubiquitous promoters include CAS and Ubc. Further embodiments include the use of self-regulating promoters (via the inclusion of high affinity binding sites for the tau DNA-binding domain) as described in U.S. Patent Publication No. 2015/0267205).

In certain embodiments, the tau modulators for use in a subject comprise ZFPs designated 57890, 65918 and/or 57930. In certain embodiments, two more such tau modulators that provide synergistic effects as compared to a single ZFP tau repressor (e.g., 57890 and 65918 ZFP repressors; 57890 and 57930 ZFP repressors; 65918 and 57930; 57890, 65918 and 57930) are provided to the subject for repression of tau and treatment and/or prevention of a tauopathy such as AD, including the amelioration of symptoms of the tauopathy.

Delivery

The proteins and/or polynucleotides (e.g., tau modulators) and compositions comprising the proteins and/or polynucleotides described herein may be delivered to a target cell by any suitable means including, for example, by injection of proteins, via mRNA and/or using an expression construct (e.g., plasmid, lentiviral vector, AAV vector, Ad vector, etc.). In preferred embodiments, the repressor is delivered using an AAV vector, including but not limited to AAV9 (see U.S. Pat. No. 7,198,951), an AAV vector as described in U.S. Pat. No. 9,585,971.

Methods of delivering proteins comprising zinc finger proteins as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 8,586,526; 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more DNA-binding protein-encoding sequences. Thus, when one or more tau modulators (e.g., repressors) are introduced into the cell, the sequences encoding the protein components and/or polynucleotide components may be carried on the same vector or on different vectors. When multiple vectors are used, each vector may comprise a sequence encoding one or multiple tau modulators (e.g., repressors) or components thereof. In preferred embodiments, the vector system is an AAV vector, for example AAV9 or an AAV variant described in U.S. Pat. No. 9,585,971 or U.S. Patent Publication No. 2017/0119906.

Conventional viral and non-viral based gene transfer methods can be used to introduce nucleic acids encoding engineered tau modulators in cells (e.g., mammalian cells) and target tissues. Such methods can also be used to administer nucleic acids encoding such repressors (or components thereof) to cells in vitro. In certain embodiments, nucleic acids encoding the repressors are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson (1992) *Science* 256:808-813; Nabel & Felgner (1993) *TIBTECH* 11:211-217; Mitani & Caskey (1993) *TIBTECH* 11:162-166; Dillon (1993) *TIBTECH* 11:167-175; Miller (1992) *Nature* 357:455-460; Van Brunt (1988) *Biotechnology* 6 (10): 1149-1154 (1988); Vigne (1995) *Restorative Neurology and Neuroscience* 8:35-36; Kremer & Perricaudet (1995) *British Medical Bulletin* 51 (1): 31-44; Haddada et al., in *Current Topics in Microbiology and Immunology* Doerfler and Böhm (eds.) (1995); and Yu et al. (1994) *Gene Therapy* 1:13-26.

Methods of non-viral delivery of nucleic acids include electroporation, lipofection, microinjection, biolistics, virosomes, liposomes, immunoliposomes, polycation or lipid: nucleic acid conjugates, naked DNA, naked RNA, artificial virions, and agent-enhanced uptake of DNA. Sonoporation using, e.g., the Sonitron 2000 system (Rich-Mar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein.

Additional exemplary nucleic acid delivery systems include those provided by Amaxa Biosystems (Cologne, Germany), Maxcyte, Inc. (Rockville, Maryland), BTX Molecular Delivery Systems (Holliston, MA) and Copernicus Therapeutics Inc, (see for example U.S. Pat. No. 6,008, 336). Lipofection is described in e.g., U.S. Pat. Nos. 5,049, 386; 4,946,787; and 4,897,355) and lipofection reagents are sold commercially (e.g., Transfectam™ and Lipofectin™ and Lipofectamine™ RNAiMAX). Cationic and neutral lipids that are suitable for efficient receptor-recognition lipofection of polynucleotides include those of Felgner, International Patent Publication Nos. WO 91/17424 and WO 91/16024. Delivery can be to cells (ex vivo administration) or target tissues (in vivo administration).

The preparation of lipid: nucleic acid complexes, including targeted liposomes such as immunolipid complexes, is well known to one of skill in the art (see, e.g., Crystal (1995) *Science* 270:404-410 (1995); Blaese et al. (1995) *Cancer Gene Ther.* 2:291-297; Behr et al. (1994) *Bioconjugate Chem.* 5:382-389; Remy et al. (1994) *Bioconjugate Chem.* 5:647-654; Gao et al. (1995) *Gene Therapy* 2:710-722; Ahmad et al. (1992) *Cancer Res.* 52:4817-4820; U.S. Pat. Nos. 4,186,183; 4,217,344; 4,235,871; 4,261,975; 4,485, 054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al. (2009) *Nature Biotechnology* 27(7):643).

The use of RNA or DNA viral based systems for the delivery of nucleic acids encoding engineered ZFPs, TALEs or CRISPR/Cas systems take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs, TALEs or CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon mouse leukemia virus (MuLV), gibbon ape leukemia virus (GaLV), Simian Immunodeficiency virus (SIV), human immunodeficiency virus (HIV), and combinations thereof (see, e.g., Buchscher et al. (1992) *J. Virol.* 66:2731-2739; Johann et al. (1992) *J. Virol.* 66:1635-1640; Sommerfelt et al. (1990) *Virol.* 176: 58-59; Wilson et al. (1989) *J. Virol.* 63:2374-2378; Miller et al. (1991) *J. Virol.* 65:2220-2224; International Patent Publication No. WO 1994/026877).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al. (1987) *Virology* 160:38-47; U.S. Pat. No. 4,797,368; International Patent Publication No. WO 93/24641; Kotin (1994) *Human Gene Therapy* 5:793-801; Muzyczka (1994) *J. Clin. Invest.* 94:1351. Construction of recombinant AAV vectors are described in a number of publications, including U.S. Pat. No. 5,173,414; Tratschin et al. (1985) *Mol. Cell. Biol.* 5:3251-3260; Tratschin et al. (1984) *Mol. Cell. Biol.* 4:2072-2081; Hermonat & Muzyczka (1984) *PNAS* 81:6466-6470; and Samulski et al. (1989) *J. Virol.* 63:03822-3828.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al. (1995) *Blood* 85:3048-305; Kohn et al. (1995) *Nat. Med.* 1:1017-102; Malech et al. (1997) *PNAS* 94 (22): 12133-12138). PA317/pLASN was the first therapeutic vector used in a gene therapy trial. (Blaese et al. (1995) *Science* 270:475-480). Transduction efficiencies of 50% or greater have been observed for MFG-S packaged vectors. (Ellem et al. (1997) *Immunol Immunother.* 44 (1): 10-20; Dranoff et al. (1997) *Hum. Gene Ther.* 1:111-2.

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al. (1998) *Lancet* 351 (9117): 1702-3, Kearns et al. (1996) *Gene Ther.* 9:748-55). Other AAV serotypes, including AAV1, AAV3, AAV4, AAV5, AAV6, AAV8, AAV 8.2, AAV9, and AAV rh10 and pseudotyped AAV such as AAV2/8, AAV2/5, AAV2/9 and AAV2/6 can also be used in accordance with the present invention. Novel AAV serotypes capable of crossing the blood-brain barrier can also be used in accordance with the present invention (see e.g. U.S. Pat. No. 9,585,971). In preferred embodiments, an AAV9 vector (including variants and pseudotypes of AAV9) is used.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al. (1998) *Hum. Gene Ther.* 7:1083-9). Additional examples of the use of adenovirus vectors for gene transfer in clinical trials include Rosenecker et al. (1996) *Infection* 24 (1): 5-10; Sterman et al. (1998) *Hum. Gene Ther.* 9 (7): 1083-1089; Welsh et al. (1995) *Hum. Gene Ther.* 2:205-18; Alvarez et al. (1997) *Hum. Gene Ther.* 5:597-613; Topf et al. (1998) *Gene Ther.* 5:507-513; Sterman et al. (1998) *Hum. Gene Ther.* 7:1083-1089.

Packaging cells are used to form virus particles that are capable of infecting a host cell. Such cells include 293 cells, which package adenovirus, and w2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) *Proc. Natl. Acad. Sci. USA* 92:9747-9751, reported that Moloney mouse leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, intrathecal, intracisternal, intracerebroventricular, or intracranial infusion, including direct injection into the brain including into any region of the brain such as the hippocampus, cortex, striatum, etc.) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

In certain embodiments, the compositions as described herein (e.g., polynucleotides and/or proteins) are delivered directly in vivo. The compositions (cells, polynucleotides and/or proteins) may be administered directly into the central nervous system (CNS), including but not limited to direct injection into the brain or spinal cord. One or more areas of the brain may be targeted, including but not limited to, the hippocampus, the substantia nigra, the nucleus basalis of Meynert (NBM), the striatum and/or the cortex. Alternatively or in addition to CNS delivery, the compositions may be administered systemically (e.g., intravenous, intraperitoneal, intracardial, intramuscular, subdermal, intrathecal, intracisternal, intracerebroventricular and/or intracranial infusion). Methods and compositions for delivery of compositions as described herein directly to a subject (including directly into the CNS) include but are not limited to direct injection (e.g., stereotactic injection) via needle assemblies. Such methods are described, for example, in U.S. Pat. Nos. 7,837,668 and 8,092,429, relating to delivery of compositions (including expression vectors) to the brain and U.S. Patent Publication No. 2006/0239966, incorporated herein by reference in their entireties.

The effective amount to be administered will vary from patient to patient and according to the mode of administration and site of administration. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. In certain embodiments, To deliver ZFPs using adeno-associated viral (AAV) vectors directly to the human brain, a dose range of about $1 \times 10^{10}$-$5 \times 10^{15}$ (or any value therebetween) vector genome per striatum can be applied. As noted, dosages may be varied for other brain structures and for different delivery protocols. Methods of delivering AAV vectors directly to the brain are known in the art. See, e.g., U.S. Pat. Nos. 9,089,667; 9,050,299; 8,337,458; 8,309,355; 7,182,944; 6,953,575; and 6,309,634.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with at least one tau modulator (e.g., repressor) or component thereof and re-infused back into the subject organism (e.g., patient). In a preferred embodiment, one or more nucleic acids of the tau modulator (e.g., repressor) are delivered using AAV9. In other embodiments, one or more nucleic acids of the tau modulator (e.g., repressor) are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein in their entireties. Various cell types suitable for ex vivo transfection are well known to those of skill in the art (see, e.g., Freshney et al., Culture of Animal Cells, *A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al. (1992) *J. Exp. Med.* 176:1693-1702).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells) (see Inaba et al. (1992) *J. Exp. Med.* 176:1693-1702).

Stem cells that have been modified may also be used in some embodiments. For example, neuronal stem cells that have been made resistant to apoptosis may be used as therapeutic compositions where the stem cells also contain the ZFP TFs of the invention. Resistance to apoptosis may come about, for example, by knocking out BAX and/or BAK using BAX- or BAK-specific TALENs or ZFNs (see, U.S. Pat. No. 8,597,912) in the stem cells, or those that are disrupted in a caspase, again using caspase-6 specific ZFNs for example. These cells can be transfected with the ZFP TFs or TALE TFs that are known to regulate a tau gene.

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's* Pharmaceutical Sciences, 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as *Spodoptera* fugiperda (Sf), and fungal cells such as *Saccharomyces*, Pischia and *Schizosaccharomyces*. Progeny, variants and derivatives of these cell lines can also be used. In a preferred embodiment, the methods and composition are delivered directly to a brain cell, for example in the striatum.

Models of CNS Disorders

Studies of CNS disorders can be carried out in animal model systems such as non-human primates (e.g., Parkinson's Disease (Johnston and Fox (2015) *Curr Top Behav Neurosci* 22:221-35); Amyotrophic lateral sclerosis (Jackson et al. (2015) *J. Med Primatol:* 44 (2): 66-75), Huntington's Disease (Yang et al. (2008) *Nature* 453 (7197): 921-4); Alzheimer's Disease (Park et al. (2015) *Int J Mol Sci* 16 (2): 2386-402); Seizure (Hsiao et al. (2016) *E Bio Med* 9:257-77), canines (e.g. MPS VII (Gurda et al. (2016) *Mol Ther* 24 (2): 206-216); Alzheimer's Disease (Schutt et al. (2016) *J Alzheimers Dis* 52 (2): 433-49); Seizure (Varatharajah et al. (2017) *Int J Neural Syst* 27 (1): 1650046) and mice (e.g. Seizure (Kadiyala et al. (2015) *Epilepsy Res* 109:183-96); Alzheimer's Disease (Li et al. (2015) *J Alzheimers Dis Parkin* 5 (3) doi 10: 4172/2161-0460), (review: Webster et al. (2014) *Front Genet* 5 (99): 1-23, doi: 10.3389f/gene.2014.00088). These models may be used even when there is no animal model that completely recapitulates a CNS disease as they may be useful for investigating specific symptom sets of a disease. The models may be helpful in determining efficacy and safety profiles of a therapeutic methods and compositions (genetic repressors) described herein.

Applications

Tau modulators (e.g., tau repressors) as described herein comprising MAPT-binding molecules (e.g., ZFPs, TALEs, CRISPR/Cas systems, Ttago, etc.) as described herein, and the nucleic acids encoding them, can be used for a variety of applications. These applications include therapeutic methods in which a MAPT-binding molecule (including a nucleic acid encoding a DNA-binding protein) is administered to a subject using a viral (e.g., AAV) or non-viral vector and used to modulate the expression of a target gene within the subject. The modulation can be in the form of repression, for example, repression of tau expression that is contributing to an AD disease state. Alternatively, the modulation can be in the form of activation when activation of expression or increased expression of an endogenous cellular gene can ameliorate a diseased state. In still further embodiments, the modulation can be repression via cleavage (e.g., by one or more nucleases), for example, for inactivation of a MAPT gene. As noted above, for such applications, the MAPT-binding molecules, or more typically, nucleic acids encoding them are formulated with a pharmaceutically acceptable carrier as a pharmaceutical composition.

The MAPT-binding molecules, or vectors encoding them, alone or in combination with other suitable components (e.g. liposomes, nanoparticles or other components known in the art), can be made into aerosol formulations (i.e., they can be "nebulized") to be administered via inhalation. Aerosol formulations can be placed into pressurized acceptable propellants, such as dichlorodifluoromethane, propane, nitrogen, and the like. Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically, retro-orbitally (RO), intracranially (e.g., to any area of the brain including but not limited to the hippocampus and/or cortex), intracisternally or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a patient should be sufficient to effect a beneficial therapeutic response in the patient over time. The dose is determined by the efficacy and $K_d$ of the particular MAPT-binding molecule employed, the target cell, and the condition of the patient, as well as the body weight or surface area of the patient to be treated. The size of the dose also is determined by the existence, nature, and extent of any adverse side-effects that accompany the administration of a particular compound or vector in a particular patient The following Examples relate to exemplary embodiments of the present disclosure in which the MAPT-modulator comprises a zinc finger protein. It will be appreciated that this is for purposes of exemplification only and that other MAPT-modulators (e.g., repressors) can be used, including, but not limited to, TALE-TFs, a CRISPR/Cas system, additional ZFPs, ZFNs, TALENs, additional CRISPR/Cas systems, homing endonucleases (meganucleases) with engineered DNA-binding domains. It will be apparent that these modulators can be readily obtained using methods known to the skilled artisan to bind to the target sites as exemplified below. Similarly, the following Examples relate to exemplary embodiments in which the delivery vehicle is any AAV vector but it will apparent that any viral (Ad, LV, etc.) or non-viral (plasmid, mRNA, etc.) can be used to deliver the tau repressors described herein.

EXAMPLES

Example 1: In Vivo MAPT Repression

Zinc finger proteins specific for MAPT (tau) target sites as described in U.S. Publication No. 2018/0153921 were used as follows:

TABLE 1

MAPT-specific designs

| SBS #, Target | Design | | | | | |
|---|---|---|---|---|---|---|
| | F1 | F2 | F3 | F4 | F5 | F6 |
| SBS# 57890 tgGTGCTGGAGCT GGTGGGTggcggag a (SEQ ID NO: 1) | LRHHLTR (SEQ ID NO: 3) | RRFTLSK (SEQ ID NO: 4) | RSDVLSE (SEQ ID NO: 5) | KHSTRRV (SEQ ID NO: 6) | RSDVLSE (SEQ ID NO: 5) | RLYTLHK (SEQ ID NO: 7) |
| SBS# 57930 cgGCAGAAGGTGG GcGGTGGCggcggc g (SEQ ID NO: 2) [Parent] | DRSHLTR (SEQ ID NO: 8) | LKQHLTR (SEQ ID NO: 9) | RSAHLSR (SEQ ID NO: 10) | TSGHLSR (SEQ ID NO: 11) | QSGNLAR (SEQ ID NO: 12) | QSGDLTR (SEQ ID NO: 13) |
| SBS# 65918 cgGCAGAAGGTGG GcGGTGGCggcggc g (SEQ ID NO: 2) | DRSHLTR (SEQ ID NO: 8) | LKQHLTR (SEQ ID NO: 9) | RSAHLSR (SEQ ID NO: 10) | TSGHLSR (SEQ ID NO: 11) | QSGNLAR (SEQ ID NO: 12) | QSGDLTR (SEQ ID NO: 13) |
| 65918 Phos contact mutants | Qm5 | none | none | none | Qm5 | none |

All ZFPs described herein were operably linked to a KRAB repression domain to form ZFP-TFs and all repressed MAPT expression.

Primate tau-specific ZFP-TFs are tested in cynomolgus monkeys (*M. fascicularis*) to observe repression of tau expression in a primate (non-human primate (NHP) model). Cynomolgus monkeys are housed in stainless steel cages equipped with an automatic watering system. The study complies with all applicable sections of the current version of the Final Rules of the Animal Welfare Act Regulations (Code of Federal Regulations, Title 9) and the *Guide for the Care and Use of Laboratory Animals*, Institute of Laboratory Animal Resources, Commission on Life Sciences, National Research Council, 8th edition.

The ZFP-TF repressors of Table 1 were cloned into an AAV vector (AAV2/9, or variants thereof) with the SYN1 promoter or CMV promoter, essentially as described in U.S. Publication No. 20180153921. The AAV vectors that were used included: a vector with a SYN1 promoter driving expression of repressors comprising 65918 and 57890 linked by a T2A peptide (SYN918-890); a vector with a CMV promoter driving expression of repressors comprising 65918 and 57890 linked by a T2A peptide (CMV918-890); a vector with a SYN1 promoter driving expression of a repressor comprising 57930 (SYN930); a vector with a SYN1 promoter driving expression of a repressor comprising 57890 (SYN890); and a vector with a SYN1 promoter driving expression of a repressor comprising 65918 (SYN918).

Fifteen NHP subjects were treated as shown in the following Table:

TABLE 2

| Cohort | AAV - promoter ZFP | rAAV vg/hemisphere |
|---|---|---|
| NHP01 | Vehicle only | 0 |
| NHP02 | Vehicle only | 0 |
| NHP03 | Vehicle only | 0 |
| NHP04 | Synapsin - 65918 and 57890 | 6E11 |
| NHP05 | Synapsin - 65918 and 57890 | 6E11 |
| NHP06 | Synapsin - 65918 and 57890 | 6E11 |
| NHP07 | CMV - 65918 and 57890 | 6E11 |
| NHP08 | CMV - 65918 and 57890 | 6E11 |
| NHP09 | Synapsin - 57930 | 6E11 |
| NHP10 | Synapsin - 57930 | 6E11 |
| NHP11 | Synapsin - 57890 | 6E11 |
| NHP12 | Synapsin - 57890 | 6E11 |
| NHP13 | Synapsin - 57890 | 6E11 |
| NHP14 | Synapsin - 65918 | 6E11 |
| NHP15 | Synapsin - 65918 | 6E11 |

In the experiment, AAV9 vectors comprising a hSYN1 or CMV driven ZFP TF are delivered at 6E11 vg/hemisphere to the left and 6E11 vg/hemisphere to the right hemisphere. Animals received a single dose of test article in a volume of 60 µL in the left and a single dose of 60 µL in the right hemisphere. For all test articles, the dose concentration was 1E13 vg/mL.

After 28 days, the animals were sacrificed, and the brains were removed and placed in a coronal brain matrix in ice-cold PBS. Brains were sliced at a 3 mm coronal slice thickness (divided into approximately 17 slices). Some brain slices (right and left hemisphere) were stored in 10% neutral-buffered formalin for histopathology and in situ hybridization analyses. All other brain slices (right and left hemisphere) were placed in RNAlater (Qiagen) and refrigerated for approximately 24 hours, after which 2-3 mm diameter punches were collected according to a predefined brain template. Punches were processed for qRT-PCR and biodistribution analysis. Additionally, CSF was collected for tau protein analysis.

Slices comprising the hippocampus and entorhinal cortex regions were used to analyze mRNA expression levels of tau, ZFP, glial and neuronal cell markers, and housekeeping genes via qRT-PCR. The results show that the ZFP-TFs were delivered by AAV to the hippocampal region leading to reduction in tau expression.

Figure 1:
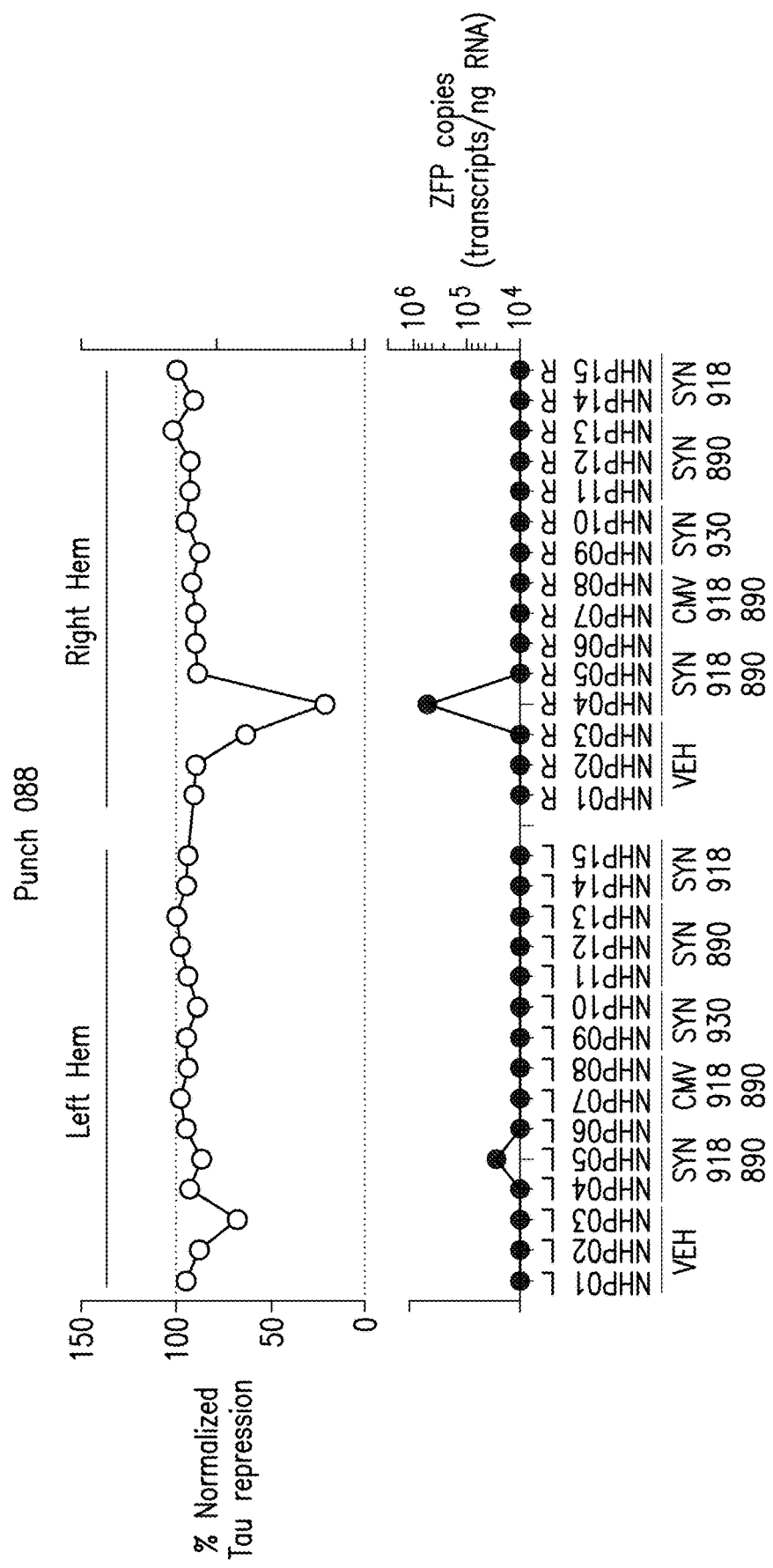
FIG. 1 is a graph depicting tau expression and ZFP transcript levels in an exemplary sample ("punch 088") taken from the caudal hippocampus of non-human primates (NHPs) treated with tau repressors as described herein. The top plot shows % normalized tau repression and the bottom plot shows ZFP mRNA copies (transcripts/ng RNA). The left half of the graph represents data from Punch 088 obtained from the left hemisphere of each animal in the study, and the right half shows data from Punch 088 obtained from the right hemisphere of each animal in the study. The promoters used in the different constructs are shown along the bottom where "CMV" indicates the use of the CMV promoter and "SYN" indicates use of the synapsin promoter.
Figure 2:
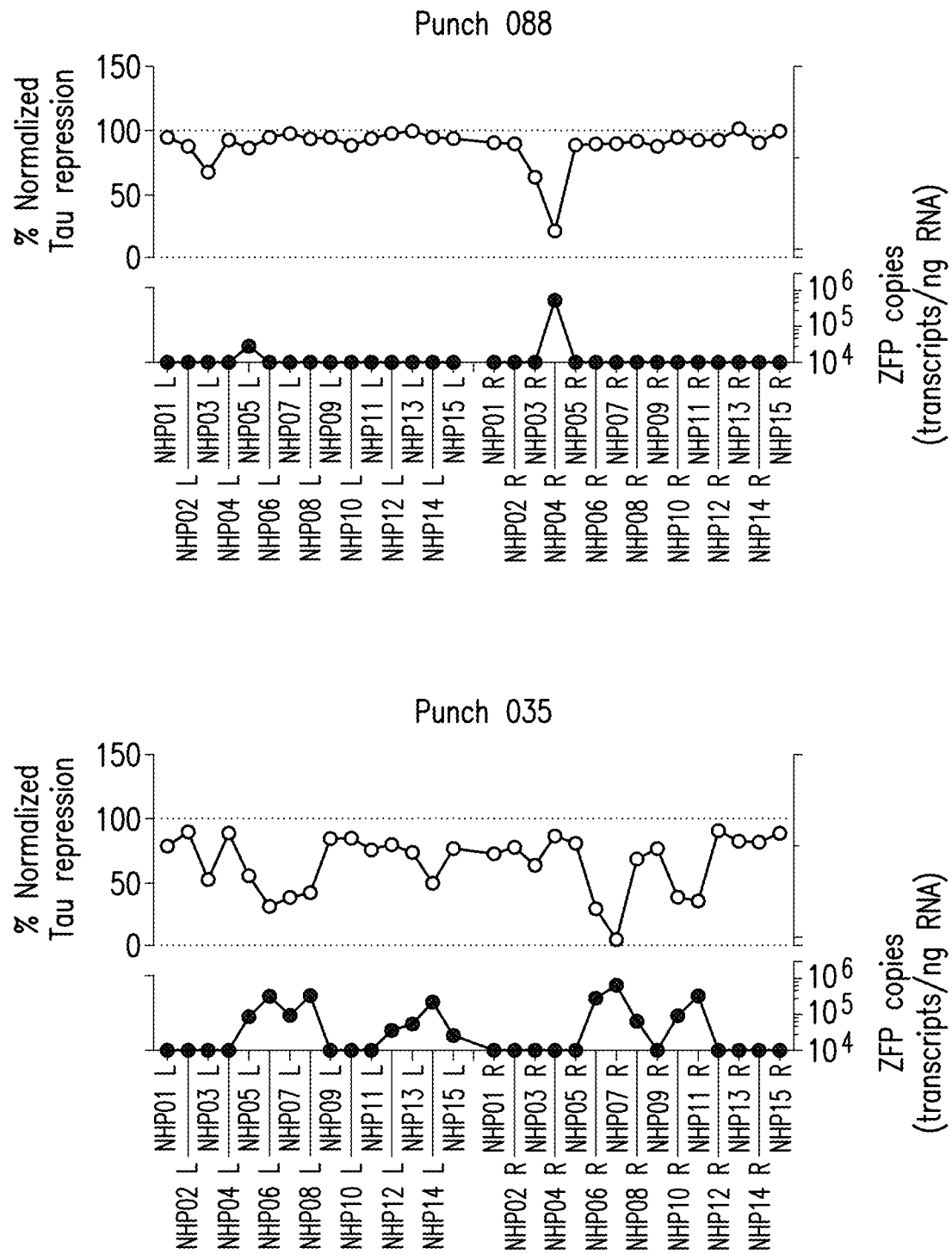
FIG. 2 are graphs depicting tau expression and ZFP levels in exemplary samples ("punch 088" in the top panel taken from the caudal hippocampus and "punch 035" in the bottom panel taken from the rostral hippocampus) taken from NHPs treated with tau repressors as described herein. The top plot in each panel shows % normalized tau repression and the bottom plot in each panel shows ZFP mRNA levels (copies/ng mRNA).

FIG. 1 and FIG. 2 show exemplary results of tau repression and ZFP mRNA levels (copies/ng mRNA) of hippocampal punches 088 and 035 using the indicated vectors in the indicated subjects.

Figure 3A:
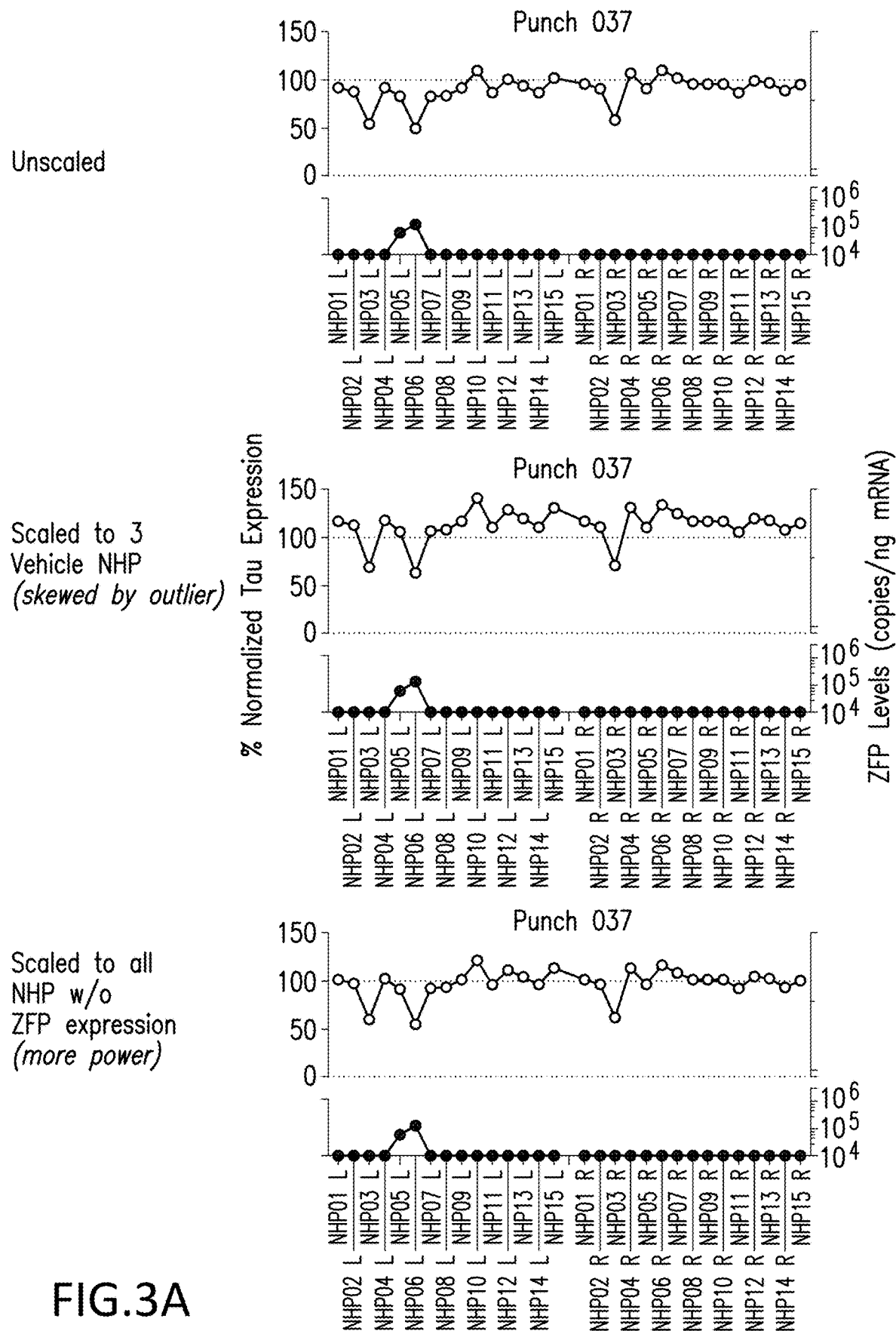
FIG. 3A through FIG. 3C show graphs depicting ZFP levels and unscaled tau protein expression levels (top graphs), scaled to the average of the three vehicle-treated animals (middle graphs), or scaled to the average of the vehicle-treated animals and ZFP-treated animals without detectable ZFP expression (bottom graphs) of the indicated NHP brain samples.
Figure 3B:
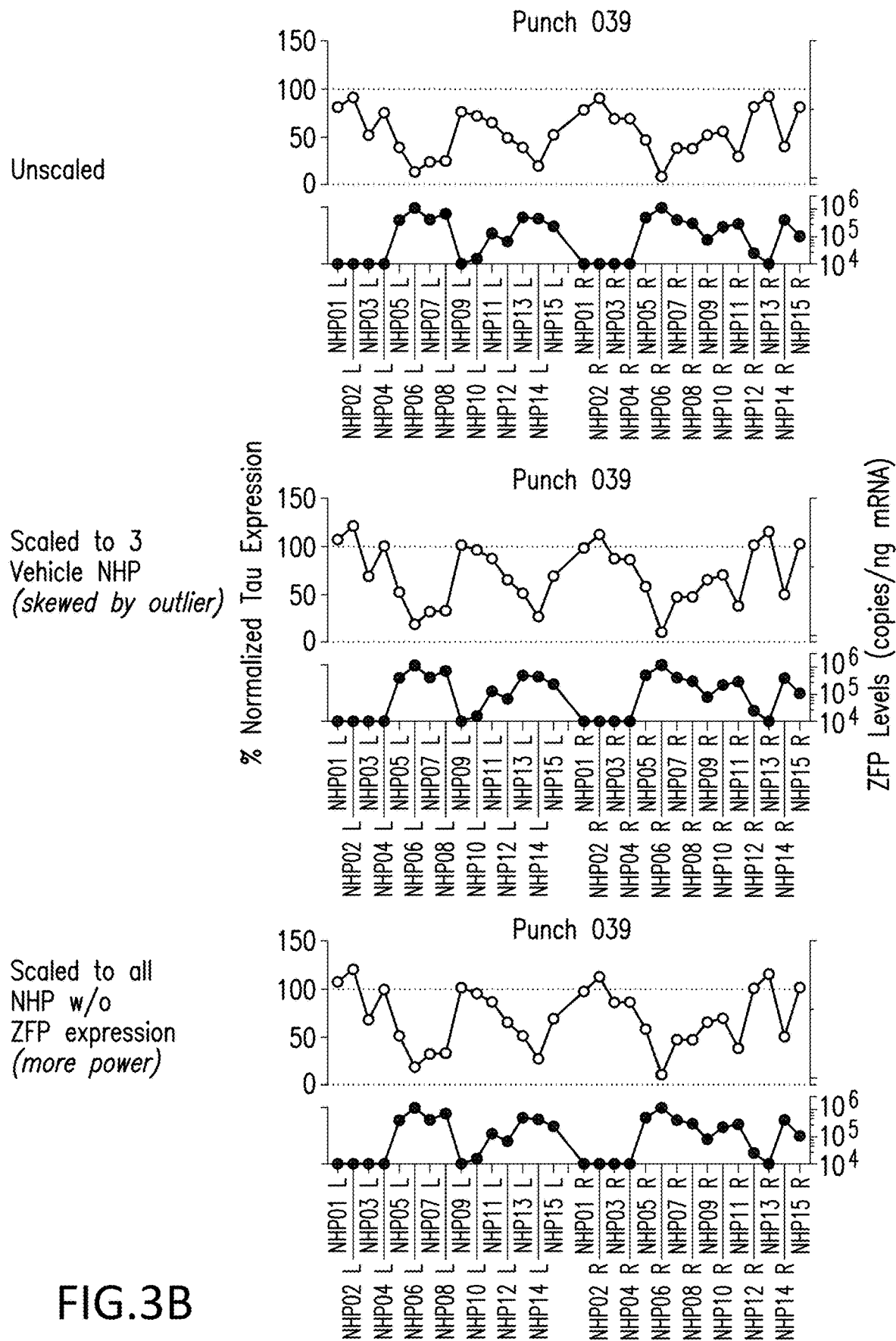
Figure 3C:
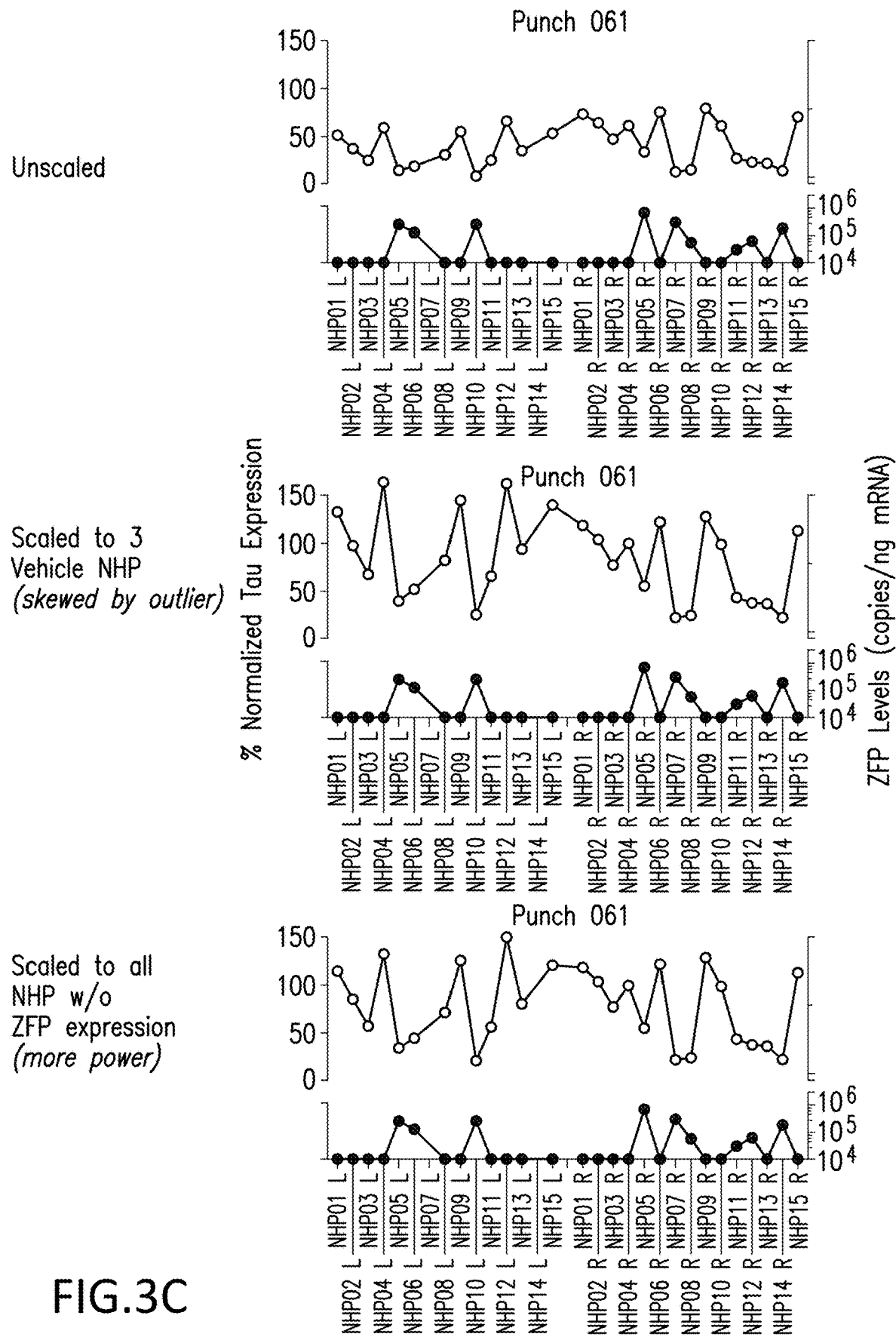

FIG. 3A through FIG. 3C show results from the indicated punch samples and three methods evaluated to establish baseline tau levels for a given punch, including no scaling (top graphs), scaling to the average of the three vehicle-treated animals (middle graphs), or scaling to the average tau expression of the vehicle-treated animals and ZFP-treated animals without detectable ZFP expression (bottom graphs). As shown, scaling by either method better approximates baseline levels across all 15 animals, with the third method (scaling to NHPs without ZFP expression) being a somewhat better representative of the tau baseline across the 15 animals in the study in some cases (e.g., Punch 037).

Figure 4:
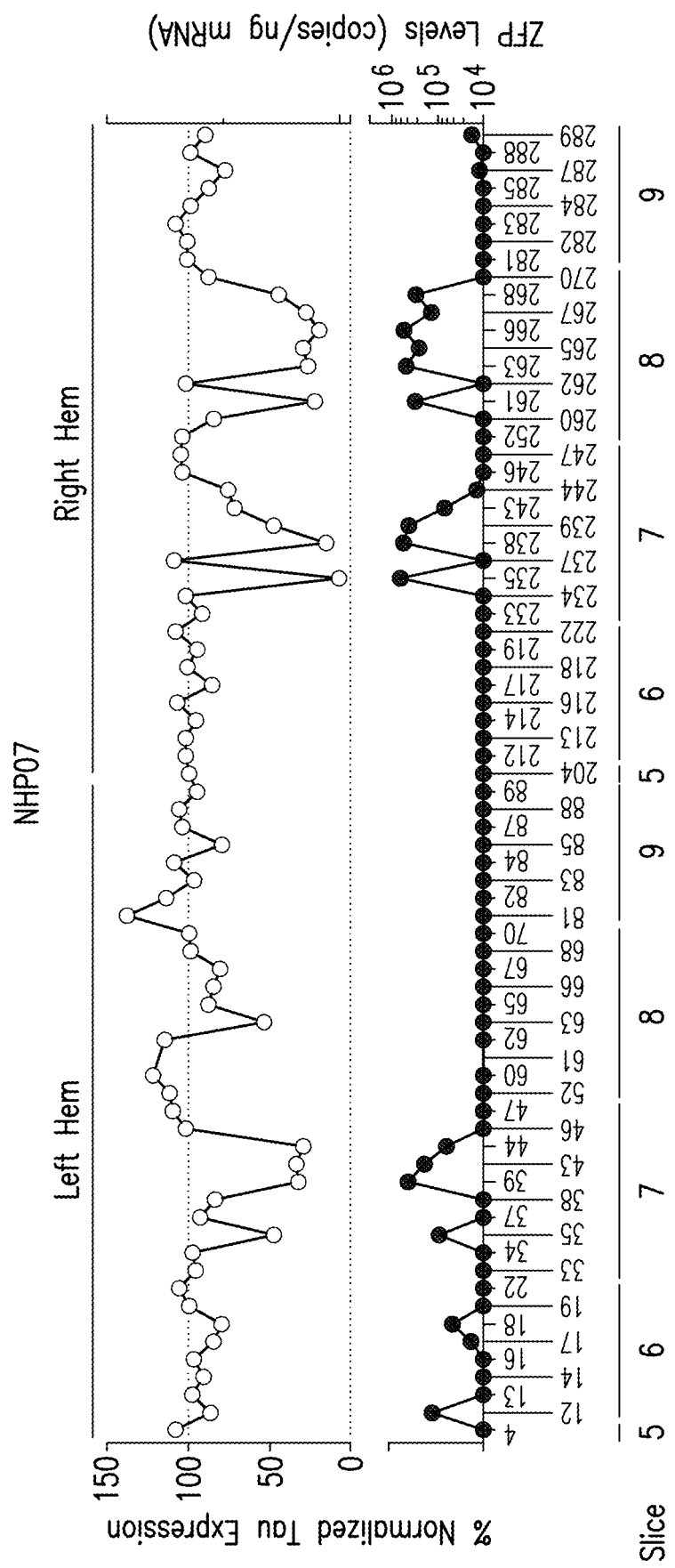
FIG. 4 is a graph depicting tau expression and ZFP levels from 74 punches taken from various brain slices ordered rostral to caudal (5, 6, 7, 8 and 9 in each hemisphere) in an exemplary NHP subject (NHP07) treated with tau repressors as described herein. The top plot in each panel shows % normalized tau repression (left axis) and the bottom plot in each panel shows ZFP mRNA levels (copies/ng mRNA) (right axis).

FIG. 4 shows tau modulation and ZFP levels in subject NHP07 which was treated with AAV CMV918-890. For this analysis, normalized tau expression was scaled to the average of the tau levels measured from vehicle-treated animals and ZFP-treated animals without detectable ZFP expression for each punch. Data from each punch for NHP07 was then extracted and grouped according to brain section analyzed. As shown, in NHP07 showed tau repression in certain brain samples.

Figure 5A:
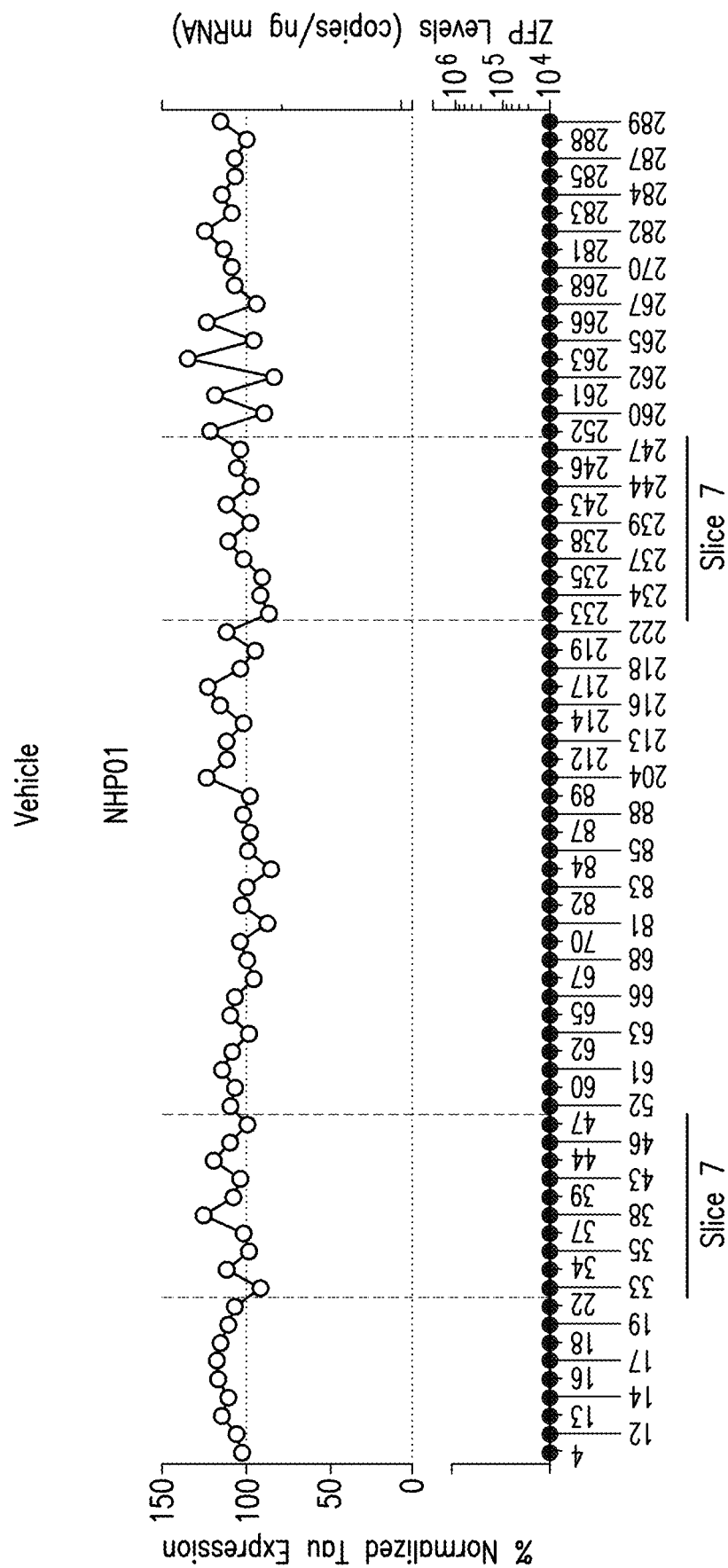
Figure 5B:
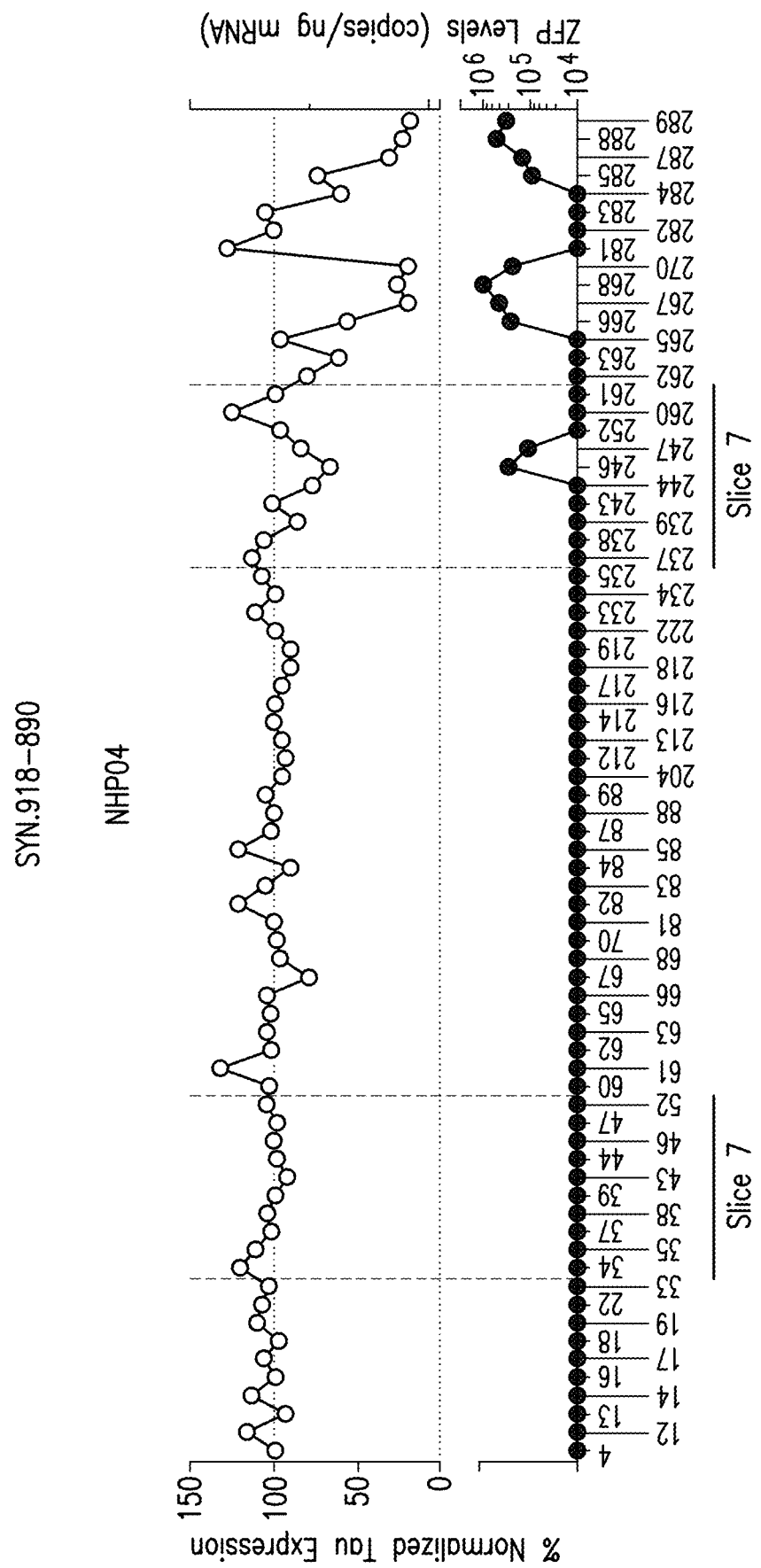

FIG. 5A and FIG. 5B show a comparison of a tau expression and ZFP levels in a control subject (Vehicle, NHP01) and a subject treated with AAV SYN918-890 (NHP04) and FIG. 5C shows MRI results from slice 7. For this analysis, normalized tau expression was scaled to the average of the tau levels measured from vehicle-treated animals and ZFP-treated animals without detectable ZFP expression for each punch.

As shown, the vehicle-treated NHP had no detectable tau reduction or ZFP expression. In contrast, NHP04 showed detectable ZFP expression in slice 7 in the right hemisphere which also correlated with two medial hippocampal punches. Increased ZFP coverage and tau reduction was observed for Sections 8 and 9 in the right hemisphere which correlated well with MRI data from those levels of the brain.

Figure 6A:
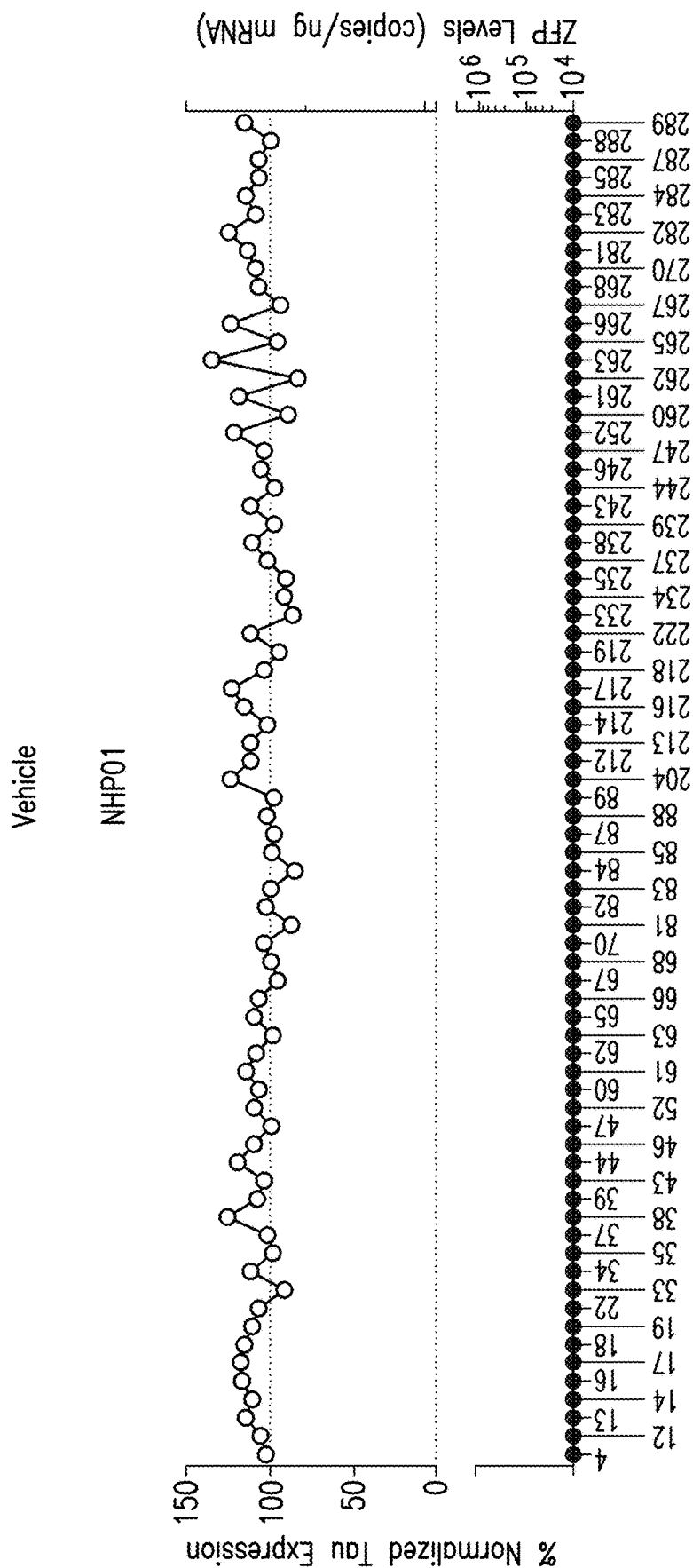
Figure 6B:
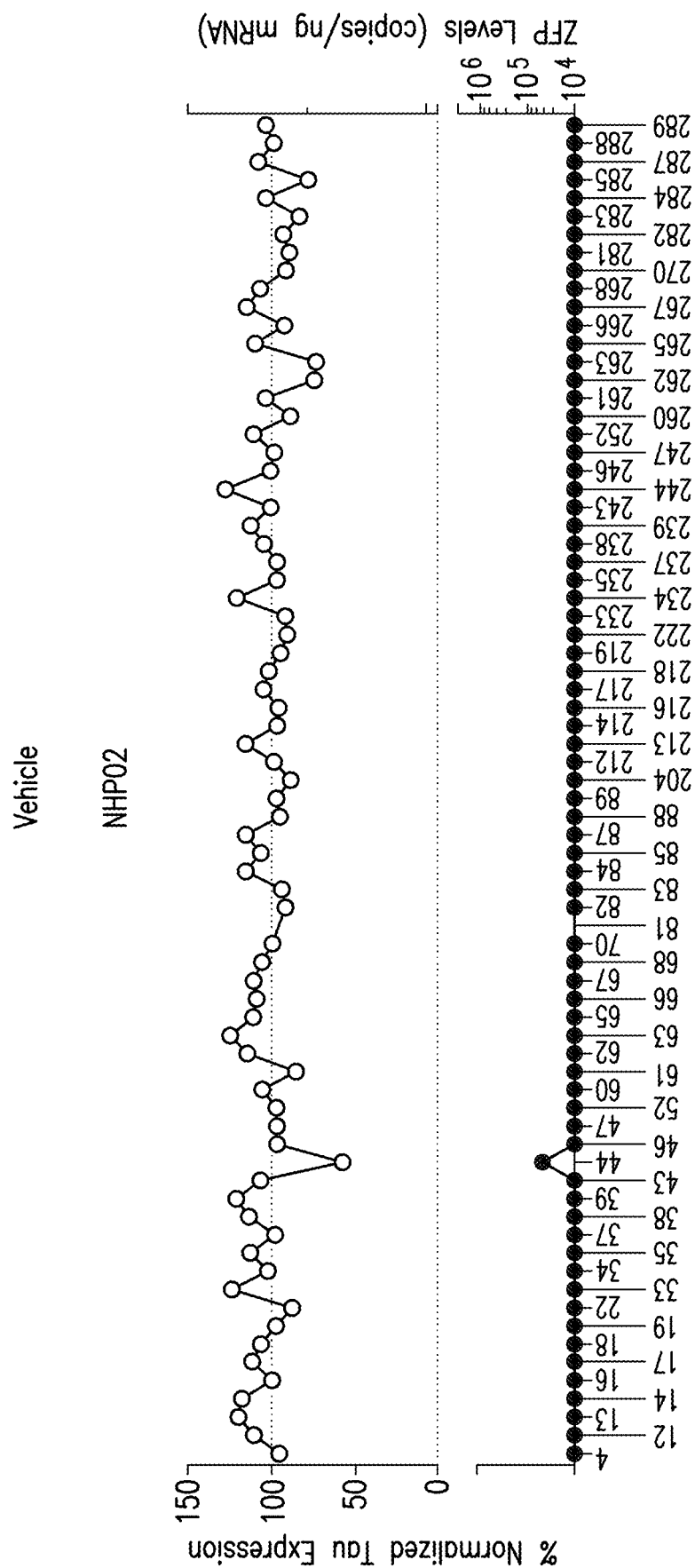
Figure 6C:
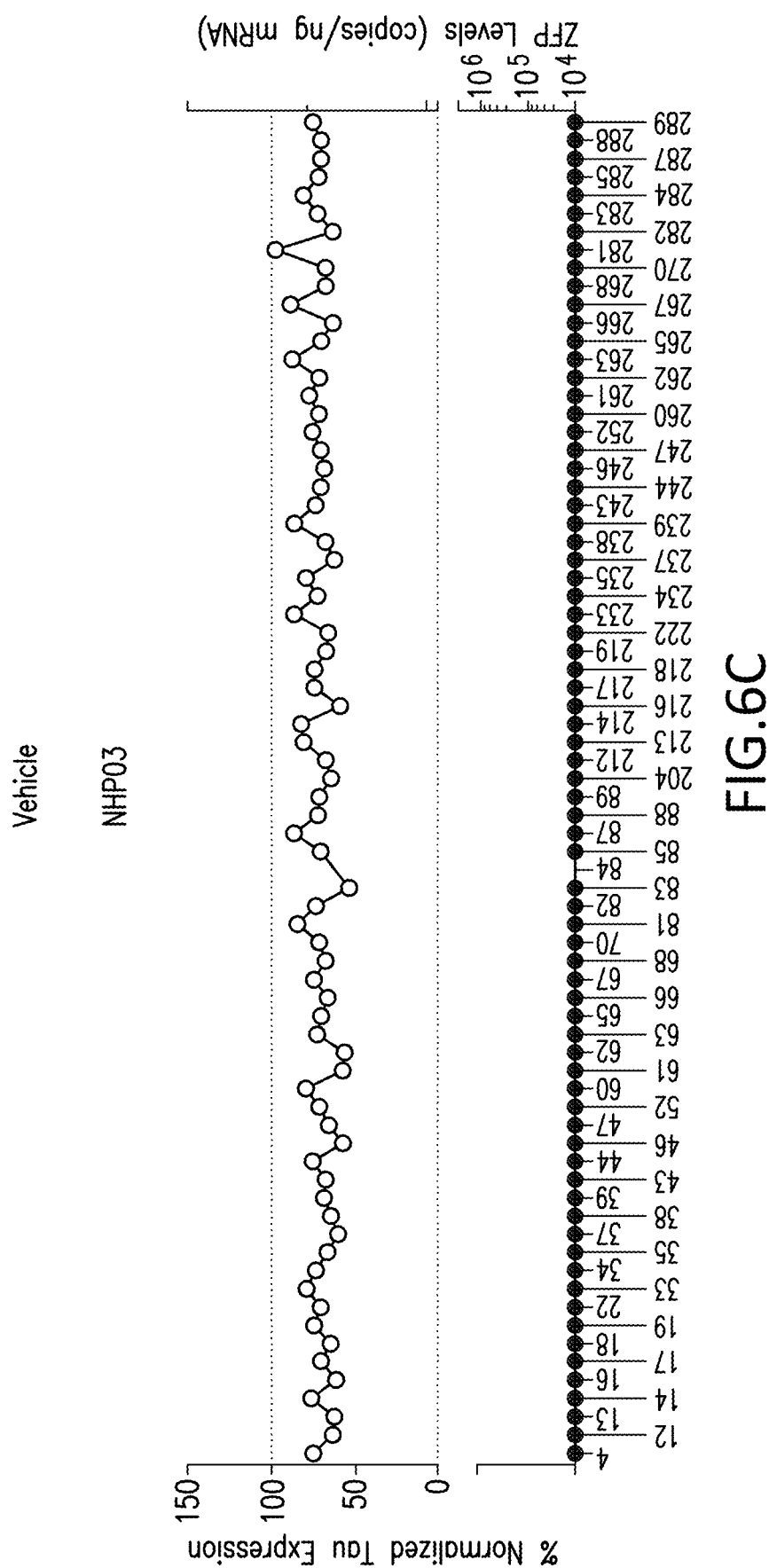
Figure 6D:
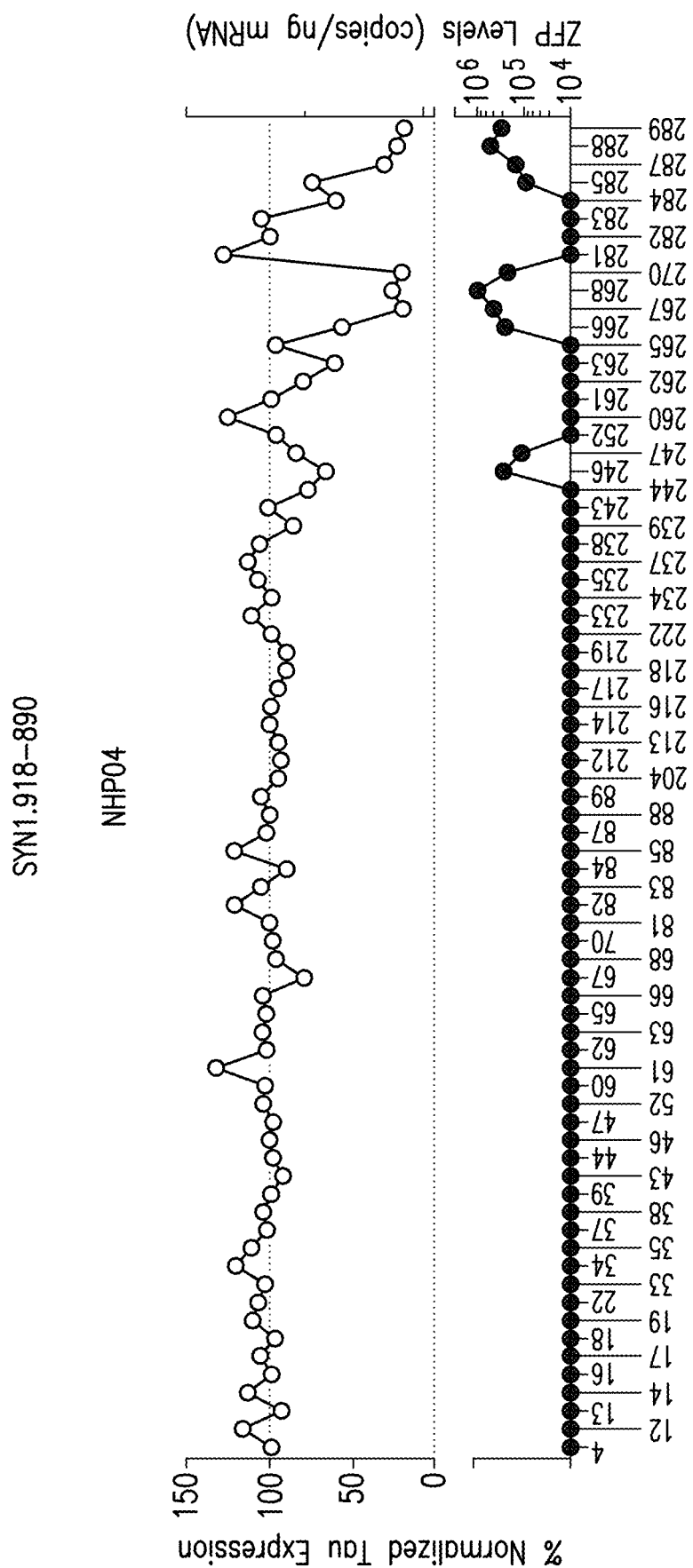
FIG. 6D through FIG. 6F show results from NHP subjects (NHP04 as shown in FIG. 6D, NHP05 as shown in FIG. 6E and NHP06 as shown in FIG. 6F) treated with genetic repressors 65918 ("918") and 57890 ("890") carried by an AAV vector (AAV9) where expression of the repressor (918 and 890) is driven by the synapsin (SYN1) promoter ("SYN1.918-890").
Figure 6E:
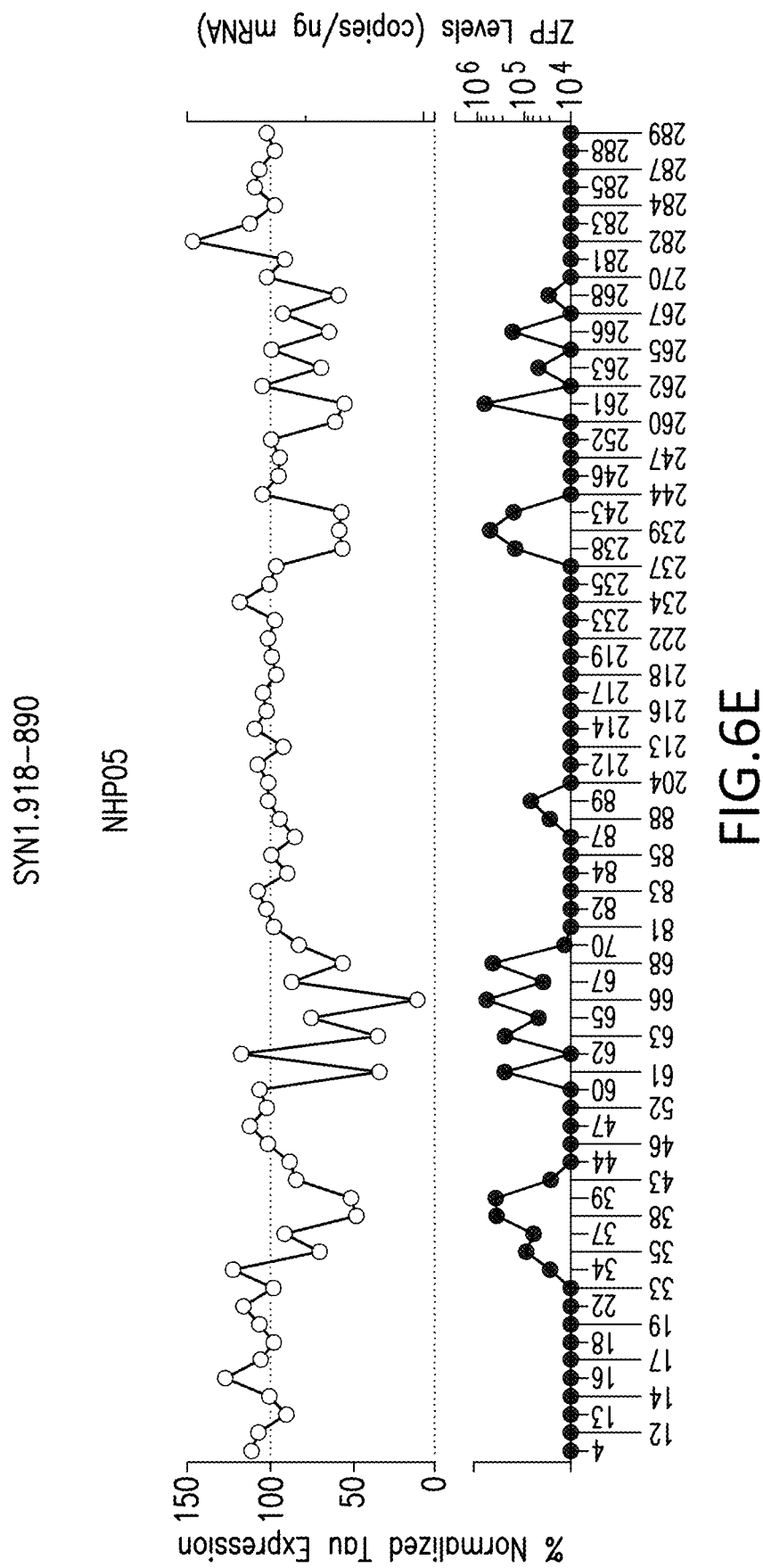
Figure 6F:
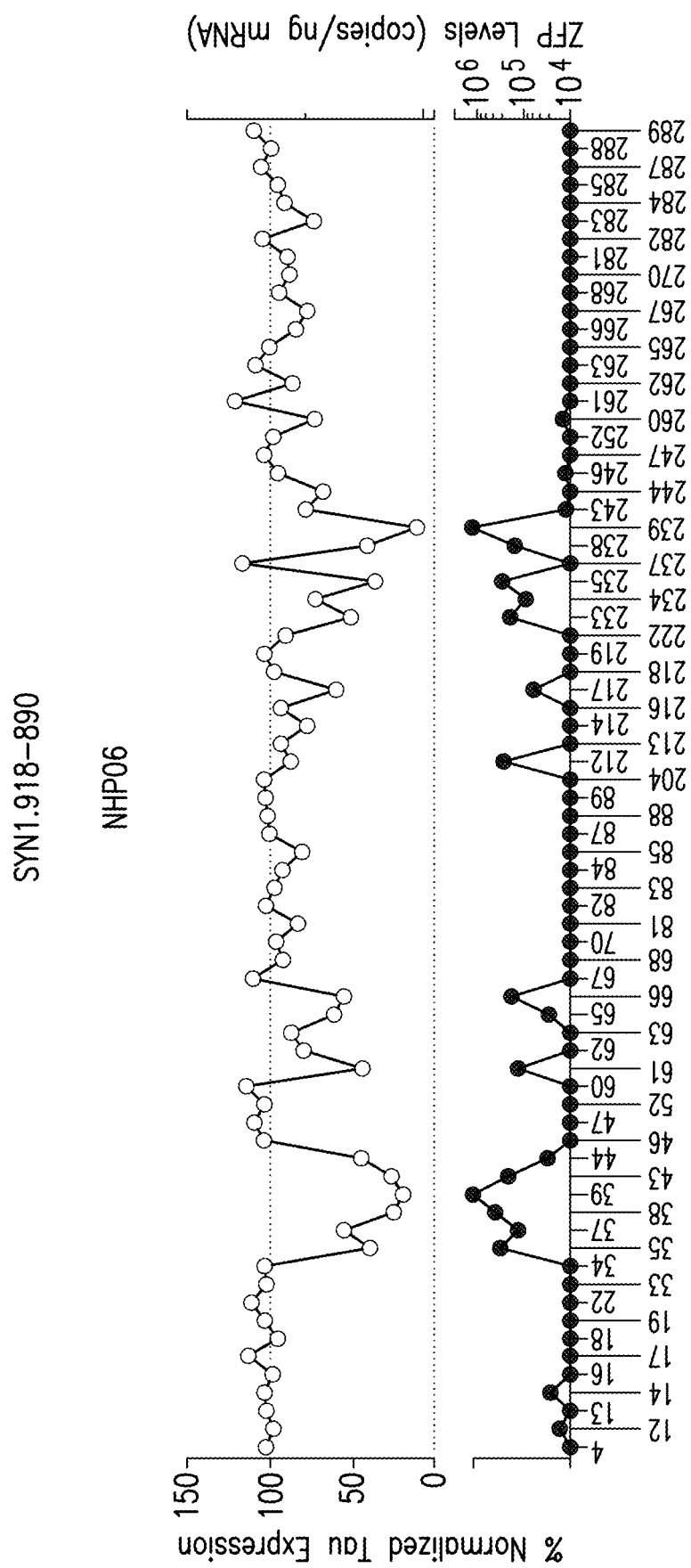
Figure 6G:
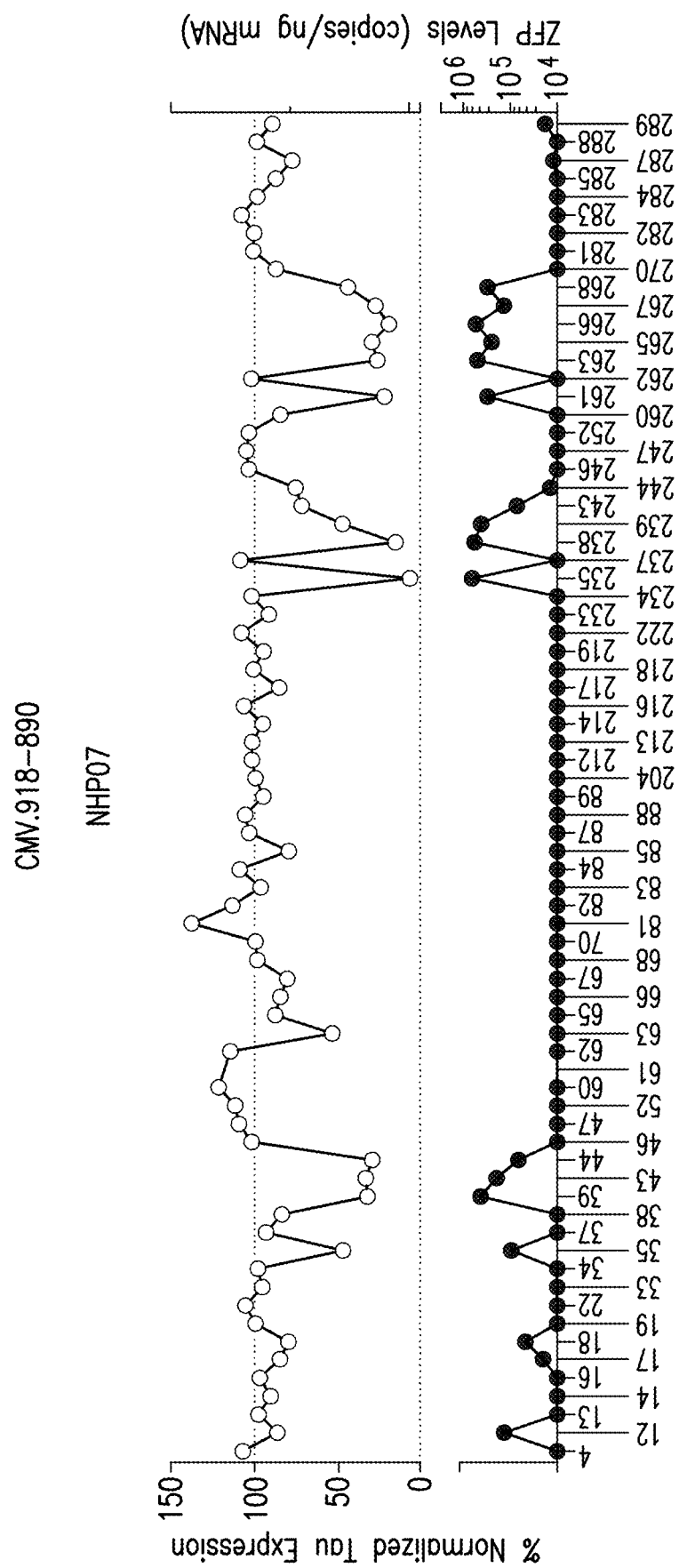
Figure 6H:
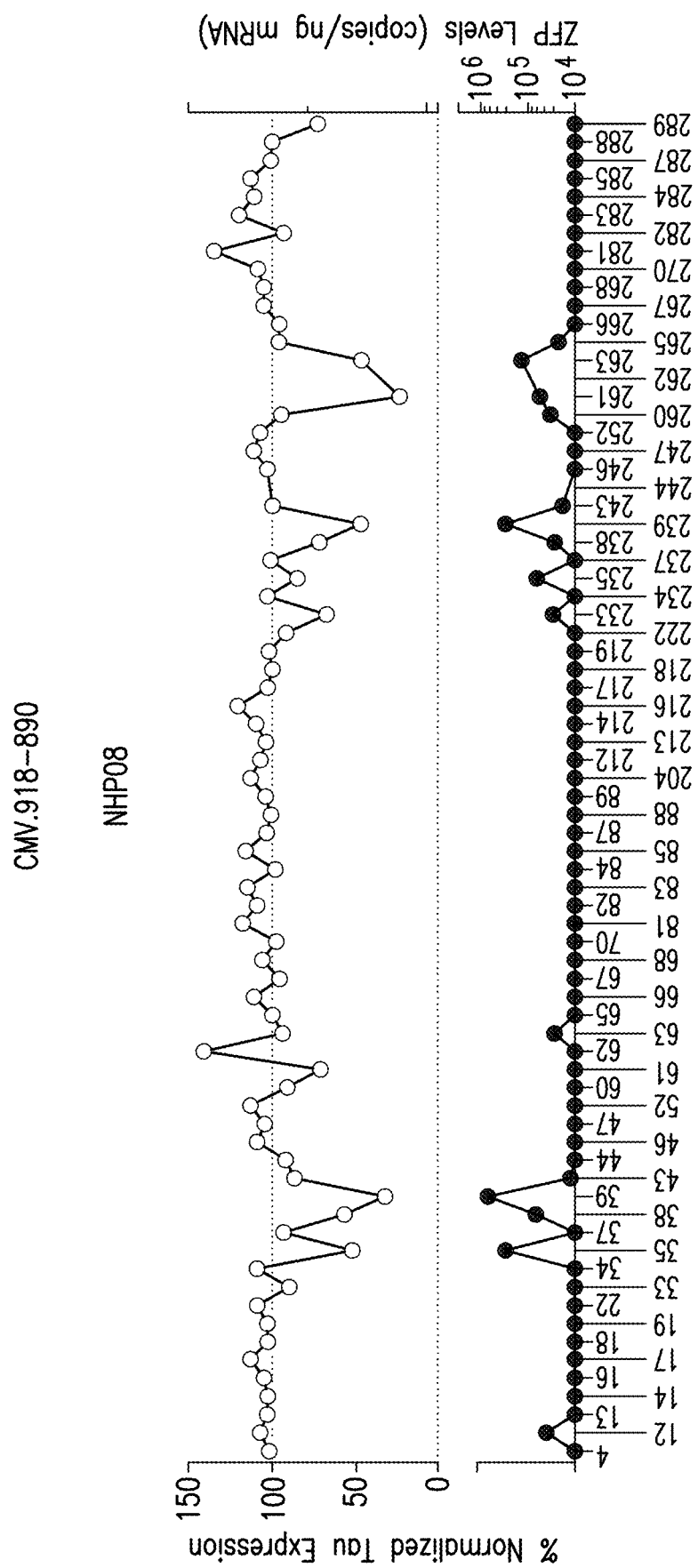
Figure 61:
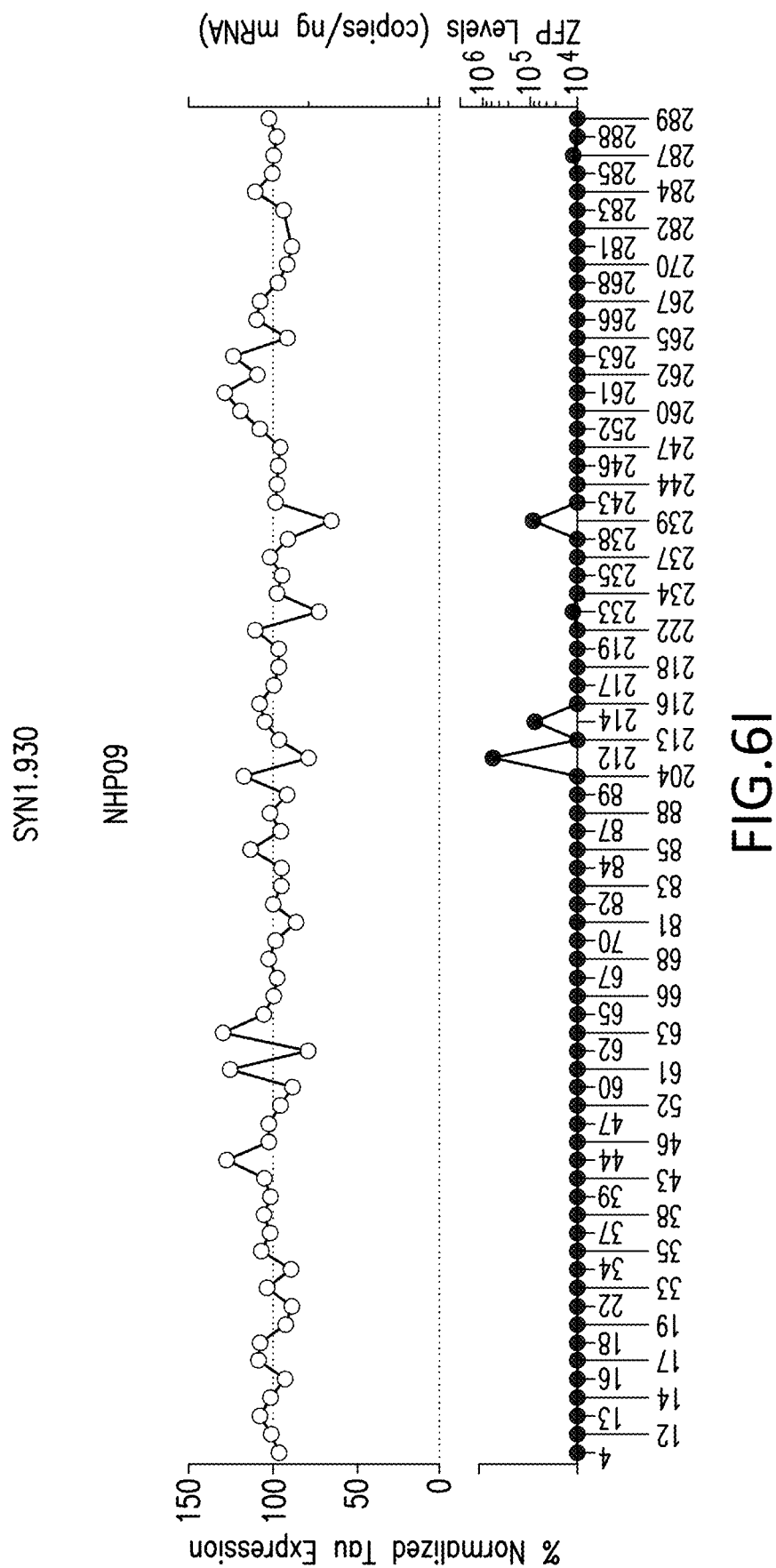
Figure 6J:
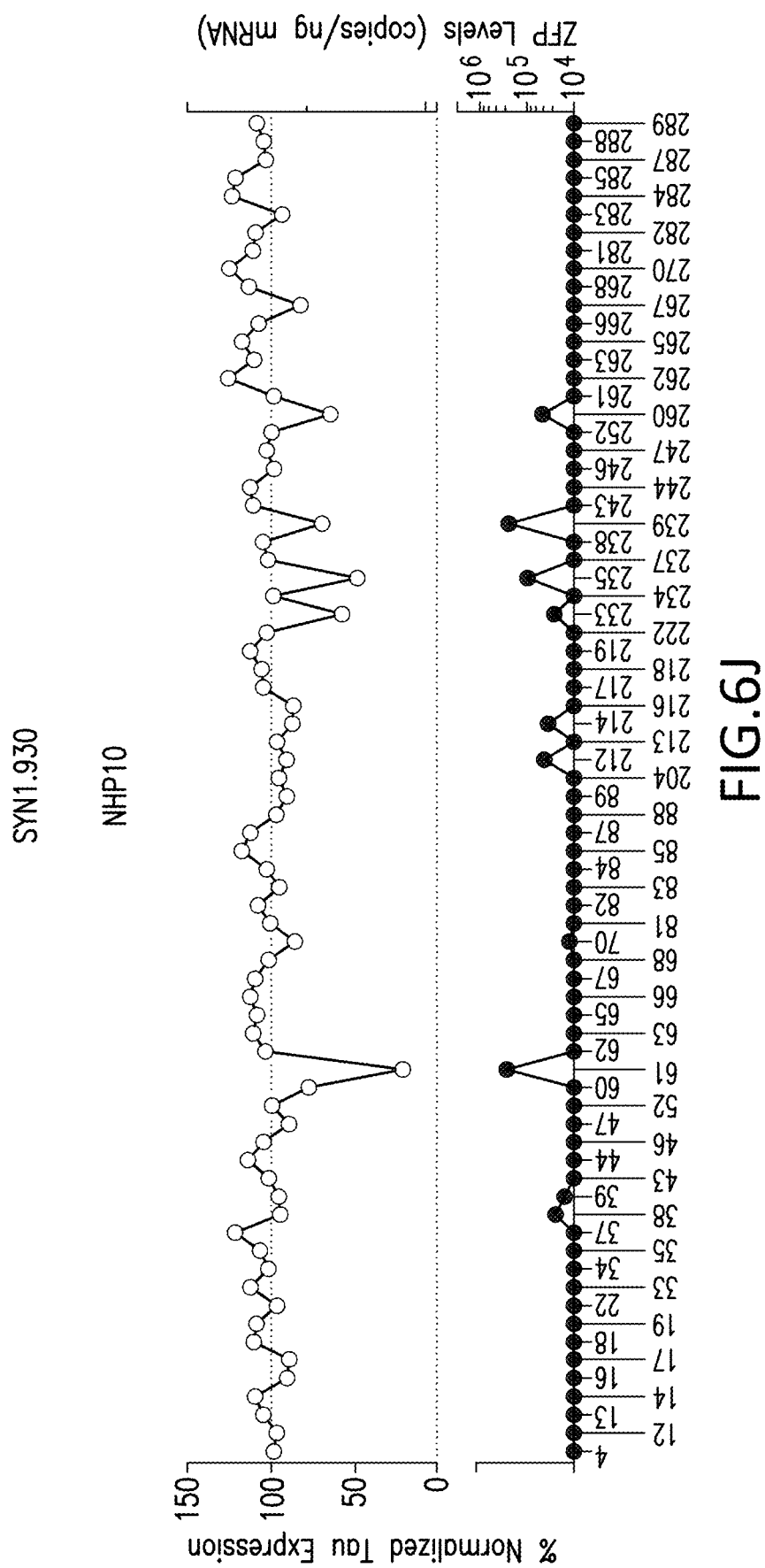
Figure 6K:
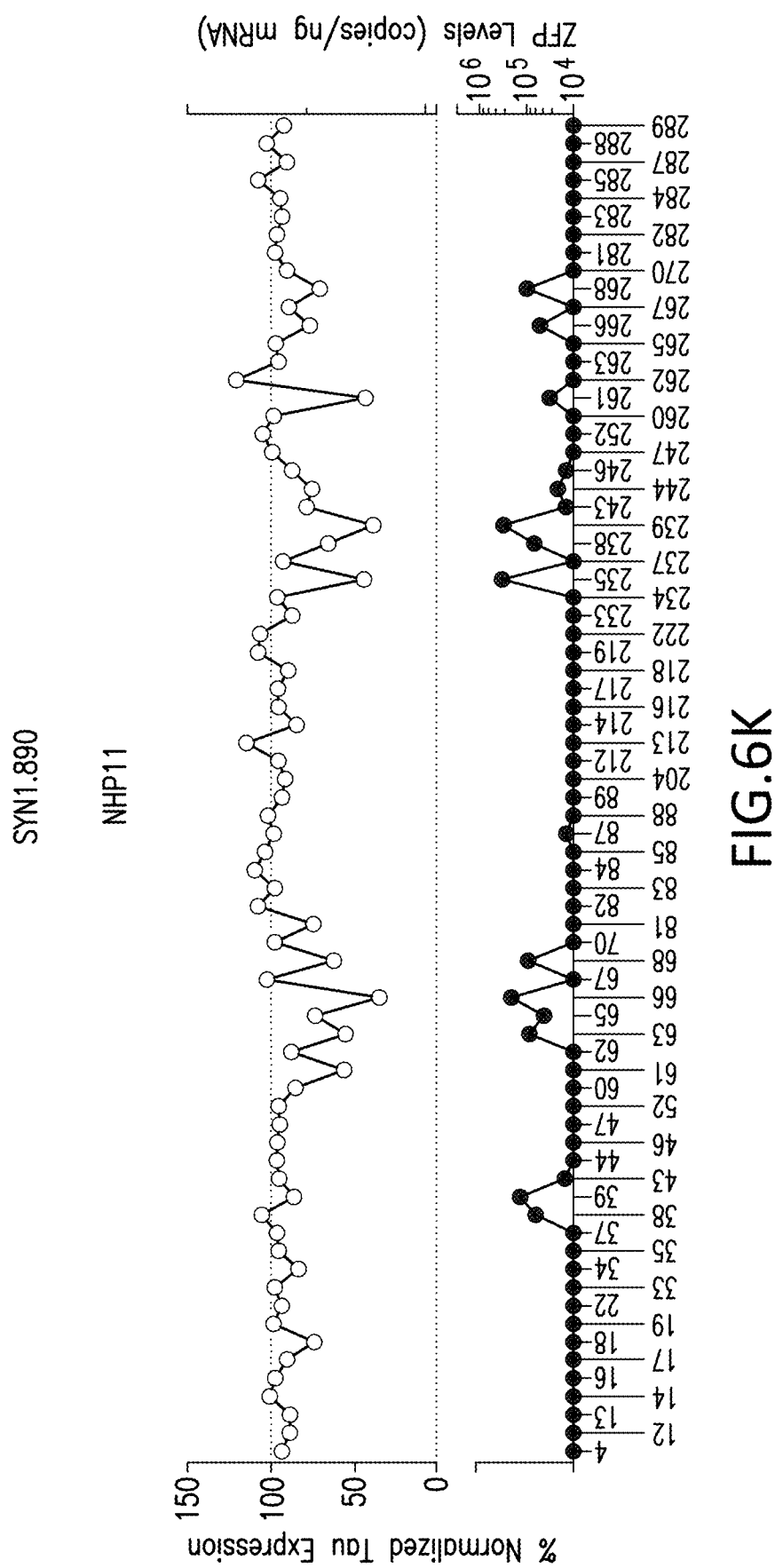
FIG. 6K through FIG. 6M show results from subjects (NHP11 as shown in FIG. 6K, NHP12 as shown in FIG. 6L and NHP13 as shown in FIG. 6M) treated with 57890 ("890") carried by an AAV vector (AAV9) where expression of the repressor is driven by the synapsin (SYN1) promoter ("SYN1.890").
Figure 6L:
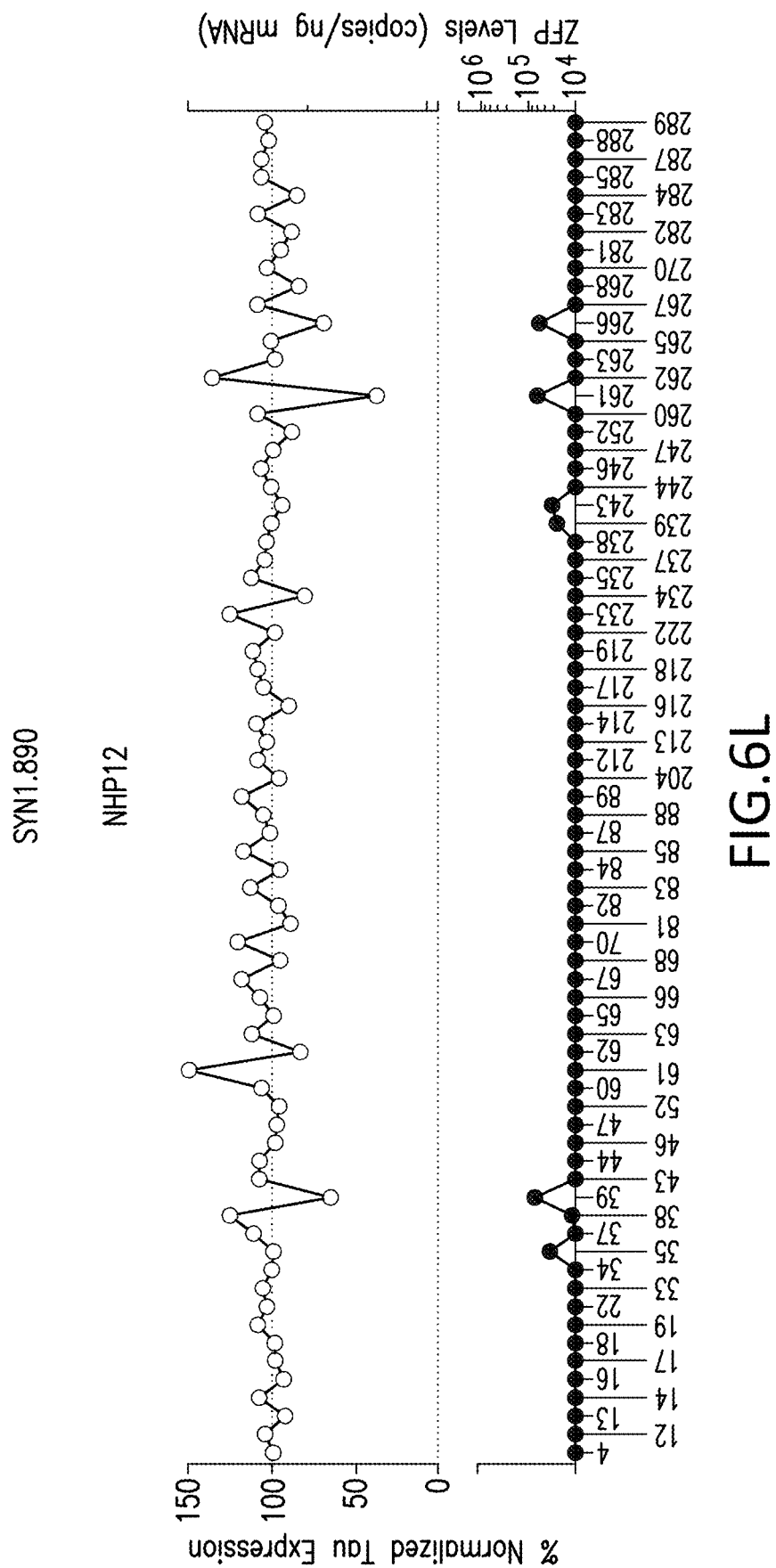
Figure 6M:
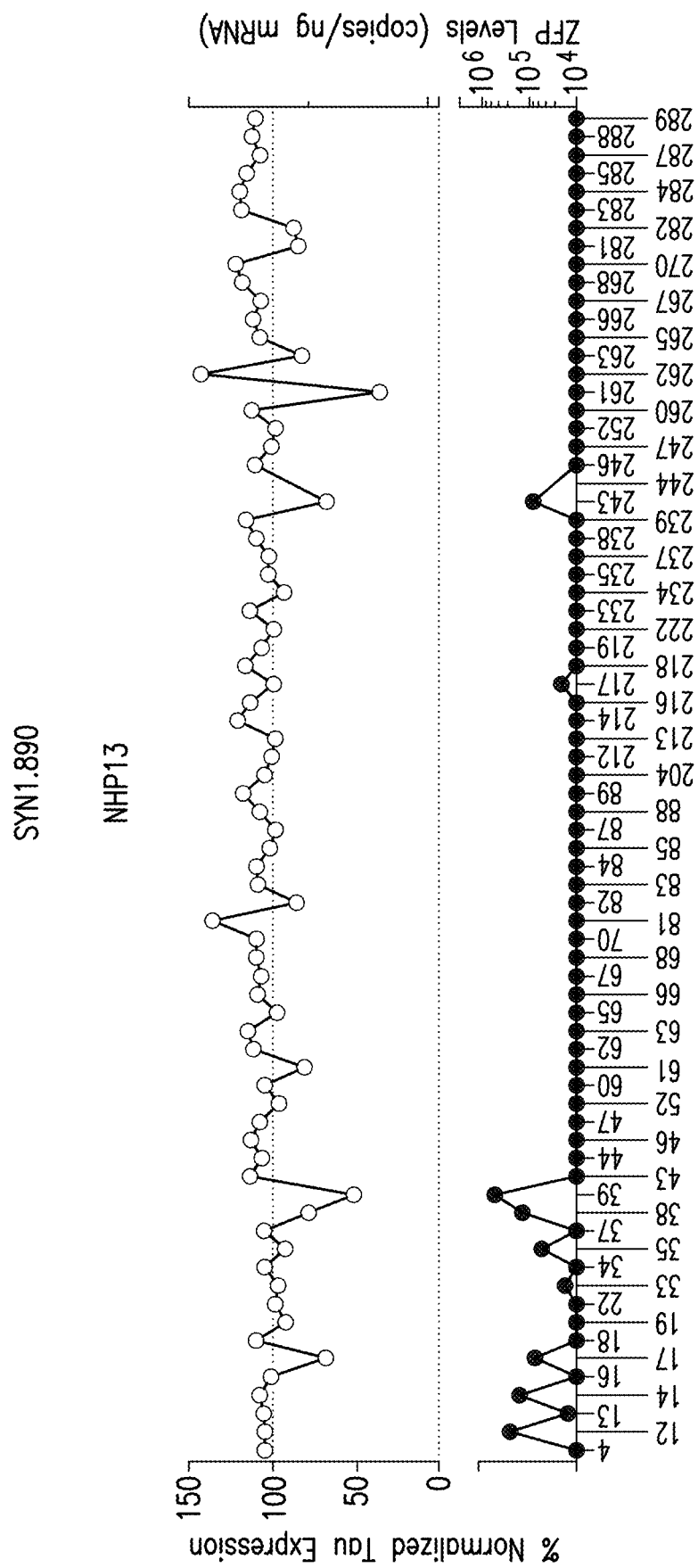
Figure 6N:
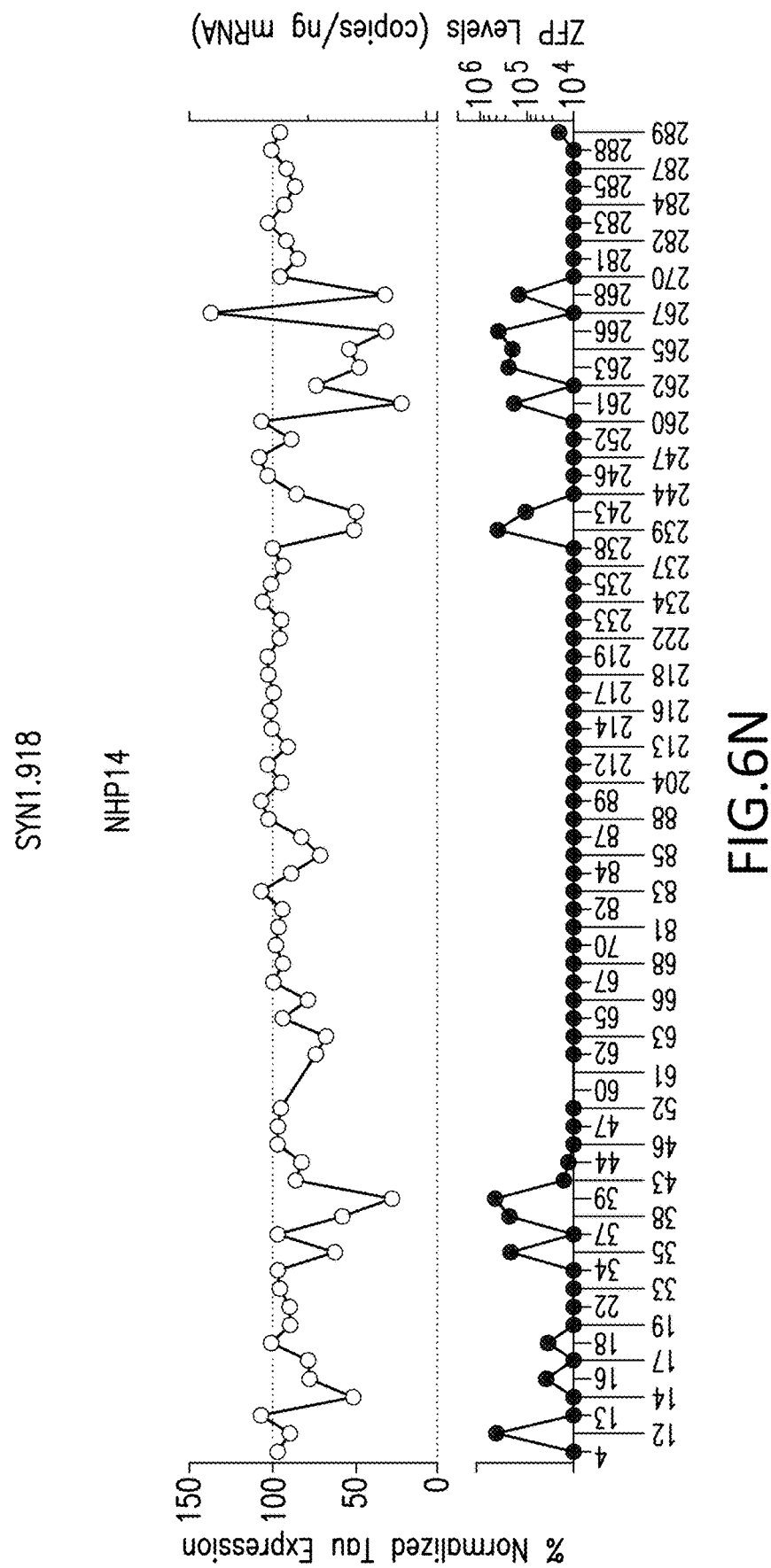
Figure 60:
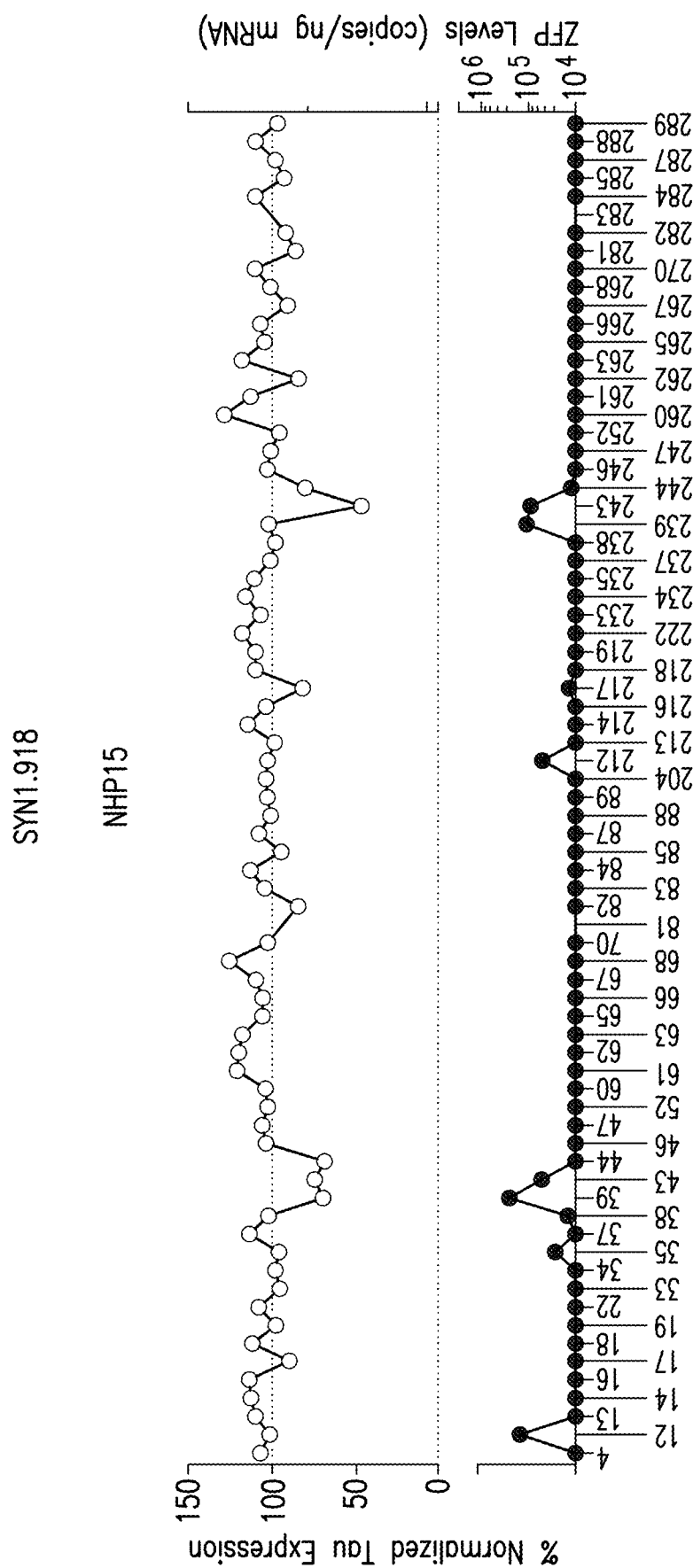

FIG. 6A through FIG. 6O show results of tau expression and ZFP levels in control subjects (FIG. 6A through FIG. 6C; NHP01, NHP02, NHP03); subjects treated with AAV SYN1.918-890 (FIG. 6D through FIG. 6F; NHP04, NHP05, NHP06); subjects treated with AAV CMV.918-890 (FIG. 6G though FIG. 6J; NHP07, NHP08); subjects treated with AAV SYN1.930 (FIG. 6G through FIG. 6J; NHP09, NHP10); subjects treated with AAV SYN1.890 (FIG. 6K through FIG. 6M; NHP11, NHP12, NHP13); and subjects treated with SYN1.918 (FIG. 6N and FIG. 6O; NHP14; NHP15).

Figure 7A:
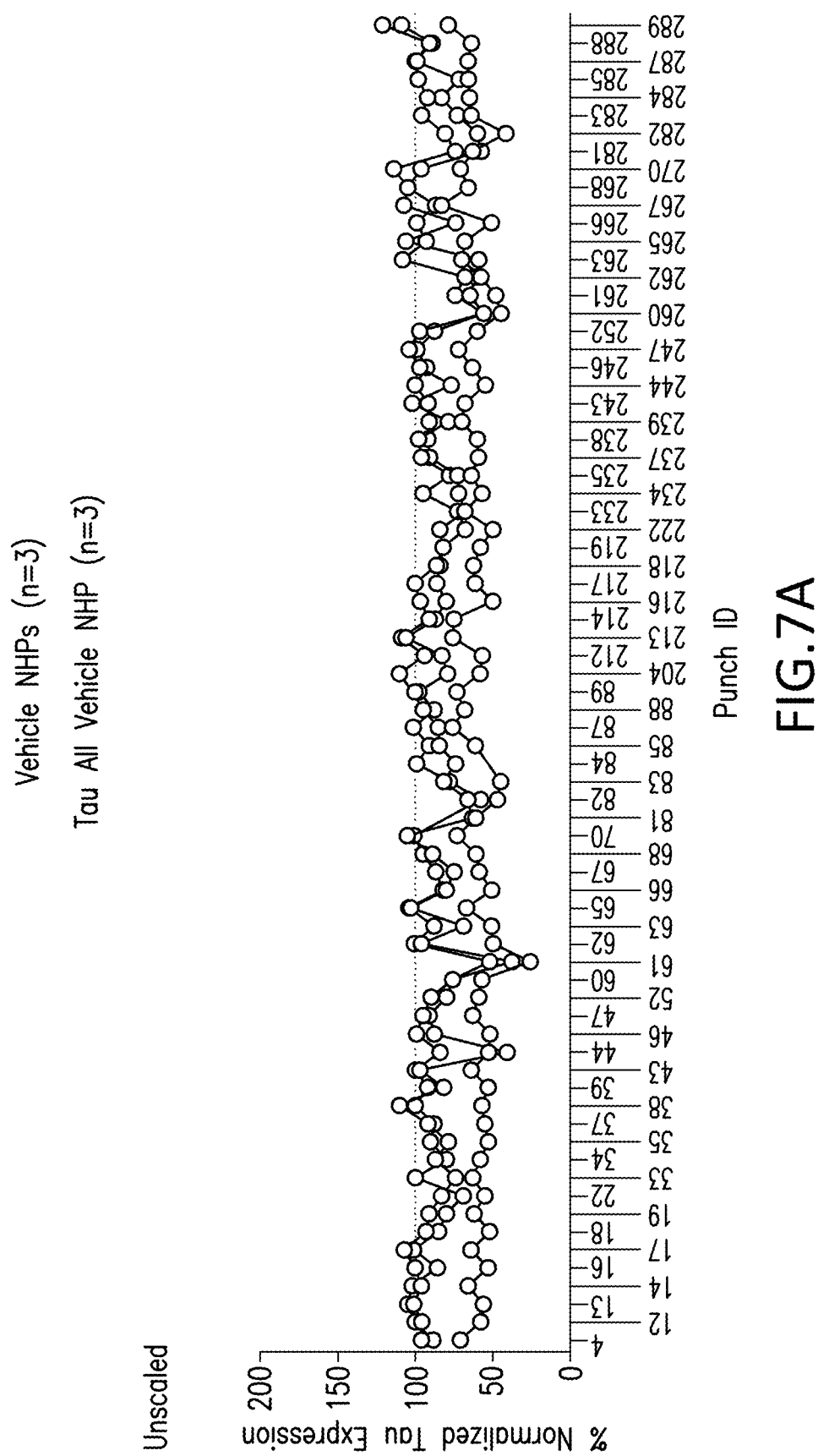
FIG. 7A through FIG. 7F are graphs depicting a composite analysis of ZFP levels and unscaled tau expression levels (FIG. 7A and FIG. 7D), or tau expression scaled to the average of the three vehicle-treated animals (FIG. 7B and FIG. 7E), or tau expression scaled to the average of the vehicle-treated animals and ZFP-treated animals without detectable ZFP expression (FIG. 7C and FIG. 7F) of the indicated NHP brain samples (punch ID on X-axis).
Figure 7B:
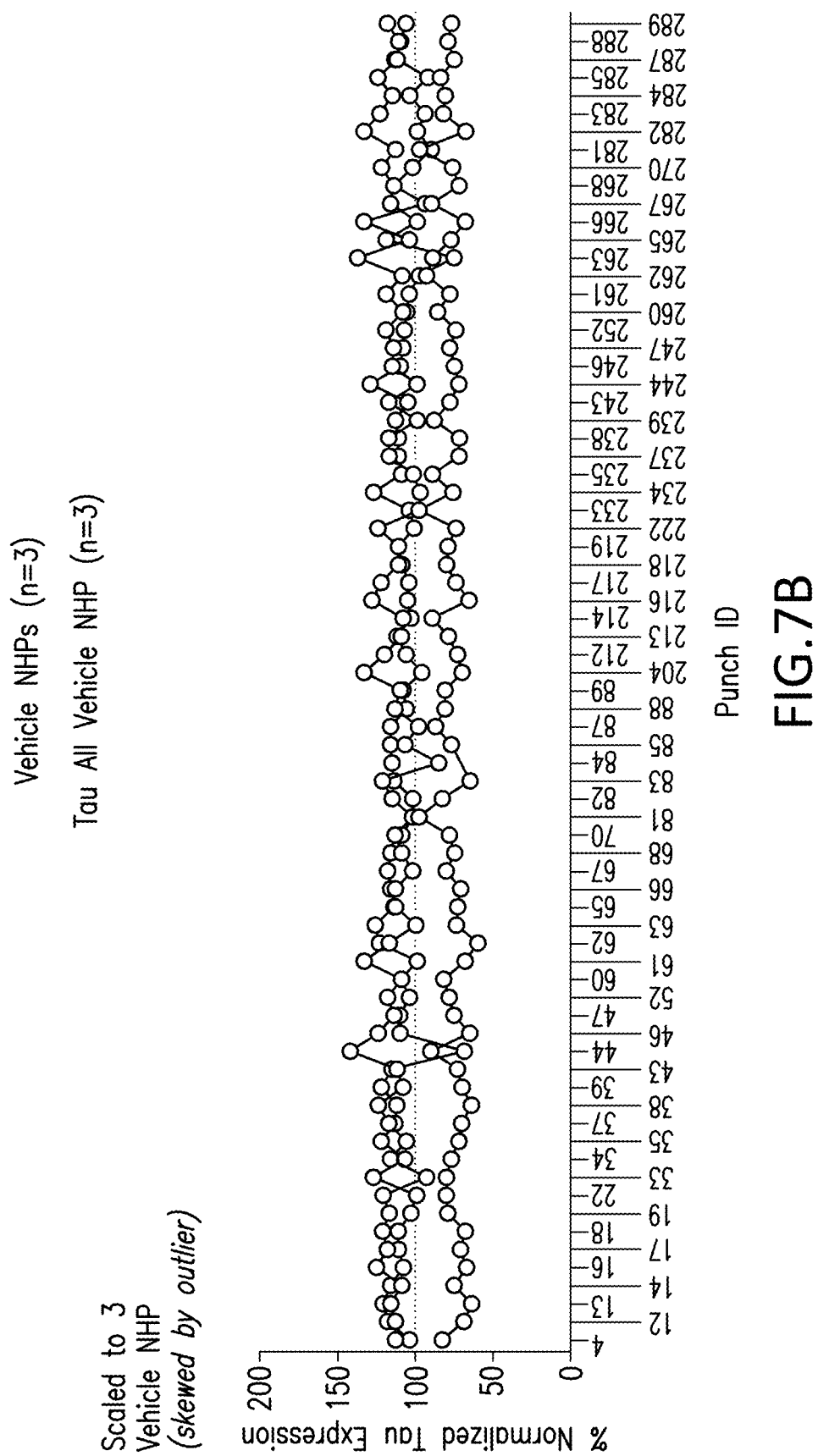
Figure 7C:
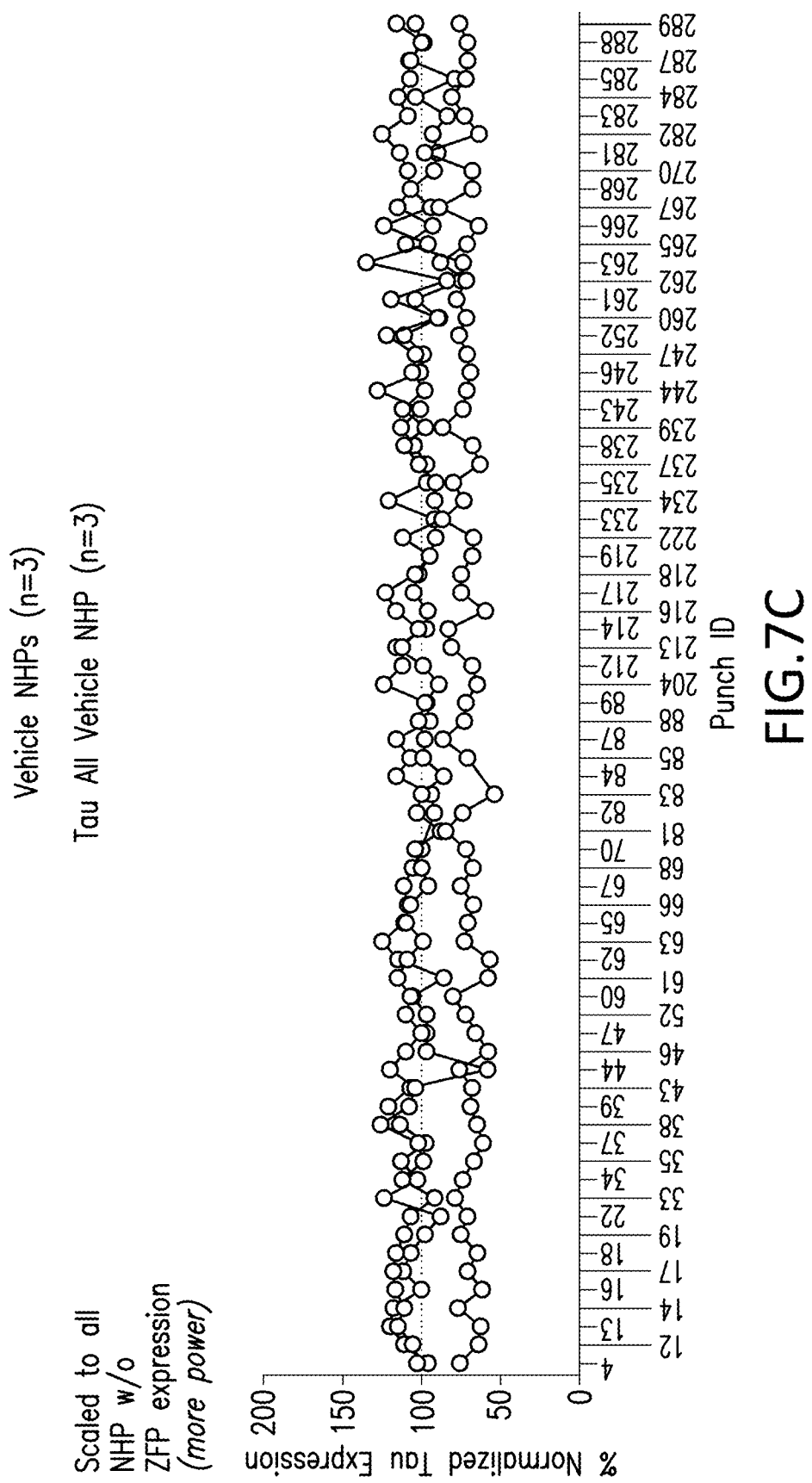
Figure 7D:
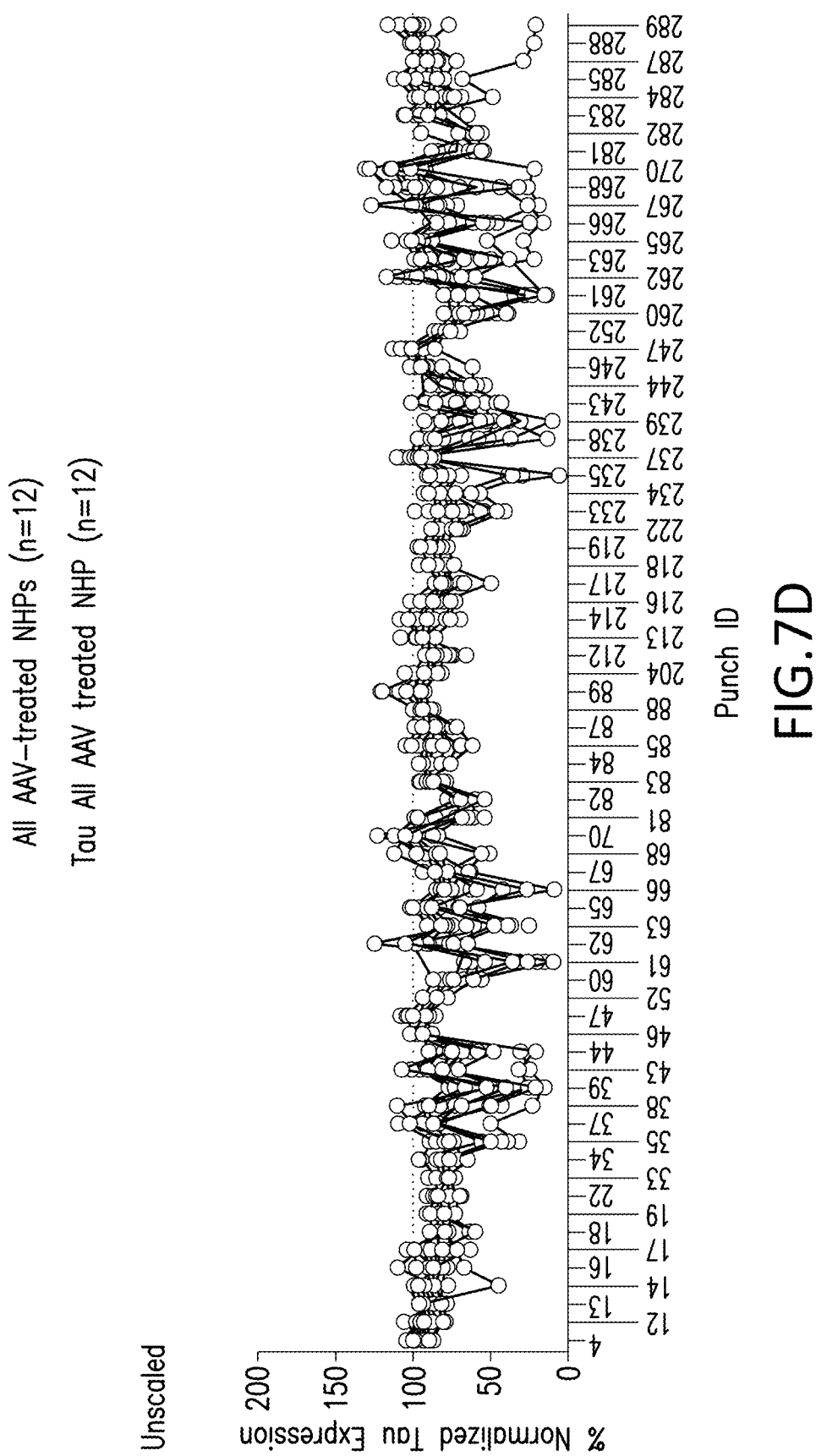
Figure 7E:
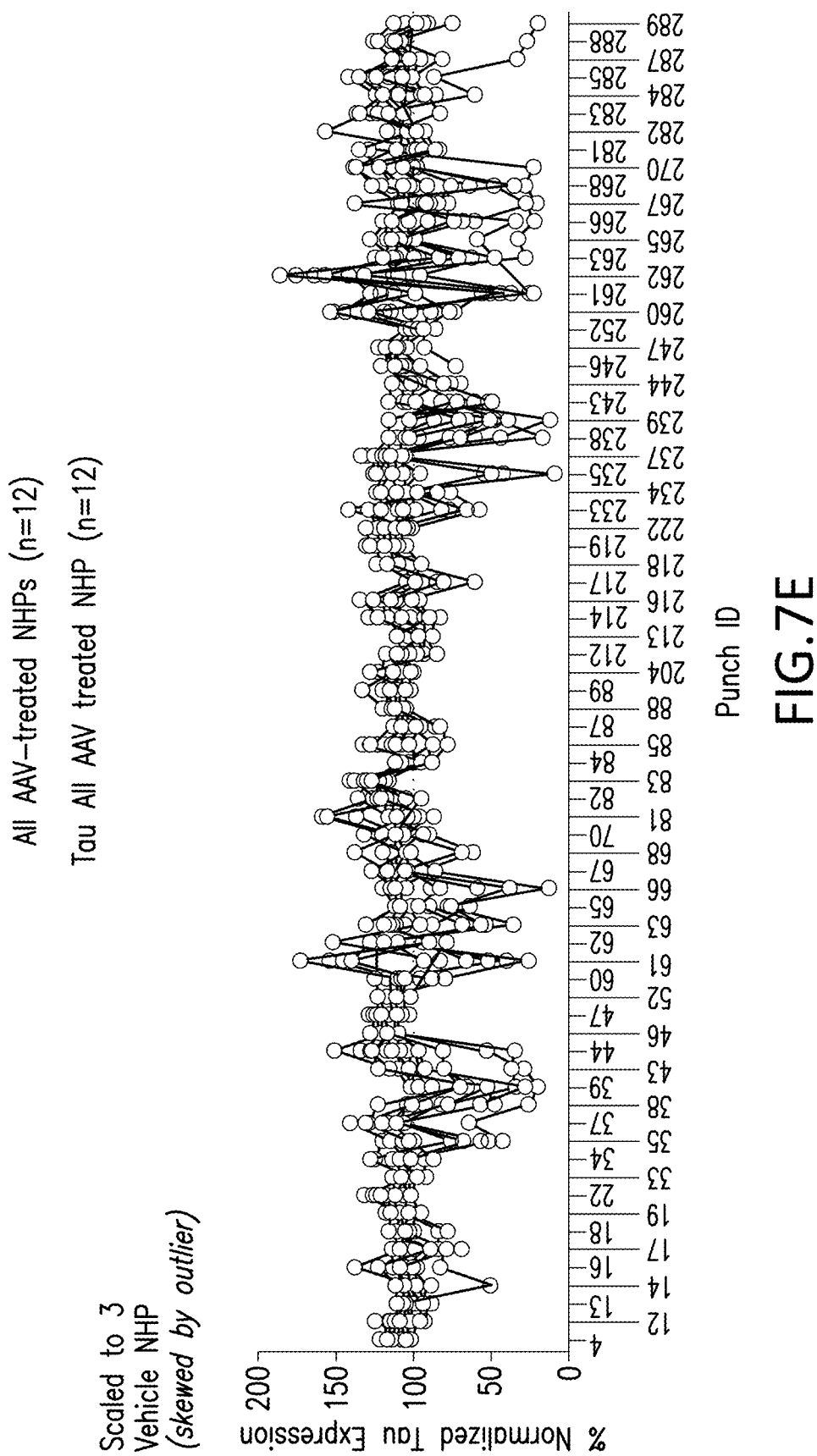
Figure 7F:
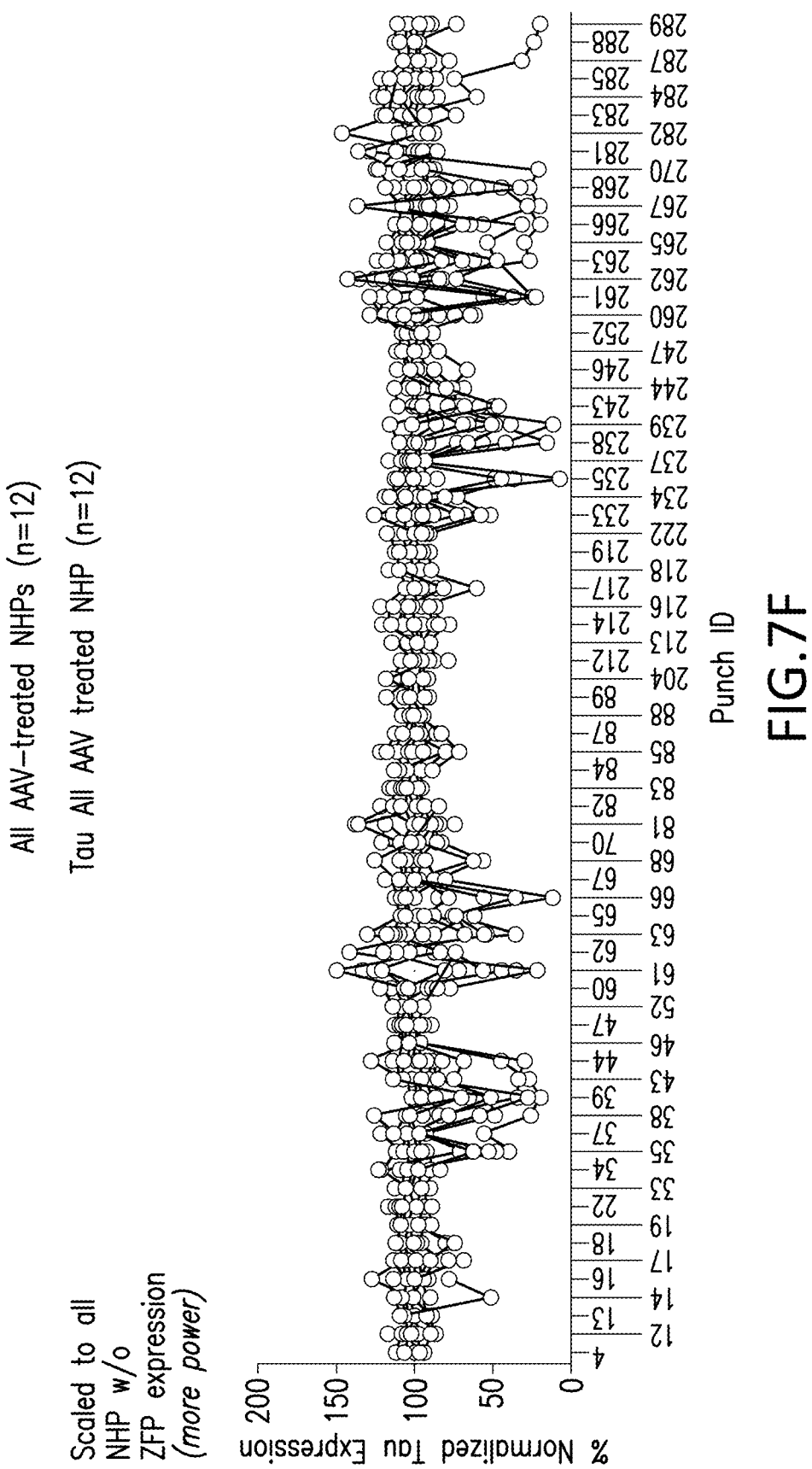
Figure 8A:
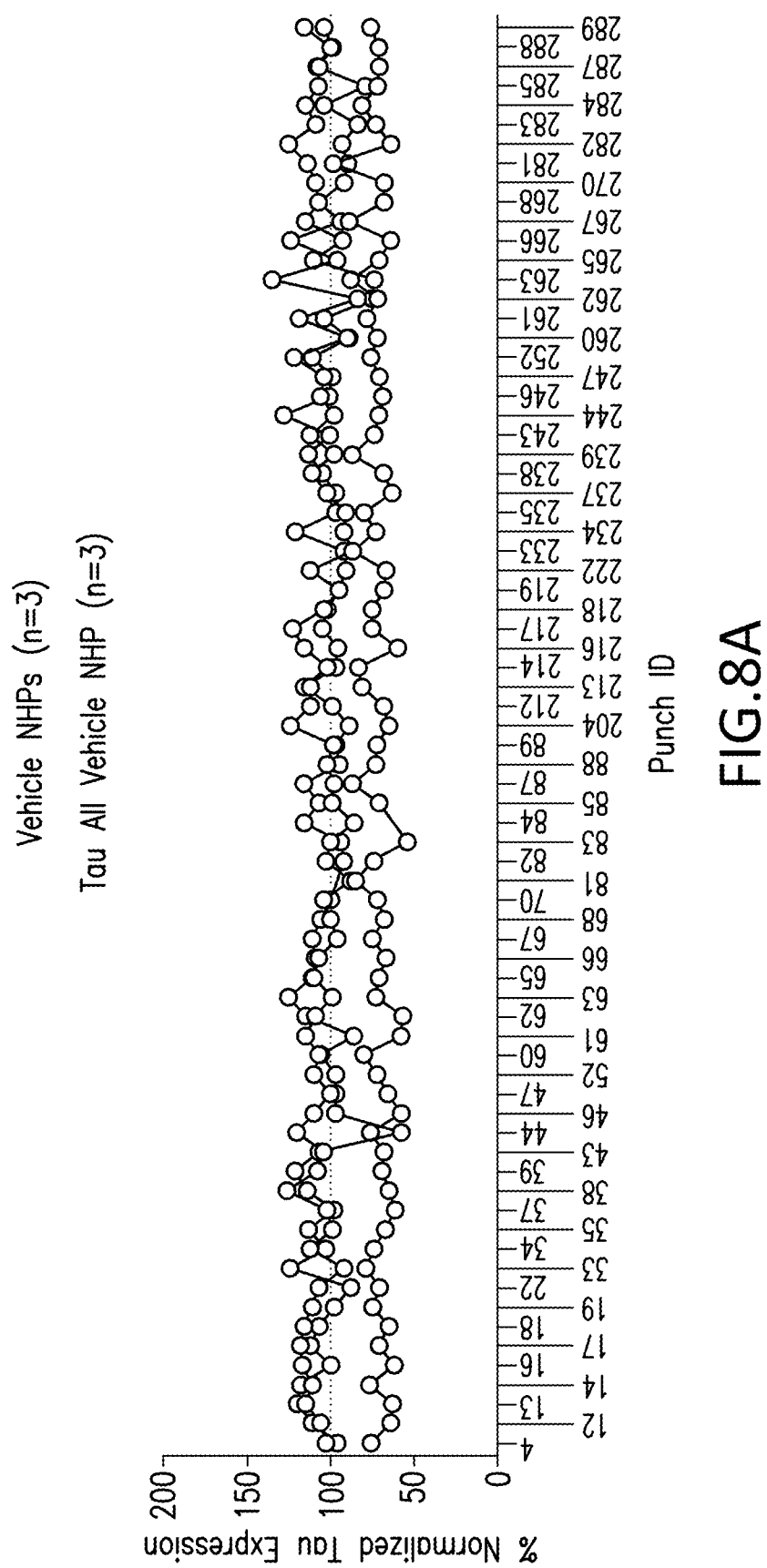
FIG. 8A through FIG. 8D are graphs depicting a composite analysis of tau expression (FIG. 8A and FIG. 8C) and ZFP levels (FIG. 8B and FIG. 8D) in control (FIG. 8A and FIG. 8B) and treated subjects (FIG. 8C and FIG. 8D) using the method of scaling tau expression to the average of the vehicle-treated animals and ZFP-treated animals without detectable ZFP expression.
Figure 8B:
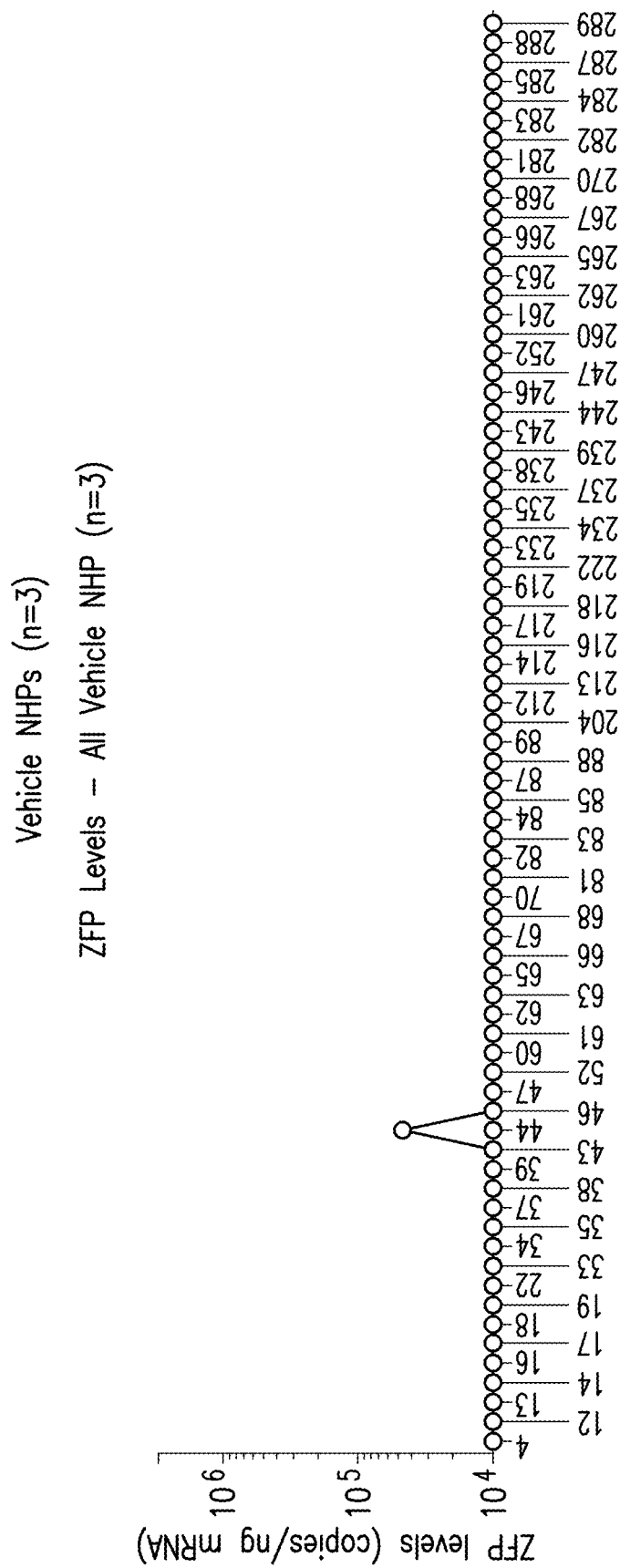
Figure 8C:
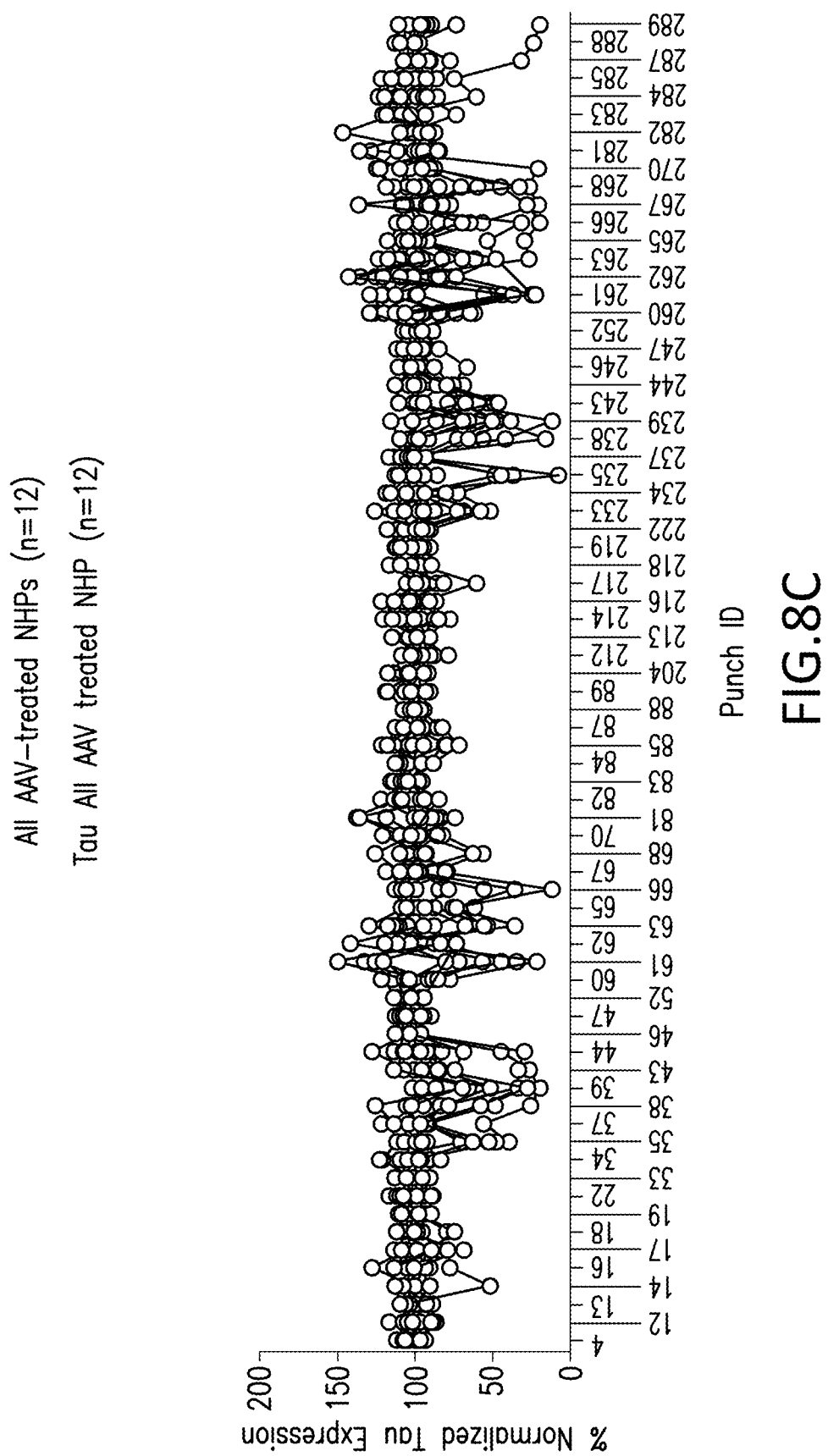
Figure 8D:
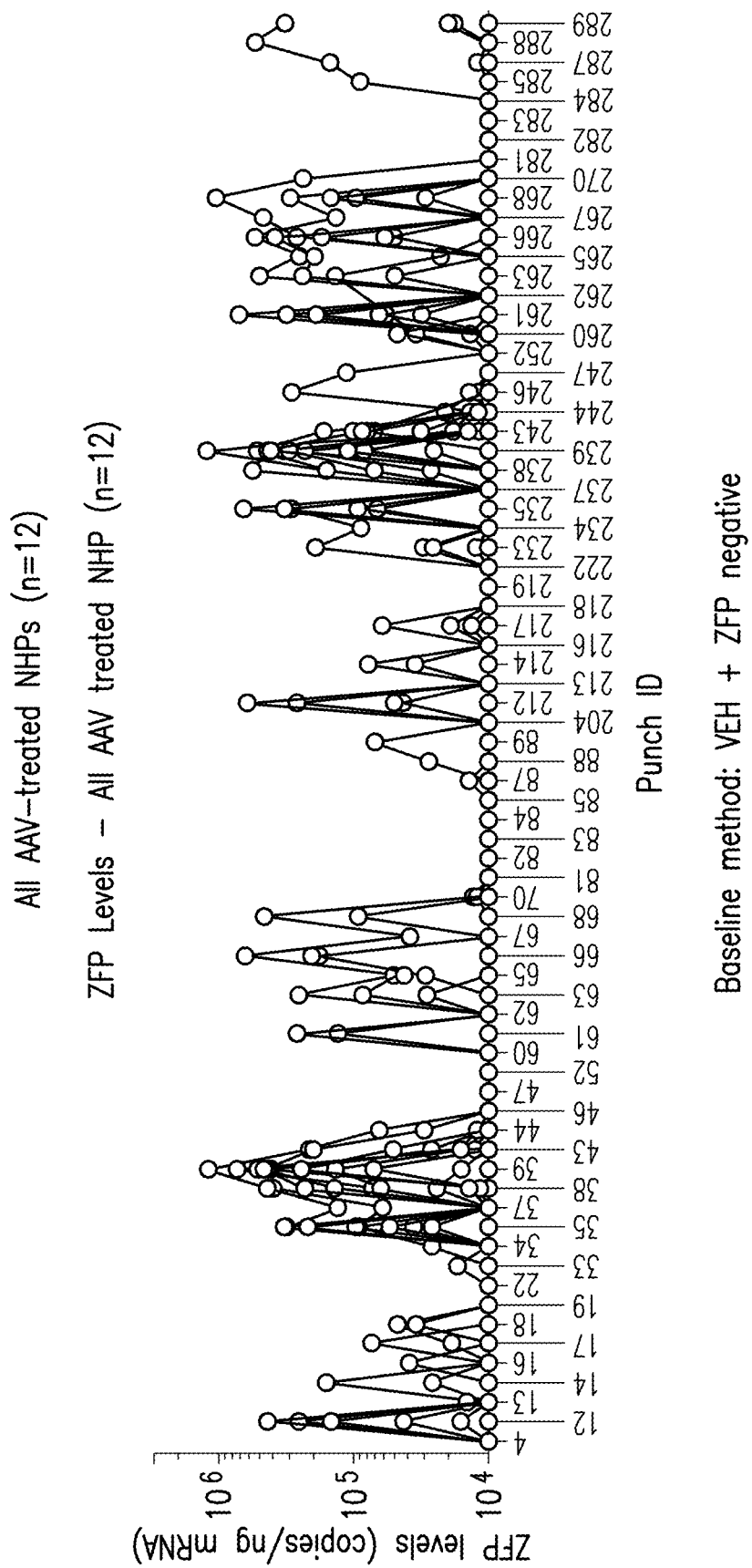

FIG. 7A through FIG. 7F show composite analysis for all punches across all animals evaluating three methods to establish baseline tau levels for a given punch, including no scaling (FIG. 7A and FIG. 7D), scaling to the average of the three vehicle-treated animals (FIG. 7B and FIG. 7E), or scaling to the average tau expression of the vehicle-treated animals and ZFP-treated animals without ZFP expression (FIG. 7C and FIG. 7F). Shown are results from the indicated subjects (vehicle NHP subjects shown in FIG. 7A through FIG. 7C) and all AAV treated subjects (FIG. 7D through FIG. 7F. As shown, scaling by either method better approximates baseline levels across all 15 animals, with the third method (scaling to vehicle- and ZFP-treated NHPs without ZFP expression) being a somewhat better representative of the tau baseline across the 3 vehicle- and 12 ZFP-treated animals in the study.

Figure 9A:
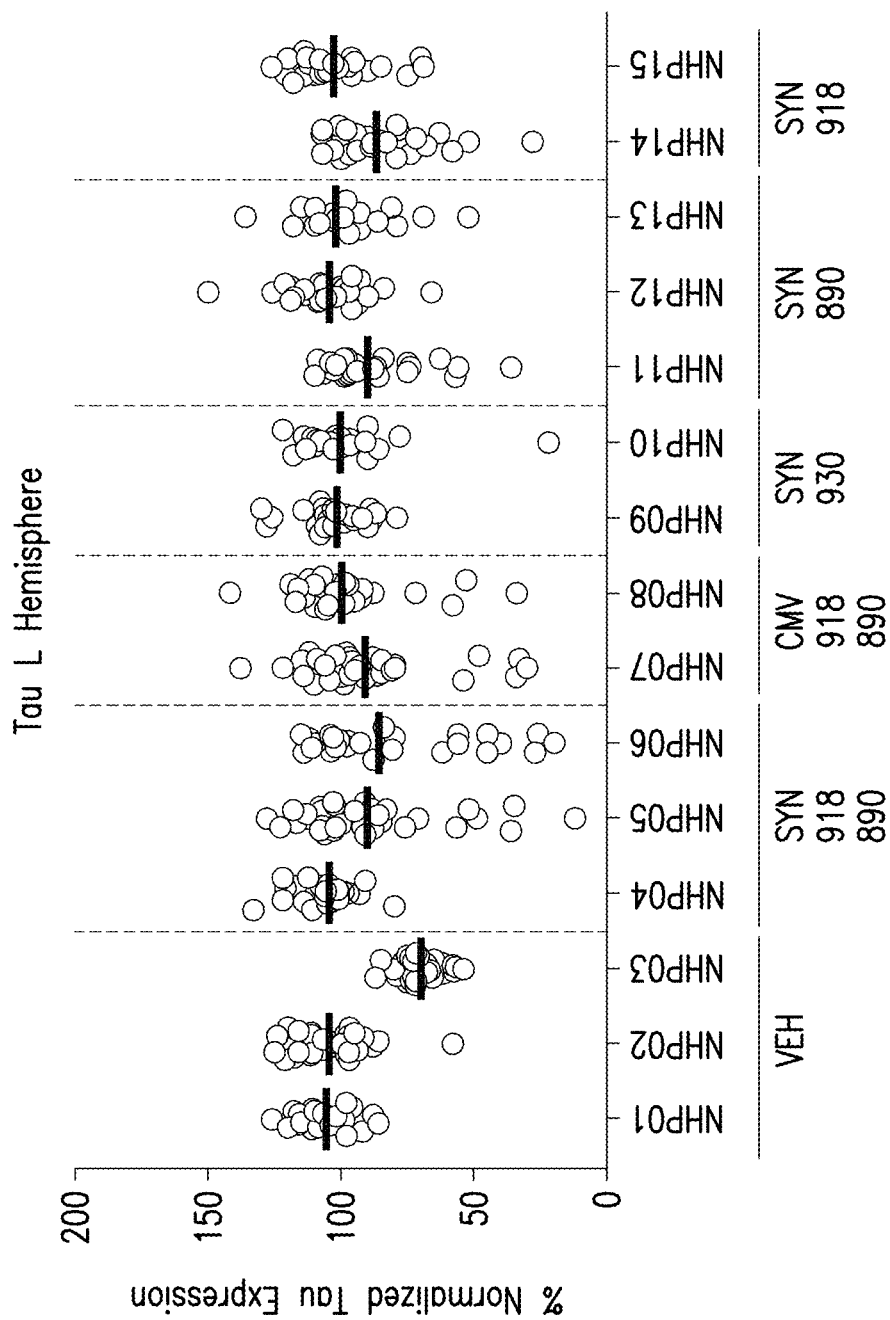
FIG. 9A and FIG. 9B are graphs depicting tau expression in the left (FIG. 9A) and right (FIG. 9B) hemispheres of control and treated subject as indicated. "VEH" indicates control subject who were administered vehicle only; "SYN918-890" refers to subjects receiving AAV vectors encoding the 65918 and 57890 genetic repressors, where expression is driven by a synapsin promoter; "CMV918-890" refers to subjects receiving AAV vectors encoding the 65918 and 57890 genetic repressors, where expression is driven by a CMV promoter; "SYN930" refers to subjects receiving AAV vectors encoding the 57930 genetic repressor, where expression is driven by a synapsin promoter; "SYN890" refers to subjects receiving AAV vectors encoding the 57890 genetic repressor, where expression is driven by a synapsin promoter; and "SYN918" refers to subjects receiving AAV vectors encoding the 65918 genetic repressor, where expression is driven by a synapsin promoter. For this analysis, normalized tau expression was scaled to the average of the tau levels measured from vehicle-treated animals and ZFP-treated animals without detectable ZFP expression for each punch.
Figure 9B:
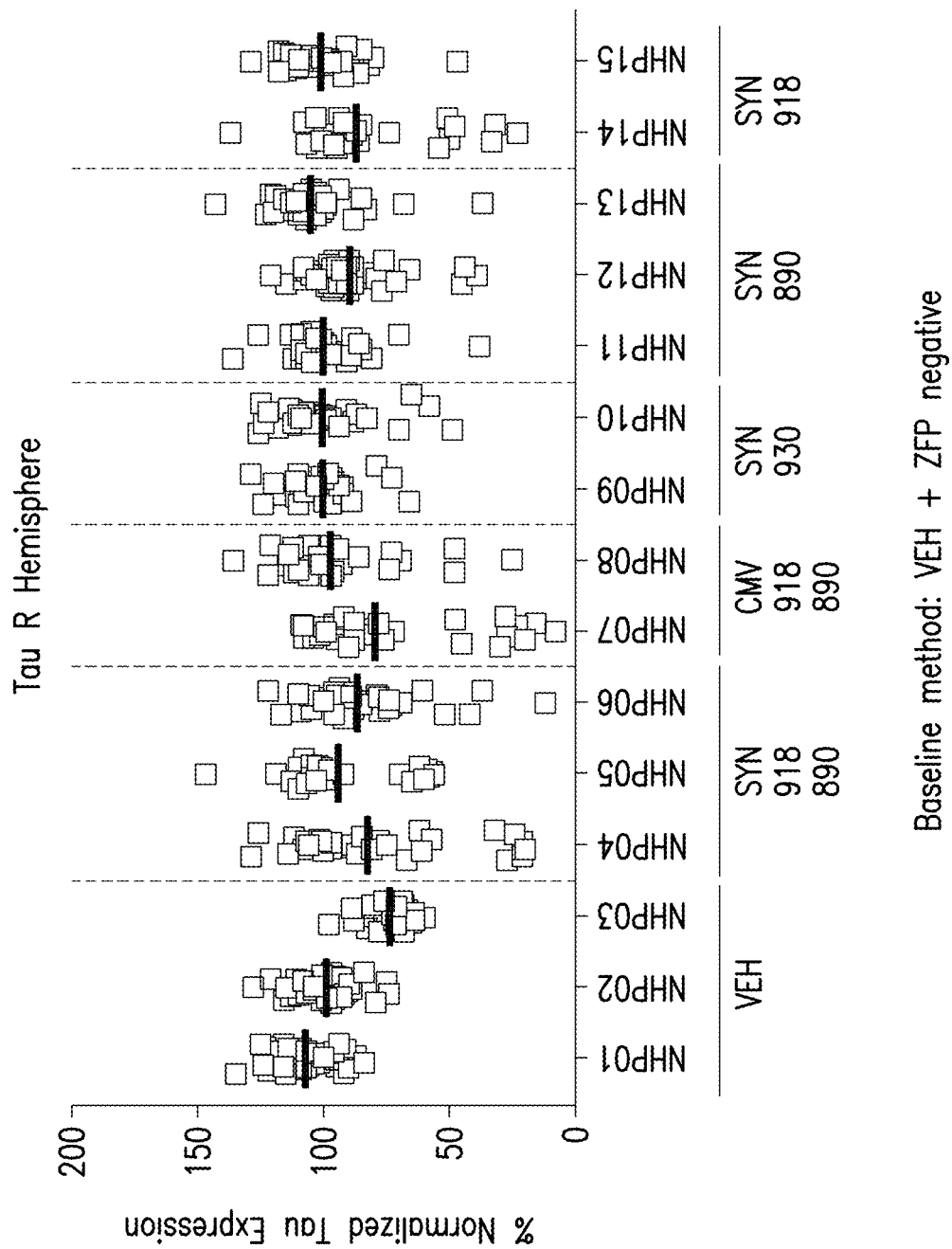
Figure 10A:
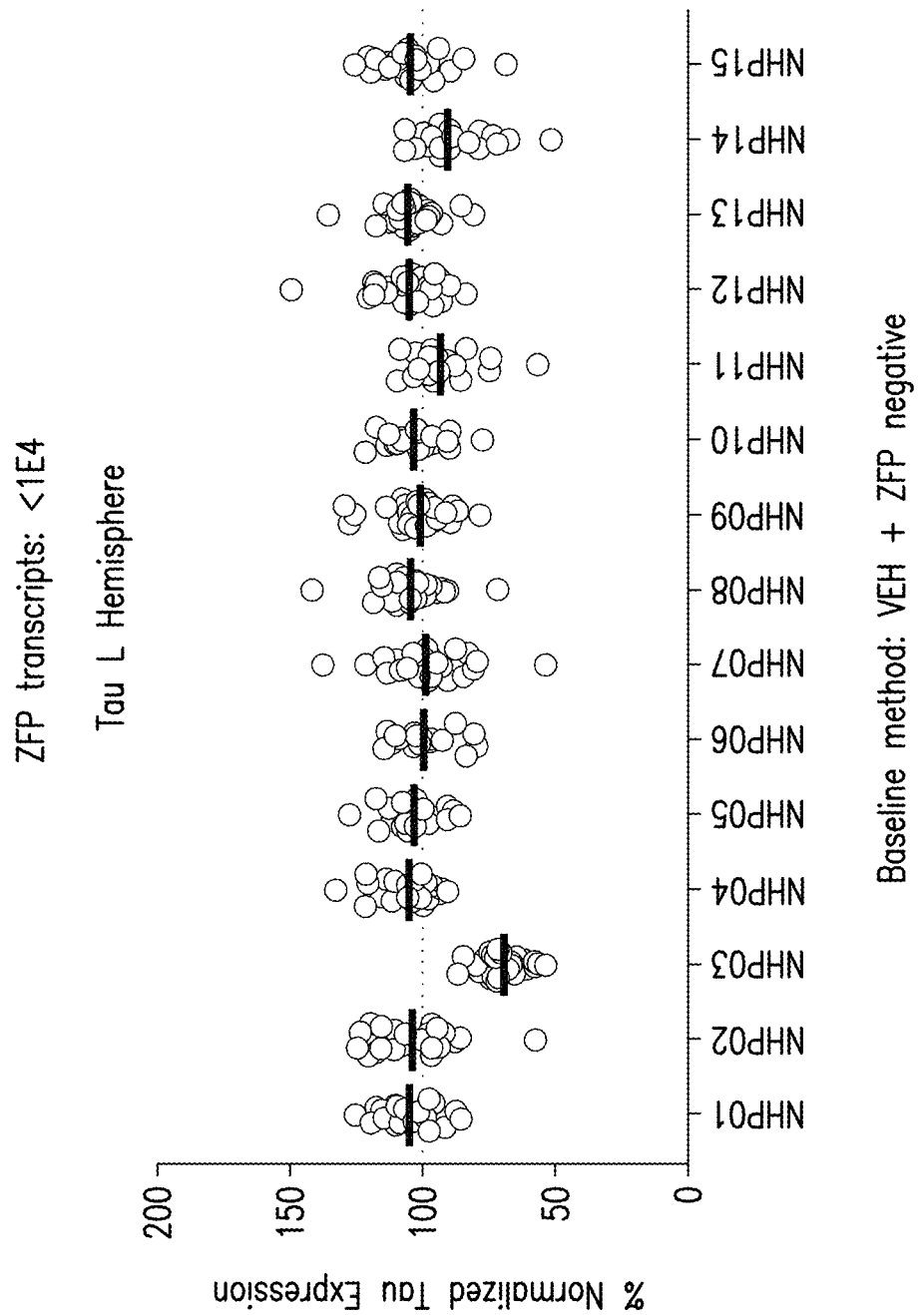
FIG. 10A through FIG. 10F are graphs depicting tau expression levels where ZFP transcript levels in the indicated NHP subjects were less than 1E4 ZFP transcripts (copies/ng mRNA) (FIG. 10A shows levels in the left hemisphere and FIG. 10B shows levels in the right hemisphere); between 1E4 and 1E5 transcripts (copies/ng mRNA) (FIG. 10C shows levels in the left hemisphere and FIG. 10D shows levels in the right hemisphere); and greater than 1E5 transcripts (copies/ng mRNA) (FIG. 10E shows levels in the left hemisphere and FIG. 10F shows in the right hemisphere). For this analysis, normalized tau expression for a given punch was scaled to the average of the tau levels measured from vehicle-treated animals and ZFP-treated animals without detectable ZFP expression.
Figure 10B:
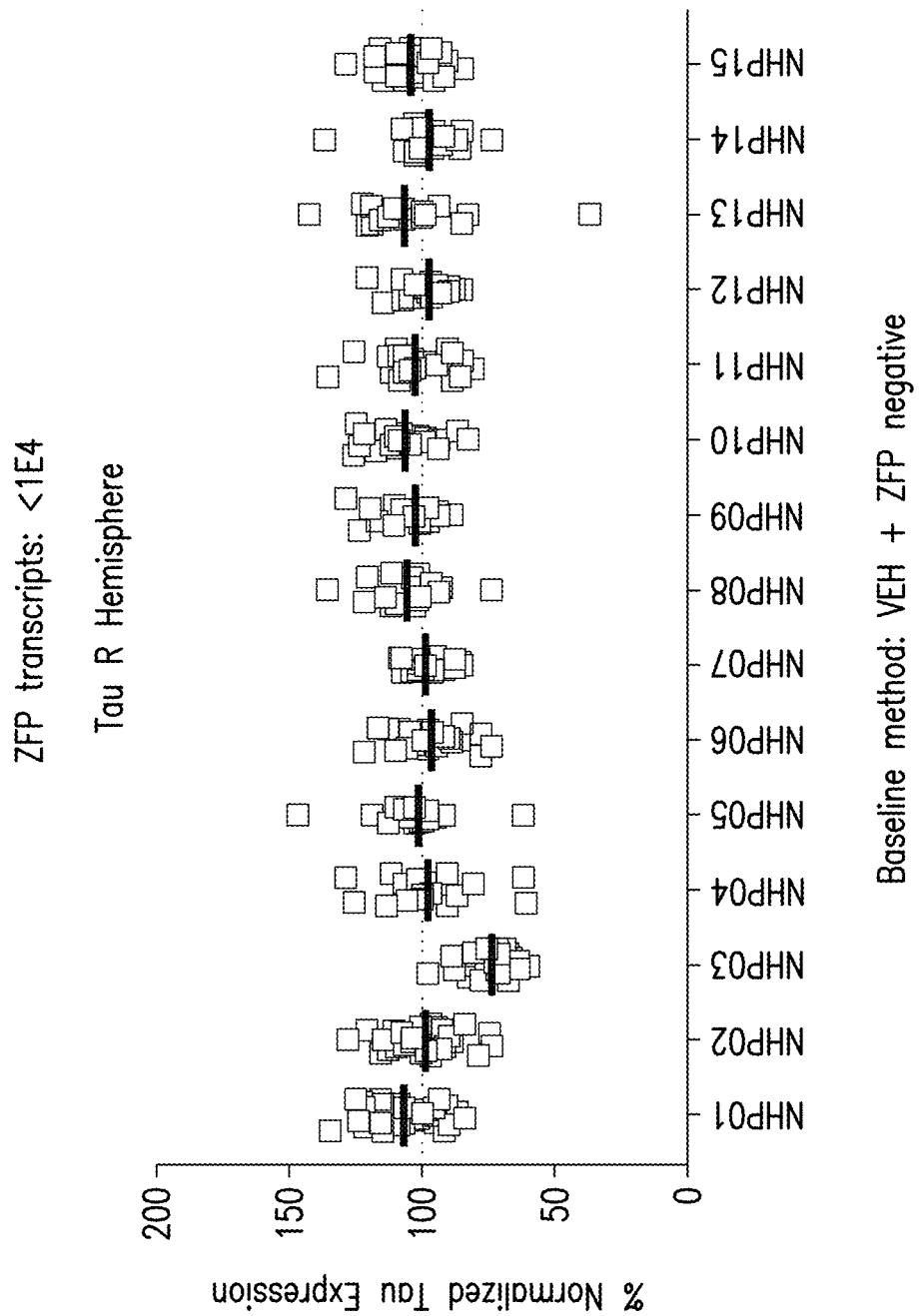
Figure 10C:
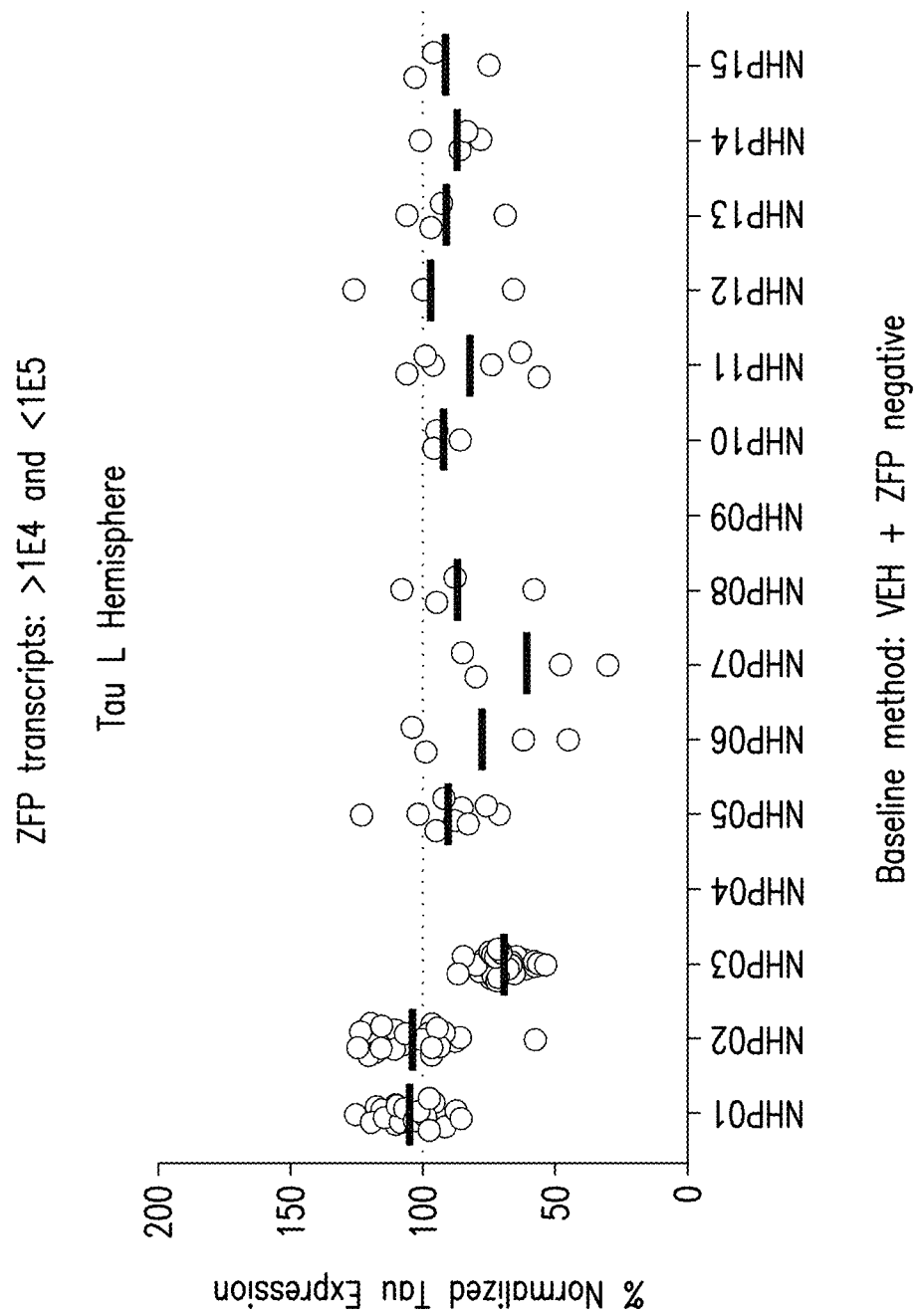
Figure 10D:
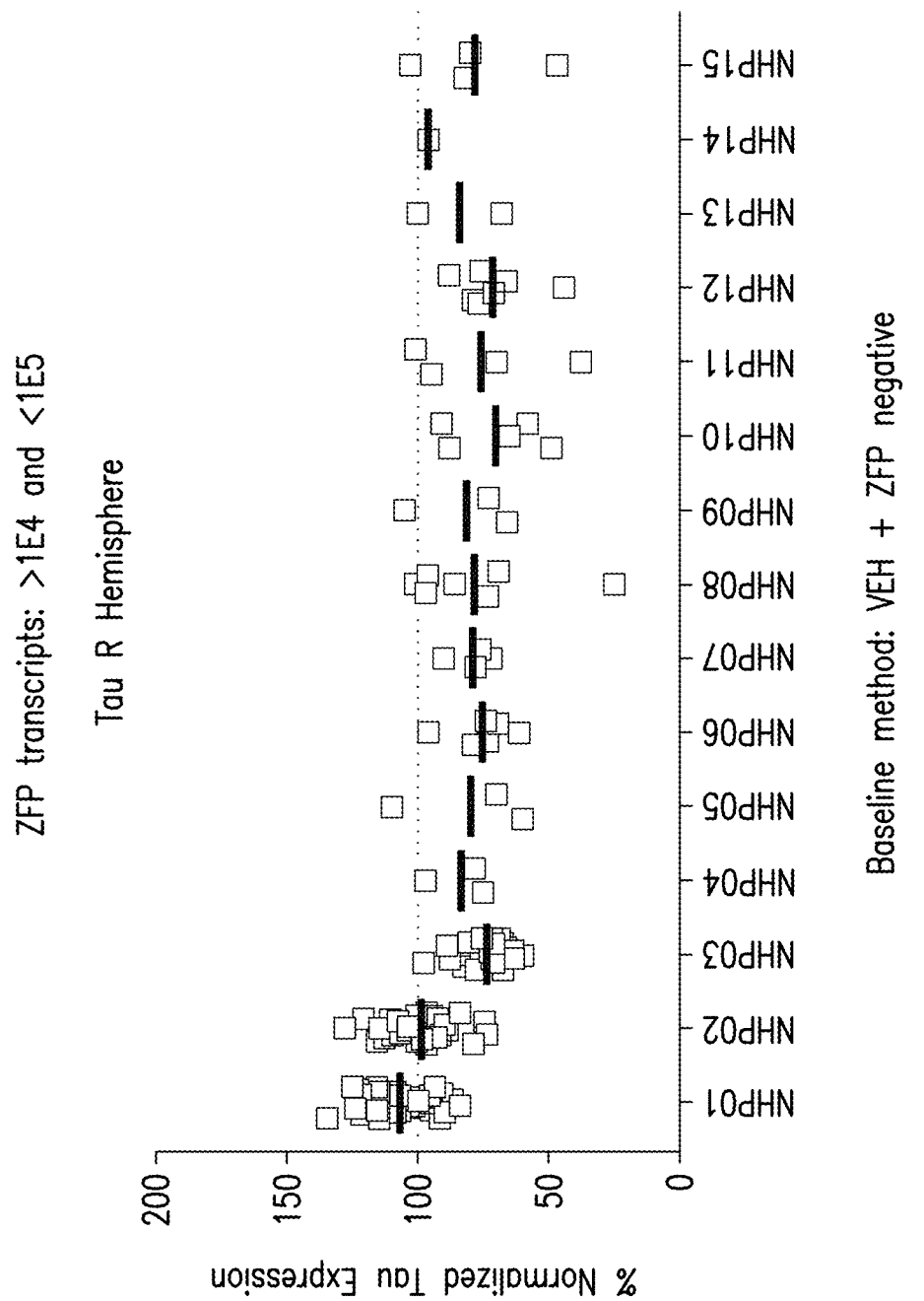
Figure 10E:
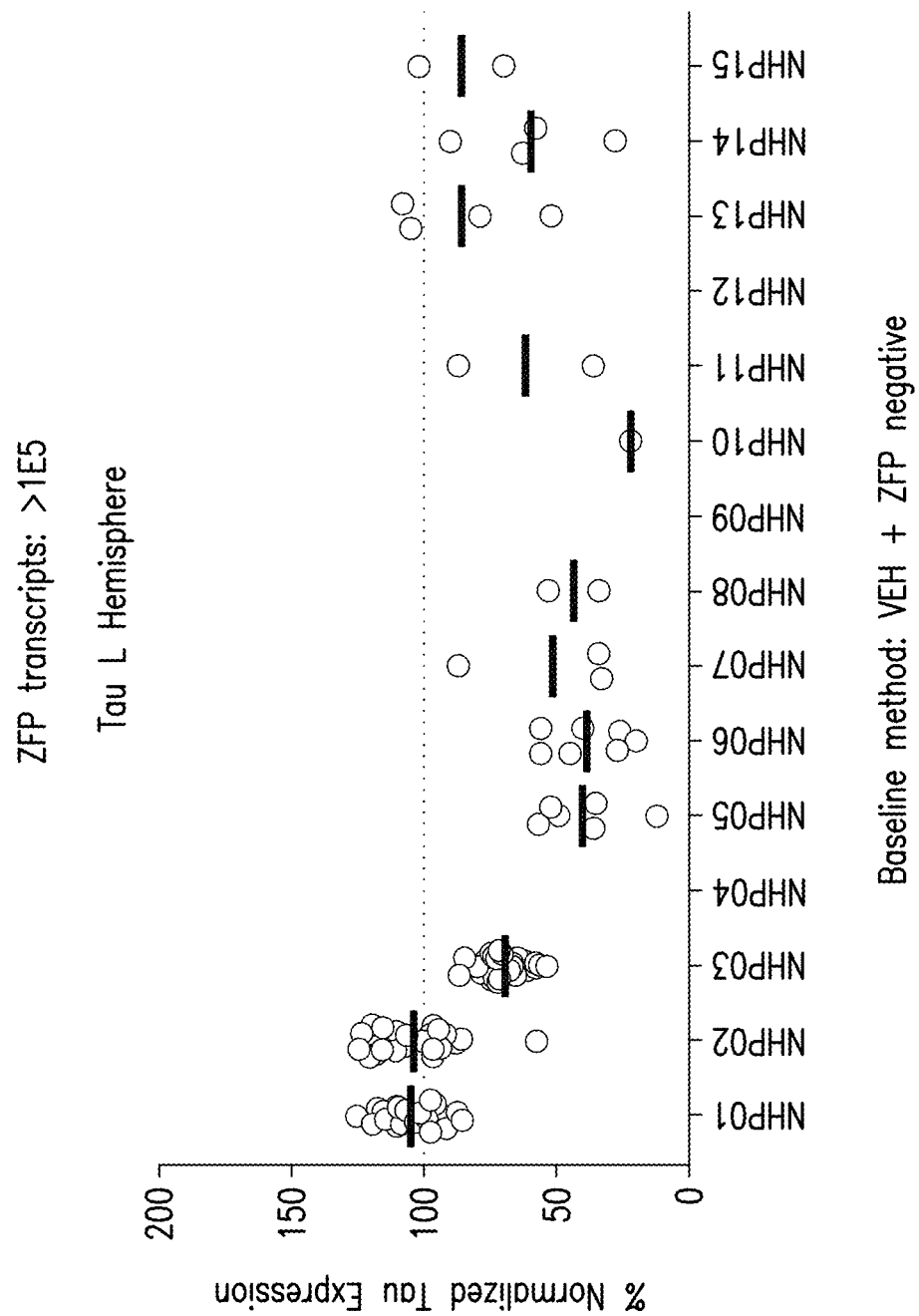
Figure 10F:
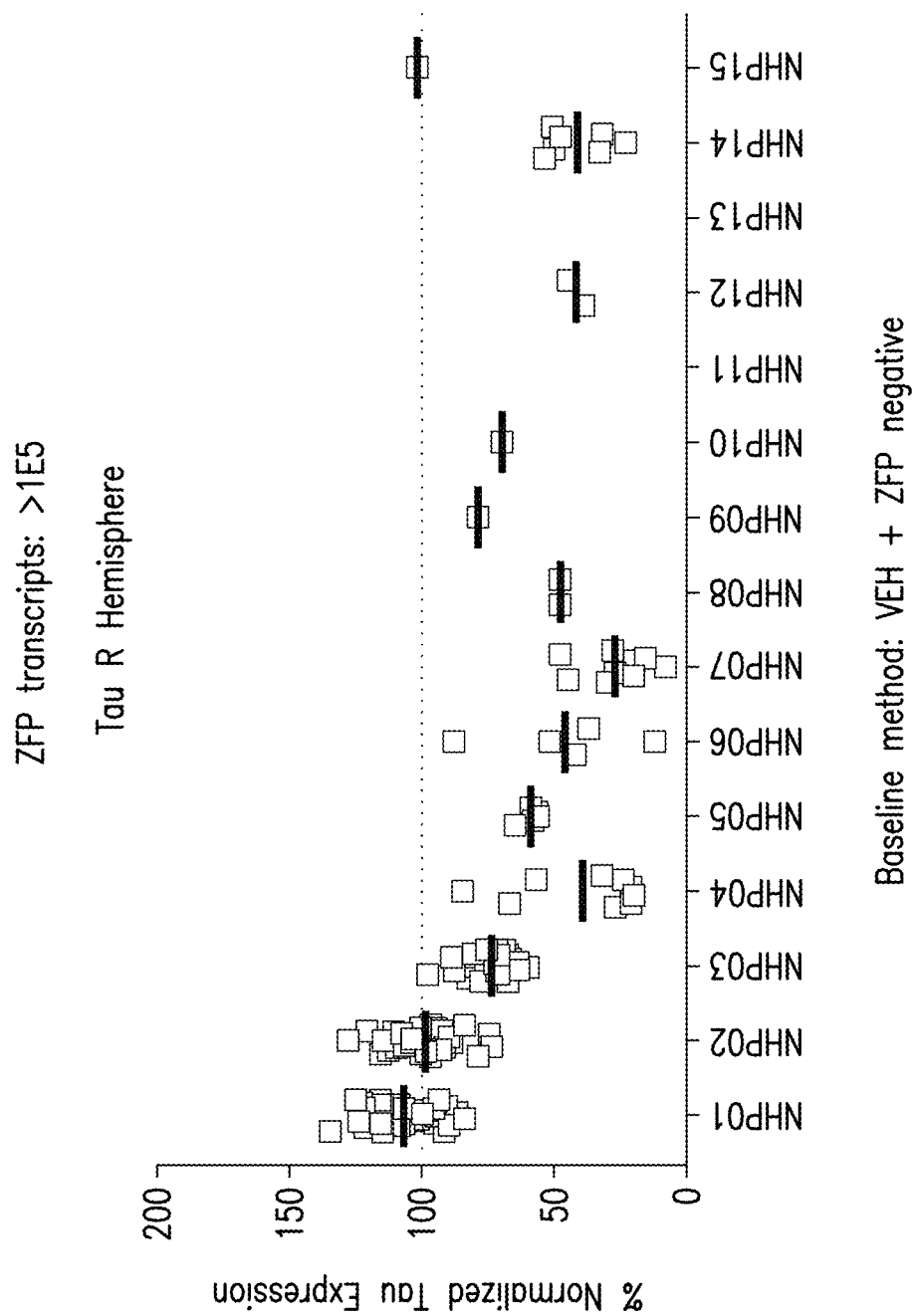
Figure 11A:
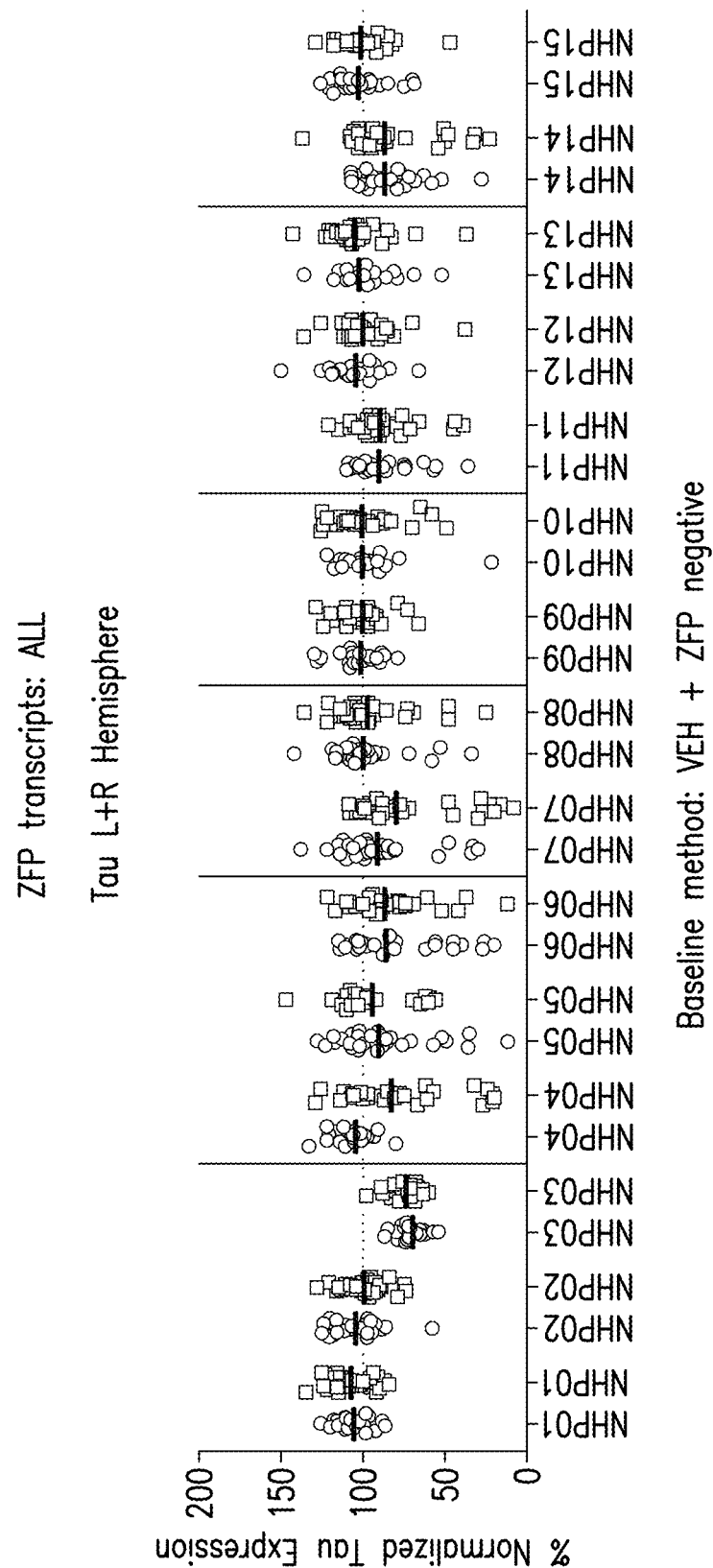
FIG. 11A through FIG. 11D are graphs depicting tau expression levels in the left and right hemispheres where ZFP transcript levels in the indicated NHP subjects are show for ZFP transcript levels (FIG. 11A) were less than 1E4 ZFP transcripts (copies/ng mRNA) (FIG. 11B); between 1E4 and 1E5 transcripts (copies/ng mRNA) (FIG. 11C); and greater than 1E5 transcripts (copies/ng mRNA) (FIG. 11D). For this analysis, normalized tau expression for a given punch was scaled to the average of the tau levels measured from vehicle-treated animals and ZFP-treated animals without detectable ZFP expression.
Figure 11B:
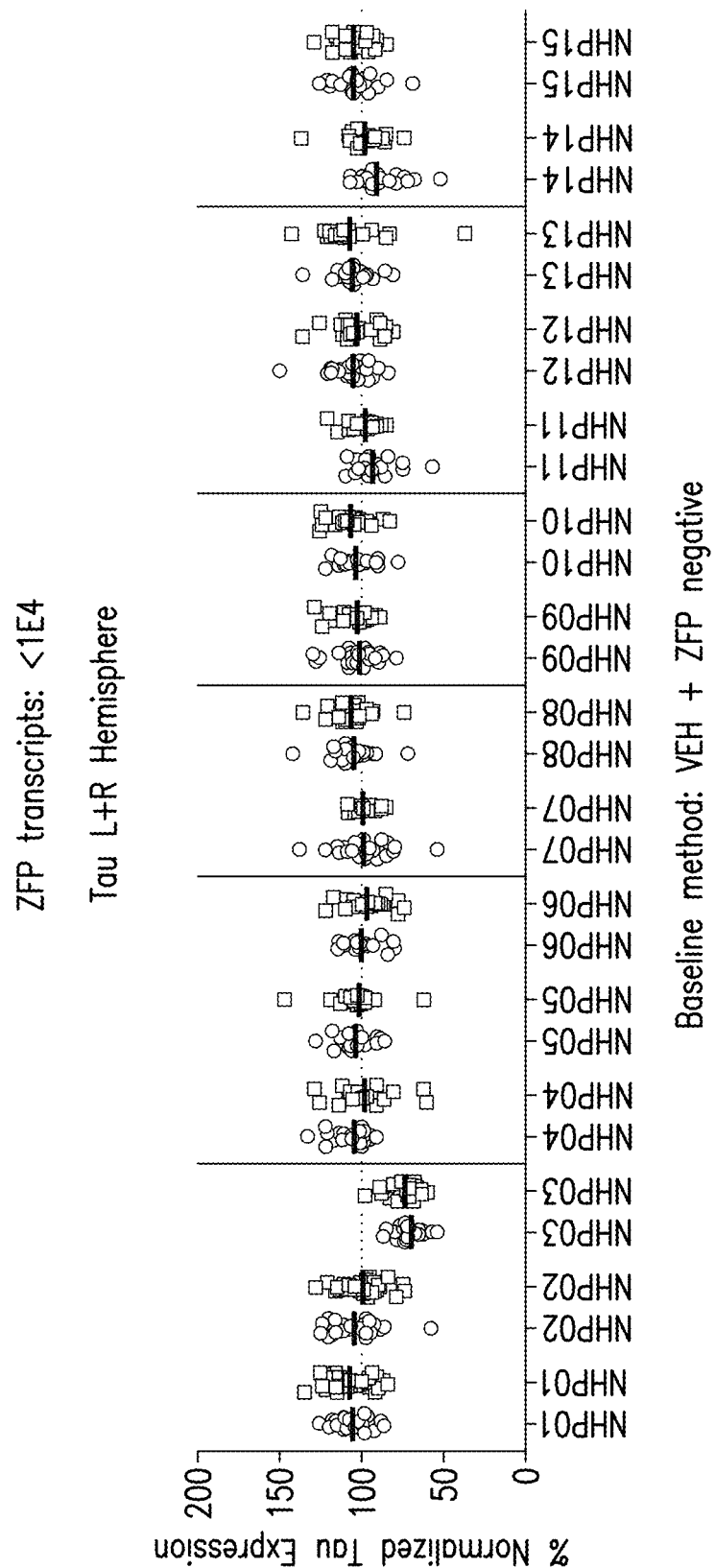
Figure 11C:
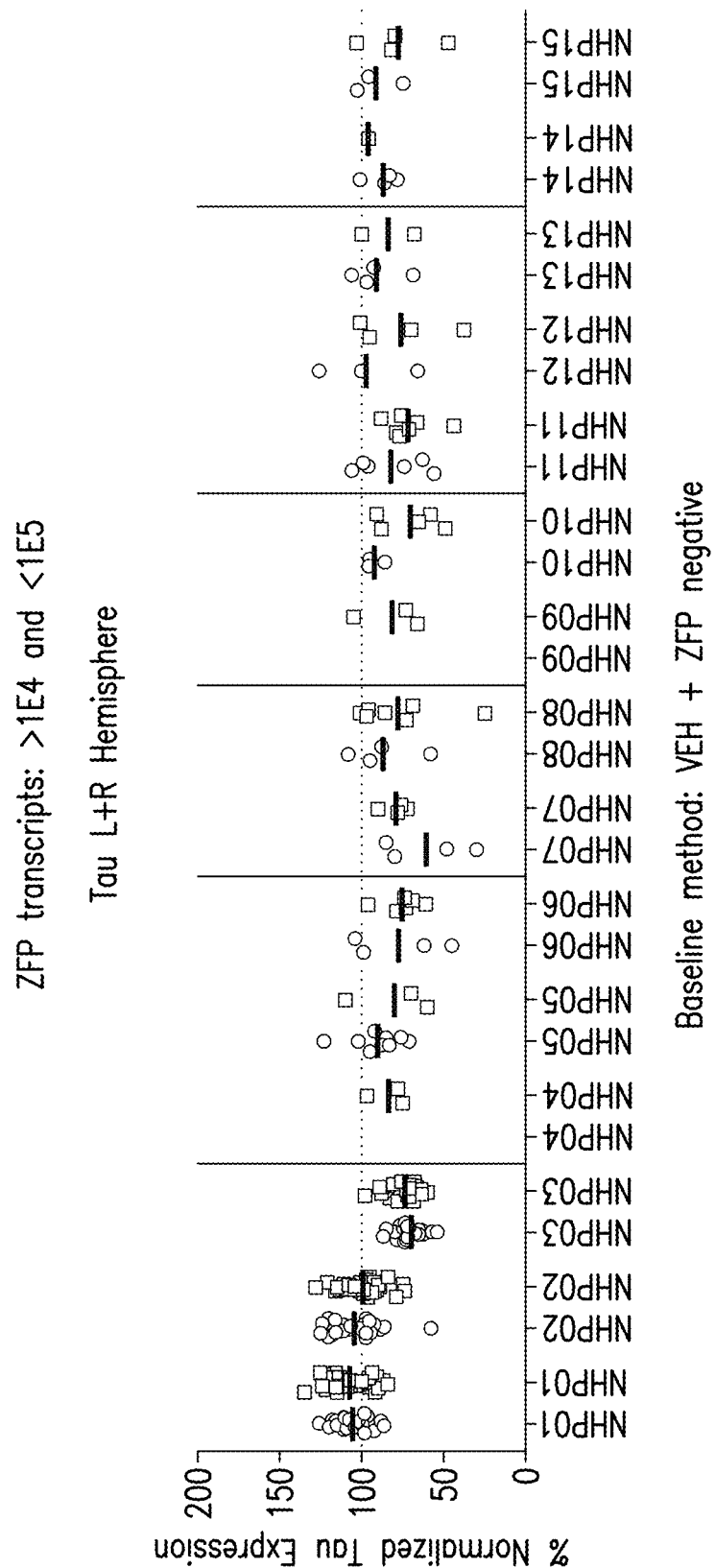
Figure 11D:
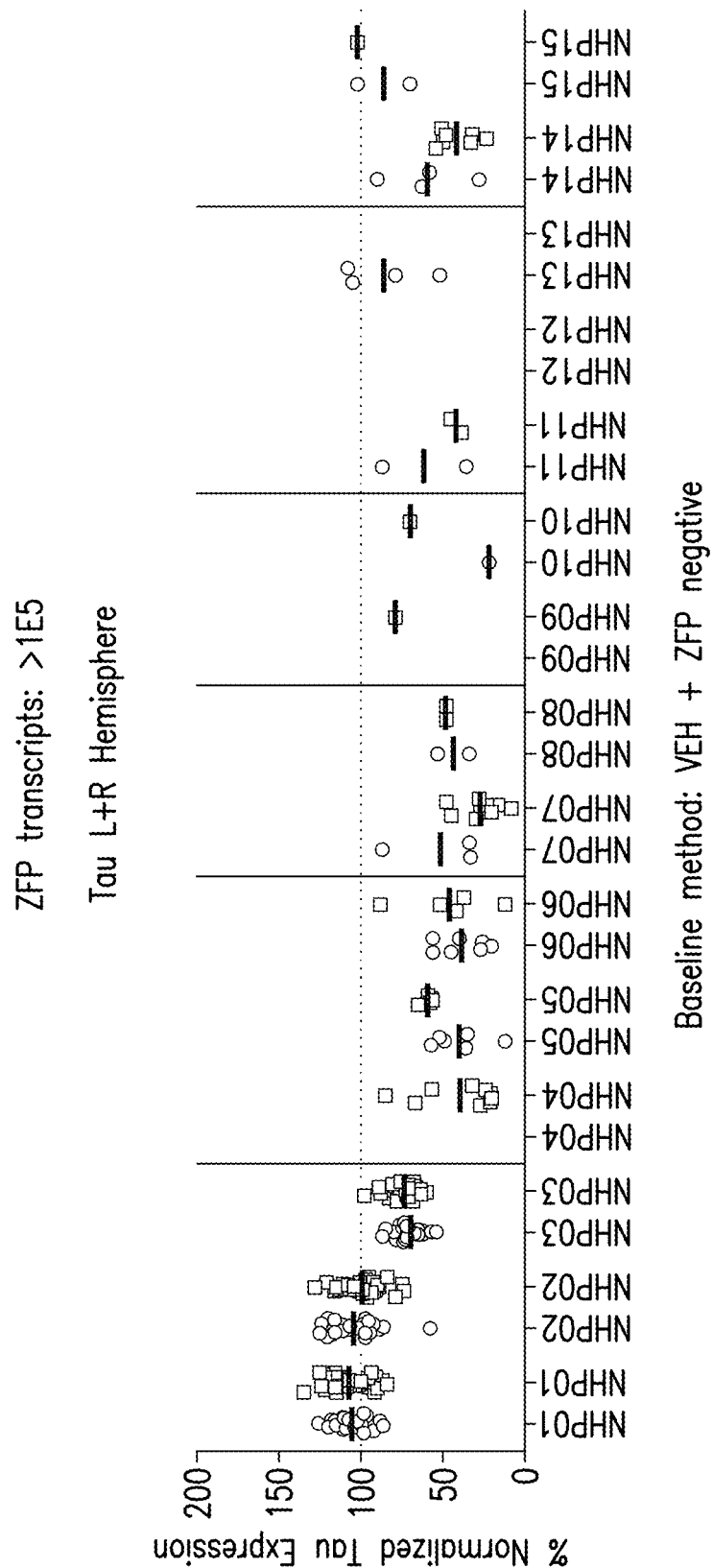

For this analysis, normalized tau expression was scaled to the average of the tau levels measured from vehicle-treated animals and ZFP-treated animals without detectable ZFP expression for each punch. FIG. 8A through FIG. 8D show results from the indicated subjects (vehicle NHP subjects shown in FIG. 8A and FIG. 8B) and all AAV treated subjects (FIG. 8C and FIG. 8D), for both scaled tau expression levels (FIG. 8A and FIG. 8C) and absolute ZFP transcript levels (copies/ng mRNA). FIG. 9A and FIG. 9B show tau expression results from the left and right hemispheres of the indicated subjects. FIG. 10A through FIG. 10F and FIG. 11A through FIG. 11D show results of the indicated animals where less than 1E4 ZFP transcripts were present (FIG. 10A and FIG. 10B, FIG. 11B); between 1E4 and 1E5 ZFP transcripts were present (FIG. 10C and FIG. 10D; FIG. 11C); where greater than 1E5 ZFP transcripts were present (FIG. 10E and FIG. 10F; FIG. 11D) and for all levels of ZFP transcripts (FIG. 11A). As shown, the large majority of punches with low levels of ZFP expression do not have significant tau reduction. However, punches between 1E4 and 1E5 ZFP transcripts/ng mRNA have intermediate tau reduction for some treatments, and those with 1E5 or greater transcripts/ng mRNA have even greater tau reduction.

FIG. 13A through FIG. 13E, FIG. 15A through FIG. 15E and FIG. 17A through FIG. 17E show the percent of normalized tau expression as a function of ZFP levels (transcripts/ng mRNA) in subjects treated as indicated. FIG. 13A through FIG. 13E show results where tau expression is scaled to the average of the Vehicle-treated animals and ZFP-treated animals without detectable ZFP expression; FIG. 15A through FIG. 15E show results where tau expression is scaled to the average of the vehicle-treated animals only; and FIG. 17A through FIG. 17E show results where tau expression was not scaled to adjust to a baseline tau level. Regardless of scaling method, the data indicate that there is a significant correlation between ZFP expression level and tau reduction for 4 of the 5 ZFP treatments, namely AAV SYN1.65918-57890, AAV CMV. 65918-57890, AAV SYN1.57890, AAV SYN1.65918. The greatest degree of tau reduction was achieved with the AAV SYN1.65918-57890 and AAV CMV.65918-57890 treatments, with some punches exceeding >80% tau reduction.

Figure 12:
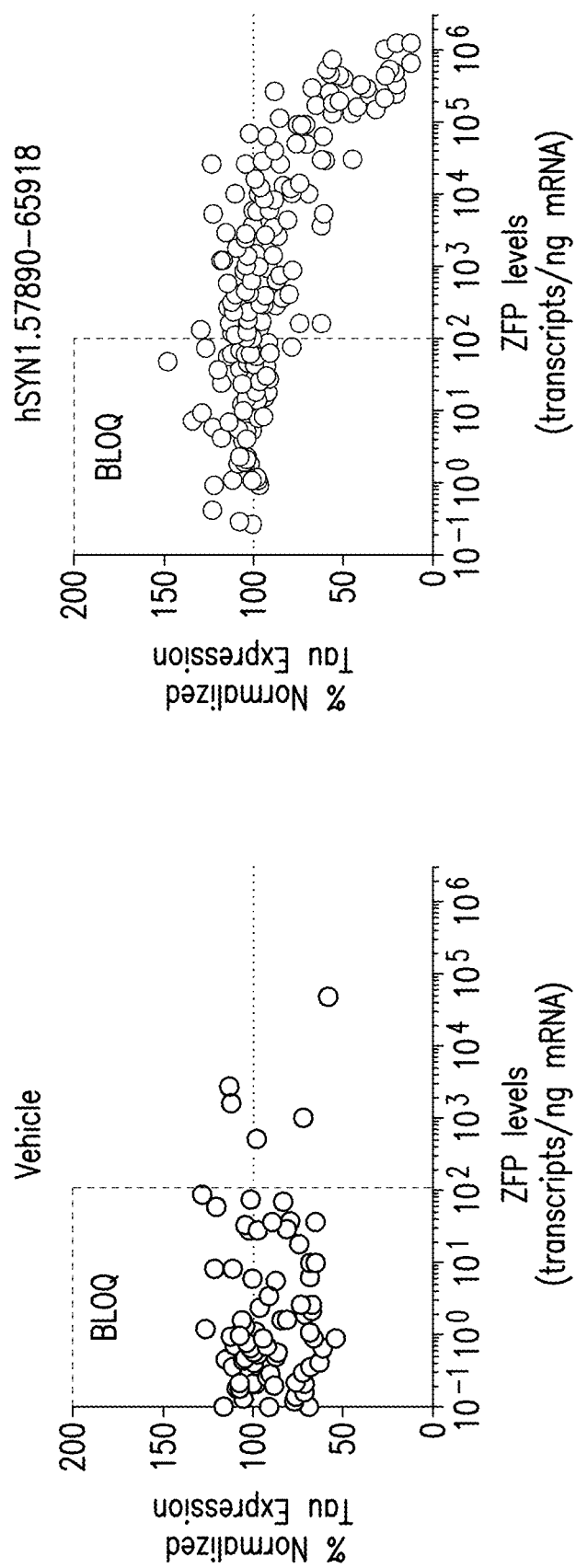
FIG. 12 are graphs depicting correlation plots showing tau expression and ZFP transcript levels in control subjects (left panel-"Vehicle") and subjects treated with AAV vectors encoding the 65918 and 57890 genetic repressors, where expression is driven by a synapsin promoter ("hSYN1.5789-65918"). The limit of the ZFP qRT-PCR assay for absolute quantitation is approximately 1E2 transcripts/ng mRNA which is indicated by Below Limit of Quantitation (BLOQ).

FIG. 12, FIG. 14 and FIG. 16 show tau expression vs. ZFP level correlation plots for NHP subjects treated with either vehicle (left panel) or AAV vectors encoding 57890 and 65918 ZFP-TF repressors whose expression is driven by the synapsin 1 promoter (right panel). The limit of the ZFP qRT-PCR assay for absolute quantitation is approximately 1E2 transcripts/ng mRNA which is indicated by Below Limit of Quantitation (BLOQ). FIG. 12 shows results where tau expression is scaled to the average of the vehicle-treated animals and ZFP-treated animals without detectable ZFP expression. FIG. 14 shows an analysis where tau expression levels are scaled to the average of the three vehicle-treated animals. FIG. 16 shows an analysis where tau expression levels were not scaled to correct for tau baseline levels. As shown repression of tau was correlated to amount of ZFP-TF present.

Example 2: Tau Repression in Humanized Tau Mouse Model

Tau reduction in the P301L mutant human tau (P301L) transgenic mouse model of tauopathy (rTg4510, Jackson Labs) and the hTau mouse model (B6.Cg-Mapt$^{tm1(EGFP)}$ $_{Kit}$Tg(MAPT)8cPdav/J, Jackson Labs) was also assessed following administration of genetic repressors as described herein. hTau mice express WT human MAPT gene and, further, the endogenous (mouse) Mapt gene knocked out and replaced with a GFP expressing construct. Treatment groups were as shown in the following Table:

| Treatment | RoA* | Dose | No. of mice | Time Point |
|---|---|---|---|---|
| Vehicle (PDS) | Ipa** (hippocampus) | 0 | 6 | 6 wk |
| AAV9.hSYN1.57890 | IPa (hippocampus) | 3E10 | 5 | 6 wk |
| AAV9.hSYN1.65918-T2a-57890 | IPa (hippocampus) | 3E10 | 6 | 6 wk |

*Route of Administration
**Intraparenchymal (Ipa)

Endpoints measured were as follows: ZFP and Tau mRNA expression levels by RT-qPCR; GFAP, Iba1, NeuN mRNA expression levels by RT-qPCR; Saitohin (STH) mRNA expression levels by RT-qPCR (STH is a protein-encoding gene in apes and humans that is nested in the intron between exons 9 and 10 of the human tau gene, see, e.g., Conrad et al. (2002) Proc Natl Acad Sci USA. 99 (11): 7751-7756.); and tau protein levels.

As shown in FIG. 18A through FIG. 18D, the synergistic pairing of 57890 and 65918 (AAV9.hSYN.65918-T2a-57890) resulted in ZFP expression levels that were at least 2-fold higher than 57890 (AAV9.hSY1.57890) alone. See, FIG. 18A. In addition, in humanized tau mice administered the construct encoding 57890 and 65918, human tau mRNA was repressed by approximately 90% repression as compared to ~60% repression in mice administered the construct encoding only 57890 (mouse tau mRNA expression was repressed by ~87% by 57890 and 65918 combination and ~81% by 57890). See, FIG. 18B. Similar results were obtained following RT-qPCR analysis of human Saitohin (hSTH), with repression by the synergistic combination of 57890 and 65918 at ~88% as compared to ~68% using 57890 alone. See, FIG. 18C. IBA1 and GFAP levels were elevated in both treatment groups as compared to control but NeuN levels were not significantly different between groups. See, FIG. 18D.

In addition, the clinical and therapeutic effectiveness of the repressors is further evaluated in this and other mouse models of AD (e.g., APPswe/PS1d9, Jackson Labs) to determine whether there is a reduction in biomarkers and symptoms of tauopathies, including by one or more the following: RNAscope ISH analysis (single cell analysis of ZFP, human tau, and mouse tau, see, e.g., Carstens et al. (2016) *J Neurosci.* 36 (23): 6312-6320); IHC ZFP/tau analysis (see, e.g., Zeitler et al. (2019) *Nature Medicine* 25:1131-1142); neurotoxicity, gliosis, dystrophic neurites, spine loss, excitotoxicity, cortical and hippocampal shrinkage, dendritic tau accumulation, cognitive (e.g., the radial arm maze and the Morris water maze, fear conditioning, etc.), and motor deficits. See, e.g., Bryan et al., (2009) *Chapter* 1: Transgenic Mouse Models of Alzheimer's Disease: Behavioral Testing and Considerations in Methods of Behavior Analysis in Neuroscience. 2nd edition, ed. Buccafusco, Boca Raton (FL): CRC Press/Taylor & Francis. Additionally, chemically induced seizure models, for example, wild-type mice treated with excitotoxic compounds such as pentylenetetrazole (PTZ, see e.g. Myers et al. (1975) *Epilepsia* 16 (2): 257-67) or kainate (Ferraro et al. (1997) *Mamm Genome* 8:200-208, are also assessed at 4-8 weeks following administration of genetic repressors as described herein, to determine whether tau reduction confers a protective effect against seizure, including, fatality related to seizure, prolonged latency to seizure, and/or reduction in seizure severity.

Example 3: Neuroinflammatory Responses

Primates treated in vivo with MAPT repressor ZFP-TFs were also evaluated for the expression levels of microglial and astrocyte markers. In particular, punches as described in Example 1 were evaluated using RT-qPCR reagents for IBA1 and GFAP expression. In addition, levels of the E1F4A housekeeping gene was also evaluated in treated primates. Briefly, brain punches were transferred to 1.5-mL Eppendorf tubes containing 0.6 mL TRI reagent (Thermo Fisher) and two 3.2-mm steel beads (BioSpec Products) on ice.

The tissue was lysed using a Qiagen TissueLyser at 4° C. using the following parameters: 5 cycles, 90 s duration, 25.1 frequency. After brief centrifugation, 70 μL of 1-bromo-3-chloropropane was added to each sample at RT. The samples were vortexed for 10 s, centrifuged at 12,000×g for 10 min at 4° C., and 120 μL of the aqueous phase from each sample was transferred to wells of a 96-well plate. Sixty microliters of isopropyl alcohol and 12 µL of MagMax magnetic beads (Thermo Scientific) were added to each sample well containing the aqueous phase samples. A Kingfisher 96 robot (Thermo Scientific) and the MagMax kit (Thermo Fisher) were used to isolate RNA from the tissue lysate following the manufacturer's instructions. One hundred microliters of the eluted RNA were separated from the magnetic beads using a magnetic stand.

RNA yield and quality were evaluated using a Nanodrop 8000 instrument (Thermo Scientific). cDNA was prepared using the High-Capacity cDNA Reverse Transcription Kit (Applied Biosystems), with 10 µL of RNA and 10 µL of RT Master Mix (10× RT buffer, 10× random primer, 25× dNTP mix, Multiscribe enzyme, and RNAse-free water) for all samples. Reverse transcription was performed on a C1000 Touch Biorad thermal cycler using the following program: 25° C. for 10 min, 37° C. for 120 min, 85° C. for 5 min, and hold at 4° C. qRT-PCR was performed using Biorad CFX384 thermal cyclers. cDNA was diluted 10-fold in nuclease-free water, and 4 µL of diluted cDNA were added to each 10 µL PCR reaction. Each sample was assayed in technical quadruplicate. Custom Taqman primer: probe assays were used in this study. 2× Fast Multiplex PCR (Qiagen) master mix was used for the tau/EIF4a2/ATP5b triplex assay, and SsoAdvanced Universal Probes Supermix (Biorad) was used for the other assays. The qPCR cycling conditions were as follows: Qiagen Fast Multiplex master mix ->95° C. for 5 min, 95° C. for 45 s, 60° C. for 45 s, plate read, 40 cycles; Biorad SsoAdvanced master mix->95° C. for 90 s, 95° C. for 12 s, 60° C. for 40 s, plate read, 42 cycles.

As shown in FIG. 19A through FIG. 19K, IBA1 and GFAP analysis showed no ZFP-dependent elevation in microglial or astrocyte marker levels in any of the primates treated with AAV constructs including the synapsin promoter. However, primates treated with AAV construct including the CMV promoter showed elevated astrocyte marker levels. Thus, no ZFP-dependent neuroinflammatory responses were observed when constructs comprising the neuronal-specific Synapsin promoter were administered to the primates.

In addition, as shown in FIG. 20A through FIG. 20D, no major bulk effect for IBA1 (FIG. 19A through FIG. 19F) or GFAP (FIG. 19G through FIG. 19K) was observed for any treatment group.

Furthermore, as shown in FIG. 21A through FIG. 21E, there was no correlation between the levels of a housekeeping gene (EIF4A2) and ZFP expression in primates treated with ZFP MAPT repressors. Any toxicity due to ZFP expression or tau reduction would be accompanied by a drop in E1F4A2 levels as ZFP levels increased.

Thus, synergistic tau repressors as described herein efficiently repress tau (up to 90% or more as compared to controls) in vivo without eliciting neuroinflammatory responses.

Example 4: Tau Protein Levels

Tau protein levels are also tested cells and subjects receiving the repressors described herein.

Briefly, neurons (derived from induced pluripotent stem cells) were administered by AAV vectors as described above and tau protein levels in the cells or punches taken from the treated subjects were evaluated by ELISA using standard techniques. Briefly, neurons derived from human IPSCs were administered via AAV6 vectors encoding single ZFPs or the synergistic 65918/57890 combination at a dose of 1E5 VG per cells (n=4 replicates). Cells were cultured for 32 days and evaluated for tau protein levels by ELISA using standard techniques.

As shown in FIG. 22, the ratio of tau to total protein in human iPSC-derived neurons was significantly reduced in cells treated with tau repressors as described herein. In particular, the 57930 repressor alone reduced tau protein expression by more than 5-fold as compared to control; the 57890 repressor alone reduced tau protein expression by 2-fold; the 65918 repressor alone reduced tau expression by more than 2-fold; and the synergistic 65918-57890 reduced tau protein expression by more than 10-fold as compared to control. Tau protein levels were also evaluated in the CSF and/or brain homogenates of humanized tau mouse models treated as described in Example 2 above using standard ELISA (Thermo). A 50% reduction of the human tau protein was seen at 6 weeks with the 65918-57890 synergy pair as compared to the control (vehicle). The 65918-57890 pair also reduced human tau protein levels as compared to animals administered 57890 alone. Furthermore, tau protein levels are further reduced at later timepoints in animals, including 8-12 weeks or more after treatment.

Thus, tau repressors as described herein reduce tau protein levels in vitro and in vivo.

The studies demonstrate that the tau ZFP-TF reagents repress tau expression (including at therapeutic levels) in a primate brain.

All patents, patent applications and publications mentioned herein are hereby incorporated by reference for all purposes in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A composition comprising a first and a second zinc finger protein transcription factor (ZFP-TF) that repress MAPT expression,
wherein the first and the second ZFP-TFs bind to capitalized nucleotides in tgGTGCTGGAGCTGGTGGGTggcggaga (SEQ ID NO: 1) and cgGCAGAAGGTGGGcGGTGGCggcggcg (SEQ ID NO: 2),
wherein binding of the first and the second ZFP-TFs that bind to SEQ ID NO: 1 and SEQ ID NO: 2 results in synergistic-repression of MAPT gene expression and wherein
(A) the DNA-binding domain of the first ZFP-TF comprises six zinc finger regions F1 to F6 comprising (i) SEQ ID Nos: 8-13, respectively, and (ii) an R-to-Q substitution at the −5 position of F1 and F5; and
(B) the DNA-binding domain of the second ZFP-TF comprises six zinc finger regions F1 to F6 comprising (i) SEQ ID NOs: 3, 4, 5, 6, 5, and 7, respectively.

2. A composition comprising a first and a second zinc finger protein transcription factor (ZFP-TF) that repress MAPT expression,
wherein the first and the second ZFP-TFs bind to capitalized nucleotides in toGTGCTGGAGCTGGTGGGTggcggaga (SEQ ID NO: 1) and cgGCAGAAGGTGGGcGGTGGCggcggcg (SEQ ID NO: 2),
wherein binding of the first and second ZFP-TFs that bind to SEQ ID NO: 1 and SEQ ID NO: 2 results in synergistic repression of MAPT gene expression wherein
(A) the DNA-binding domain of the first ZFP-TF comprises six zinc finger regions F1 to F6 comprising (i) SEQ ID NOs: 3, 4, 5, 6, 5, and 7, respectively (SBS #57890); and
(B) the DNA-binding domain of the second ZFP-TF comprises six zinc finger regions F1 to F6 comprising SEQ ID Nos: 8-13, respectively (SBS #57930).

3. The composition of claim 1, wherein the first and the second ZFP-TF are encoded by polynucleotides carried by one or more viral vectors.

4. The composition of claim 3, wherein the one or more viral vectors are AAV vectors.

5. The composition of claim 4, wherein one AAV vector comprises the polynucleotides encoding the first and the second ZFP-TF.

6. The composition of claim 5, wherein the AAV vector is an AAV9 vector.

7. The composition of claim 3, wherein the one or more viral vectors comprise a CMV or synapsin (SYN) promoter.

8. The composition of claim 1, wherein the first and the second ZFP-TF are encoded by a single expression cassette in an AAV vector.

9. The composition of claim 8, wherein the coding sequences for the first and the second ZFP-TF are connected in frame by a coding sequence for a T2A peptide.

* * * * *

SEQUENCE LISTING

<160> NUMBER OF SEQ ID NOS: 13

<210> SEQ ID NO 1
<211> LENGTH: 28
<212> TYPE: DNA
<213> ORGANISM: Unknown
<220> FEATURE:
<223> OTHER INFORMATION: Description of Unknown:
      Human or mouse oligonucleotide

<400> SEQUENCE: 1
tggtgctgga gctggtgggt ggcggaga                                        28

<210> SEQ ID NO 2
<211> LENGTH: 28
<212> TYPE: DNA
<213> ORGANISM: Mus sp.

<400> SEQUENCE: 2
cggcagaagg tgggcggtgg cggcggcg            28

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Arg His His Leu Thr Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Arg Phe Thr Leu Ser Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ser Asp Val Leu Ser Glu
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys His Ser Thr Arg Arg Val
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Leu Tyr Thr Leu His Lys

```
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Arg Ser His Leu Thr Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Lys Gln His Leu Thr Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Ala His Leu Ser Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Ser Gly His Leu Ser Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ser Gly Asn Leu Ala Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
    peptide

<400> SEQUENCE: 13

Gln Ser Gly Asp Leu Thr Arg
1               5
```